(12) United States Patent
Ehrich et al.

(10) Patent No.: US 8,722,336 B2
(45) Date of Patent: *May 13, 2014

(54) RESTRICTION ENDONUCLEASE ENHANCED POLYMORPHIC SEQUENCE DETECTION

(75) Inventors: Mathias Ehrich, San Diego, CA (US); Dirk Johannes Van Den Boom, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,612

(22) Filed: May 25, 2012

(65) Prior Publication Data

US 2012/0270217 A1    Oct. 25, 2012

Related U.S. Application Data

(63) Continuation of application No. 12/411,329, filed on Mar. 25, 2009, now Pat. No. 8,206,926.

(60) Provisional application No. 61/039,747, filed on Mar. 26, 2008.

(51) Int. Cl.
*C12Q 1/68* (2006.01)
*C12P 19/34* (2006.01)

(52) U.S. Cl.
USPC .................................. 435/6.12; 435/91.2

(58) Field of Classification Search
None
See application file for complete search history.

(56) References Cited

U.S. PATENT DOCUMENTS

| | | |
|---|---|---|
| 4,656,127 A | 4/1987 | Mundy |
| 4,683,195 A | 7/1987 | Mullis et al. |
| 4,683,202 A | 7/1987 | Mullis et al. |
| 4,851,331 A | 7/1989 | Vary et al. |
| 4,965,188 A | 10/1990 | Mullis et al. |
| 5,210,015 A | 5/1993 | Gelfand et al. |
| 5,387,505 A | 2/1995 | Wu |
| 5,484,701 A | 1/1996 | Cocuzza et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,547,835 A | 8/1996 | Koster |
| 5,589,330 A | 12/1996 | Shuber |
| 5,605,798 A | 2/1997 | Koster |
| 5,641,658 A | 6/1997 | Adams et al. |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,786,183 A | 7/1998 | Ryder et al. |
| 5,834,189 A | 11/1998 | Stevens et al. |
| 5,849,483 A | 12/1998 | Shuber |
| 5,849,542 A | 12/1998 | Reeve et al. |
| 5,851,770 A | 12/1998 | Babon et al. |
| 5,869,242 A | 2/1999 | Kamb |
| 5,876,934 A | 3/1999 | Duthie et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,952,174 A | 9/1999 | Nikiforov et al. |
| 5,958,692 A | 9/1999 | Cotton et al. |
| 5,976,802 A | 11/1999 | Ansorge et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,043,031 A | 3/2000 | Koster et al. |
| 6,045,996 A | 4/2000 | Cronin et al. |
| 6,046,005 A | 4/2000 | Ju et al. |
| 6,087,095 A | 7/2000 | Rosenthal et al. |
| 6,110,684 A | 8/2000 | Kemper et al. |
| 6,136,541 A | 10/2000 | Gulati |
| 6,140,054 A | 10/2000 | Wittwer et al. |
| 6,142,681 A | 11/2000 | Gulati |
| 6,143,496 A | 11/2000 | Brown |
| 6,156,501 A | 12/2000 | McGall et al. |
| 6,183,958 B1 | 2/2001 | Stanton, Jr. |
| 6,194,144 B1 | 2/2001 | Koster |

(Continued)

FOREIGN PATENT DOCUMENTS

| | | |
|---|---|---|
| CN | 1930303 A | 3/2007 |
| WO | WO 97/035589 | 10/1997 |
| WO | WO 00/028081 | 5/2000 |
| WO | WO 00/052625 | 9/2000 |
| WO | WO 01/020039 | 3/2001 |
| WO | WO 01/025485 | 4/2001 |
| WO | WO 01/027326 | 4/2001 |
| WO | WO 01/027327 | 4/2001 |
| WO | WO 01/027329 | 4/2001 |
| WO | WO 01/029259 | 4/2001 |

(Continued)

OTHER PUBLICATIONS

Ausubel, et al., Current protocols in Molecular Biology, Greene Publishing, 1995.

(Continued)

*Primary Examiner* — Kenneth R. Horlick
*Assistant Examiner* — David Thomas
(74) *Attorney, Agent, or Firm* — Grant Anderson LLP

(57) ABSTRACT

Provided in part herein is an improved method for the detection of specific polymorphic alleles in a mixed DNA population. The method comprises enriching the relative percentage of a given polymorphic allele that is exponentially amplifiable by PCR. Provided also are methods for selectively enriching target nucleic acid, for example, fetal nucleic acid in a maternal sample. In the case of detecting fetal nucleic acid in a maternal sample, a restriction enzyme is introduced that can discriminate between the alleles of a polymorphic site. In some embodiments, the maternal allele is digested and nucleic acid comprising the paternal allele is relatively enriched.

18 Claims, 20 Drawing Sheets

(56) References Cited

U.S. PATENT DOCUMENTS

| | | |
|---|---|---|
| 6,197,506 B1 | 3/2001 | Fodor et al. |
| 6,210,891 B1 | 4/2001 | Nyren et al. |
| 6,221,601 B1 | 4/2001 | Koster et al. |
| 6,221,605 B1 | 4/2001 | Koster |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,258,538 B1 | 7/2001 | Koster et al. |
| 6,261,768 B1 | 7/2001 | Todd et al. |
| 6,268,144 B1 | 7/2001 | Koster |
| 6,277,573 B1 | 8/2001 | Koster |
| 6,300,076 B1 | 10/2001 | Koster |
| 6,602,662 B1 | 8/2003 | Koster |
| 6,814,934 B1 | 11/2004 | Higuchi |
| 8,206,926 B2 | 6/2012 | Ehrich et al. |
| 2001/0031467 A1 | 10/2001 | Dapprich et al. |
| 2002/0022224 A1 | 2/2002 | Hornby et al. |
| 2002/0064791 A1 | 5/2002 | Whitaker et al. |
| 2003/0027135 A1 | 2/2003 | Ecker |
| 2003/0082539 A1 | 5/2003 | Ecker |
| 2003/0124556 A1 | 7/2003 | Ecker |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0190605 A1 | 10/2003 | Ecker |
| 2003/0211522 A1 | 11/2003 | Landes |
| 2003/0232351 A1 | 12/2003 | Feinberg |
| 2004/0009518 A1 | 1/2004 | Lo |
| 2004/0137470 A1 | 7/2004 | Dhallan |
| 2004/0180328 A1 | 9/2004 | Ecker |
| 2004/0219517 A1 | 11/2004 | Ecker |
| 2004/0229224 A1 | 11/2004 | Frazer |
| 2005/0042639 A1 | 2/2005 | Knapp et al. |
| 2005/0079521 A1 | 4/2005 | Beaulieu et al. |
| 2005/0164241 A1 | 7/2005 | Hahn |
| 2005/0272070 A1 | 12/2005 | Ehrich |
| 2005/0287592 A1 | 12/2005 | Kless |
| 2006/0099581 A1 | 5/2006 | Berlin |
| 2006/0269925 A1 | 11/2006 | Nunes et al. |
| 2007/0048735 A1 | 3/2007 | Ecker |
| 2007/0059707 A1 | 3/2007 | Cantor et al. |
| 2008/0299562 A1 | 12/2008 | Oeth et al. |
| 2009/0317818 A1 | 12/2009 | Ehrich et al. |

FOREIGN PATENT DOCUMENTS

| | | |
|---|---|---|
| WO | WO 2005/035725 | 4/2005 |
| WO | WO 2006/056480 | 6/2006 |
| WO | WO 2007/028155 | 3/2007 |
| WO | WO 2007/140417 | 12/2007 |
| WO | WO 2007/147063 | 12/2007 |
| WO | WO 2008/157264 | 6/2008 |
| WO | WO 2008/118988 | 10/2008 |
| WO | WO 2009/032779 | 3/2009 |
| WO | WO 2009/032781 | 3/2009 |

OTHER PUBLICATIONS

Boom et al., 1990, J. Clin. Microbiol. 28: 495-503.
Boom et al., 1991, J. Clin. Microbiol. 29: 1804-1811.
Chen & Kwok, Nucleic Acids Research 25: 347-353 (1997).
Chen et al., Proc. Natl. Acad. Sci. USA 94/20: 10756-10761 (1997).
Cheung et al., 1994, J. Clin. Microbiol. 32: 2593-2597.
Chirgwin et al., 1979, Biochem. 18: 5294-5299.
Chiu et al., 2001, Clin. Chem. 47: 1607-1613.
Chomczynski and Mackey, 1995, Anal. Biochem. 225: 163-164.
Chomczynski and Mackey, 1995, Biotechniques 19: 942-945.
Chomczynski and Sacchi, 1987, Analytical Biochem. 162: 156-159.
Chomczynski, 1993, Biotech. 15: 532-537.
Dallan et al., "A non-invasive test for prenatal diagnosis based on fetal DNA present in maternal blood: a preliminary study", Lancet, Feb. 20, 2007, vol. 369, pp. 474-481.
Fournie et al.,1986 Anal. Biochem. 158: 250-256.
Fuery et al., Detection of Rare Mutant Alleles by Restriction Endonuclease-mediated Selective-PCR: Assay Design and Optimization:, Clinical Chemistry, 2000, vol. 46, pp. 620-624.
Grompe et al., Proc. Natl. Acad. Sci. USA 86: 5855-5892 (1989).
Grompe, Nature Genetics 5: 111-117 (1993).
Hatcher et al., Prenatal Diagnosis by exzymatic amplification and restriction endonuclease digestion for detection of haemoglobins A, S and C, Molecular and Cellular Probes, Academic Press, London. GB. vol. 6, No. 4., Aug. 1, 1992 pp. 343-348.
Innis et al., PCR Protocols: A Guide to Methods and Applications, Innis et al., eds, 1990.
Jurinke, C., Oeth, P., van den Boom, D., MALDI-TOF mass spectrometry: a versatile tool for high-performance DNA analysis. Mol. Biotechnol. 26, 147-164 (2004).
Lo et al. Am J Hum Genet. Apr. 1998;62(4):768-75.
Lo et al. Lancet. Aug. 16, 1997;350(9076):485-7.
Nasis et al. Clin Chem. Apr. 2004;50(4):694-701.
NCBI: Single Nucleotide Polymorphisms rs432950, May 25, 2006, (online), (Retrieved on Jun. 3, 2008), Retrieved from the National Center for Biotechnology Information (at NIH) database using internet: <URL: http:ncbi.nlm.nih.gov/SNP/snp_ref.cgi?type=rs&rs=4329520>.
Oeth, P. et al., iPLEX™ Assay: Increased Plexing Efficiency and Flexibility for MassARRAY® System through single base primer extension with mass-modified Terminators. SEQUENOM Application Note (2005).
Orita et al., Proc. Natl. Acad. Sci. U.S.A 86: 27776-2770 (1989).
Poch et al., "Sth132I, a novel class-IIs restriction endonuclease of Streptococcus thermophilus ST132" Gene 195: 201-206 (1997).
Reference Single Nucleotide Polymorphism rs12007, submitted to NCBI as ss44816763 by ABI, Jul. 19, 2005, pp. 1-13.
Reference Single Nucleotide Polymorphism rs910500, submitted to NCBI as ss5159471 by TSC-CSHL, Sep. 19, 2001, pp. 1-8.
Sambrook et al., Molecular Biology: A laboratory Approach, Cold Spring Harbor, N.Y. 1989.
Sekizawa et al., "Recent advances in non-invasive prenatal DNA diagnosis through maternal blood", J. Obstet. Gynacol. Res, Dec. 2007, vol. 33. No. 6, pp. 747-764.
Sheffield et al., Proc. Natl. Acad. Sci. USA 49: 699-706 (1991).
Weber et al., "A real-time Polymerase chain reaction assay for quantification of allele ratios and correction of amplification bias," Analytical Biochemistry, Academic Press Inc, New York, vol. 320, No. 2, Sep. 15, 2003, pp. 252-258.
White et al., Genomics 12: 301-306 (1992).
International Preliminary Report on Patentability mailed on: Oct. 8, 2009 in International Application No. PCT/US2008/58317, filed on Mar. 26, 2008.
International Search Report and Written Opinion mailed on: Dec. 18, 2009 in International Application No. PCT/US2009/038304, filed on Mar. 25, 2009.
International Search Report and Written Opinion mailed on: Jun. 30, 2008 in International Application No. PCT/US2008/58317, filed on Mar. 26, 2008.
Supplementary European Search Report dated Mar. 3, 2011 in European Application No. EP 08744402.2 filed Mar. 26, 2008.
Supplementary European Search Report dated: Sep. 1, 2011 in European Application No. EP 09726123 filed: Mar. 26, 2008 based on International Application No. PCT/US2009/038304.
Office Action mailed: Mar. 21, 2012 in U.S. Appl. No. 12/532,824, filed Mar. 15, 2010.
Office Action mailed: Apr. 27, 2011 in U.S. Appl. No. 12/411,329, filed Mar. 25, 2009 and published as: 2009/0317818 on: Dec. 24, 2009.
Office Action mailed: Feb. 29, 2012 in U.S. Appl. No. 12/411,329, filed Mar. 25, 2009 and published as: 2009/0317818 on: Dec. 24, 2009.
International Preliminary Report on Patentability mailed on Mar. 11, 2010 in International Application No. PCT/US2008/074689, filed on Aug. 28, 2008.
International Search Report and Written Opinion mailed on Mar. 23, 2009 in International Application No. PCT/US2008/074689, filed on Aug. 28, 2008.

(56) References Cited

OTHER PUBLICATIONS

International Preliminary Report on Patentability mailed on Oct. 7, 2010 in International Application No. PCT/US2009/038304, filed on Mach 25, 2009.
Office Action mailed Jul. 26, 2012 in U.S. Appl. No. 12/532,824, filed Mar. 15, 2010 and published as 2012-0115737 on May 10, 2012.
New England Biolabs, Inc. 1998/99 Catalog, Beverly, MA, USA pp. 256-257.
Office Action mailed Dec. 27, 2012 in U.S. Appl. No. 12/532,824, filed Mar. 15, 2010 and published as 2012-0115737 on May 10, 2012.
International Search Report and Written Opinion mailed on Oct. 9, 2008 in International Application No. PCT/US2007/071232, filed on Jun. 14, 2007.
International Preliminary Report on Patentability mailed on Mar. 12, 2009 in International Application No. PCT/US2007/071232, filed on Jun. 14, 2007.
Amicucci et al., (2000) Clin Chem 46:301-302.
Anker and Stroun, Clin. Chem. (2002) 48:1210-1211.
Anker et al., Cancer Metastasis Rev. (1999) 18:65-73.
Bischoff et al., Hum. Reprod. Update. (2005) Jan.~Feb.;11(1):59-67.
Chan et al, Clin Chem. Jan. 2004;50(1):88-92.
Chan KC and Lo YM, Histol Histopathol (2002) 17,937-943.
Chen XQ, et al. Nat Med (1996) 2,1033-1035.
Chiu RWK, et al. (2002) Lancet 360:998-1000.
Costa JM, Ernault P (2002) Clin Chem 48:679-680.
Costa JM, et al. Prenat Diagn 21:1070-1074.
Finning KM, et al. (2002) Transfusion 42:1079-1085.
Fournie et al., Cancer Lett 1995;91:221-227.
Fournie et al., Gerontology 1993;39:215-221.
Fucharoen G, et al. (2003) Prenat Diagn 23:393-396.
Gonzalez-Gonzalez MC, et al. (2002) Prenat Diagn 22:946-948.
Gonzalez-Gonzalez MC, et al. (2003) Prenat Diagn 23:232-234.
Jahr S, et al. Cancer Res (2001) 61,1659-1665.
Li et al, Clin Chem. Jun. 2004;50(6):1002-1011.
Lo et al. (1998) N. Engl J Med 339:1734-1738.
Lo et al. Am J Hum Genet (1999) 64:218-224.
Lo KW, et al. Clin Chem (1999) 45,1292-1294.
Lo et al., Lancet 1998;351:1329-1330.
Lo et al., Clin Chem 2000;46:319-323.
Nawroz H et al., Nat Med 1996;2:1035-1037.
Nelson, Crit. Rev. Clin. Lab Sci. (1998) 35(5):369-414.
Ng EK, et al. Proc Natl Acad Sci USA (2003) 100, 4748-4753.
Rijnders RJ, et al. (2001) Obstet Gynecol 98:374-378.
Rumore and Steinman J Clin Invest. Jul. 1990;86(1):69-74.
Saito H, et al. (2000) Lancet 356:1170.
Stroun M, et al. Oncology (1989) 46,318-322.
Wang et al. Clin Chem. Jan. 2004;50(1):211-213.
Widlak et al, J Biol Chem. Mar. 17, 2000;275(11):8226-8232.
Office Action mailed Oct. 7, 2013 in U.S. Appl. No. 12/532,824, filed Mar. 15, 2010 and published as 2012-0115737 on May 10, 2012.
Office Action mailed Oct. 28, 2013 in U.S. Appl. No. 12/532,824 filed Mar. 15, 2010 and published as 2012-0115737 on May 10, 2012.

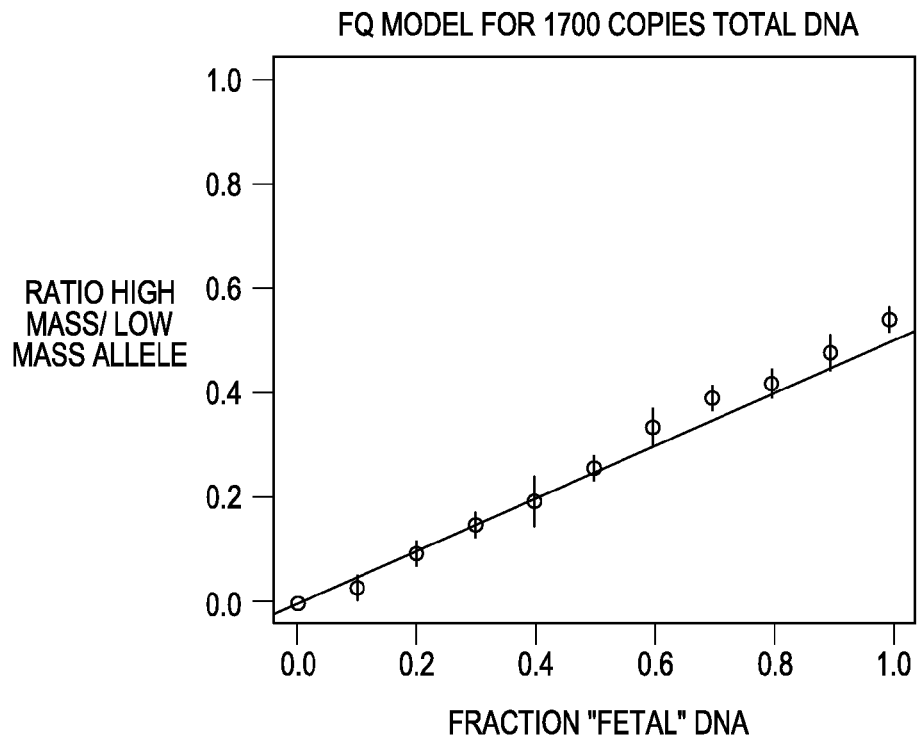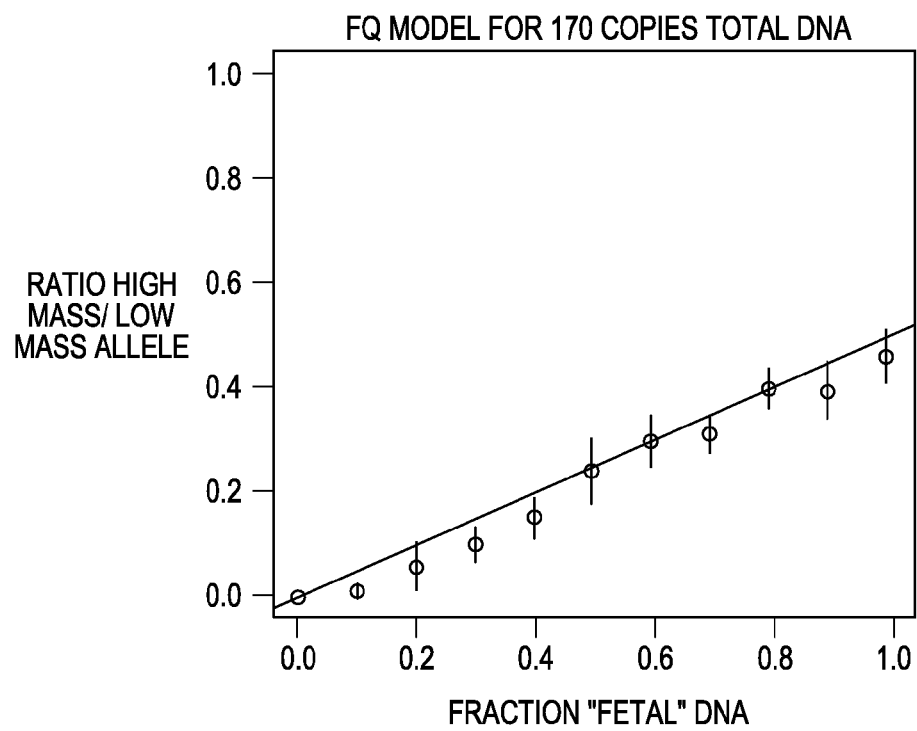
FIG. 6

FIG. 8A

| FIG. 8AA |
|----------|
| FIG. 8AB |

NON-INVASIVE PRENATAL SEX TEST - AMG_(F/M)-

```
                10        20        30        40        50        60
AM-X.SEQ  ACCTCATCCTGGCACCCTGGTTATATCAACTTCAGCTATGAGTAATTTTCTCTTTAC
          X:::::::::::::::::::::::::::::::::::::::::::::::::::::::::
AM-Y.SEQ  ACCTCATCCTGGGCACCCTGGTTATATCAACTTCAGCTATGAGTAATTTTCTCTTTAC
                10        20        30        40        50        60

70        80        90       100       110       120
AM-X.SEQ  TAATTTTGACCATTGTTTGCGTTAACAATGCCCCTGGGCTCTGTAAAGAATAGTGTGTTGA
          ::::::::  ::::: ::::::::::::  ::::::::::::::::::::::::::::
AM-Y.SEQ  TAATTTTGATCACTGTTTGCATTAGCAGTGCCCCCTGGGCTCTGTAAAGAATAGTGGGTGGA
                70        80        90       100       110       120

130       140       150       160       170
AM-X.SEQ  TTCTTTATCCCAGAT------GTTTCTCAAGTGGTCCTGATTTTACAGTTCCTACCACCA
          ::::: ::::X ::       ::::::::::::::::::::::::::::::::::::
AM-Y.SEQ  TTCTTCATCCCAAATAAAGTGTTTCTCAAGTGGTCCCAATTTTACAGTTCCTACCATCA
               130       140       150       160       170       180

180       190       200       210
AM-X.SEQ  GCTTCCCAGTTTAAGCTCTGATGGTTGGCCCTCAAGCCT
          :::::::::::::::::::::::::::::::::::::::
AM-Y.SEQ  GCTTCCCAGTTTAAGCTCTGATGGTTGGCCCTCAAGCCT
               190       200       210
```

*FIG. 8AA*

PRIMERS FOR NON-INVASIVE PRENATAL SEX TESTING USING AMG AS TARGET:

PCR PRIMERS:
AMG-F:  5'-ACGTTGGATGCCCTGGGCTCTGTAAAGAAT-3'
AMG-R:  5'-ACGTTGGATGAGGCTTGAGGCCAACCATCAG-3'

EXTEND PRIMERS:
AMG-E:  5'-TTCTTCATCCCAAATAAAGT-3'

COMPETITORS:
AMG-X-S:
5'-CCCTGGGCTCTGTAAAGAATAGTGTGTTGATTCTTTATCCCAGAaGTTTCTCAAGTGGTCCTGATTTTACAGTTCCTACCACCA
GCTTCCCAGTTTAAGCTCTGATGGTTGGCCCTCAAGCCT-3'

AMG-X-AS:
5'-AGGCTTGAGGCCAACCATCAGAGCTTAAACTGGGAAGCTGGTGTAGGAACTGTAAAATCAGGACCACTTGAGAAActTCTGGGATAAAGA
ATCAACACACTATTCTTTACAGAGCCCAGGG-3'

AMG-Y-S:
5'-CCCTGGGCTCTGTAAAGAATAGTGGGTGGATTCTTCATCCCAAATAAAGTcGTTTCTCAAGTGGTCCCAATTTACAGTTCCTACCATCA
GCTTCCCAGTTTAAGCTCTGATGGTTGGCCCTCAAGCCT-3'

AMG-Y-AS:
5'-AGGCTTGAGGCCAACCATCAGAGCTTAAACTGGGAAGCTGATGGTAGGAACTGTAAAATTGGGACCACTTGAGAAACgACTTTATTTGGGATGA
AGAATCCACCCACTATTCTTTACAGAGCCCAGGG

| FIG. 8BA |
|---|
| FIG. 8BB |

NON-INVASIVE PRENATAL SEX TEST - AMG-XY-5-i

```
                      10        20        30        40        50        60
AM-X.SEQ     ACCTCATCCTGGGCACCCTGGTTATATCAACTTCAGCTATGAGGTAATTTTCTCTTTAC
             X:::::::::::::::::::::::::::::::::::::::::::::::::::::::::::
AM-Y.SEQ     ACCTCATCCTGGGCACCCTGGTTATATCAACTTCAGCTATGAGGTAATTTTCTCTTTAC
                      10        20        30        40        50        60

70        80        90       100       110       120
AM-X.SEQ     TAATTTTGACCATTGTTGTTGCGTTAACAATGCCCTGGGCTCTGTAAAGAATAGTGTTGA
             ::::::::::  :::  ::::::  :: ::::::::::::::::::::::::::: ::
AM-Y.SEQ     TAATTTTGATCACTGTTTGCATTAGCAGTGCCCTGGGCTCTGTAAAGAATAGTGGGTGGA
                      70        80        90       100       110       120

130       140       150       160       170
AM-X.SEQ     TTCTTTTATCCCAGAT------GTTTCTCAAGTGGTCCTGATTTTACAGTTCCTACCACCA
             :::::::: ::::::X ::    :::::::::::::::::::::::::::::::: ::
AM-Y.SEQ     TTCTTTCATCCCAAATAAAGTGGTTTCTCAAGTGGTCCCAATTTTACAGTTCCTACCATCA
                     130       140       150       160       170       180

180       190       200       210
AM-X.SEQ     GCTTCCCAGTTTAAGCTCTGATGGTTGGCCCTCAAGCCT
             :::::::::::::::::::::::::::::::::::::::
AM-Y.SEQ     GCTTCCCAGTTTAAGCTCTGATGGTTGGCCCTCAAGCCT
                     190       200       210
```

*FIG. 8BA*

PRIMERS FOR NON-INVASIVE PRENATAL SEX TESTING USING AMG AS TARGET:
PCR PRIMERS:
AMG-XY-5-i-F:      5'-ACGTTGGATGTATCAACTTCAGCTATGAGG-3'
AMG-XY-5-i-R:      5'-ACGTTGGATGCACTATTCTTTACAGAGC-3'

EXTEND PRIMERS:
AMG-XY-5-i-E:      5'-CTTTACAGAGCCCAGGG-3'

COMPETITORS:
AMG-XY-5-i-S:
5'-TATCAACTTCAGCTATGAGGTAATTTTCTCTTTACTAATTTGAYCAYTGTTTGCRTTARCARTaCCCTGGGCTCTGTAAAGAATAGTG-3'

AMG-XY-5-i-AS:
5'-CACTATTCTTTACAGAGCCCAGGGtARTGRTAARGCAAACAYTGYTCAAAATTAGTAAAGAGAAAAATTACCTCATAGCTGAAGTTGATA-3'

FIG. 8BB

| FIG. 8C | FIG. 8CA |
|---|---|
|  | FIG. 8CB |

NON-INVASIVE PRENATAL SEX TEST

```
                  10        20        30        40        50        60
AM-X.SEQ    ACCTCATCCTGGGCACCCTGGTTATATCAACTTCAGCTATGAGGTAATTTTCTCTTTAC
            X:::::::::::::::::::::::::::::::::::::::::::::::::::::::::::
AM-Y.SEQ    ACCTCATCCTGGGCACCCTGGTTATATCAACTTCAGCTATGAGGTAATTTTCTCTTTAC
                  10        20        30        40        50        60

70        80        90       100       110       120
AM-X.SEQ    TAATTTTGACCATTGTTTGCGTTAACAATGCCCTGGGCTCTGTAAAGAATAGTGTGTTGA
            ::::::::: ::  ::::::::  ::::: ::::::::::::::::::::::: ::  ::
AM-Y.SEQ    TAATTTTGATCACTGTTTGCATTAGCAGTCCCCTGGGCTCTGTAAAGAATAGTGGGTGGA
                  70        80        90       100       110       120

130       140       150       160       170
AM-X.SEQ    TTCTTTTATCCCAGAT------GTTTCTCAAGTGGTCCTGATTTTACAGTTCCTACCACCA
            :::::: ::::::::X ::    ::::::::::::::::::::::::::::::::: ::
AM-Y.SEQ    TTCTTTCATCCCAAATAAAGTGGTTTCTCAAGTTGTTCTCAAGTGGTCCCAATTTTACAGTTCCTACCATCA
                 130       140       150       160       170       180

180       190       200       210
AM-X.SEQ    GCTTCCCAGTTTAAGCTCTGATGGTTGGCCCTCAAGCCT
            :::::::::::::::::::::::::::::::::::::::
AM-Y.SEQ    GCTTCCCAGTTTAAGCTCTGATGGTTGGCCCTCAAGCCT
                 190       200       210
```

*FIG. 8CA*

NEW PRIMERS FOR NON-INVASIVE PRENATAL SEX TESTING USING AMG AS TARGET:
PCR PRIMERS:
AMG-F:     5'-CCCTGGGCTCTGTAAAGAAT-3'
AMG-R:     5'-GAGCTTAAACTGGGAAGCTG-3'

EXTEND PRIMERS:
AMG-Y:     5'-TTCTTCATCCCAAATAAAGT-3'
AMG-CON:   5'-CCCTGGGCTCTGTAAAGAATAGT-3'

EXTEND PRODUCTS:
Y CHROMOSOME:        TTCTTCATCCCAAATAAAGTG
TEMPLATE POSITIVE:   CCCTGGGCTCTGTAAAGAATAGTG

RESULTS TABLE

| SEQUENCE NAME | PRIMER SEQUENCE | NO. OF NUCLEOTIDES | MASS |
|---|---|---|---|
| AMG-Y PRIMER | TTCTTCATCCCAAATAAAGT | 20 | 6011 |
| YCHROMOSOME POSITIVE | TTCTTCATCCCAAATAAAGTg | 21 | 6340.2 |
| AMG-CON PRIMER | CTGGGCTCTGTAAAGAATAGT | 21 | 6457.2 |
| TEMPLATE POSITIVE | CTGGGCTCTGTAAAGAATAGTg | 22 | 6786.4 |
| SRY PRIMER | caggacagcagtagagca | 18 | 5550.6 |
| SRY EXTENSION PRODUCT | caggacagcagtagagcag | 19 | 5879.8 |

FIG. 8CB

NON-INVASIVE PRENATAL ALBUMIN TEST

QUERY    1  GCTCAGTATCTTCAGCAGTGTCCATTTGAAGATCATGTAAAATTAGTGAATGAAGTAACT  60
            ||||||||||||||||||||||||||||||||||||||||||||||||||||||||||||
SBJCT  193  GCTCAGTATCTTCAGCAGTGTCCATTTGAAGATCATGTAAAATTAGTGAATGAAGTAACT  252

QUERY   61  GAATTTGC  68
            ||||||||
SBJCT  253  GAATTTGC  260

ALB ASSAY:

PCR-F: 5'-ACGTTGGATGCAGTATCTTCAGCAGTGTCC-3'
PCR-R: 5'-ACGTTGGATGGCAAATTCAGTTACTTCATTC-3'

EXTEND: 5'-CAGTGTCCATTTGAAGATC-3'

COMPETITOR-S:
5'-CAGTATCTTCAGCAGTGTCCATTTGAAGATCtTGTAAAATTAGTGAATGAAGTAACTGAATTTGC-3'

COMPETITOR-AS:
5'-GCAAATTCAGTTACTTCATTCATTCACTAATTTTACAaGATCTTCAAATGGACACTGCTGAAGATACTG-3'

FIG. 9

RESTRICTION ENDONUCLEASE ENHANCED POLYMORPHIC SEQUENCE DETECTION

RELATED PATENT APPLICATIONS

This patent application is a continuation of U.S. patent application Ser. No. 12/411,329, filed on Mar. 25, 2009, which claims the benefit of U.S. Provisional Patent Application No. 61/039,747, filed on Mar. 26, 2008, entitled RESTRICTION ENDONUCLEASE ENHANCED POLYMORPHIC SEQUENCE DETECTION. This patent application also is related to U.S. Provisional Patent Application No. 60/908,167, filed on Mar. 26, 2007, and Patent Cooperation Treaty International Patent Application No. PCT/US2008/058317, filed on Mar. 26, 2008, and published as Publication No. WO2008/118988 on Oct. 2, 2008, each entitled RESTRICTION ENDONUCLEASE ENHANCED POLYMORPHIC SEQUENCE DETECTION. The entirety of each of these three patent applications is hereby incorporated herein by reference.

FIELD OF THE INVENTION

The invention in part pertains to methods for detecting specific alleles in a mixed nucleic acid sample. Methods provided herein can be used to detect the presence or absence of fetal nucleic acid in a maternal sample.

BACKGROUND

The analysis of circulating nucleic acids has revealed applications in the non-invasive diagnosis, monitoring, and prognostication of many clinical conditions. For example, for prenatal applications, circulating fetal-specific sequences have been detected and constitute a fraction of the total DNA in maternal plasma. The diagnostic reliability of circulating DNA analysis depends on the fractional concentration of the targeted sequence, the analytical sensitivity, and the specificity. The robust discrimination of sequence differences (e.g., single-nucleotide polymorphisms, or SNPs) between circulating DNA species is technically challenging and demands the adoption of highly sensitive and specific analytical methods.

Current techniques to detect sequence differences in a DNA sample include allele-specific PCR, restriction digest and Southern blot hybridization, restriction endonuclease-mediated selective-PCR (REMS-PCR), and competitive PCR methods involving the use of fluorescent detection probes. Currently available techniques present several disadvantages. For allele-specific PCR, it is often difficult to design assays with a high degree of allele specificity (Nasis et al. *Clin Chem.* 2004 April; 50(4):694-701). Restriction digest/Southern blot methods require higher amounts of DNA template than the method provided herein, and lack the sensitivity to detect polymorphic sequences comprising a low relative proportion of total DNA. Restriction endonuclease-mediated selective-PCR (REMS-PCR) has the drawback of requiring a thermostable restriction enzyme that cleaves the wild-type allele. REMS-PCR is described in U.S. Pat. No. 6,261,768, which is hereby incorporated by reference. Use of the technique may not always be possible, and this requirement limits the general utility of the REMS-PCR approach. Competitive PCR lacks the sensitivity to detect polymorphic sequences comprising a low relative proportion (<5%) of total DNA. Competitive PCR with allele-specific fluorescent probes lacks the ability to multiplex assays higher than 2-3 assays in a single tube format. In addition, similar methods utilizing methylation differences between DNA species (for example, US Patent Application Publication No. 20070059707, entitled, "Methods for prenatal diagnosis of chromosomal abnormalities", which is hereby incorporated by reference) are not effective at low copy numbers of genomic DNA.

SUMMARY

The invention in part provides sequence-specific cleavage of nucleic acid to selectively enrich for a particular target nucleic acid. Polymorphic loci are chosen such that only one allele at the polymorphic locus is cleaved by a given cleavage agent, such as a restriction endonuclease. Oligonucleotide primer pairs designed to flank the polymorphism allow amplification of the polymorphic region, or amplicon, by amplification (e.g., PCR). Prior to or during amplification, nucleic acid samples are incubated with the given restriction endonuclease. In some embodiments, the cleavage agent is introduced prior to amplification. This approach results in cleavage of the polymorphic allele or sequence comprising the polymorphic allele that is recognized by the restriction endonuclease, if this allele is present. Cleavage of any template nucleic acid within the amplicon sequence (i.e., between primer pairs) prevents PCR amplification of this template. Therefore, if only one allele of a polymorphism is recognized by the cleavage agent and the corresponding nucleic acid sequence is cleaved by the restriction endonuclease, the relative percentage of the amplifiable alternate polymorphic allele is increased in a manner dependent on the efficiency and specificity of the restriction endonuclease activity. After amplification, the amplified polymorphic alleles can be genotyped or otherwise detected or discriminated by any method known in the art (e.g., using Sequenom's MassARRAY® technology or by RT-PCR).

In some embodiments, the invention in part provides a method for detecting the presence or absence of a target allele at a polymorphic locus in a sample, where the sample contains nucleic acid, which comprises: cleaving a nucleic acid comprising a non-target allele at or near the polymorphic locus with a cleavage agent that recognizes and cleaves the non-target allele, but not the target allele; amplifying uncleaved nucleic acid but not cleaved nucleic acid; and analyzing the amplification products from the previous step to determine the presence or absence of the target allele. In certain embodiments, the method also comprises first obtaining a sample suspected of comprising nucleic acid with target and non-target alleles. In some embodiments, the method is used to distinguish between two individuals, for example, between a mother and a fetus, where the sample comprises both maternal and fetal nucleic acid. Optionally, the method may be used to quantify the target nucleic acid relative to the non-target nucleic acid.

The invention also in part provides methods for enriching for target nucleic acid, comprising cleaving nucleic acid comprising a non-target allele with a restriction endonuclease that recognizes the nucleic acid comprising the non-target allele but not the target allele; and amplifying uncleaved nucleic acid but not cleaved nucleic acid, where the uncleaved, amplified nucleic acid represents enriched target nucleic acid relative to non-target nucleic acid. In some embodiments, methods provided herein may be utilized to determine the presence or absence of target nucleic acid in a background of non-target nucleic acid. In certain embodiments, the amplification products can be analyzed to diagnose, monitor or prognose a clinical condition. Likewise, the amplification products can be analyzed to assist in the diagnosis, prognosis or monitoring of a clinical condition or chromosomal abnormality. Nucleic acid may be selected such that it comprises an allele having a polymorphic site that is susceptible to selective digestion by a cleavage agent, for example.

Methods provided herein are useful for analyzing nucleic acid including, but not limited to, DNA, RNA, mRNA, oligonucleosomal, mitochondrial, epigenetically-modified, single-stranded, double-stranded, circular, plasmid, cosmid, yeast artificial chromosomes, artificial or man-made DNA, including unique DNA sequences, and DNA that has been reverse transcribed from an RNA sample, such as cDNA, and combinations thereof. In some embodiments, methods provided herein are used to detect or selectively enrich RNA.

A nucleic acid may also be characterized as target nucleic acid or non-target nucleic acid, where target nucleic comprises the target allele and non-target nucleic acid comprises the non-target allele. In some embodiments, the target nucleic acid comprises the paternal allele and the non-target nucleic acid comprises the maternal allele. In certain embodiments, the nucleic acid is cell-free nucleic acid or partially cell-free nucleic acid. In some embodiments, the target nucleic acid is apoptotic or partially apoptotic. In certain embodiments, the target nucleic acid is less than 2000, 1200, 1100, 1000, 900, 800, 700, 600, 500, 400, 300, 200, 100, 80, 70, 60, 50, 40 or less base pairs in length.

Methods provided herein may be used to detect target nucleic acid in a biological sample. In some embodiments, the biological sample is from an animal, often a human. In certain embodiments, the biological sample is selected from the group of whole blood, serum, plasma, umbilical cord blood, chorionic villi, amniotic fluid, cerbrospinal fluid, spinal fluid, lavage fluid, biopsy sample, urine, feces, sputum, saliva, nasal mucous, prostate fluid, semen, lymphatic fluid, bile, tears, sweat, breast milk, breast fluid, embryonic cells and fetal cells, and mixture thereof. In some embodiments, the sample is from a crime scene (e.g., used for forensic analysis). In certain embodiments, the biological sample is obtained through non-invasive means, for example, a blood draw from a pregnant female. In another some embodiments, the biological sample is cell-free. In certain embodiments, the sample is a previously isolated sample of nucleic acids.

In some embodiments, the invention in part provides a method for detecting the presence or absence of fetal nucleic acid in a maternal sample, where the sample contains nucleic acid, which comprises: cleaving nucleic acid comprising a maternal allele with a restriction endonuclease that recognizes and cleaves the nucleic acid comprising the maternal allele but not the paternal allele; amplifying uncleaved nucleic acid but not cleaved nucleic acid; and analyzing the amplification products from the previous step to determine the presence or absence of fetal nucleic acid. In certain embodiments, the sample comprises a mixture of nucleic acids. For example, the mixture may comprise nucleic acid from different species or from different individuals. In some embodiments, the sample is from a pregnant female. Samples can be collected from human females at 1-4, 4-8, 8-12, 12-16, 16-20, 20-24, 24-28, 28-32, 32-36, 36-40, or 40-44 weeks of fetal gestation, and sometimes between 5-28 weeks of fetal gestation. In certain embodiments, methods provided herein may be used to detect the presence or absence of fetal Y-chromosome nucleic acid, thereby determining the sex of the fetus.

In some embodiments, the target nucleic acid comprises a paternal allele. In certain embodiments, the mother is homozygous at the polymorphic site and the fetus is heterozygous at the polymorphic site. In the case when the mother is homozygous at the polymorphic site and the fetus is heterozygous at the polymorphic site, the polymorphic site is considered informative (e.g., see FIG. 5A for examples of informative and non-informative cases). In certain embodiments, the maternal genotype is determined in conjunction with methods provided herein. In some embodiments, the mother is first genotyped (for example, using peripheral blood mononuclear cells (PBMC) from a maternal whole blood sample) to determine the non-target allele that will be recognized and cleaved by the cleavage agent. When the method is used for forensic purposes, the victim may be first genotyped to determine the non-target allele that will be recognized and cleaved by the cleavage agent. Likewise, when used for organ transplant-related applications, the transplant recipient may be first genotyped to determine the non-target allele that will be recognized and cleaved by the cleavage agent.

In certain embodiments, the sample contains nucleic acid from two different individuals. Such instances include, but are not limited to, organ transplant recipients, transfusion recipients, and forensic applications.

In certain embodiments, the sample is from an individual suspected of suffering from a disease, and the non-target allele is a wild-type allele that is selectively cleaved in order to enrich for a disease-related point mutation. In certain embodiments, the disease is cancer. The ras proto-oncogenes, K-ras, N-ras, and H-ras, and the p53 tumor suppressor gene are examples of genes which are frequently mutated in human cancers. Specific mutations in these genes leads to activation or increased transforming potential.

The invention also in part provides methods useful for detecting rare alleles or low copy number alleles. In some embodiments, the target allele is undetectable by conventional or unmodified genotyping methods if the non-target allele is not selectively cleaved. In certain embodiments, the target allele is not detectable unless it is selectively enriched, for example, by methods provided herein. In certain embodiments, the target allele concentration (e.g., allele concentration in a sample) is about 0.1% to about 40%, e.g., about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34% or 35%, of total nucleic acid (e.g., total nucleic acid in a composition or sample), or is less than one of the foregoing percentages. Total nucleic acid includes maternal nucleic acid and any fetal nucleic acid, and total nucleic acid includes non-target allele and any target allele. When fetal nucleic acid is present, target allele is about 50% of the fetal nucleic acid, and non-target allele often includes the other about 50% of the fetal nucleic acid and all maternal nucleic acid, in some embodiments. In certain embodiments, the target nucleic acid number is about 1 to about 5,000 molecules, e.g., about 5, 6, 7, 8, 9, 10, 11, 12, 13, 14, 15, 16, 17, 18, 19, 20, 25, 30, 35, 40, 50, 55, 60, 70, 80, 90, 100, 150, 200, 250, 300, 400, 500, 600, 700, 800, 900 or 1000 molecules, or is less than one of the foregoing numbers of molecules. In certain embodiments, the target allele is a mutation, and the non-target allele is the wild-type allele. In certain embodiments, the target allele may be either a somatic or germline mutation. In certain embodiments, another allele or sequence identifier in the same amplicon as the polymorphic locus may be detected. For example, a sequence comprising a target allele may be selectively enriched using methods provided herein, and another sequence identifier may be detected by any method known in the art.

In certain embodiments, there are no other polymorphic loci within the amplicon that may be recognized by the cleavage agent. For example, there is only one polymorphic locus in the amplicon recognized by the cleavage agent in some embodiments.

In certain embodiments, the method optionally comprises first isolating nucleic acid from the sample. DNA isolation from blood, plasma, or serum of the pregnant mother can be performed using any method known to one skilled in the art. Any standard DNA isolation technique can be used to isolate the fetal DNA and the maternal DNA including, but not limited to, QIAamp DNA Blood Midi Kit supplied by QIAGEN. Other standard methods of DNA isolation are described, for example, in (Sambrook et al., Molecular Biology: A laboratory Approach, Cold Spring Harbor, N.Y. 1989; Ausubel, et al., Current protocols in Molecular Biology, Greene Publishing, Y, 1995). A method for isolation of plasma DNA is described in Chiu et al., 2001, *Clin. Chem.* 47: 1607-1613, which is herein incorporated by reference in its entirety. Other suitable methods are provided in Example 2 of PCT International Application Publication Number 2007/028155, filed on Sep. 1, 2006.

Methods described herein allow for the use of any cleavage agent capable of distinguishing between two different sequences, and cleaving somewhere within the amplicon sequence thereby preventing amplification of the cleaved sequence. The difference between the sequences may be the result of different alleles at one or more polymorphic sites within the sequence. In another example, the difference between the sequences may be the result of two homologous sequences, for example, between paralogous genes or between highly homologous genes such as the RhD gene, which encodes the D polypeptide, and the RHCE gene, which encodes the CcEe polypeptide. An example of a cleavage agent is a restriction enzyme, also referred to as a restriction endonuclease. Multiple restriction endonucleases (available from various vendors) may be selected that correspond to appropriate sequence differences. In some embodiments, the restriction enzyme is a thermostable restriction enzyme. In certain embodiments, the restriction enzyme is Tsp509I. In certain embodiments, a step is added to end the cleaving activity of the cleavage agent, for example, by introducing a protease and/or high temperature prior to amplification.

A restriction endonuclease may be added prior to or during amplification, for example, during an incubation step. In some embodiments, the restriction endonuclease is added less than 5 minutes, 5 minutes, 10 minutes, 20 minutes, 30 minutes, 40 minutes, 50 minutes, 60 minutes, 90 minutes or 120 or more minutes before amplification. Incubation time may be shortened if additional units of restriction enzyme are added to the reaction. Conversely, longer incubation times are often used to allow a reaction to proceed to completion with fewer units of enzyme. This is contingent on how long a particular enzyme can survive (maintain activity) in a reaction. Some enzymes survive for long periods (>16 hours) while others survive only an hour or less in a reaction. In certain embodiments, the restriction enzyme digests greater than 40%, 50%, 60%, 70%, 80%, 90%, 91%, 92%, 93%, 94%, 95%, 96%, 97%, 98% or 99% of the non-target nucleic acid. However, if digestion of non-target nucleic acid of less than 40% allows for useful enrichment of target nucleic acid, it is within the scope of the invention. In certain embodiments, the restriction enzyme digests substantially all of the non-target nucleic acid. In certain embodiments, the restriction endonuclease is a thermostable restriction endonuclease. Examples of thermostable endonucleases include, but are not limited to, Bst NI, Bsl I, Tru 9I and Tsp 509 I. In certain embodiments, the cleavage agent is not thermostable, especially when the digestion occurs prior to the amplification step. In some embodiments, the cleavage agent is thermostable and a majority of the digestion of the non-target nucleic acid occurs prior to the amplification step during a pre-incubation step. In certain embodiments, the restriction enzyme digests greater than 80%, 85%, 86%, 87%, 88%, 89%, 90%, 91%, 92%, 93%, 94%, 95%, 96%, 97%, 98% or 99% of the non-target nucleic acid prior to amplification. In another embodiment, one or more incubation steps may be introduced during thermal cycling. Incubation steps are ideally at the optimal temperature for digestion to occur. For example, for Tsp509I the incubation temperature may be 65 degrees C. In certain embodiments, a step is introduced to prevent or to reduce digestion during the amplification step, for example, by introducing a protease to disable a cleavage agent that is a protein.

In some embodiments, the units of restriction enzyme added to the sample is 0.10, 0.25, 0.50, 0.75, 1.0, 2.0 or more. Note that DNA substrates are digested at varying rates, therefore, the actual number of units required for a complete or substantially complete digestion may vary from assay to assay.

In certain embodiments, only one restriction endonuclease is used to digest one or more non-target alleles in a single reaction. For example, a multiplexed assay may be designed where a single restriction endonuclease performs multiple (e.g., greater than 5, 10, 15, 20, 25, 50, 100) digestions across the genome. In certain embodiments, more than one restriction endonuclease (e.g., greater than or equal to 2, 3, 4, 5, 6, 7, 8, 9, 10) is used to make multiple (e.g., greater than 5, 10, 15, 20, 25, 50, 100) digestions across the genome.

Amplification may be performed after or during the cleavage of the non-target allele, and prior to the detection of the target allele. In some embodiments, amplification is performed after cleavage of the non-target allele. Amplification can be performed by any method known in the art, including but not limited to polymerase chain reaction (PCR), ligase chain reaction, transcription-based amplification, restriction amplification, or rolling circle amplification, using primers that anneal to the selected fetal DNA regions. Oligonucleotide primers are selected such that they anneal to the sequence to be amplified. In some embodiments, primers are designed such that one or both primers of the primer pair contain sequence recognizable by one or more restriction endonucleases.

Following amplification, the relative enrichment of the target allele in the sample allows accurate detection of allele frequencies using practically any method of nucleic acid detection known in the art. For example, any of the following methods may be used, including, but not limited to, primer extension or microsequencing methods, ligase sequence determination methods, mismatch sequence determination methods, microarray sequence determination methods, restriction fragment length polymorphism (RFLP) procedures, PCR-based assays (e.g., TAQMAN® PCR System (Applied Biosystems)), nucleotide sequencing methods, hybridization methods, conventional dot blot analyses, single strand conformational polymorphism analysis (SSCP), denaturing gradient gel electrophoresis (DGGE), heteroduplex analysis, mismatch cleavage detection, detection by mass spectrometry, real time-PCR and pyrosequencing.

Methods provided herein may also be multiplexed at high levels in a single reaction. For example, one or more alleles can be detected simultaneously. Multiplexing embodiments are particularly important when the genotype at a polymorphic locus is not known. In some instances, for example when the mother is heterozygous at the polymorphic locus, the assay may not be informative. See FIG. 5A, which further describes the use of polymorphic variants to detect fetal nucleic acid from a maternal sample. In some embodiments, 1 to 1,000 target alleles are assayed (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 target alleles are assayed), or a number of target alleles more than one of the foregoing number of target alleles is assayed, where each of the target alleles assayed may or may not be informative (e.g., not every target allele is informative). In certain embodiments, the genotype at the polymorphic locus is known. In certain embodiments, 5 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more or 90 or more target alleles are assayed (e.g., informative target alleles are assayed). The invention in part also includes combinations of different multiplex schemes provided herein.

In certain embodiments, the invention in part provides a method for quantifying a target allele at a polymorphic locus in a sample, where the sample contains nucleic acid, that comprises: digesting nucleic acid containing a maternal allele at the polymorphic locus with an enzyme, such as a restriction endonuclease, that selectively digests the maternal allele, where the selective digestion yields a DNA sample enriched for fetal DNA; determining the maternal or paternal allele frequency using polymorphic markers within the amplicon, and comparing the paternal or maternal allele frequency to a control DNA sample. In some embodiments, a difference in allele frequency is indicative of a chromosomal abnormality. In certain embodiments, the control DNA sample is a competitor oligonucleotide that is introduced to the assay in known quantities.

In certain embodiments, the present invention provides a kit for detecting the presence or absence of target nucleic acid. One component of the kit is primers for amplifying the region of interest. Another component of the kit comprises probes for discriminating between the different alleles of each nucleic acid species.

Certain non-limiting embodiments of the invention are further described in the following Brief Description of the Drawings, Detailed Description and claims.

BRIEF DESCRIPTION OF THE DRAWINGS

FIG. 6 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers.

FIGS. 8A-8C provide the location design of the AMG primers. The amplification primers are underlined once and the extend primers are underlined twice. In addition, competitor sequences are provided. Competitor sequences may be used for quantitative methods. FIG. 8C includes a Results Table that shows the different masses generated by each of the AMG and SRY assays, which may be used to interpret the results from the assays. FIG. 8A (FIG. 8AA, FIG. 8AB) discloses SEQ ID NOS 1,169-1,177, respectively, in order of appearance. FIG. 8B (FIG. 8BA, FIG. 8BB) discloses SEQ ID NOS 1,169-1,170 and 1,178-1,182, respectively, in order of appearance. FIG. 8C (FIG. 8CA, FIG. 8CB) discloses SEQ ID NOS 1,169-1,170, 1,183-1,184, 1,173, 1,185-1,187, 1,173, 1,186 and 1,188-1,191, respectively, in order of appearance.

FIG. 9 provides the location design of the albumin (ALB) primers. The amplification primers are highlighted and the extend primer is underlined twice. Where the PCR primers are provided alone, the sequence-specific portion of the primer is underlined, and the multiplex tag is not underlined. In addition, competitor sequences are provided. Competitor sequences may be used for quantitative methods. FIG. 9 discloses SEQ ID NOS 1,192 and 1,192-1,197, respectively, in order of appearance.

DETAILED DESCRIPTION

Figure 1:
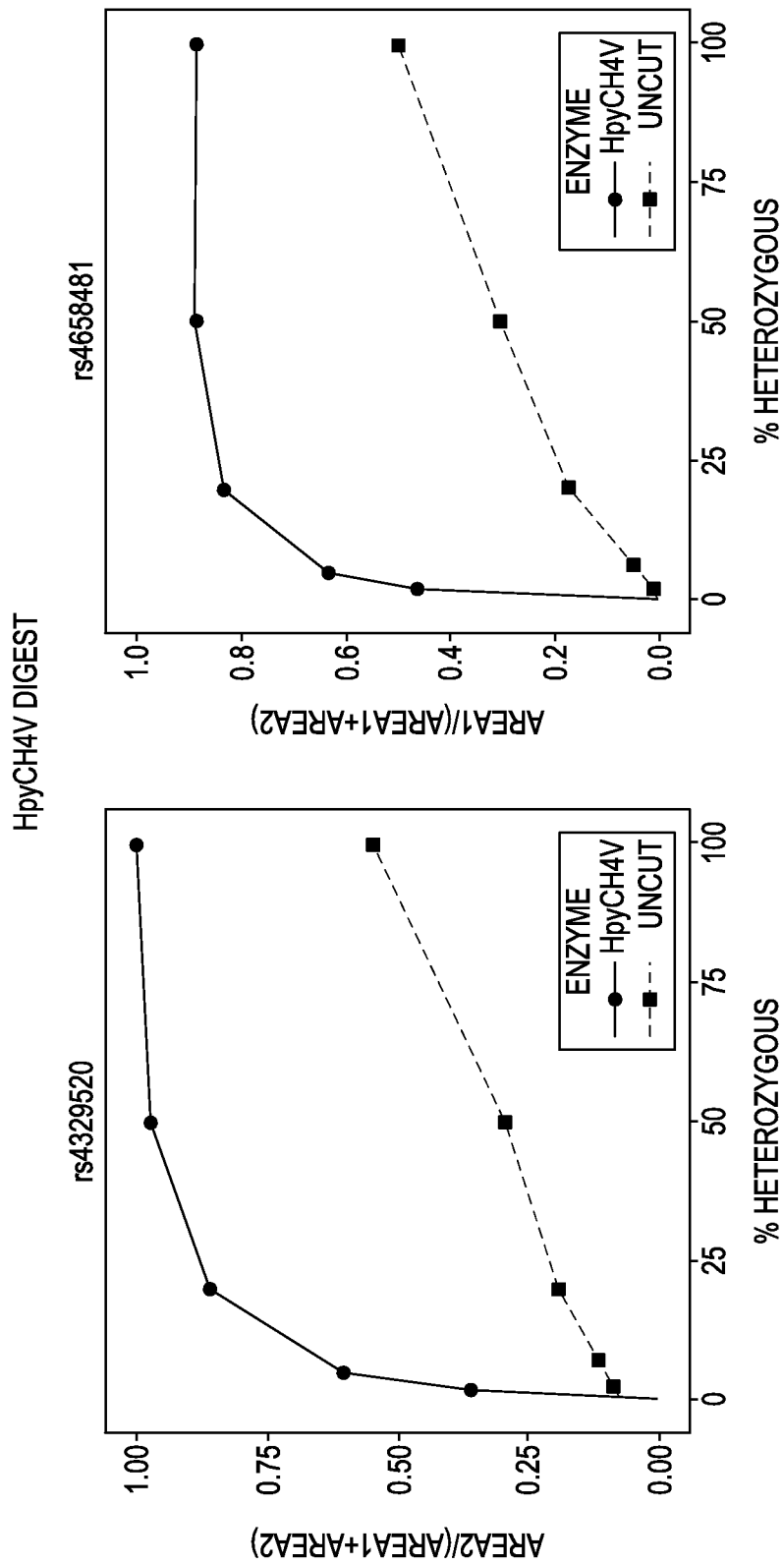
FIG. 1 is the HpyCH4V digest, which shows allele peak area ratios in a DNA mixture series. Peak area ratio is determined by dividing the calculated peak area of the SNP allele not recognized by HpyCH4V (i.e., target allele) by the total peak area of both SNP alleles present in the mass spectrum.

It has been determined in the fields of biology and diagnostics that certain nucleic acids are present at very low concentrations in humans. In particular, fetal DNA has been found to exist in maternal plasma (Lo et al. *Lancet.* 1997 Aug. 16; 350(9076):485-7). This discovery has facilitated the development of non-invasive prenatal diagnostic approaches based simply on the analysis of a maternal blood sample (Lo et al. *Am J Hum Genet.* 1998 April; 62(4):768-75). The non-invasive nature of maternal plasma-based approaches represents a major advantage over conventional methods of prenatal diagnosis, such as amniocentesis and chorionic villus sampling, which are associated with a small but finite risk of fetal loss. However, a technical challenge experienced by many workers in the field relates to the ability to discriminate the relatively small amount of fetal DNA from the coexisting background of maternal DNA in maternal plasma. During pregnancy, fetal DNA amounts to approximately 3-6% of the total DNA in maternal plasma. Hence, the diagnostic reliability of fetal DNA analysis in maternal plasma generally has depended on the accurate detection of fetal-specific markers.

Methods described herein solve this problem by enriching, relatively, the amount of low copy number nucleic acid before detecting or quantifying the alleles present in the sample. In the case of prenatal diagnostics, the use of restriction endonuclease enhanced polymorphic sequence detection allows for the selective, sensitive detection of fetal nucleic acid from maternal samples. The fetal DNA in the maternal plasma sample is selectively enriched before detecting the alleles present in the maternal sample. To enrich for fetal DNA present in plasma of the mother to allow accurate detection of fetal alleles present in the sample, methods provided herein allow for the cleavage of maternal nucleic acid or nucleic acid of maternal origin. Thus, the maternal DNA can be substantially reduced, masked, or destroyed completely, and the sample is left with DNA enriched for DNA of fetal origin. The selective reduction of maternal DNA can be performed using one or more enzymes, such as restriction endonucleases, which selectively digest nucleic acids which comprise maternal alleles.

The term "sample" as used herein refers to a composition, specimen or culture (e.g., microbiological cultures) that includes nucleic acids. The term "sample" includes biological and environmental samples. A sample may include a specimen of synthetic origin. Biological samples include whole blood, serum, plasma, umbilical cord blood, chorionic villi, amniotic fluid, cerebrospinal fluid, spinal fluid, lavage fluid (e.g., bronchoalveolar, gastric, peritoneal, ductal, ear, athroscopic), biopsy sample, urine, feces, sputum, saliva, nasal mucous, prostate fluid, semen, lymphatic fluid, bile, tears, sweat, breast milk, breast fluid, embryonic cells and fetal cells. A biological sample can be maternal blood, including maternal plasma or serum. In some circumstances, a biological sample is acellular. In other circumstances, a biological sample does contain cellular elements or cellular remnants in maternal blood. In some embodiments, a nucleic acid sample is, or is obtained from, an extracellular or acellular composition (e.g., blood plasma, blood serum, urine).

In some embodiments, a sample comprises a mixture of nucleic acids. For example, the mixture may comprise nucleic acid from different species or from different individuals. In some embodiments, a sample is from a pregnant female or a female suspected of being pregnant. In certain embodiments, the sample is procured through non-invasive means (e.g., a blood draw). In some embodiments the sample is from any animal, including but not limited to, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may be tested for the presence of target nucleic acid.

In some embodiments, the biological sample is blood, and sometimes plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water, crime scene samples, and industrial samples, as well as samples obtained from food and dairy processing instruments, apparatus, equipment, utensils, disposable and non-disposable items. These examples are not to be construed as limiting the sample types applicable to the present invention.

The term "non-invasive" as used herein refers to a method for collecting a sample that poses minimal risk to an individual (e.g., the mother, fetus, victim, etc.). An example of a non-invasive method is a blood draw; whereas examples of invasive methods include amniocentesis and chorionic villus sampling, both of which constitute a finite risk to the fetus.

The terms "target" or "target nucleic acid" as used herein refer to any molecule whose presence is to be detected or measured or whose function, interactions or properties are to be studied, where target nucleic acid comprises the target allele and non-target nucleic acid comprises the non-target allele. Fetal nucleic acid may comprise both target nucleic acid and non-target nucleic when the fetus is heterozygous at a polymorphic locus. Other examples of target nucleic acid include, but are not limited to, trace nucleic acid, mutated nucleic acid, viral nucleic acid and transplant nucleic acid.

The terms "nucleic acid" and "nucleic acid molecule" may be used interchangeably herein. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/non-naturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties.

In the case of RNA, an RNA may be placentally-expressed RNA in maternal plasma. Background maternal RNA may be selectively digested according to methods provided herein. Also, methods herein may further comprise an additional step of discriminating alleles of RNA which involves reverse transcriptase polymerase chain reaction (RT-PCR). In certain embodiments, fetal RNA may be extracted from maternal body fluids, sometimes whole blood, and sometimes plasma or serum using e.g. RNA extraction methods such as, but not limited to, gelatin extraction method; silica, glass bead, or diatom extraction method; guanidinium thiocyanate acid-phenol based extraction methods; guanidinium thiocyanate acid based extraction methods; guanidine-hydrochloride based extraction methods; methods using centrifugation through cesium chloride or similar gradients; phenol-chloroform based extraction methods; and/or other available RNA extraction methods, as are known in the art for use in extraction of intracellular RNA, including commercially available RNA extraction methods, e.g. by using or adapting or modifying methods of Boom et al. (1990, J. Clin. Microbiol. 28: 495-503); Cheung et al. (1994, J. Clin. Microbiol. 32: 2593-2597); Boom et al. (1991, J. Clin. Microbiol. 29: 1804-1811); Chomczynski and Sacchi (1987, Analytical Biochem. 162: 156-159); Chomczynski, (1993, Biotech. 15: 532-537); Chomczynski and Mackey (1995, Biotechniques 19: 942-945); Chomczynski and Mackey (1995, Anal. Biochem. 225: 163-164); Chirgwin et al. (1979, Biochem. 18: 5294-5299); Fournie et al. (1986 Anal. Biochem. 158: 250-256); and WO97/35589.

The term "amplification reaction" as used herein refers to any in vitro means for multiplying the copies of nucleic acid. "Amplifying" as used herein refers to a step of submitting a sample to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step. "Polymerase chain reaction" or "PCR" as used herein refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Oligonucleotides often comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a nucleic acid template and facilitates the amplification of the nucleic acid template, or otherwise plays a role in the detection of the nucleic acid molecule. In amplification embodiments, an oligonucleotide primer serves as a point of initiation of nucleic acid synthesis. Primers can be of a variety of lengths and are often less than 50 nucleotides in length, for example 12-25 nucleotides, in length. The length and sequences of primers for use in PCR can be designed based on principles known to those of skill in the art.

The term "template" refers to any nucleic acid molecule that can be used for amplification in methods described herein. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term "amplicon" as used herein refers to amplified DNA that has been "copied" once or multiple times, e.g. by polymerase chain reaction. The amplicon sequence falls between the amplification primers.

The term "polymorphic locus" as used herein refers to a nucleic acid region that comprises a polymorphism. The nucleic acid region may be 1, 2, 3, 4, 5, 6, 7, 8, 9, 10, 11, 12, 13, 14, 15, 20, 25, 30, 35, 40, 50, 60, 70, 80, 90, 100, 200, 300, 400, 500 or more nucleotides in length.

The term "polymorphism" as used herein refers to an allelic variant. Polymorphisms can include single nucleotide polymorphisms (SNP's) as well as simple sequence length polymorphisms, for example. A polymorphism can be due to one or more nucleotide substitutions at one allele in comparison to another allele or can be due to an insertion or deletion, duplication, inversion and other alterations of one or more nucleotides. Certain polymorphisms include, but are not limited to, restriction fragment length polymorphisms (RFLPs), insertions/deletions, short tandem repeats, such as di-, tri- or tetra-nucleotide repeats (STRs), and the like. As used herein, the term "polymorphism" includes epigenetic variants, as long as cleavage by non-epigenetic-specific cleavage agents is utilized.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

Alleles can have an identical sequence or can vary by a single nucleotide or more than one nucleotide. With regard to organisms that have two copies of each chromosome, if both chromosomes have the same allele, the condition is referred to as homozygous. If the alleles at the two chromosomes are different, the condition is referred to as heterozygous. For example, if the locus of interest is SNP X on chromosome 1, and the maternal chromosome contains an adenine at SNP X (A allele) and the paternal chromosome contains a guanine at SNP X (G allele), the individual is heterozygous A/G at SNP X.

As used herein, the term "mutant alleles" may refer to variant alleles that are associated with a disease state, e.g., cancer. The term "sequence identifier" as used herein refers to any sequence difference that exists between two sequences that can be used to differentiate the sequences. In some embodiments, the sequence identifier does not include methylation differences.

As used herein, the term "genotype" refers to the identity of the alleles or non-homologous variants present in an individual or sample. The term "genotyping a sample" or "genotyping an individual" refers to determining a specific allele or specific nucleotide(s) or polymorphism(s) in a sample or carried by an individual at particular region(s).

The term "selectively" as used herein does not suggest an absolute event, but instead a preferential event. For example, "selectively cleaved" is used to indicate one sequence (for example, the non-target sequence) is preferentially cleaved or digested over another sequence (for example, the target sequence). However, some of a target sequence may also be cleaved due to a lack of specificity with the cleavage agent or other variables introduced during the cleavage process.

The term "cleavage agent" as used herein refers to any means that is capable of differentially cleaving two or more sequences based on a sequence difference that exists between the two or more sequences. The cleavage agent may be an enzyme in some embodiments. The cleavage agent may be natural, synthetic, unmodified or modified. In some embodiments, the cleavage agent is a restriction endonuclease. Restriction endonucleases, alternatively called restriction enzymes, are a class of bacterial enzymes that cut or digest DNA at specific sites. Type I restriction endonucleases occur as a complex with the methylase and a polypeptide that binds to the recognition site on DNA. They are often not very specific and cut at a remote site. Type II restriction endonucleases are the classic experimental tools. They have very specific recognition and cutting sites. The recognition sites are short, 4-8 nucleotides, and are usually palindromic sequences. Because both strands have the same sequence running in opposite directions the enzymes make double-stranded breaks, which, if the site of cleavage is off-center, generates fragments with short single-stranded tails; these can hybridize to the tails of other fragments and are called sticky ends. They are generally named according to the bacterium from which they were isolated (first letter of genus name and the first two letters of the specific name). The bacterial strain is identified next and multiple enzymes are given Roman numerals. For example the two enzymes isolated from the R strain of *E. coli* are designated Eco RI and Eco RII. In some embodiments, the restriction enzyme is a type II restriction endonuclease. In another some embodiments, the restriction enzyme is thermostable.

The term "chromosomal abnormality" as used herein refers to a deviation between the structure of the subject chromosome and a normal homologous chromosome. The term "normal" refers to the predominate karyotype or banding pattern found in healthy individuals of a particular species. A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. A chromosomal abnormality can be correlated with presence of a pathological condition or with a predisposition to develop a pathological condition.

Uses and Advantages Associated with Methods Described Herein

The invention in part provides nucleic acid-based assays that are particularly useful for non-invasive prenatal testing. Methods provided herein may be used, inter alia, to determine the presence of fetal nucleic acid in a sample, to determine the amount of fetal nucleic acid in a sample, to determine the sex of a fetus, and to enrich for a target nucleic acid sequence. The invention in part may be combined with other prenatal methods, such as those described in U.S. application Ser. No. 12/027,954, filed Feb. 7, 2008; PCT Application No. PCT/US07/69991, filed May 30, 2007; PCT Application No. PCT/US07/071232, filed Jun. 15, 2007; PCT Patent Publication Numbers WO 2009/032779 and WO 2009/032781, both filed Aug. 28, 2008, PCT Patent Publication Number WO 2008/118988, filed Mar. 26, 2008, and PCT Patent Application Number PCT/EP05/012707, filed Nov. 28, 2005; or any of the prenatal diagnostic (both invasive and non-invasive) methods disclosed in PCT Patent Publication No. WO 2008/157264, filed on Jun. 12, 2008, all of which are hereby incorporated by reference.

The invention in part may be used to more accurately detect fetal DNA using high frequency polymorphisms that match the criteria provided herein. These polymorphisms are alternatively called fetal identifiers. The criteria includes one or more of the following:

1) One allele of the SNP is recognized by the cleavage agent;

2) The alternate SNP allele is not recognized by the same cleavage agent;

3) No other sites for the cleavage are found +/−50 base pair of the SNP within the PCR amplicon; and 4) (Optionally) The minor allele frequency is greater than 0.4 (sometimes across a range of populations).

Examples of fetal identifiers are set forth in Table 16. In some embodiments, the method of detecting the presence or absence of fetal nucleic acid in a sample comprises obtaining or possessing a nucleic acid sample known to be of maternal origin and suspected of comprising fetal nucleic acid; analyzing the nucleic acid sample to determine the maternal genotype at one or more nucleotide polymorphisms selected from the group consisting of the polymorphisms set forth in Table 16; and analyzing the nucleic acid sample to determine the fetal genotype of one or more nucleotide polymorphisms selected from the group consisting of the polymorphisms set forth in Table 16, where a fetal genotype possessing a paternally-inherited allele indicates the presence of fetal nucleic acid, further where nucleic acid comprising a maternal allele is digested using methods provided herein. In some embodiments, one or more of the polymorphisms set forth in Table 16 are used in conjunction with methods provided herein. In another some embodiments, one or more of the multiplex schemes provided in Table 11 is used according to methods provided herein. In certain embodiments, the maternal genotypes are first determined from DNA that is substantially free of fetal nucleic acid. For example, where the sample is blood of from blood, the maternal genotypes may be determined from the portion of the blood that comprises nucleated maternal cells (e.g., white blood cells). In some embodiments, the DNA that is substantially free of fetal nucleic acid is from peripheral blood mononuclear cells. In certain embodiments, the amount of fetal DNA is determined by comparing the relative amount of paternally-inherited alleles to an internal control (e.g., competitor oligonucleotide).

In Table 11, each primer of the amplification primer pair may comprise the entire sequence shown or only the non-underlined sequence, where the underlined portion of the primer is a tag sequence (ACGTTGGATG) (SEQ ID NO: 1) for improved multiplexing and the non-underlined portion is a sequence-specific primer sequence. The tag sequence may be any tag sequence known in the art that improves multiplexing. In certain embodiments, the invention in part includes primers that are substantially similar to the primers provided herein, for example, about 90% or more identical (e.g., primers differ by 1, 2, 3, 4, 5, 6, 7, 8, 9 or 10 nucleotide mismatches, or 1-3 nucleotide mismatches, when aligned with one another), and further where the primers are still specific for a given nucleic acid region. For example, one or more bases of a primer sequence may be changed or substituted, for example with an inosine, but the primer still maintains the same specificity and plexing ability. Bases indicated by uppercase text are complementary to the nucleic acid sequence to which the primer hybridizes, and bases indicated by lowercase text are not complementary to the nucleic acid sequence to which the primer hybridizes. Bases indicated in lower case text can be selected to shift or adjust the mass of primers and amplification products.

In particular embodiments, a sequence tag is attached to a plurality of primary and secondary primer pairs provided in Table 11. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGTTGGATG- (SEQ ID NO: 1), and is attached to the 5' end of each primary and secondary primer. In particular embodiments of methods provided herein, only a single primer pair is used to amplify each particular nucleic acid target-region.

In certain embodiments, methods provided herein may be used to improve the detection the Y-chromosome in a maternal sample, which may be used to determine the sex of a fetus. The presence or absence of the Y-chromosome in a maternal sample may be determined by performing the SRY assay described in Example 3. The SRY assay is a highly sensitive quantitative internal standard assay that detects trace amounts of the Y-chromosome. In certain embodiments, other polymorphisms located on the Y-chromosome may be assayed according to methods provided herein.

The presence or absence of the Y-chromosome in a maternal sample may also be determined by performing the AMG assay provided herein. The presence or absence of a target nucleic acid may be determined in combination with other assays, such as an RhD assay, blood type assay or sex test assay. Methods provided herein may also be used for other applications, including but not limited to, paternity testing, forensics or quality control assays.

In addition to prenatal applications, methods provided herein find utility in a range of applications, including, but not limited to, detecting rare cancer mutations, detecting transplant rejection and forensics.

In certain embodiments, the total copy number of nucleic acid molecules for the human serum albumin (ALB) gene is determined. Methods for determining the total copy number of nucleic acid present in a sample comprise detecting albumin-specific extension products and comparing the relative amount of the extension products to competitors introduced to the sample. In certain embodiments, the invention in part provides compositions and methods to determine the relative amount of fetal DNA in a sample (e.g., when the sample is plasma from a pregnant woman carrying a male fetus), which comprises annealing one or more albumin gene sequences to the fetal DNA, the primers provided in FIG. 9; performing a primer extension reaction; and analyzing the primer extension products to determine the relative amount of ALB extension products, where maternal albumin nucleic acid has been reduced using methods provided herein. In certain embodiments, the fetal ALB amplicon is first amplified using the amplification primers provided in FIG. 9. The assay is useful to measure how much nucleic acid (e.g., total copy number) is present in a sample or loaded into a particular reaction. The assay may serve as an internal control and a guide to the likelihood of success for a particular PCR reaction. For example, if only 400 copies of ALB are measured then the probability of detecting any fetal DNA may be considered low. In certain embodiments, the competitors provided in FIG. 9 are introduced as an internal standard to determine copy number. In some embodiments, 200, 300, 400, 500, 600, 700, 800 or more competitor molecules are introduced to the assay.

Methods described herein provide a number of advantages. Methods provided herein allow a high sensitivity to detect polymorphic alleles (e.g., fetal identifiers) present at low relative percentages in a DNA mixture and present at low copy number, for example. Methods provided herein may also be incorporated into multiplexed assays in a single reaction in certain embodiments. Methods described herein are readily implemented, and only add a single additional step to the many current detection methods, for example.

Nucleases

Cleavage methods and procedures for selecting restriction enzymes for cutting nucleic acid at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Nucleic acid to be cleaved often is/are free of certain contaminants such as phenol, chloroform, alcohol, EDTA, detergents, or excessive salts, all of which can interfere with restriction enzyme activity, in certain embodiments.

Embodiments of the invention can be assembled from multiple restriction endonucleases (available from various vendors) that are chosen to correspond to appropriate polymorphic alleles, as long as a restriction endonuclease selects for one polymorphic allele over another and performs a digestion within the amplicon sequence such that it prevents a subsequent amplification event. In some embodiments, the amplicon is chosen such that it contains a variable nuclease restriction site and sequence identifier, which may or may not be the same as the restriction site. Also, the restriction enzyme need not cleave at the polymorphic site, for example, at the variable nucleotide of a SNP.

Restriction enzymes are traditionally classified into three types on the basis of subunit composition, cleavage position, sequence-specificity and cofactor-requirements. However, amino acid sequencing has uncovered extraordinary variety among restriction enzymes and revealed that at the molecular level there are many more than three different kinds.

Type I enzymes are complex, multisubunit, combination restriction-and-modification enzymes that cut DNA at random far from their recognition sequences. Originally thought to be rare, we now know from the analysis of sequenced genomes that they are common. Type I enzymes are of considerable biochemical interest but they have little practical value since they do not produce discrete restriction fragments or distinct gel-banding patterns.

Type II enzymes cut DNA at defined positions close to or within their recognition sequences. They produce discrete restriction fragments and distinct gel banding patterns, and they are the only class used in the laboratory for DNA analysis and gene cloning. Type II enzymes frequently differ so utterly in amino acid sequence from one another, and indeed from every other known protein, that they likely arose independently in the course of evolution rather than diverging from common ancestors.

The most common type II enzymes are those like HhaI, HindIII and NotI that cleave DNA within their recognition sequences. Enzymes of this kind are available commercially. Most recognize DNA sequences that are symmetric because they bind to DNA as homodimers, but a few, (e.g., BbvCI: CCTCAGC) recognize asymmetric DNA sequences because they bind as heterodimers. Some enzymes recognize continuous sequences (e.g., EcoRI: GAATTC) in which the two half-sites of the recognition sequence are adjacent, while others recognize discontinuous sequences (e.g., BglI: GCCNNNNNGGC (SEQ ID NO: 2)) in which the half-sites are separated. Cleavage leaves a 3'-hydroxyl on one side of each cut and a 5'-phosphate on the other. They require only magnesium for activity and the corresponding modification enzymes require only S-adenosylmethionine. They tend to be small, with subunits in the 200-350 amino acid range.

The next most common type II enzymes, usually referred to as 'type IIs' are those like FokI and AlwI that cleave outside of their recognition sequence to one side. These enzymes are intermediate in size, 400-650 amino acids in length, and they recognize sequences that are continuous and asymmetric. They comprise two distinct domains, one for DNA binding, the other for DNA cleavage. They are thought to bind to DNA as monomers for the most part, but to cleave DNA cooperatively, through dimerization of the cleavage domains of adjacent enzyme molecules. For this reason, some type IIs enzymes are much more active on DNA molecules that contain multiple recognition sites. A wide variety of Type IIS restriction enzymes are known and such enzymes have been isolated from bacteria, phage, archeabacteria and viruses of eukaryotic algae and are commercially available (Promega, Madison Wis.; New England Biolabs, Beverly, Mass.). Examples of Type IIS restriction enzymes that may be used with methods described herein include, but are not limited to enzymes such as those listed in Table IA.

| Enzyme-Source | Recognition/Cleavage Site | Supplier |
|---|---|---|
| Alw I - *Acinetobacter lwoffii* | GGATC(4/5) | NE Biolabs |
| Alw26 I - *Acinetobacter lwoffi* | GTCTC(1/5) | Promega |
| Bbs I - *Bacillus laterosporus* | GAAGAC(2/6) | NE Biolabs |
| Bbv I - *Bacillus brevis* | GCAGC(8/12) | NE Biolabs |
| BceA I - *Bacillus cereus* 1315 | IACGGC(12/14) | NE Biolabs |
| Bmr I - *Bacillus megaterium* | CTGGG(5/4) | NE Biolabs |
| Bsa I - *Bacillus stearothermophilus* 6-55 | GGTCTC(1/5) | NE Biolabs |
| Bst71 I - *Bacillus stearothermophilus* 71 | GCAGC(8/12) | Promega |
| BsmA I - *Bacillus stearothermophilus* A664 | GTCTC(1/5) | NE Biolabs |
| BsmB I - *Bacillus stearothermophilus* B61 | CGTCTC(1/5) | NE Biolabs |
| BsmF I - *Bacillus stearothermophilus* F | GGGAC(10/14) | NE Biolabs |
| BspM I - *Bacillus* species M | ACCTGC(4/8) | NE Biolabs |
| Ear I - *Enterobacter aerogenes* | CTCTTC(1/4) | NE Biolabs |
| Fau I - *Flavobacterium aquatile* | CCCGC(4/6) | NE Biolabs |
| Fok I - *Flavobacterium okeonokoites* | GGATG(9/13) | NE Biolabs |
| Hga I - *Haemophilus gallinarum* | GACGC(5/10) | NE Biolabs |
| Ple I - *Pseudomonas lemoignei* | GAGTC(4/5) | NE Biolabs |
| Sap I - *Saccharopolyspora* species | GCTCTTC(1/4) | NE Biolabs |
| SfaN I - *Streptococcus faecalis* ND547 | GCATC(5/9) | NE Biolabs |
| Sth132 I - *Streptococcus thermophilus* ST132 | CCCG(4/8) | No commercial supplier (Gene 195: 201-206 (1997)) |

A third major kind of type II enzyme, more properly referred to as "type IV" are large, combination restriction-and-modification enzymes, 850-1250 amino acids in length, in which the two enzymatic activities reside in the same protein chain. These enzymes cleave outside of their recognition sequences; those that recognize continuous sequences (e.g., Eco57I: CTGAAG) cleave on just one side; those that recognize discontinuous sequences (e.g., BcgI: CGANNNNNNTGC (SEQ ID NO: 3)) cleave on both sides releasing a small fragment containing the recognition sequence. The amino acid sequences of these enzymes are varied but their organization are consistent. They comprise an N-terminal DNA-cleavage domain joined to a DNA-modification domain and one or two DNA sequence-specificity domains forming the C-terminus, or present as a separate subunit. When these enzymes bind to their substrates, they switch into either restriction mode to cleave the DNA, or modification mode to methylate it.

As discussed above, the length of restriction recognition sites varies. For example, the enzymes EcoRI, SacI and SstI each recognize a 6 base-pair (bp) sequence of DNA, whereas NotI recognizes a sequence 8 bp in length, and the recognition site for Sau3AI is only 4 bp in length. Length of the recognition sequence dictates how frequently the enzyme will cut in a random sequence of DNA. Enzymes with a 6 bp recognition site will cut, on average, every $4^6$ or 4096 bp; a 4 bp recognition site will occur roughly every 256 bp.

Different restriction enzymes can have the same recognition site—such enzymes are called isoschizomers. Table IB shows that the recognition sites for SacI and SstI are identical. In some cases isoschizomers cut identically within their recognition site, but sometimes they do not. Isoschizomers often have different optimum reaction conditions, stabilities and costs, which may influence the decision of which to use. Table IB is provided only to show exemplary restriction enzymes, and does not limit the scope of the invention in any way.

TABLE IB

| Enzyme | Recognition Sequence |
|---|---|
| BamH I | GGATCC |
|  | CCTAGG |
| Not I | GCGGCCGC |
|  | CGCCGGCG |
| Sau3A I | GATC |
|  | CTAG |
| Sac I | GAGCTC |
|  | CTCGAG |
| Sst I | GAGCTC |
|  | CTCGAG |
| Hinf I | GANTC |
|  | CTNAG |
| Xho II | PuGATCPy |
|  | PyCTAGPu |

Restriction recognition sites can be unambiguous or ambiguous. The enzyme BamHI recognizes the sequence GGATCC and no others; therefore it is considered "unambiguous." In contrast, HinfI recognizes a 5 bp sequence starting with GA, ending in TC, and having any base between (in Table IB, "N" stands for any nucleotide). HinfI has an ambiguous recognition site. XhoII also has an ambiguous recognition site: Py stands for pyrimidine (T or C) and Pu for purine (A or G), so XhoII will recognize and cut sequences of AGATCT, AGATCC, GGATCT and GGATCC.

The recognition site for one enzyme may contain the restriction site for another. For example, note that a BamHI recognition site contains the recognition site for Sau3AI. Consequently, all BamHI sites will cut with Sau3AI. Similarly, one of the four possible XhoII sites will also be a recognition site for BamHI and all four will cut with Sau3AI.

Also from Table IB, most recognition sequences are palindromes—they read the same forward (5' to 3' on the top strand) and backward (5' to 3' on the bottom strand). Most, but certainly not all recognition sites for commonly-used restriction enzymes are palindromes. Most restriction enzymes bind to their recognition site as dimers (pairs).

Nucleic Acid Detection

Whether detecting sequence differences, detecting amplification products or primer extension products, any detection or discrimination method known may be utilized. These methods include, but are not limited to, primer extension reactions, mass spectrometry, hybridization using at least one probe, hybridization using at least one fluorescently labeled probe, direct sequencing, cloning and sequencing, and electrophoresis. Polymorphism detection methods known may also include, for example, microsequencing methods, ligase sequence determination methods (e.g., U.S. Pat. Nos. 5,679, 524 and 5,952,174, and WO 01/27326), digital PCR (U.S. Pat. No. 6,143,496), mismatch sequence determination methods (e.g., U.S. Pat. Nos. 5,851,770; 5,958,692; 6,110,684; and 6,183,958), microarray sequence determination methods, restriction fragment length polymorphism (RFLP) procedures, PCR-based assays (e.g., TAQMAN® PCR System (Applied Biosystems)), nucleotide sequencing methods, hybridization methods, conventional dot blot analyses, single strand conformational polymorphism analysis (SSCP, e.g., U.S. Pat. Nos. 5,891,625 and 6,013,499; Orita et al., *Proc. Natl. Acad. Sci. U.S.A* 86: 27776-2770 (1989)), denaturing gradient gel electrophoresis (DGGE), heteroduplex analysis, mismatch cleavage detection, and techniques described in Sheffield et al., *Proc. Natl. Acad. Sci. USA* 49: 699-706 (1991), White et al., *Genomics* 12: 301-306 (1992), Grompe et al., Proc. *Natl. Acad. Sci. USA* 86: 5855-5892 (1989), and Grompe, *Nature Genetics* 5: 111-117 (1993), detection by mass spectrometry (e.g., US 20050079521, which is hereby incorporated by reference), real time-PCR (e.g., U.S. Pat. Nos. 5,210,015, 5,487,972, both of which are hereby incorporated by reference), or hybridization with a suitable nucleic acid primer specific for the sequence to be detected. Suitable nucleic acid primers can be provided in a format such as a gene chip.

Primer extension polymorphism detection methods, also referred to herein as "microsequencing" methods, typically are carried out by hybridizing a complementary oligonucleotide to a nucleic acid carrying the polymorphic site. In these methods, the oligonucleotide typically hybridizes adjacent to the polymorphic site. As used herein, the term "adjacent" refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656, 127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, *Nucleic Acids Research* 25: 347-353 (1997) and Chen et al., *Proc. Natl. Acad. Sci. USA* 94/20: 10756-10761 (1997)) and by mass spectrometric methods (e.g., MALDI-TOF mass spectrometry). Oligonucleotide extension methods using mass spectrometry are described, for example, in U.S. Pat. Nos. 5,547,835; 5,605,798; 5,691,141; 5,849,542; 5,869,242; 5,928,906; 6,043,031; 6,194,144; and 6,258,538.

Microsequencing detection methods often incorporate an amplification process that precedes the extension step. The amplification process typically amplifies a region from a nucleic acid sample that comprises the polymorphic site. Amplification can be carried out by utilizing a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683,202, 4,965,188; 5,656,493; 5,998,143; 6,140,054; WO 01/27327; and WO 01/27329 for example. PCR primer pairs may also be used in any commercially available machines that perform PCR, such as any of the GENEAMP® Systems available from Applied Biosystems, for example.

A microarray can be utilized for determining whether a polymorphic variant is present or absent in a nucleic acid sample. A microarray may include any oligonucleotides described herein, and methods for making and using oligonucleotide microarrays suitable for prognostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259, for example. A microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphic site within a nucleotide sequence

EXAMPLES

The Examples hereafter illustrate embodiments of the invention and are not limiting.

Example 1

Restriction Endonuclease Enhanced Polymorphic Sequence Detection Using HpyCH4V And NlaIII The effectiveness of restriction endonuclease enhanced polymorphic sequence detection was demonstrated using several restriction endonucleases (REs), including HpyCH4V and NlaIII (purchased from New England BioLabs, Inc). Both of these enzymes were separately tested in multiplexed genotyping reactions for their ability to specifically cleave one allele of a given polymorphism while allowing PCR amplification of the remaining allele of the polymorphism. See Table 2 for the polymorphisms tested with each enzyme.

Two CEPH DNA samples were mixed in varying ratios to generate DNA samples composed of 0%, 2%, 5%, 20%, 50% and 100% DNA heterozygous for both alleles of the SNP, with the remaining DNA being homozygous for the allele recognized by the RE. Table 3 shows DNA samples used in these studies and corresponding genotype information. Mixtures composed of NA05995 and NA10849 were used for experiments with HpyCH4V enzyme, and mixtures composed of NA10862 and NA10846 were used for experiments with NlaIII enzyme.

TABLE 2

Restriction enzymes recognizing SNPs

| Restriction Enzyme | Polymorphism | SNP Alleles | Allele Digested by RE |
|---|---|---|---|
|  | rs10430091 | A/T |  |
| NlaIII | rs2050927 | A/T | A |
| NlaIII, HpyCH4V | rs4329520 | A/T | T, T* |
|  | rs4657868 | A/T |  |
| HpyCH4V | rs4658481 | A/T | A |
|  | rs6693568 | A/T |  |
|  | rs860954 | A/T |  |
|  | rs9431593 | A/T |  |

*Both enzymes, NlaIII and HpyCH4V, digest the T allele.

TABLE 3

DNA samples used and genotypes

|  |  | SNP genotypes | | |
|---|---|---|---|---|
| Restriction Enzyme | DNA* | rs2050927 | rs4329520 | rs4658481 |
| HpyCH4V | NA05995 |  | TA | TA |
|  | NA10849 |  | T | A |
| NlaIII | NA10862 | AT | TA |  |
|  | NA10846 | A | T |  |

*DNA samples were obtained from Coriell CEPH DNA collection

TABLE 4

DNA mixtures (Listed as ng DNA per reaction)

|  |  | Relative percentage unrecognized SNP allele | | | | | |
|---|---|---|---|---|---|---|---|
|  |  | 0% | 2% | 5% | 20% | 50% | 100% |
| HpyCH4V | NA05995 | 0 | 0.6 | 0.6 | 0.6 | 0.6 | 0.6 |
|  | NA10849 | 0.6 | 29.4 | 11.4 | 2.4 | 0.6 | 0 |
| NlaIII | NA10862 | 0 | 0.6 | 0.6 | 0.6 | 0.6 | 0.6 |
|  | NA10846 | 0.6 | 29.4 | 11.4 | 2.4 | 0.6 | 0 |

NOTE:
Based on 3 pg DNA for haploid human genomic equivalent, 0.6 ng DNA is equal to 200 copies of genomic target DNA in the mixtures.

After preparation of the sample DNA mixtures, PCR cocktail was prepared according to Table 5 below (using multiplexed PCR primers as shown in Table 6) to either include no restriction endonuclease or 0.25U of restriction endonuclease per each sample reaction. PCR cocktail was aliquoted to a 96-well plate to include 7 replicates of each DNA mixture for each enzyme condition. After addition of DNA to the PCR cocktail mixtures, samples were incubated at 37° C. for 1 hour to allow enzyme digestion of DNA samples and then immediately thermal cycled using standard conditions (Table 7).

TABLE 5

PCR cocktail preparation for each multiplex without DNA addition

| Reagents | Final Conc | No RE N = 1 (uL) | HpyCH4V N = 1 (uL) | NlaIII N = 1 (uL) |
|---|---|---|---|---|
| Water | n/a | 3 | 2.95 | 2.975 |
| 10xPCR Buffer (HotStar Taq Buffer) | 1.25x | 3.125 | 3.125 | 3.125 |
| MgCl$_2$ (25 mM) | 1.625 mM | 1.625 | 1.625 | 1.625 |
| PCR Nucleotide Mix (for UNG use) (10 mM dATP, dCTP, dGTP, dUTP) | 0.2 mM | 0.5 | 0.5 | 0.5 |

TABLE 5-continued

PCR cocktail preparation for each multiplex without DNA addition

| Reagents | Final Conc | No RE N = 1 (uL) | HpyCH4V N = 1 (uL) | NlaIII N = 1 (uL) |
|---|---|---|---|---|
| F/R Primer mix (0.5 uM) | 0.1 μM | 5 | 5 | 5 |
| 5 U/ul HpyCH4V or 10 U/ul NlaIII | 0.25 U/rxn | — | 0.05 | 0.025 |
| 1 U/μl Uracil-DNA-Glycosylase (UDG) | 1.25 U/rxn | 1.25 | 1.25 | 1.25 |
| HotStar Taq (5 U/uL) | 2.5 U/rxn | 0.5 | 0.5 | 0.5 |
| DNA - added separately | varies | 10 | 10 | 10 |
| Total volume | n/a | 25 | 25 | 25 |

TABLE 6A

PCR Primer sequences for SNPs

| SNP | SEQ ID NO: | Forward PCR Primer | SEQ ID NO: | Reverse PCR Primer |
|---|---|---|---|---|
| rs10430091 | 4 | ACGTTGGATGCACAAGATTCTGAAACTTAG | 12 | ACGTTGGATGGCTGTTTAACTCAGCATG |
| rs2050927 | 5 | ACGTTGGATGTTGGGTGCAGAGTAGTCATC | 13 | ACGTTGGATGTTCTAGCTTGCTTCTCCTCC |
| rs4329520 | 6 | ACGTTGGATGATGTCCACCTCCTGCTCCAC | 14 | ACGTTGGATGGAAAGTTGTCGTGGTAGAGG |
| rs4657868 | 7 | ACGTTGGATGCTAGCGTACCCAATGGAATC | 15 | ACGTTGGATGCTAACCAGGAAAAGACACCC |
| rs4658481 | 8 | ACGTTGGATGGTGGTAGAAACAAATGTCAGC | 16 | ACGTTGGATGCTGCTAAGCATGAGAGAAAG |
| rs6693568 | 9 | ACGTTGGATGGGCCTGTTCATTCTCAGAAA | 17 | ACGTTGGATGTGACTAGGAAATCACACTGG |
| rs860954 | 10 | ACGTTGGATGTAGCCTTTAGTCTTGATGCC | 18 | ACGTTGGATGCCATTCTTGTATGTTTTGTC |
| rs9431593 | 11 | ACGTTGGATGGCCTCAGTAGTCACATAAGG | 19 | ACGTTGGATGTTGAGATCAGTGTCGGTTCC |

TABLE 6B

Extend Primers

| SNP | SEQ ID NO: | Extend Primer |
|---|---|---|
| rs10430091 | 20 | gTGTTTAACTCAGCATGTGGGAA |
| rs2050927 | 21 | CCTCCATCATCCTTAGC |
| rs4329520 | 22 | GCGTGGTTCTAGACTTATGC |
| rs4657868 | 23 | cAAGACACCCCATACATTA |
| rs4658481 | 24 | TAAGCATGAGAGAAAGGGAAAG |
| rs6693568 | 25 | atGAAATCACACTGGACATTTT |
| rs860954 | 26 | GTTTTGTCTTTTTCTGTATACTCATG |
| rs9431593 | 27 | TGTTCCTGACTCTCAAAAT |

TABLE 7

Thermal cycling conditions

| Temp. | Time | Cycles |
|---|---|---|
| 37° C. | 1 hour | 1 |
| 94° C. | 15 min | 1 |
| 94° C. | 20 sec | |
| 56° C. | 30 sec | ] 45 cycles |
| 72° C. | 1 min | |

TABLE 7-continued

Thermal cycling conditions

| Temp. | Time | Cycles |
|---|---|---|
| 72° C. | 3 min | 1 |
| 4° C. | forever | 1 |

Amplicons generated during PCR were genotyped with the extend primers in Table 5 using standard iPLEX™ assay and MassARRAY® technology (Jurinke, C., Oeth, P., van den Boom, D., MALDI-TOF mass spectrometry: a versatile tool for high-performance DNA analysis. *Mol. Biotechnol.* 26, 147-164 (2004); and Oeth, P. et al., iPLEX™ Assay: Increased Plexing Efficiency and Flexibility for MassAR-RAY® System through single base primer extension with mass-modified Terminators. SEQUENOM Application Note (2005), both of which are hereby incorporated by reference).

Results

Figure 2:
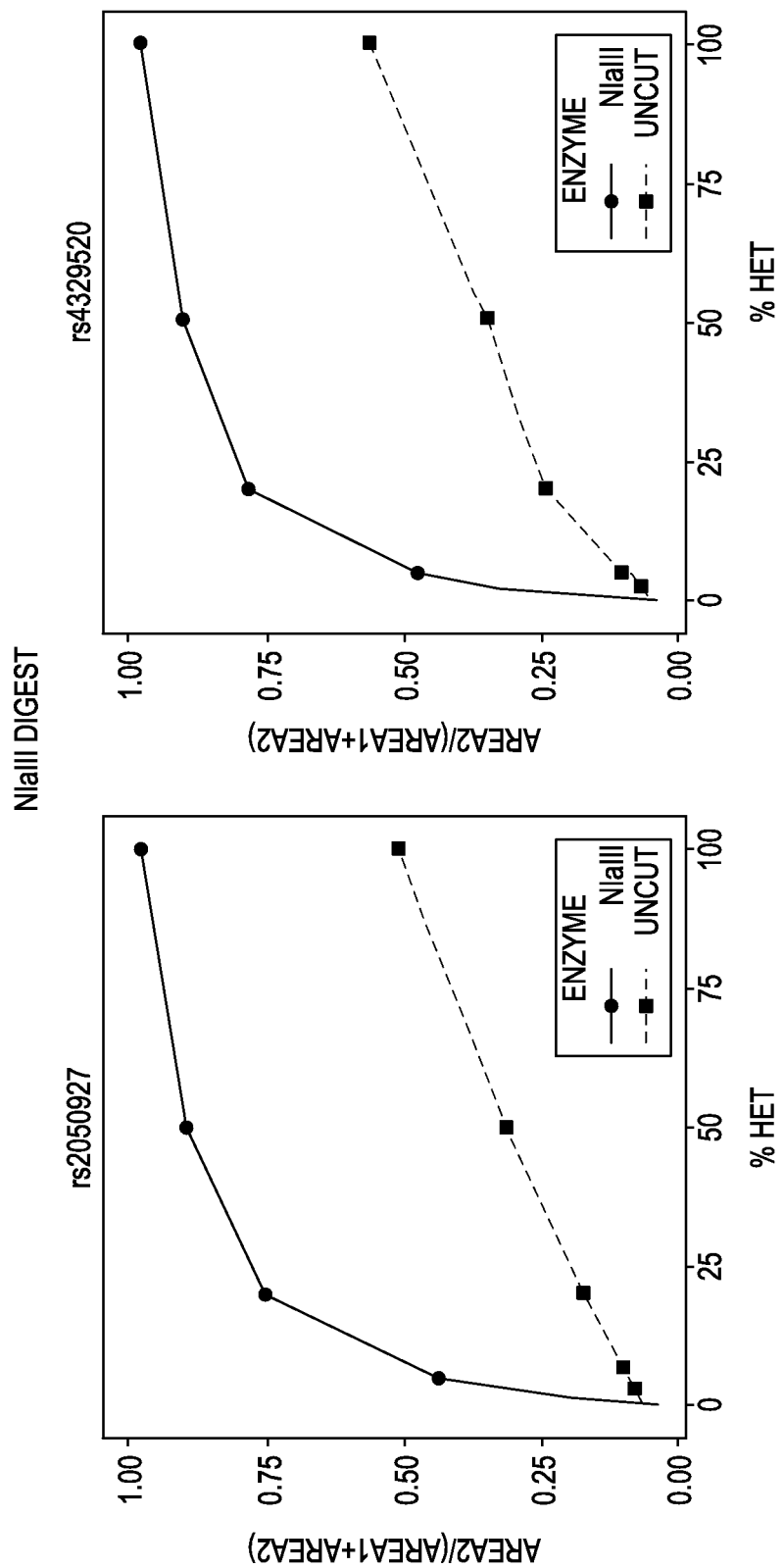
FIG. 2 is the NlaIII digest, which shows allele peak area ratios in a DNA mixture series. Peak area ratio is determined by dividing the calculated peak area of the SNP allele not recognized by NlaIII (i.e., target allele) by the total peak area of both SNP alleles present in the mass spectrum.
Figure 3A:
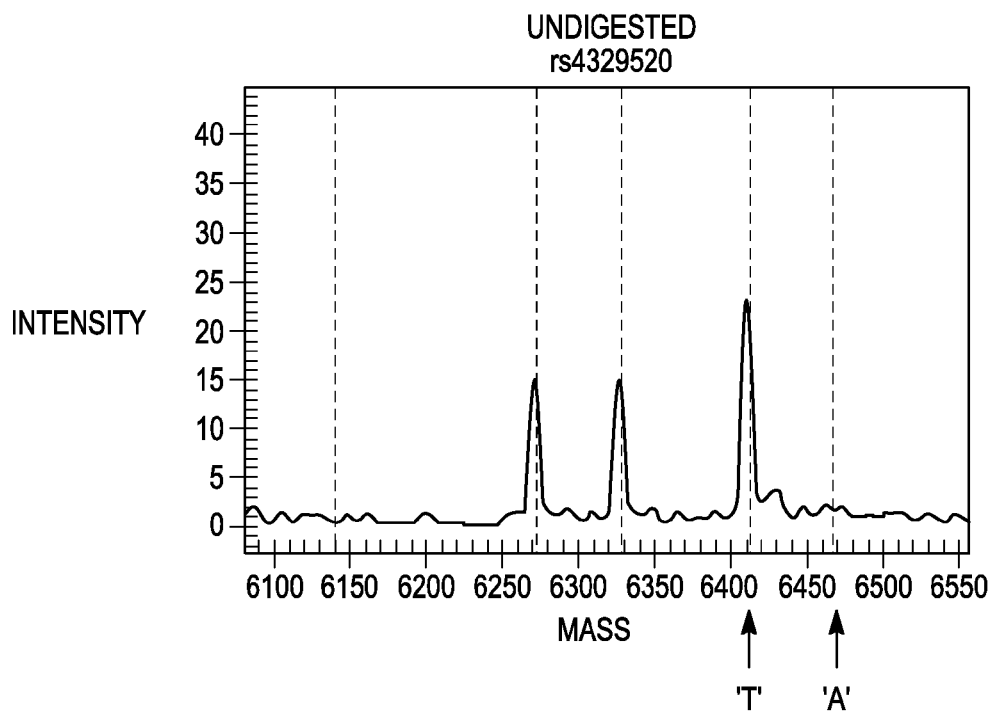
FIG. 3 (FIG. 3A-FIG. 3D) is the HpyCH4V screenshots of 2% heterozygous DNA mixture. Note the appearance of the 'A' and 'T' alleles after HpyCH4V digestion of the DNA samples for rs4329520 and rs4658481, respectively.
Figure 3B:
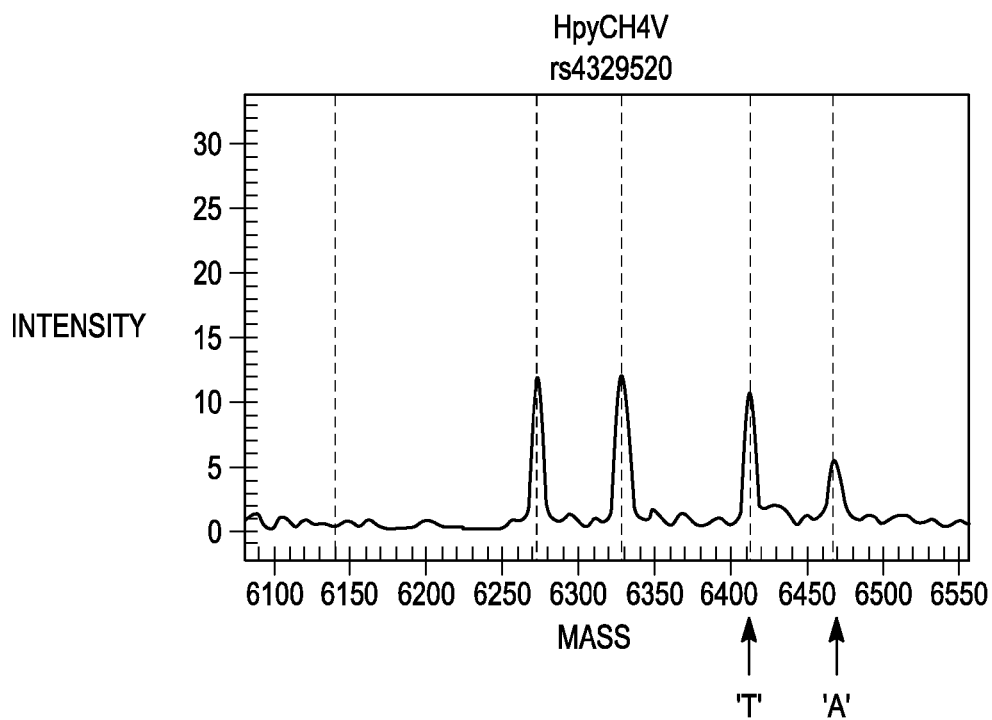
Figure 3C:
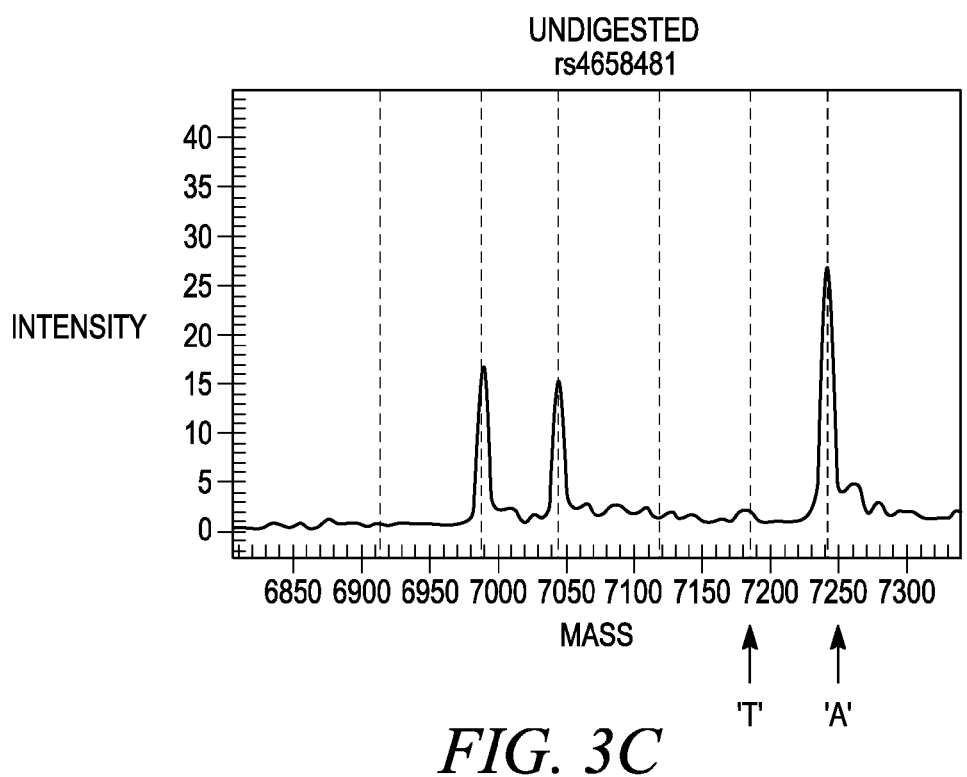
Figure 3D:
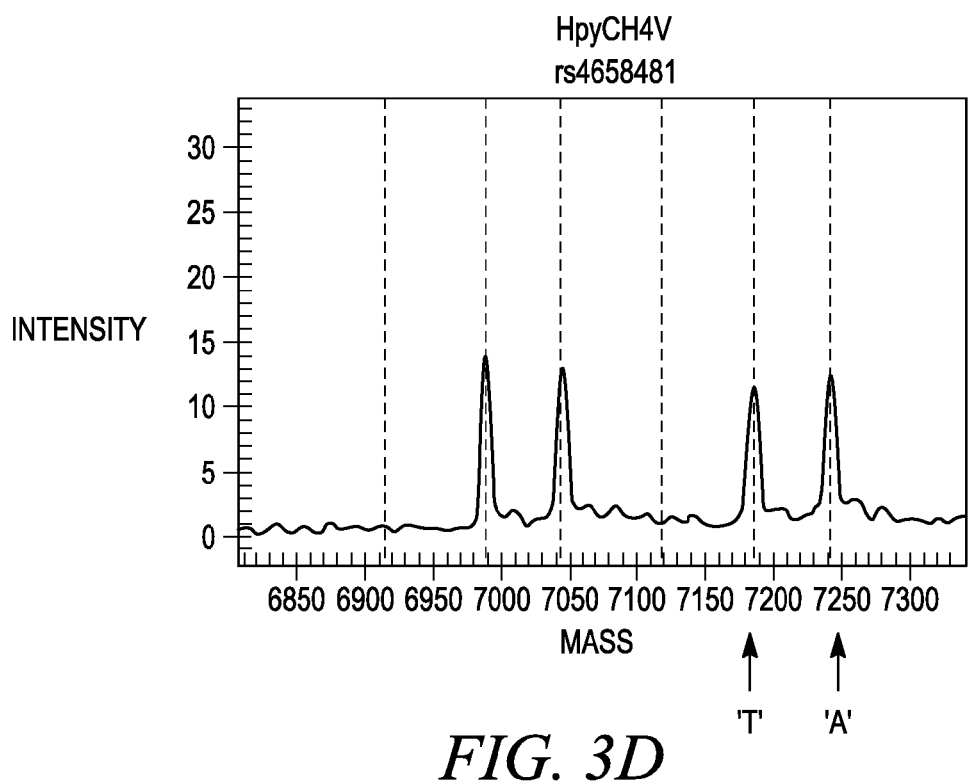
Figure 4A:
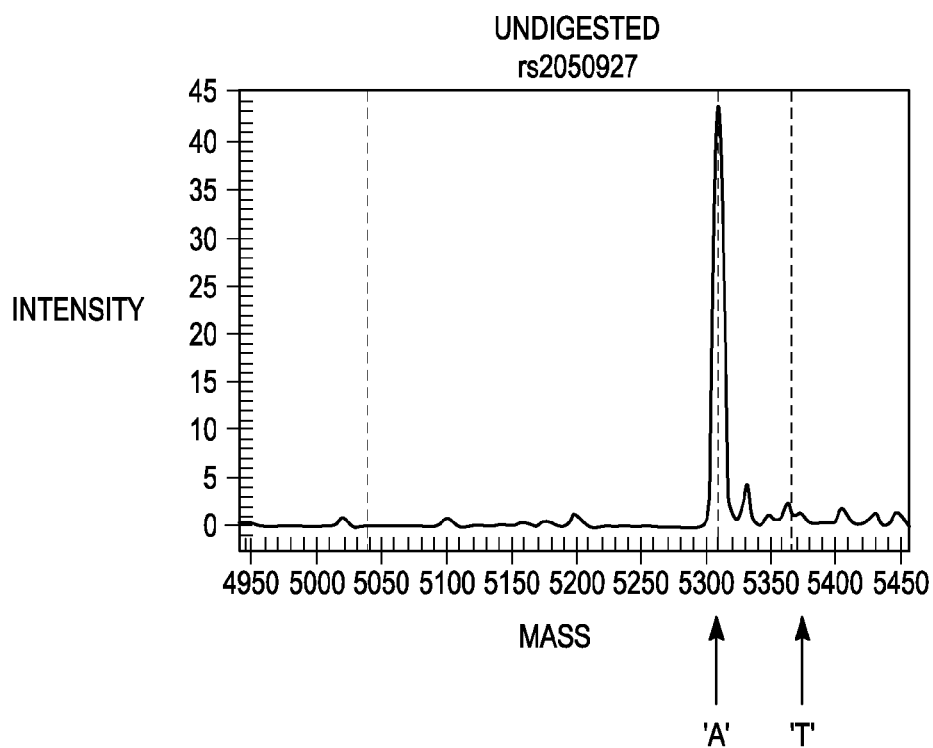
FIG. 4 (FIG. 4A-FIG. 4D) is the NlaIII screenshots of 2% heterozygous DNA mixture. Note the appearance of the 'T' and 'A' alleles after NlaIII digestion of the DNA samples for rs2050927 and rs4329520, respectively.
Figure 4B:
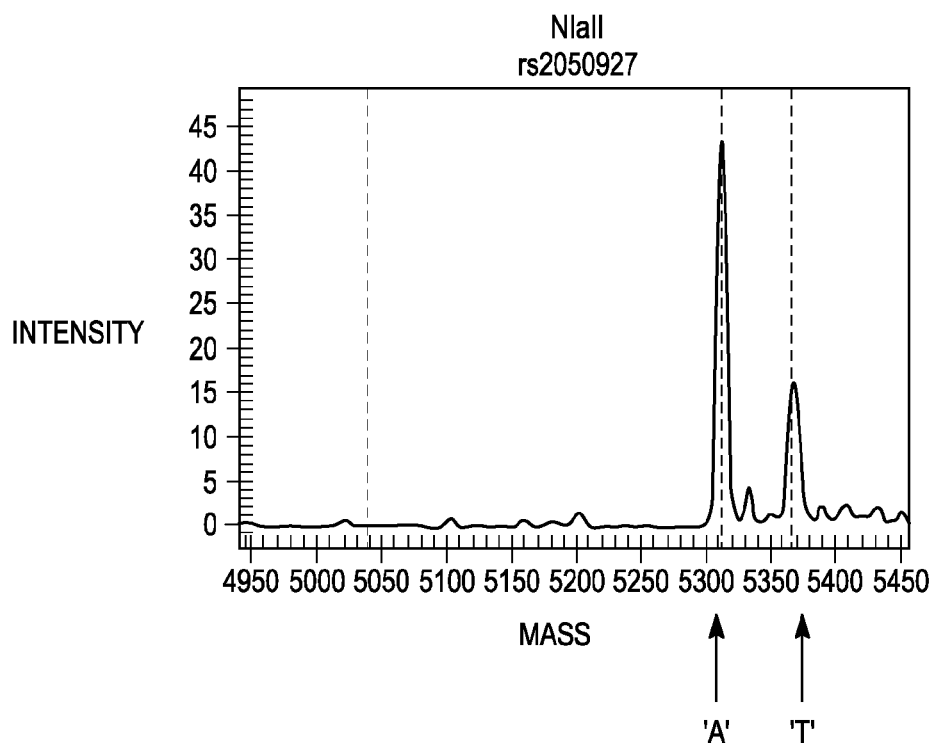
Figure 4C:
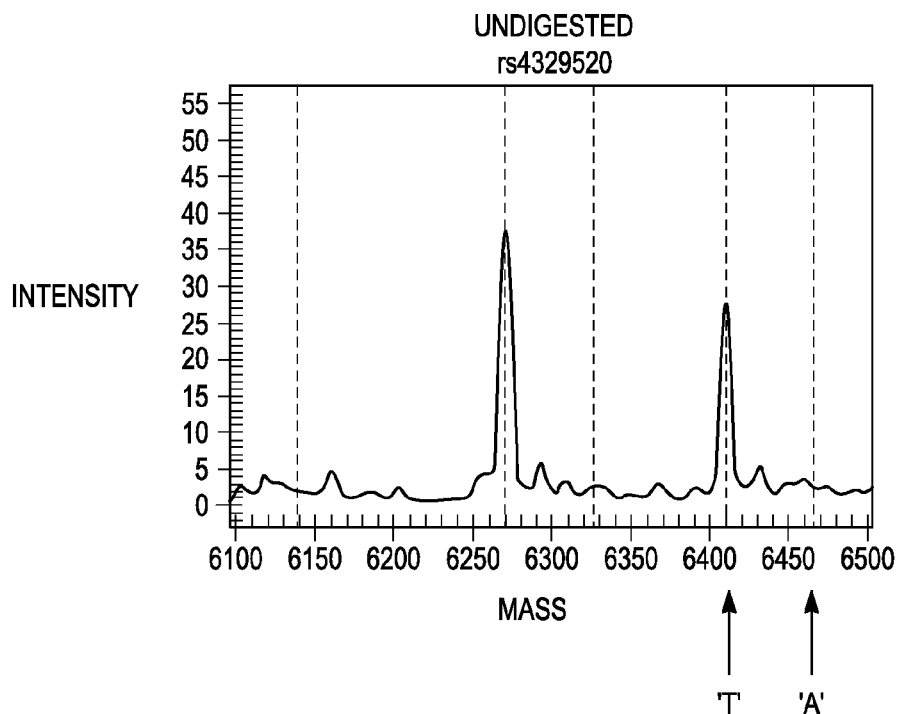
Figure 4D:
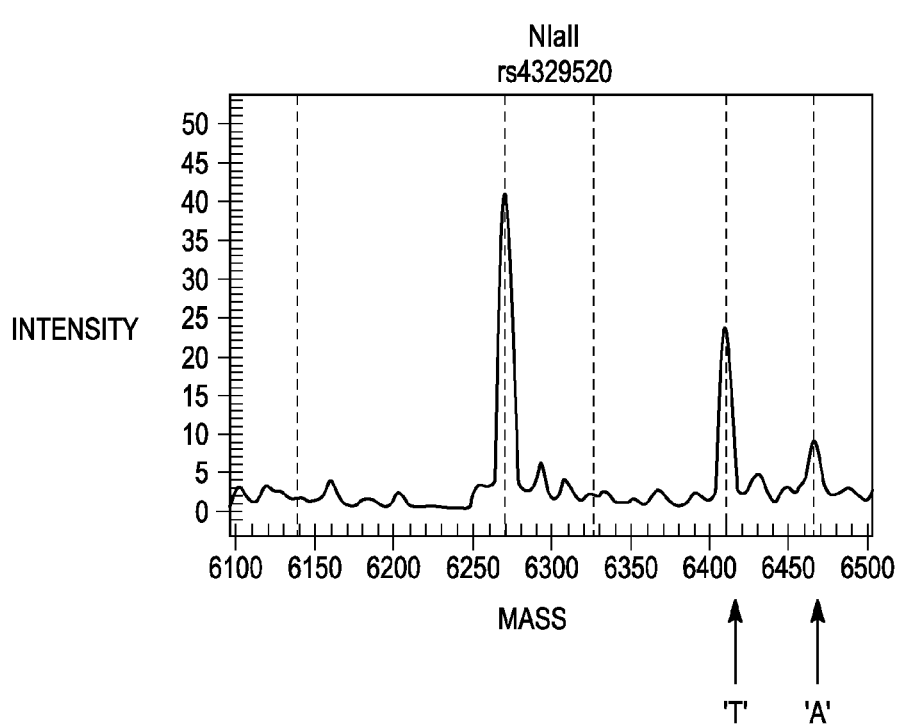

Digestion of DNA with both restriction enzymes allowed detection of minor alleles when they were present at ratios as low as 2% heterozygous DNA. This is in contrast to undigested DNA samples where minor alleles were only reliably detected when present at ratios of 20% heterozygous DNA and higher. When allele peak area ratios are considered, the effect of restriction endonuclease digest is even more apparent. HpyCH4V digested samples showed minor allele peak area ratios of 0.35-0.45 in 2% heterozygous DNA mixtures, while minor allele peak area ratios of 2% heterozygous DNA mixtures were at background levels without enzyme digestion (FIG. 1). While the increases in allele peak area ratio were not as high when using the NlaIII restriction endonuclease, the results were similar (FIG. 2). Example screen shots of the mass spectrum in 2% heterozygous DNA mixtures with and without HpyCH4V (FIG. 3) or NlaIII (FIG. 4) are shown below.

Optimization Studies

Initial optimization studies for enzyme concentration and pre-PCR incubation time of HpyCH4V digestion were performed using 5% heterozygous DNA mixtures (0.6 ng heterozygous DNA, 11.4 ng homozygous DNA). Based on these experiments, maximal peak area ratios were obtained with incubation times as short as 5 minutes and 0.25U HpyCH4V enzyme.

Example 2

Restriction Endonuclease Enhanced Polymorphic Sequence Detection Using TfiI

A similar experiment was performed as described in Example 1 using a different restriction endonuclease, TfiI. In this experiment, the TfiI restriction endonuclease selectively recognized and cleaved the 'C' allele of the 'C/T' SNP, rs4487973. The SNP rs4487973 occurs in the following genomic sequence on chromosome 1: CACACAGTTAG-GATT[C/T]ACCTGAGCTTGTCCC (SEQ ID NO: 28). For these studies, two CEPH DNA samples, one homozygous 'C' and the other heterozygous 'C/T' for the rs4487973 SNP, were mixed in varying ratios to generate DNA mixtures containing 0%, 1%, 2.5%, 10%, 50% of the rs4487973 'T' allele. The TfiI restriction endonuclease was either added or not added to each mixture to determine the endonucleases' effect on detecting the polymorphic sequence. Of the mixtures not digested with TfiI enzyme, the rs4487973 'T' allele was detected in the 10%, and 50% 'T' allele mixtures, but not the 0%, 1%, and 5% 'T' allele DNA mixtures. However, of samples digested with TfiI enzyme, the rs4487973 'T' allele was detectable in 1%, 5%, 10% and 50% 'T' allele mixtures. These results indicate the utility of this method to improve detection of polymorphic alleles present at low relative concentrations in a sample.

Example 3

Fetal Identifiers, Sex Test and Copy Number Determination

Selection of SNPs

Analysis of paternally-inherited alleles in clinical samples and correlation with Y-chromosome frequency in male fetuses was performed with a total of 16 SNPs. SNP assays for analysis of clinical samples were multiplexed as 8-plexes. All SNPs had a minor allele frequency (maf) of ~0.4 in all ethnic groups and were unlinked.

For performance evaluation of a universal Fetal Identifier panel that can be multiplexed with disease-specific markers, a new panel of 87 NT SNPs with a pan-ethnic maf>0.4 was selected and multiplexed into 16-plexes.

Method of SNP Analysis

Figure 5A:
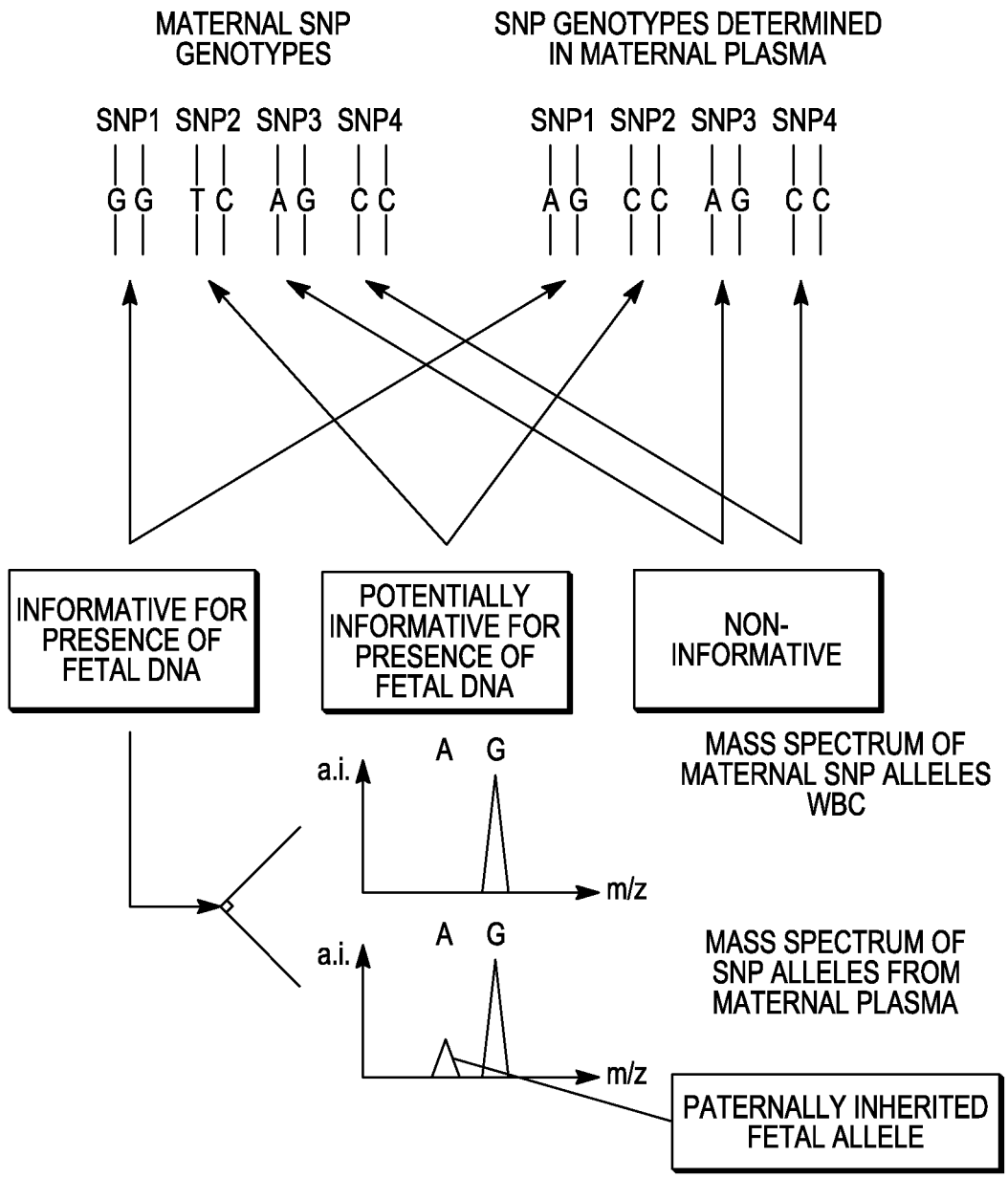
FIG. 5A shows the use of single nucleotide polymorphisms (SNP's) Fetal Identifiers to confirm the presence of fetal DNA by paternally-inherited alleles.
Figure 5B:
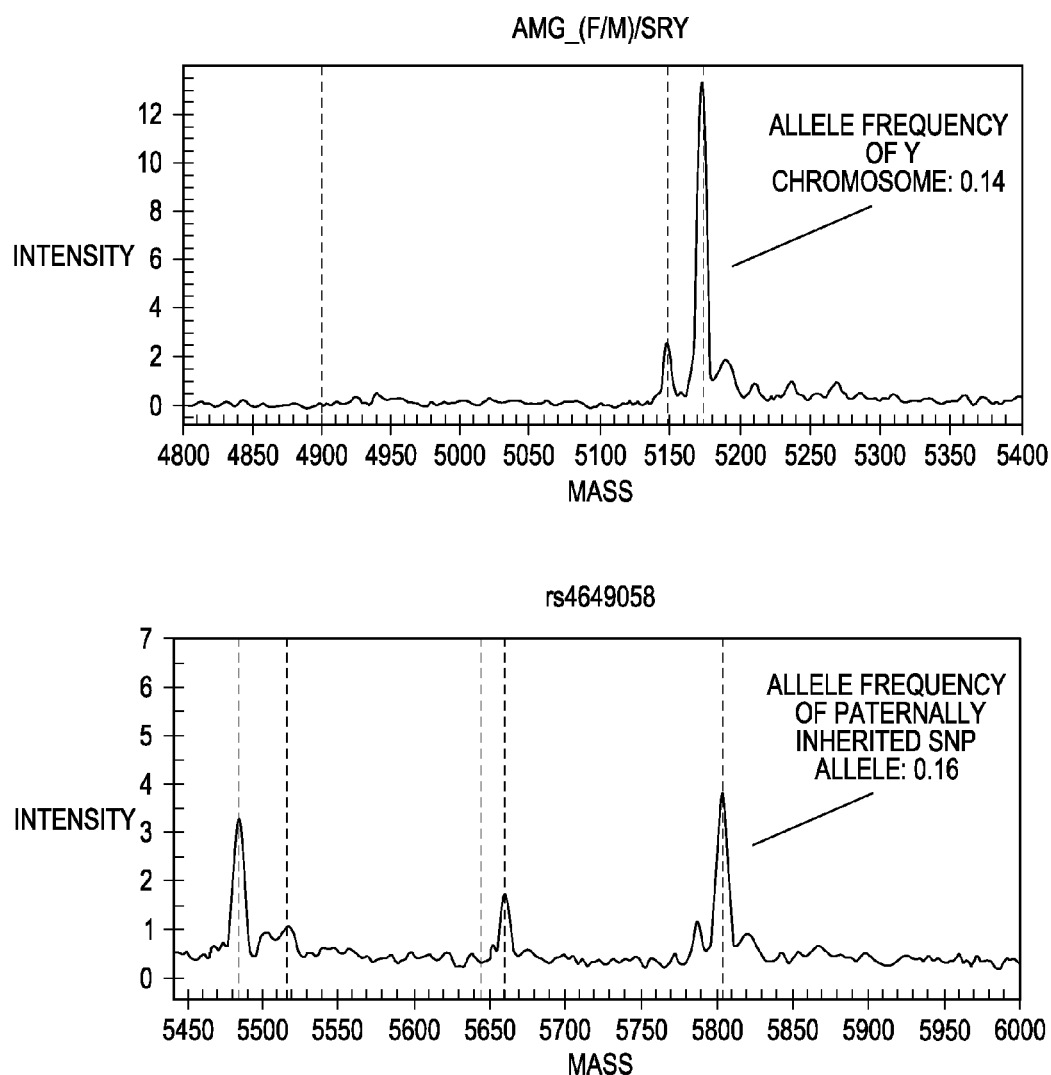
FIG. 5B shows representative mass spectra demonstrating the correlation between fetal DNA amounts estimated from AMG XY and from Fetal Identifier assays. The results were generated using the AMG primers provided in FIG. 9A-9C.

Analysis of SNPs in maternal buffy coat and maternal plasma was performed using the iPLEX™ assay and MassARRAY® technology. In brief, the target region surrounding the SNP is first amplified by PCR. Subsequently an oligonucleotide primer is annealed to the PCR product and is extended allele-specifically by a single nucleotide using a mixture of 4 terminator nucleotides and a DNA polymerase. The extension products are transferred to a miniaturized chip array and are analyzed by MALDI-TOF Mass Spectrometry. Determination of the molecular mass of extension products allows unambiguous identification of the SNP allele present in the sample. The peak area ratio of mass signals allows the estimation of the relative abundance of the alleles in a given sample. FIG. 5A provides an overview of the assay used for SNP analysis.

Clinical Samples

The total sample set consisted of 35 paired blood/plasma samples from pregnant Caucasian woman (nine 1st trimester; twelve 2nd trimester; fourteen 3rd trimester). The subset of samples used for correlation of Y-chromosome frequency and paternally-inherited alleles in maternal plasma consisted of 19 samples of pregnant Caucasian woman carrying a male fetus.

DNA Extraction

DNA extraction was performed from 1 ml of maternal plasma using the Qiagen® MinElute kit for fetal genotyping. DNA extraction from frozen blood (minus plasma) was performed from 4 ml using Qiagen's PureGene kit for maternal genotyping.

Results

An assay targeting sequence differences in the Amelogenin region on the X and Y chromosome was used to assess the relative amount of fetal DNA extracted from plasma of pregnant woman carrying a male fetus. Details of the AMG assay are depicted in FIGS. 8A-8C. X and Y-specific sequences can be discriminated by sequence specific iPLEX extension products and their respective mass signals. The peak area ratio of the extension products allows estimation of the relative amount of fetal DNA, because the Y-specific sequences represent 50% of the total fetal DNA contribution.

Sixteen of nineteen (84%) plasma samples with a male fetus showed a Y-chromosome frequency of higher than 5%, indicating presence of at least 10% fetal DNA in the extracted DNA. FIG. 6 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers Table 8 provides a list of SNPs that were multiplexed at 10+ plexing level and passed all phases of the validation. The following shows the validation scheme, performance criteria and model system used to qualify multiplex SNP assays for their utility in identifying the presence for fetal DNA.:

Phase I
  Step 1: Initial Fetal Identifier (FI) screening parameters
    FI's are multiplexed from pool of 87 NT SNPs (mass difference 56 Da)
    Genotyping of control DNAs (CEPH populations)
  Step 2: Advance screening criteria
    Reproducibility of genotyping calls in 4 replicates
    Unambiguous genotype data (assay shows no interfering or unpredicted mass signals)
    Allelic skew in heterozygous DNAs
    Variance of allelic ratio in heterozygous DNAs
  Step 3: Replex successful SNPs and repeat Phase 1 screening to generate multiplexes of 10+ SNPs
Multiplexed SNPs passing Phase I test criteria are tested in Phase II
Phase II
  Step 1: Mixtures of Genomic DNA are used for assessing FI reliability
    Mix Mother: 2000 copies of DNA1
    Mix 10%: 3600 copies DNA 1/400 copies of DNA 2
    Mix 20%: 1600 copies DNA 1/400 copies of DNA 2
  Analysis of allele frequency variation in 4 mixture series and 8 replicate measurements. Sensitivity and specificity are calculated for the detection of low copy number allele in background of high copy number allele
Multiplexed SNPs passing Phase II test criteria are tested in Phase III
Phase III
  Step 1: Various DNAs are mixed to emulate different maternal-fetal combinations
    Plate 1: 3600 copies DNA maternal/400 copies DNA fetal
    Plate 2: 1600 copies DNA maternal/400 copies DNA fetal Each plate contains 88 sample mixtures, 4 positive and 4 negative controls. Analysis of allele frequency variation in 4 mixture series, where sensitivity and specificity are calculated for the detection of low copy number allele in background of high copy number allele Application of this assay panel to a model system for the detection of fetal DNA in maternal background showed that paternally-inherited fetal alleles can be detected with a sensitivity of 95% at 100% specificity if the sample preparation method can enrich the relative amount of fetal DNA to 20%. In Table 8, the minor allele frequency (MAF) for each SNP from different ethnic populations is provided. The ethnic populations are defined by the HapMap Project, where CEU represents individuals of Northern and Western Europe descent, HCB represents Han Chinese in Beijing, JAP represents Japanese in Tokyo, and YRI represents the Yoruba in Ibadan, Nigeria.

TABLE 8

| SNP | MAF CEU | MAF HCB | MAF JAP | MAF YRI |
|---|---|---|---|---|
| rs11166512 | 0.43 | 0.41 | 0.50 | 0.49 |
| rs11184494 | 0.50 | 0.40 | 0.48 | 0.50 |
| rs11247894 | 0.43 | 0.39 | 0.32 | 0.44 |
| rs12089156 | 0.46 | 0.49 | 0.44 | 0.43 |
| rs12125888 | 0.40 | 0.43 | 0.48 | 0.43 |
| rs12136370 | 0.42 | 0.48 | 0.42 | 0.48 |
| rs12143315 | 0.40 | 0.42 | 0.42 | 0.42 |
| rs12759642 | 0.39 | 0.48 | 0.48 | 0.42 |
| rs156988 | 0.46 | 0.40 | 0.45 | 0.41 |
| rs2050927 | 0.44 | 0.50 | 0.41 | 0.49 |
| rs213624 | 0.48 | 0.44 | 0.40 | 0.34 |
| rs2454175 | 0.46 | 0.48 | 0.43 | 0.40 |
| rs4329520 | 0.45 | 0.43 | 0.40 | 0.44 |
| rs4487973 | 0.47 | 0.43 | 0.44 | 0.40 |
| rs454782 | 0.48 | 0.40 | 0.41 | 0.46 |
| rs4648888 | 0.33 | 0.30 | 0.33 | 0.46 |
| rs635364 | 0.49 | 0.40 | 0.46 | 0.43 |
| rs660279 | 0.41 | 0.49 | 0.50 | 0.39 |
| rs6687785 | 0.48 | 0.46 | 0.48 | 0.44 |
| rs7551188 | 0.46 | 0.49 | 0.45 | 0.46 |
| rs9431593 | 0.41 | 0.43 | 0.49 | 0.40 |

A multiplexed panel of 16 SNPs was analyzed with maf>0.3 in the same maternal plasma DNA extraction and established a baseline of maternal genotypes by analyzing DNA from PBMCs. Using the maternal genotype information, paternally-inherited alleles were identified in plasma samples and estimated the amount of fetal DNA from the peak area ratio of extension products representing paternally-inherited fetal alleles and maternal alleles.

Figure 7:
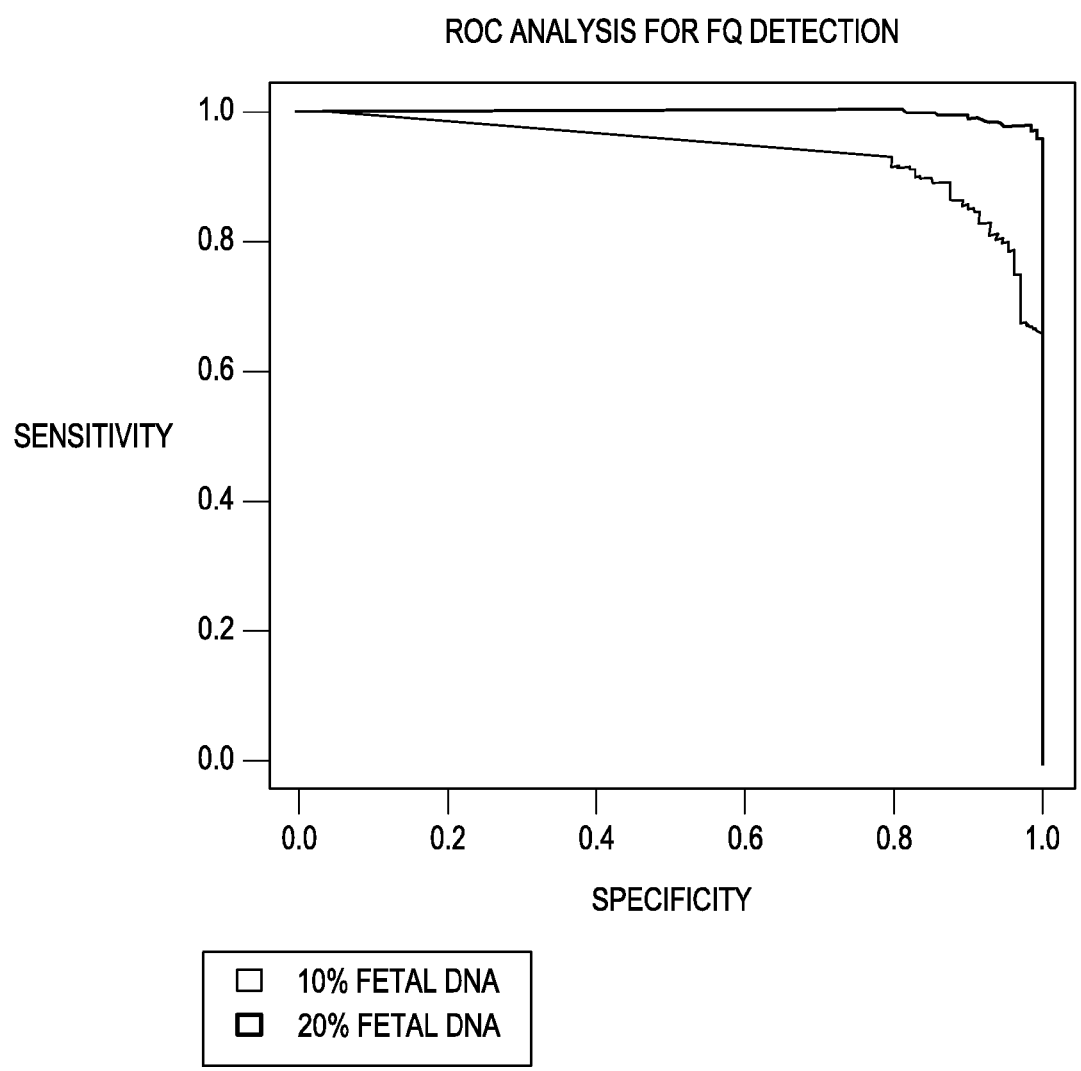
FIG. 7 shows the performance of multiplexed SNP assays (21 assays total) for detection of paternally-inherited alleles in a model system.

The AMG XY frequency was then compared with the allele-frequency of paternally-inherited fetal alleles in informative SNPs. This comparison revealed that samples with a positive Y-frequency of 10% (used as a Limit-of-quantitation threshold) or more have significantly higher differences between maternally and paternally-inherited fetal allele-frequencies (p-value<0.001; Fishers' exact test). This data suggests that Fetal Identifiers can be used as a non-gender specific approach for identification of the presence of fetal DNA. FIG. 7 exemplifies those results.

Example 4

Restriction Endonuclease Enhanced Polymorphic Sequence Detection Using Tsp509I

The effectiveness of restriction endonuclease enhanced polymorphic sequence detection was demonstrated using Tsp509I (purchased from New England BioLabs, Inc). Tsp509I was tested in multiplexed genotyping reactions for its ability to specifically cleave one allele of a given polymorphism while allowing PCR amplification of the remaining allele of the polymorphism. See Table 9 for Tsp509I enzyme characteristics.

TABLE 9

| | |
|---|---|
| Enzyme source | E. coli expressing cloned Tsp509I gene from Thermus species ITI346 |
| Recognition sequence | 5' . . . ↓AATT . . . 3' |
| Vendor | New England Biolabs, Inc. |
| Catalogue Numbers | R0576S, R0576L |
| Stock concentration | 10 U/ul |
| Digestion temperature | 65° C. |
| Thermostable? | Yes |
| Timesaver Enzyme? | Yes |
| Heat Inactivated at ≤80° C. | No |

Potential SNPs for use with Tsp509I

SNPs meeting the allele frequency criteria above were further screened for three characteristics:
1) one allele of the SNP is recognized by Tsp509I
2) the alternate SNP allele is not recognized by the Tsp509I
3) no other sites for Tsp509I are found +/−50 bp of the SNP within the PCR amplicon 338 SNPs passing these criteria are shown in Table 10.

TABLE 10

SNPs meeting criteria for Tsp509I screening

| | | | | | | |
|---|---|---|---|---|---|---|
| rs10021843 | rs11221268 | rs1447660 | rs2367059 | rs4130306 | rs623052 | rs7703746 |
| rs10030074 | rs11221881 | rs1458207 | rs2373814 | rs4311632 | rs6431221 | rs7725509 |
| rs1003016 | rs11227624 | rs1462685 | rs2401505 | rs4399565 | rs644818 | rs7737946 |
| rs10034384 | rs11249671 | rs1470207 | rs2427102 | rs4420242 | rs6468296 | rs7741525 |
| rs1004395 | rs11563997 | rs1503660 | rs2435556 | rs4420719 | rs6488494 | rs7763815 |
| rs10102733 | rs11635372 | rs1514424 | rs2451984 | rs4438888 | rs6494229 | rs7769867 |
| rs1010479 | rs11655850 | rs1536069 | rs2462049 | rs4442368 | rs650616 | rs7810506 |
| rs10110766 | rs11685586 | rs1540885 | rs247852 | rs4452041 | rs6542638 | rs7818415 |
| rs10139699 | rs11727770 | rs1543513 | rs2507947 | rs4488809 | rs6556642 | rs7820949 |
| rs10179379 | rs11759755 | rs1548605 | rs2517540 | rs4489023 | rs6569474 | rs7828293 |
| rs10234234 | rs11771935 | rs1593443 | rs2522215 | rs4533845 | rs6575809 | rs7831906 |
| rs10260483 | rs11773909 | rs1597205 | rs263025 | rs453609 | rs6582294 | rs7845628 |
| rs1026791 | rs11835780 | rs163027 | rs264039 | rs4589569 | rs6592545 | rs7899028 |
| rs10276221 | rs12007 | rs166576 | rs2647415 | rs4667489 | rs6595267 | rs7900002 |
| rs10278812 | rs12034424 | rs16830436 | rs2657300 | rs4673821 | rs664358 | rs7915178 |
| rs1029176 | rs12107918 | rs17074340 | rs2676403 | rs4674824 | rs6707911 | rs7985274 |
| rs1041409 | rs12158945 | rs17079191 | rs269882 | rs4678766 | rs6766358 | rs8016543 |
| rs10421748 | rs12439908 | rs17152417 | rs2723307 | rs4680921 | rs6807437 | rs8063107 |
| rs10510379 | rs12442455 | rs17156383 | rs273172 | rs4683161 | rs683262 | rs880385 |

TABLE 10-continued

SNPs meeting criteria for Tsp509I screening

| | | | | | | |
|---|---|---|---|---|---|---|
| rs1054067 | rs12450474 | rs17170027 | rs2734574 | rs4684986 | rs686851 | rs910500 |
| rs1070036 | rs1259733 | rs1720839 | rs2792780 | rs4708590 | rs6878291 | rs9285190 |
| rs10740169 | rs12607335 | rs1789529 | rs2804649 | rs4716945 | rs6897414 | rs9312864 |
| rs10754776 | rs12618834 | rs179596 | rs2820107 | rs474077 | rs691 | rs9314663 |
| rs10777944 | rs12674093 | rs1797700 | rs2821312 | rs4762447 | rs6929257 | rs9322744 |
| rs10784847 | rs12675087 | rs1822243 | rs2826737 | rs4764597 | rs6941784 | rs9352730 |
| rs10785736 | rs12783667 | rs1850422 | rs2828793 | rs4783152 | rs6962207 | rs9356029 |
| rs10795112 | rs12903747 | rs1870836 | rs2834712 | rs4815732 | rs7002630 | rs9428474 |
| rs10806232 | rs1297215 | rs1885121 | rs2846589 | rs4845519 | rs7041138 | rs9515625 |
| rs10818726 | rs13110085 | rs1904161 | rs2865878 | rs4869315 | rs7076662 | rs9554894 |
| rs10822434 | rs13130326 | rs1904185 | rs2889515 | rs4889072 | rs7082218 | rs9555581 |
| rs10832561 | rs13155942 | rs1910369 | rs2903113 | rs4894467 | rs7084321 | rs9594249 |
| rs10840805 | rs13255815 | rs1912619 | rs2928668 | rs4897019 | rs7094883 | rs9599645 |
| rs10851704 | rs13269702 | rs1916803 | rs2937415 | rs4928169 | rs7144509 | rs9630712 |
| rs10860857 | rs13331222 | rs2007475 | rs2984523 | rs494220 | rs7151741 | rs9652080 |
| rs10880400 | rs1335075 | rs2030926 | rs299080 | rs4952502 | rs7205009 | rs9692857 |
| rs10884498 | rs1342995 | rs2034877 | rs2993531 | rs4953843 | rs725849 | rs9787011 |
| rs10893402 | rs1346718 | rs2038710 | rs3010003 | rs4974594 | rs726395 | rs9818611 |
| rs10898954 | rs1363267 | rs2063506 | rs302137 | rs514714 | rs7266163 | rs9838013 |
| rs10901705 | rs1367452 | rs2092797 | rs309564 | rs550408 | rs7294836 | rs9864594 |
| rs10953770 | rs1372688 | rs2126316 | rs3128688 | rs558692 | rs7320201 | rs9886292 |
| rs10956363 | rs1376827 | rs2168524 | rs313937 | rs561470 | rs7323716 | rs9929404 |
| rs10964719 | rs1378933 | rs2191076 | rs331893 | rs586030 | rs7356482 | rs9987005 |
| rs10996924 | rs1401454 | rs2207800 | rs356643 | rs6005754 | rs748773 | rs9989393 |
| rs11017936 | rs1418136 | rs2241491 | rs373321 | rs6019378 | rs7588807 | rs9992168 |
| rs11079666 | rs1420562 | rs2247858 | rs3816551 | rs6043856 | rs7604667 | |
| rs11082446 | rs1432865 | rs2298810 | rs3902451 | rs6139756 | rs7679285 | |
| rs11099210 | rs1439047 | rs2304748 | rs3902595 | rs614004 | rs7688917 | |
| rs11105611 | rs1444647 | rs230526 | rs3912319 | rs6142841 | rs7689368 | |
| rs11125229 | rs1445496 | rs2322301 | rs3913810 | rs614290 | rs7691446 | |

Multiplexing Tsp509I SNPs

Multiplexed assays were designed using 274 SNPs from Table 10. The resulting multiplexed SNPs are shown in Table 11A with associated PCR primers and Extend primer for each SNP, and genomic sequence comprising the amplicon sequence (with the SNP allele variants indicated by brackets) are shown in Table 11B.

TABLE 11A

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W1 | rs644818 | 29 | ACGTTGGATGTGTCAGACTTGTCTGAAGGC | 303 | ACGTTGGATGCAGATAGTGCTTGAGAGGAG | 577 | GAAGGCCCACAGAAA |
| W1 | rs11685586 | 30 | ACGTTGGATGCCAAAGTGAACTTGGGTCTC | 304 | ACGTTGGATGGGGAGAAAGAACAACCTGC | 578 | CGGGGACTCCAGGAA |
| W1 | rs7094883 | 31 | ACGTTGGATGAAGCCTGTGGACTGTTAACC | 305 | ACGTTGGATGACATTAAGCCCAAAACAGG | 579 | AACCTGCTGACTTCAA |
| W1 | rs10021843 | 32 | ACGTTGGATGGTGAACTTTTTTGCAAGGG | 306 | ACGTTGGATGAAAGTGGCCAGGGATATAG | 580 | TTGCAAGGGAGGAAAA |
| W1 | rs7588807 | 33 | ACGTTGGATGCATCAGCAGTGTGTAAGAG | 307 | ACGTTGGATGCTGGTGAGTAAGCATTGAAG | 581 | CTTCACCAGCACTAAGA |
| W1 | rs1297215 | 34 | ACGTTGGATGTCCAAGGTGGTCTTTTGAG | 308 | ACGTTGGATGGTTGGTAAATGGTAGAGCCG | 582 | tcTGGCTCTGGGTTCAA |
| W1 | rs4667489 | 35 | ACGTTGGATGTTTGTTAGCAACAGCTGG | 309 | ACGTTGGATGGGAGTAGTCTTCACCTGTAG | 583 | cGCTATGCTGGAGCAAA |
| W1 | rs7082218 | 36 | ACGTTGGATGGTCTCTTAAGCAACGAGCGG | 310 | ACGTTGGATGTAGAGAAGGGCAACCAACACTG | 584 | CGGGTGCAGTGGGTGCAA |
| W1 | rs2903113 | 37 | ACGTTGGATGACACTGTTCGCATCTGCATC | 311 | ACGTTGGATGTAGCTCCAGGCAAGGAGAATT | 585 | ccacTCCCAAGCCACACAAAT |
| W1 | rs10139699 | 38 | ACGTTGGATGTGTTTCTCAGGAGTTCCCAG | 312 | ACGTTGGATGGCAGGAGAGAGAAAAAGAC | 586 | ccaGAGTTCCCAGCAGAAT |
| W1 | rs4452041 | 39 | ACGTTGGATGTGTGTCCAGTGACCAATAGG | 313 | ACGTTGGATGGTTGACGCAAAGCAAGTGAC | 587 | tcCCTGTCAGTGAGGAAAA |
| W1 | rs13130326 | 40 | ACGTTGGATGTGGTTCCAGTTCTCAAGCTC | 314 | ACGTTGGATGTCTTAGGAAAACCACGTCCAC | 588 | CCTTTGATGAGGAGCTGTA |
| W1 | rs2865878 | 41 | ACGTTGGATGATTGTGGCTGTGTCTCCTC | 315 | ACGTTGGATGCGTATCTGTCTTGGATCCTG | 589 | gagaGGGGACGATGCAGAA |
| W1 | rs11079666 | 42 | ACGTTGGATGGGAACACCTCCATTCTGATG | 316 | ACGTTGGATGACACAAGTGGGAGAGGTTTG | 590 | cctcGGGGTCCTGAACCCTA |
| W1 | rs2401505 | 43 | ACGTTGGATGACACCATCCGGTAGGAAAG | 317 | ACGTTGGATGCCAGTTTGTTAGGTTCTCTGG | 591 | AGTTTGACAGGAAGAAGAAA |
| W1 | rs4889072 | 44 | ACGTTGGATGCAGGAGGTATATGAGATCTGG | 318 | ACGTTGGATGTACACAGTAAGTTCCCTGAG | 592 | AGATCTGGAGGATGGAGAAA |
| W1 | rs7151741 | 45 | ACGTTGGATGAAGGGTGAGTGCTTTGATCCAG | 319 | ACGTTGGATGGTTCCAGCACAAGATTGTTG | 593 | AGATAACGTGATCCATTTAAT |
| W1 | rs10034384 | 46 | ACGTTGGATGCTCACAGTGAAAGTGAACAG | 320 | ACGTTGGATGCCGTATATGTAGCCACTTT | 594 | cGAAAGTGCATAGCTTGTTAA |
| W1 | rs1822243 | 47 | ACGTTGGATGGACATATATAACCTTGGTCCC | 321 | ACGTTGGATGCGTCTCTTCCTTCATAGAG | 595 | tctATGCTTTCAGCTCCAAAA |
| W1 | rs7604667 | 48 | ACGTTGGATGGAGGAGGTTGGGAAAAATGTG | 322 | ACGTTGGATGGAAGATGCACCACTTTCTG | 596 | caCTTGGTCCCTTATTGTTCAA |
| W1 | rs7845628 | 49 | ACGTTGGATGAGCTTTCCTAAACCTGTGAC | 323 | ACGTTGGATGAAACCACTTCCTGCTTTCCG | 597 | gaaacTGTGAAGAAAGAGGAGG |
| W1 | rs7915178 | 50 | ACGTTGGATGACCACCATCACAAAAGAGG | 324 | ACGTTGGATGAAACCACTTCCTGCTTTCCG | 598 | ctacACCTGTGACATTGGTTTAA |
| W1 | rs7691446 | 51 | ACGTTGGATGACCACCATCACAAAAGAGG | 325 | ACGTTGGATGTATGTTTGCATGTTGTTTG | 599 | aaCATCACAAAAGAGGCTCTAA |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W1 | rs4684986 | 52 | ACGTTGGATGCCATGTGAGGAGGCATGTTT | 326 | ACGTTGGATGTTAATGCCAGACAAGCCTCC | 600 | tttggGAGGTACATGAGGGAAA |
| W1 | rs4894467 | 53 | ACGTTGGATGGTATTGGGTTACATGATG | 327 | ACGTTGGATGAGAAGTCCTGTTAGTAGGG | 601 | ATGATGTAATAACTAAAATGCAAT |
| W1 | rs1830436 | 54 | ACGTTGGATGGCCGTGCATGGACTTCACAAG | 328 | ACGTTGGATGCCACTGGCCTTTTCAAAGTC | 602 | ACAAGAAGAAATGTCTAGATTTAA |
| W1 | rs7810506 | 55 | ACGTTGGATGGAGCATCTTCAAATATCCCC | 329 | ACGTTGGATGAACAACCGTTTTCTCTTGGG | 603 | ctataCCCTTTAGAATGACATTCAA |
| W1 | rs11017936 | 56 | ACGTTGGATGAATCCATTTCAGACGCAGCC | 330 | ACGTTGGATGATGTCAGAGATCACAAGCC | 604 | ttacCTCATCAATGCAATCTGAAA |
| W1 | rs17170027 | 57 | ACGTTGGATGGAACTGATGAAGAAAAGC | 331 | ACGTTGGATGCCTTTTGTGAGCAAGATGCC | 605 | cAGAATAGAATAGGAACTCAGAAAA |
| W1 | rs1378933 | 58 | ACGTTGGATGGTGGGCACTGTAATACAAGG | 332 | ACGTTGGATGTCCACACATGGTATCACAAC | 606 | gggcgTTCAATGGAGAAGACAGAAT |
| W1 | rs4438888 | 59 | ACGTTGGATGCTGTTGCCTAAAGTTCTCGC | 333 | ACGTTGGATGACATTACTTGAGACCCACAC | 607 | CTCGCTATTGTTAGCATTAATAAGAT |
| W1 | rs2846589 | 60 | ACGTTGGATGGTGATATTGAGTCTCACCTG | 334 | ACGTTGGATGCTCTTTCTTCATTATCATTC | 608 | GAAAGCAAAATGTGTATTTTTACAAA |
| W1 | rs2298810 | 61 | ACGTTGGATGGTTCCAGTAGGAAAACAGG | 335 | ACGTTGGATGTTCACTGACTCATGGATGGG | 609 | ccctAAAACAGTTCGTATTTCAGAAT |
| W1 | rs2034877 | 62 | ACGTTGGATGCATTTTGGGAAAATATACC | 336 | ACGTTGGATGGGAAGTCAGGATGAAAGTG | 610 | cttgTGGGAAATATACCACATCCAAT |
| W1 | rs269882 | 63 | ACGTTGGATGTACCTTCTATATCCAAGGAC | 337 | ACGTTGGATGATCTCCCCTTTTGAAACTTG | 611 | gggGACATAAAACTTCAATGATAGAA |
| W1 | rs10102733 | 64 | ACGTTGGATGCTCAGAAGAGAAGTACCAGC | 338 | ACGTTGGATGCTAGGATTACACGTGTGAG | 612 | gggcCCAGCCTTGATGTGGGAAAAA |
| W1 | rs1259733 | 65 | ACGTTGGATGCTGTCTGTGTGATCATCAGG | 339 | ACGTTGGATGTGACGCTAAAGACTGAGTGG | 613 | gatggCTGTGTGATCATCAGGGAGAAT |
| W1 | rs9555581 | 66 | ACGTTGGATGCATTGAAACCTGGGATACAC | 340 | ACGTTGGATGAAAGCAATCTCGACCTCAC | 614 | tctcTGCTGAGGTATCATCTAAGAAT |
| W1 | rs10510379 | 67 | ACGTTGGATGTGCTCACACAAAGCCTGTTG | 341 | ACGTTGGATGGAATAACTATGAGCTCATGG | 615 | ggtcgCTTCACACGGACATGCGTGACAA |
| W2 | rs11835780 | 68 | ACGTTGGATGTGAATCCCATGAGCATGAGC | 342 | ACGTTGGATGATTCACACAGCATTGCCTC | 616 | GAGCCCACTGCTACA |
| W2 | rs166576 | 69 | ACGTTGGATGGCCTTATTAGCTTCACTTG | 343 | ACGTTGGATGCATCTCATGAGAAAAGGCATC | 617 | ACATGGTCGCCAAAA |
| W2 | rs880385 | 70 | ACGTTGGATGGAAAGGCCACAAAGCTGTTG | 344 | ACGTTGGATGTCCACATGCATGATATGGAC | 618 | ACTGGCTGGGAAAAA |
| W2 | rs4708590 | 71 | ACGTTGGATGTGCAGAGTGCGAGAAGAAG | 345 | ACGTTGGATGAAGAGAGAGGGCTTTCATCC | 619 | aCACTGCACAGCCAAT |
| W2 | rs13110085 | 72 | ACGTTGGATGAGCAAGTGTTCCCTTTTGG | 346 | ACGTTGGATGCACGCCTAGGCTATGTTTA | 620 | GGGGCTGGTAGAAAT |
| W2 | rs1797700 | 73 | ACGTTGGATGAAGTGCTGGATTACAGGAG | 347 | ACGTTGGATGAGAGCAGGCAAAGATGCAAC | 621 | TGCCAGAACTAATCAA |
| W2 | rs1885121 | 74 | ACGTTGGATGGACGATTCTTCAGGAAAC | 348 | ACGTTGGATGCCATGACTCTAGTGACCTTC | 622 | AAGACAAAGGACACCAA |
| W2 | rs1904161 | 75 | ACGTTGGATGTAAGCATCCATGACCTACC | 349 | ACGTTGGATGCAGGTGGTAAATGTGCTCAG | 623 | caGACCTACCACCCAAAT |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W2 | rs10901705 | 76 | ACGTTGGATGTCTGAAGTAGACCTGGATG | 350 | ACGTTGGATGCTCAGGATATCATTACACACC | 624 | aCTGAGAGCAACCACTAA |
| W2 | rs7820949 | 77 | ACGTTGGATGCGAGTTGAAGATCCCATACG | 351 | ACGTTGGATGCTCGGTGAACTATAGGAATC | 625 | CATACGAGTGGGAGAAAT |
| W2 | rs7144509 | 78 | ACGTTGGATGAAGCAACTGGCACTCCTAAG | 352 | ACGTTGGATGGAGTGTTGTGATGCATGCC | 626 | TGGCACTCCTAAGACCAAA |
| W2 | rs8016543 | 79 | ACGTTGGATGTTATACAGGTTCCAGCCAGC | 353 | ACGTTGGATGCAGAGAGAAAAGGGAGTAGG | 627 | ACCTGATACTGAAGCCAAA |
| W2 | rs1458207 | 80 | ACGTTGGATGTCTCAAATATCTAAGTGGG | 354 | ACGTTGGATGCAAAACTTCACCTCAATAA | 628 | ggTCTAAGTGGGAGTCCAA |
| W2 | rs13155942 | 81 | ACGTTGGATGCGGTTCTTTTTGAGGACTGG | 355 | ACGTTGGATGCTCAGTGTCTGACAAAAGC | 629 | ctcTCTTTCTCCAGGATGA |
| W2 | rs3912319 | 82 | ACGTTGGATGACTGGCCATGCAGATGTAAG | 356 | ACGTTGGATGCACTGCCATAGACCCTGAACAC | 630 | gCCAACAGAGAAGTAACAA |
| W2 | rs9929404 | 83 | ACGTTGGATGGAGATGAGAGCAGGTG | 357 | ACGTTGGATGCTCATAGACCCTGAACAC | 631 | GAGCAGGTGAAATGTTCTA |
| W2 | rs4974594 | 84 | ACGTTGGATGGAGAAAATCCATCCTCTGAACC | 358 | ACGTTGGATGCCATGGCTCGTGTTCTTAAC | 632 | cTCCTCTGAACCTTATCAAAA |
| W2 | rs4673821 | 85 | ACGTTGGATGGTCACTGAACTCTGGAGTAG | 359 | ACGTTGGATGCAGTTTTCAAAGGAAACCC | 633 | agCAGATAGCCTCTTGTGAAT |
| W2 | rs10784847 | 86 | ACGTTGGATGTCCCCCTACTTGCTTGAAAG | 360 | ACGTTGGATGTGAAAGAGTGAAGGAGGAC | 634 | ggggaTTGAAAGCAGGGCATA |
| W2 | rs1444647 | 87 | ACGTTGGATGCTCCCATCTATGATTTCCAG | 361 | ACGTTGGATGCATATCTGAGACACAC | 635 | ccacATCATGCCTCTATTGACA |
| W2 | rs12007 | 88 | ACGTTGGATGAATGAATGAGAGCTTGCTTACTTC | 362 | ACGTTGGATGTCGTTCAGACACTAGC | 636 | ctAGCTTGCTTACTTCTAAAAA |
| W2 | rs6569474 | 89 | ACGTTGGATGCATTGCAGTAACTGGAGGTC | 363 | ACGTTGGATGTAGTAACTTCAGTTACC | 637 | gATCATTGTATAGGTTCCCAGA |
| W2 | rs7076662 | 90 | ACGTTGGATGAATGAACACCAAGGAAAGCGATG | 364 | ACGTTGGATGTGCTTAGTAACTCATGTG | 638 | AGCGGATGAAGCAATACATTAA |
| W2 | rs6043856 | 91 | ACGTTGGATGTAATACCCTGAGCAAGGACG | 365 | ACGTTGGATGTGCATTAAAATCCATGTG | 639 | cccatGACGTCACCCTGTAAAAA |
| W2 | rs6142841 | 92 | ACGTTGGATGGTCCATTAACGTGTGAG | 366 | ACGTTGGATGGGTTCATGAAAATGTTAGTTCC | 640 | ccccGTGTGGAGAAGTGCGAGT |
| W2 | rs748773 | 93 | ACGTTGGATGCACCAGTGCAAACACAAC | 367 | ACGTTGGATGCCTGATTGTTTTGGAGGAG | 641 | gaagtAATGAGAACCTGGTTAA |
| W2 | rs1363267 | 94 | ACGTTGGATGTGTGCAGCACTTTTCACAAG | 368 | ACGTTGGATGATCCAGGGTCACATCACAGATTG | 642 | ccCCAAGTTGAAAACTTATTCCAA |
| W2 | rs2723307 | 95 | ACGTTGGATGGGATCAAGAGAGAAAAATGGG | 369 | ACGTTGGATGATGTAGTTTCAATCTCTGTCTG | 643 | cATGGGAAACATGCCTCAATAAAT |
| W2 | rs4589569 | 96 | ACGTTGGATGTACATTCAGACGATAGTGCC | 370 | ACGTTGGATGAGAACCAAGTAACCCCAAACC | 644 | ggtaAGACGATAGTGCCAGAAAAT |
| W2 | rs6766358 | 97 | ACGTTGGATGCACATGCTAGAGAAAGAGGG | 371 | ACGTTGGATGTATGTCTTCCTTCCCTGATTTC | 645 | ccctcAATCATTCATGAAGCCAAT |
| W2 | rs7689368 | 98 | ACGTTGGATGAGTTGCCATGTTTCCACAGG | 372 | ACGTTGGATGACTAATACTCCAGGTTGAGG | 646 | ccCAGGATCCTCTAGATTGTGAAAA |
| W2 | rs7900002 | 99 | ACGTTGGATGCTACGTGACCCAAAGTTCAG | 373 | ACGTTGGATGTCTCACTCCTGGTTACCTAC | 647 | ggggcCCCAAAGTTCAGGATGGTAA |

TABLE 11A-continued

SNPs and PCR and Extend primer sequences used for multiplex assays with Tsp509I enzyme

| Multiplex | SNP_ID | SEQ ID NO: 2nd-PCR Primer | SEQ ID NO: 1st-PCR Primer | SEQ ID NO: Extend Primer |
|---|---|---|---|---|
| W2 | rs4489023 | 100 ACGTTGGATGGGGCTCTTATTATTGTACTC | 374 ACGTTGGATGAACAAGCCCAAGTTCCAG | 648 cGGCTCTTATTATTGTACTCTATAAA |
| W2 | rs10260483 | 101 ACGTTGGATGAGAAGGAGGTCATTCTAGGC | 375 ACGTTGGATGACATGACTCTAAAGCCACC | 649 gggcGGTCATTCTAGGCCATTAATAA |
| W2 | rs4533845 | 102 ACGTTGGATGGGCAGAACAAGGACAGATAG | 376 ACGTTGGATGAGTGTCTAGTAAAAGTTCTGCC | 650 atcGGTGATGTTTCAGGAAGTAAA |
| W2 | rs6556642 | 103 ACGTTGGATGGCCAGCTTGTCCATTAAAGG | 377 ACGTTGGATGCTGGCTTATAAATAAAAGACC | 651 cACTTGAAAAATACTTTAGACTTTCTT |
| W2 | rs12674093 | 104 ACGTTGGATGTTTCACAGGGTTAGGATGGG | 378 ACGTTGGATGCTAGCAAAGGCTGGATTCTG | 652 acatGGAGTTTCCTGTACTTTAAAAAA |
| W2 | rs7741525 | 105 ACGTTGGATGTGTGGAAGGCAGAGTGATATAC | 379 ACGTTGGATGGCTTTCTTCACTCAGAAGGG | 653 agagACTGAGACAGCAGTAGCCTAAT |
| W2 | rs2462049 | 106 ACGTTGGATGGGGAAGGTGTTTGTCTCATA | 380 ACGTTGGATGGTACAGTTTGAAAGGAGC | 654 ggtcCTTTCTGCAGCTCATATTCTGCAA |
| W2 | rs11105611 | 107 ACGTTGGATGAGAAGATATGTTGAGAGGGC | 381 ACGTTGGATGTATTCCCTTTCTGGCTGTGG | 655 ccctAGAGGGCAGATAAATAGTTAAAT |
| W3 | rs2191076 | 108 ACGTTGGATGTATGGTGCCTCCACAAAAG | 382 ACGTTGGATGCCTCTGATATATGTCCAGT | 656 ACTGTTTGACCCAGG |
| W3 | rs163027 | 109 ACGTTGGATGATGTGGTGGCAATATTGGG | 383 ACGTTGGATGCCAAAAGCAGGCTTCTTC | 657 TGGGAGGGGAATAA |
| W3 | rs4420719 | 110 ACGTTGGATGACCATTATTGGCCCTGCTC | 384 ACGTTGGATGATGGCAACATCTGCTTTCCC | 658 GGCACCTTAGGTGATG |
| W3 | rs2038710 | 111 ACGTTGGATGAGAATGACAAACCCAAGGGC | 385 ACGTTGGATGGACCTGTGCAAAACTTTGG | 659 tAGGGCACGTAGTAGA |
| W3 | rs1850422 | 112 ACGTTGGATGTAGGTTAAGAGGGAAAGGG | 386 ACGTTGGATGACTTGCCTTGTTCTTGACTG | 660 AGGGAAAGGGTGAAAA |
| W3 | rs1447660 | 113 ACGTTGGATGAAAGTCAGCACACAGTCACTGG | 387 ACGTTGGATGTCTCGAACAAGCTAGAGGAC | 661 ttAAAGCAACCCCAGGA |
| W3 | rs11221268 | 114 ACGTTGGATGTCGAACTCCTGACCTCAAAC | 388 ACGTTGGATGCCTGTAATCCCAGCACTTTG | 662 GACCTCAAACAATCCAAT |
| W3 | rs4845519 | 115 ACGTTGGATGGTGTTCATACTGTAGGCTTG | 389 ACGTTGGATGTAAACCAACCCCCTTCTTGC | 663 cCTGTAGGCTTGAAGAGA |
| W3 | rs1514424 | 116 ACGTTGGATGGTGTAAATAGGCTTGTGAGAG | 390 ACGTTGGATGTCTTTGGATTAAATGCCTGC | 664 GGCTTGTGAGAGGTAAAT |
| W3 | rs2092797 | 117 ACGTTGGATGTGCTTCATAACTCTGTCACG | 391 ACGTTGGATGCAAAACAGTATCGTAACAG | 665 tTCTGTCACGTTTCAGTAA |
| W3 | rs3902595 | 118 ACGTTGGATGCAGTCTCCCTAGCTAAGTG | 392 ACGTTGGATGTAGGAGAGATCCTGGAAGGTG | 666 gTCAGATCAACACCAAGTA |
| W3 | rs10276221 | 119 ACGTTGGATGCATTTGCGCGGAAAGAGGGAG | 393 ACGTTGGATGAATGTCCCACACATGAAGAG | 667 GGAGCCAGAAGAGATATAAT |
| W3 | rs11249671 | 120 ACGTTGGATGCACCCTATGCGACTTCTTTG | 394 ACGTTGGATGTGGAGCTGTTATTCTAGTG | 668 tttcCCACCGTCGAGACAAT |
| W3 | rs9992168 | 121 ACGTTGGATGTATCCCCCAAAACCTCACATC | 395 ACGTTGGATGGACTGGACTATAGTGATGC | 669 CCAGAGGATGTGTACACTAA |
| W3 | rs2937415 | 122 ACGTTGGATGAATCATGAAGTGATGAGAGG | 396 ACGTTGGATGCCACATTCAACTGCAGTTC | 670 GAAGTGATGAGAGAACTAA |
| W3 | rs10421748 | 123 ACGTTGGATGAGGACCTGGAGCTCAGCAAC | 397 ACGTTGGATGTCAGCTGTCTCCATGCTC | 671 gggTGGGAGAATGCCAAA |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W3 | rs11227624 | 124 | ACGTTGGATGTGTGCAGCAATGATCACAG | 398 | ACGTTGGATGCTCAGCCATCTCCTGTCATC | 672 | AGCAATGATCACAGCTATAAT |
| W3 | rs6595267 | 125 | ACGTTGGATGACAAGTAAGGTTGGGTGTG | 399 | ACGTTGGATGCCTATTCATGGAACCTCCAC | 673 | ggaaGTTGGGTGTGCCTTTG |
| W3 | rs614290 | 126 | ACGTTGGATGGGATGCTATATCATAGCCAC | 400 | ACGTTGGATGCTTCCCCCGCTCTCTTTAAAC | 674 | CCACATACCTTGAAAAAGAAT |
| W3 | rs1536069 | 127 | ACGTTGGATGCTCTGCTCTGCACACATAAG | 401 | ACGTTGGATGCCCTGAGATTATGTGACACC | 675 | gctaTGCACACATAAGGAGTAA |
| W3 | rs7688917 | 128 | ACGTTGGATGGGTGTTAGTCAACTAGGAGG | 402 | ACGTTGGATGAGAGCTTGGACTCTAGCATC | 676 | TAGGAGGTAATGAGGAGAAATAAT |
| W3 | rs4420242 | 129 | ACGTTGGATGAGAGGAAGCAAAGCTAAGGG | 403 | ACGTTGGATGCCCAGACACCACTTTATAGCC | 677 | ccctcCAGATCCAGAAACAGGAA |
| W3 | rs1432865 | 130 | ACGTTGGATGACCGCTAATGCTCCTCATTC | 404 | ACGTTGGATGCTTTGCACTTACTGCTTCCC | 678 | ggacACTGAATGACAAGAAGGAA |
| W3 | rs2821312 | 131 | ACGTTGGATGGGGCTTGGCTAATGCTCCTCATTC | 405 | ACGTTGGATGGCATGTTTAGTACTGCCAAG | 679 | ctcccCTCATTCAACTCAATGTAA |
| W3 | rs1910369 | 132 | ACGTTGGATGACCGCTAATGCTATAGCTAC | 406 | ACGTTGGATGCTTAACCTAGCTAGAGATCTGG | 680 | GCTTGAATAGCTATATACCCAAAT |
| W3 | rs2030926 | 133 | ACGTTGGATGGGGATTTCTGTGAAGCTGCTC | 407 | ACGTTGGATGGTAGTTAAAGGTGAGCAGGG | 681 | atagcCACAGGACAAGAAACCAAA |
| W3 | rs4399565 | 134 | ACGTTGGATGCCATGAATGAATGGCAAGTGTCTG | 408 | ACGTTGGATGAAAGTGTTGACCCCAGTGTG | 682 | tggaTGCTCTAGAGATGAGGACAA |
| W3 | rs1367452 | 135 | ACGTTGGATGTTGGTAGCATATGGGTCTCC | 409 | ACGTTGGATGCCTTGGGTTCTGAGGATTTGC | 683 | ccccCTTCAGGCCAAATCGAGAAT |
| W3 | rs2828793 | 136 | ACGTTGGATGGCCAGGGATTGTATTGGAAG | 410 | ACGTTGGATGCCTTTCTGATGAATGAAGCC | 684 | ctTAGCATATGGTCTCCTTTAA |
| W3 | rs2427102 | 137 | ACGTTGGATGCTTCTATGAACCACCAAGGC | 411 | ACGTTGGATGCTGGATATTGTTCAGCTGGG | 685 | gggtTCAGGAAGCTCTGGAATCAAT |
| W3 | rs10860857 | 138 | ACGTTGGATGTAGGAACGTGTACACTG | 412 | ACGTTGGATGATGATCCATGAACAGCCAAACCATGTC | 686 | ccacaACCAAGGCAAGCGACAAGTC |
| W3 | rs9692857 | 139 | ACGTTGGATGCCTATTTCTTGTGACCC | 413 | ACGTTGGATGATGTCTATACTGCCACCTTAGAACC | 687 | AACTATAAAGCATTGCTAAAAGAAT |
| W3 | rs4762447 | 140 | ACGTTGGATGATGACATACTCCCATGTGCC | 414 | ACGTTGGATGAAGAGAATCAGAGCCAGC | 688 | gggagGGTTTTTTGCCAGTATGTAAA |
| W3 | rs1540885 | 141 | ACGTTGGATGCTATGTAAAAGTAGCA | 415 | ACGTTGGATGCTTCCAAAGTTCATATGCAG | 689 | gaagGTGCCCCCAGGTTTTGAACAAT |
| W3 | rs17156383 | 142 | ACGTTGGATGCACGCTATGTAAAAGTAGCA | 416 | ACGTTGGATGCTTCCAAAGTTCATATGCAG | 690 | ccAGCTACTGAAAATGAAAATGTATAA |
| W3 | rs10278812 | 143 | ACGTTGGATGAATGGATAGAAGAATCTG | 417 | ACGTTGGATGACTACCCTGACTGCTATCTC | 691 | gggcATGGATAGAGAATCTGTCATAA |
| W3 | rs6575809 | 144 | ACGTTGGATGCCTGAGTCAACCTTGGAAAG | 418 | ACGTTGGATGTAATAGCTCCCCAACAGTC | 692 | gGGAAAGATAAGAGAGATATCAGAAAT |
| W3 | rs1029176 | 145 | ACGTTGGATGAGCCTGAATCTCTAGCAGTC | 419 | ACGTTGGATGGAGAGACACTGTCTCACTCA | 693 | aaggCATAAATATGCTTTCAACTACATG |
| W3 | rs3010003 | 146 | ACGTTGGATGCTGCAAGCTAAGAAACCAC | 420 | ACGTTGGATGCGTACCATATACCTAGGGTG | 694 | gcttGGTGATTTATGCAGAAAAGAATA |
| W4 | rs2241491 | 147 | ACGTTGGATGCCATTATTTCTCCCAAAGTC | 421 | ACGTTGGATGAAATAAGACCCTTGCACCCG | 695 | CCAAAGCTCTCCCAA |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W4 | rs11635372 | 148 | ACGTTGGATGTGTGGAAGGAGGCAAGGG | 422 | ACGTTGGATGATGTCTGTCTTGGCTATGGG | 696 | TCTGCAGTCTGGCAA |
| W4 | rs4952502 | 149 | ACGTTGGATGAGAAGAGATGGTGGTTGTGC | 423 | ACGTTGGATGACTGTTAGCTAGCACTGTGG | 697 | TGGTTGTCAGCCAA |
| W4 | rs2063506 | 150 | ACGTTGGATGAGTAGATCCTCCAGTTAAGGG | 424 | ACGTTGGATGGGACTCCCTACTCATTCAAG | 698 | GCCTCAGGGGAAGAA |
| W4 | rs650616 | 151 | ACGTTGGATGGTTGTGCTAGTAGACCGAG | 425 | ACGTTGGATGTCTAGTTTTCTTCTTCCCAGC | 699 | gCCGAGGGGTGGGAAT |
| W4 | rs10179379 | 152 | ACGTTGGATGTTTAGTGACACCTCCCATCC | 426 | ACGTTGGATGGGGTAGTAGGAGAAGTGGTTAG | 700 | CCAATCTGTCCGAAAT |
| W4 | rs2657300 | 153 | ACGTTGGATGGGCATGCAACATAGACTTGG | 427 | ACGTTGGATGTTAGTGAGCATCAGAGGCAG | 701 | ccTCCTAGACCTGTCAA |
| W4 | rs9886292 | 154 | ACGTTGGATGAGGCTTTCAGGATCTGCTTC | 428 | ACGTTGGATGCTCAAGGGCCATAGAAACAC | 702 | ggGCTTCCTGGGAAGAA |
| W4 | rs247852 | 155 | ACGTTGGATGTGGTGGACACAGGACAGCATTG | 429 | ACGTTGGATGTCATCCCATCATGCATCCTC | 703 | aCCTGGAAAGGAAGGAAC |
| W4 | rs2517540 | 156 | ACGTTGGATGATGTGTCAAGACCATCTGGG | 430 | ACGTTGGATGACGAGCAAGCAAGAGACTCGTCTC | 704 | tccaCAGTGCTCCCCAAAC |
| W4 | rs1335075 | 157 | ACGTTGGATGAGTTATTCTCCCGAGAAGGC | 431 | ACGTTGGATGGCTAGGCAGATTGTGCTGTG | 705 | CCACAATAGGATCTGCAAT |
| W4 | rs9630712 | 158 | ACGTTGGATGGACATGGTTGTGTTGTGAAG | 432 | ACGTTGGATGAAGCACCGCTGGTGATAATG | 706 | GTGAAGTAAAAGCTGGAAT |
| W4 | rs4928169 | 159 | ACGTTGGATGACTATGGTAGTACATGGG | 433 | ACGTTGGATGATGCATCATTGAATATTCACAC | 707 | tGGGGTCAGTAAGGAATA |
| W4 | rs11771935 | 160 | ACGTTGGATGTCCAAGCCCACAGGACAAAC | 434 | ACGTTGGATGTTCTTGTGGATTCCACTCCG | 708 | gaCAACAAGTACCAGCAGTA |
| W4 | rs13255815 | 161 | ACGTTGGATGGTTGGTAATAGCTACAGCCC | 435 | ACGTTGGATGAGAGAAGAGCTGACTGTCAGCG | 709 | ccatCCCTGCTCCCCTGAAT |
| W4 | rs9838013 | 162 | ACGTTGGATGTTTTGTCCCCAAACATCCC | 436 | ACGTTGGATGTTTAGTGAGGGTGCTGGAAG | 710 | ccACTACCATTGAGGTTCAC |
| W4 | rs9599645 | 163 | ACGTTGGATGAGACATCAGAGAGAAGGGAC | 437 | ACGTTGGATGTATTAAAGATGAGAGCCACAG | 711 | GGACATACAAATCAGACTAAT |
| W4 | rs453609 | 164 | ACGTTGGATGTGTTCCTGACTTCAAGGGC | 438 | ACGTTGGATGACCAGTTCTACCCATGAAG | 712 | aTTCATAATGAAGCAGGAAAT |
| W4 | rs8063107 | 165 | ACGTTGGATGAGGTGCTGTGGCAAGTTAG | 439 | ACGTTGGATGCTGCTGGGTATTCAGTTC | 713 | gggaTGGAGGGTTTTCACAA |
| W4 | rs9594249 | 166 | ACGTTGGATGTGGAAGAGAAACTCAAAAG | 440 | ACGTTGGATGACACAGGGTCTGTACATTGCAG | 714 | cCTTCAAAAGTTTAGAACCTGAA |
| W4 | rs7828293 | 167 | ACGTTGGATGCCAGGTCTCAAACTGATTG | 441 | ACGTTGGATGCCATTATGTGAAATCAGCG | 715 | gtaaCAAGTAGAGTGCTGAAT |
| W4 | rs7041138 | 168 | ACGTTGGATGGAAATACTTCCCTCGGGCTC | 442 | ACGTTGGATGAACCGCAGGTAAGGATTCAG | 716 | TTCAGGCTTTAAATACCTTCAAA |
| W4 | rs10818726 | 169 | ACGTTGGATGCTTCCCTGGCTTCATTTTCC | 443 | ACGTTGGATGCGATCTCCATCCAAAAGAGGC | 717 | CTTCATTTTCCAGGGTTGTTAAT |
| W4 | rs1548605 | 170 | ACGTTGGATGAGAGATTGAGCTTCAGTCCC | 444 | ACGTTGGATGTCAGTCTTGTGTAGATAGGG | 718 | AGTCCCCAGTGTAATAGGAAAT |
| W4 | rs6139756 | 171 | ACGTTGGATGCCACTTACAGAACAGAGGG | 445 | ACGTTGGATGTATACCTACCCCCAATGAC | 719 | ccccCAGGCTGCCTTGAAAT |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W4 | rs2126316 | 172 | ACGTTGGATGTGCTGCTGGATTCAGTTTGC | 446 | ACGTTGGATGGAACACTTTAGGCCAATATCC | 720 | gggTGCTAGTAGTATTTTGTTGACAAT |
| W4 | rs1420562 | 173 | ACGTTGGATGTTGATATGAGCCTCTGAGAC | 447 | ACGTTGGATGAGCTGAAGTTCGTGAGATGC | 721 | gagagGAGCCTCTGAGACTGAAAT |
| W4 | rs2647415 | 174 | ACGTTGGATGGGACGTGAGCAAGAAAAGAC | 448 | ACGTTGGATGTGCTACGATTCAGTAATGAG | 722 | ggGAAAAGACACTATGATGGTAAT |
| W4 | rs12607335 | 175 | ACGTTGGATGTGGTCTATTGAGGCAATGG | 449 | ACGTTGGATGAGGTTCATTTATGTGGTAGC | 723 | ccccTCTGACAACAAAAGGAAATAA |
| W4 | rs9322744 | 176 | ACGTTGGATGGACCCATGTCTGTCATACTG | 450 | ACGTTGGATGTGGAGCACTTTTGATGTG | 724 | AGCATCATTAAAGTATTTAGCCAAT |
| W4 | rs9864594 | 177 | ACGTTGGATGTGTCAAAACCCCATCTCTAC | 451 | ACGTTGGATGGGGCTCAAGTGATTTTCCAG | 725 | cttaAAAACCCCATCTCTACTAAAAA |
| W4 | rs4680921 | 178 | ACGTTGGATGGCCAAGCAACACTATGGTAT | 452 | ACGTTGGATGAAGACCAAGTGAACTGTGCC | 726 | gCACCTTTTAGTCTAAGGAGAGAAAT |
| W4 | rs4716945 | 179 | ACGTTGGATGAATGCCATTTCCTCAGGAGC | 453 | ACGTTGGATGGAAGCATCTAAGCACACGTC | 727 | gggcAGAATGAGGTGCTCTTTTCAAA |
| W4 | rs1543513 | 180 | ACGTTGGATGGACTGTGGTAGAGTAAGTCTG | 454 | ACGTTGGATGGAGAATTCCACATTCAGAGACAAC | 728 | ggggTGTTTAAAGCAGGCAAAATAAA |
| W4 | rs7266163 | 181 | ACGTTGGATGGTGTTGATCTGTCACATGGC | 455 | ACGTTGGATGGATGGACAAATAGCCCTGAAG | 729 | cttcCACATGGCAATATAAATGACCAA |
| W4 | rs9515625 | 182 | ACGTTGGATGGAGGTGCCAGCTAATCTAAC | 456 | ACGTTGGATGCATGAGGCCACAAAATCGTTTTCATCC | 730 | cCCGTGATTTACTAATAAGTATCAAAT |
| W4 | rs10953770 | 183 | ACGTTGGATGTATTACATCGAAATCAAGG | 457 | ACGTTGGATGTGCTCACTGGAGCATTTCAG | 731 | gACATCGAAATCAAGGTTTATGTTATA |
| W4 | rs1070036 | 184 | ACGTTGGATGGAAGTGTTTAGGATTTGAG | 458 | ACGTTGGATGGCAATCTTAAAGAGGGTTG | 732 | ccctCATACTTAGGTTGATTATCCCTAAT |
| W4 | rs10822434 | 185 | ACGTTGGATGAAGTCTTGACATAAGGTAG | 459 | ACGTTGGATGACAGGACCCTTGCTTTCAAC | 733 | ttacGTCTTGACATAAGGTAGTAAAAT |
| W4 | rs4953843 | 186 | ACGTTGGATGCAAAGCTTTGCGCATCAGG | 460 | ACGTTGGATGAATGAATCTCGCCAGGAAGTTG | 734 | aggcgCAAAATCTAAAGCAGAGATAAAT |
| W5 | rs2804649 | 187 | ACGTTGGATGTTAGGCCAAGCTCATGCTTC | 461 | TCTTTCCAGGCCCAA | 735 | |
| W5 | rs7323716 | 188 | ACGTTGGATGCAGTGATTTCAAATCCGGC | 462 | GCCGCACATCAGAAT | 736 | |
| W5 | rs10785736 | 189 | ACGTTGGATGCAATCAGCTACTGCTGATCC | 463 | ACGTTGGATGTGGTTTGGTTTCTCAGCTGG | 737 | TGATCCACTGGCTCAA |
| W5 | rs7831906 | 190 | ACGTTGGATGCTGTCAAAAGCCAGGCTAAG | 464 | ACGTTGGATGAGGTTCAAAGAGTATAAAG | 738 | CCAGGCTAAGGCAAAT |
| W5 | rs2928668 | 191 | ACGTTGGATGGCCAACCAGTTATCCCCATTC | 465 | ACGTTGGATGTACTTTGTGACCTTGAGGC | 739 | cTCCCCATTCCACAAT |
| W5 | rs12903747 | 192 | ACGTTGGATGCTTGAGAGGTTCACTAAC | 466 | ACGTTGGATGTGAGGCCATTAAAAGCAGGG | 740 | gATACAGCTTGGCCAAT |
| W5 | rs4869315 | 193 | ACGTTGGATGTAGAGCTCACAGAGCACTTC | 467 | ACGTTGGATGAGCACTTAACTGAGTCTGGG | 741 | GCACTTCCTACAAACAA |
| W5 | rs6542638 | 194 | ACGTTGGATGCTCAGTTTAAAGTCACTGCC | 468 | ACGTTGGATGTAACCCTGCAAAGACTAGAG | 742 | cCACTGCCAGTGACCTAA |
| W5 | rs686851 | 195 | ACGTTGGATGTTTACAGACTAGCGTGACGG | 469 | ACGTTGGATGATCTCACGATCCCCATTTC | 743 | cGACGGACCAATCTAAT |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W5 | rs9987005 | 196 | ACGTTGGATGGAGGAGGATGAAATCAGTGTC | 470 | ACGTTGGATGATGAGAACATGCCAGAAAGTGCC | 744 | GGTGTTGCCTGTTATTGA |
| W5 | rs10030074 | 197 | ACGTTGGATGTTTTTCTGTCTCAGCCTCCC | 471 | ACGTTGGATGATGAGGCTGAGAAACCTGTCTCTAC | 745 | ggaaACCAGGCCAGGCTAA |
| W5 | rs1346718 | 198 | ACGTTGGATGTATGATGGATGCAAGGCTTTCC | 472 | ACGTTGGATGATGAGGCTGAAGAATGCTTTCCC | 746 | GACTATCCTCTTCAGACCAA |
| W5 | rs2007475 | 199 | ACGTTGGATGAGCTTGGGCTGAATGTTAGG | 473 | ACGTTGGATGTAAAAGCAAAACAGCTTCC | 747 | ctAGCGTTTCACGTTCAAAA |
| W5 | rs10110766 | 200 | ACGTTGGATGGGCTCTAGTTTTCAGCAGAC | 474 | ACGTTGGATGCTCAAAACCTGGCTACCTTG | 748 | gCCTGGGAAAGAAAACAA |
| W5 | rs11099210 | 201 | ACGTTGGATGGTTACACTGACAATCAAGGG | 475 | ACGTTGGATGACTCTCATGTACCCTCTG | 749 | cGAGGAGGGCAGAGAAGAAT |
| W5 | rs4130306 | 202 | ACGTTGGATGAACTGATGATGGCTCGTACTACC | 476 | ACGTTGGATGGCTCTTTTCCCTATGATGTG | 750 | tGTACTACCCAGTGGAATAAA |
| W5 | rs1401454 | 203 | ACGTTGGATGGATAATATTGTGCTGCATGCT | 477 | ACGTTGGATGACCTTGTTCTGTGTGTGTGG | 751 | gggtTGCTGCATGCTGTAAAT |
| W5 | rs179596 | 204 | ACGTTGGATGCTGGATCTTTACCTCCATAGC | 478 | ACGTTGGATGACTAGAATCGTGCAGAGAAC | 752 | agCTTACCTCCATAGCATCTAA |
| W5 | rs9787011 | 205 | ACGTTGGATGGAGCACTTATCACAGGTCAG | 479 | ACGTTGGATGGAAGTGGGATAAACAAGGG | 753 | gtaatTGCCCCTTCAAGTGAAT |
| W5 | rs9989393 | 206 | ACGTTGGATGACTGAAGCATAACGCCTCTG | 480 | ACGTTGGATGGGTGCCAAACATGTTATGC | 754 | gaCTCTGGGACTACTAAGAAGA |
| W5 | rs664358 | 207 | ACGTTGGATGATCTTCATGTCCCAAGGAGG | 481 | ACGTTGGATGCCAAGTTATGAAACGTAG | 755 | ggaTGGAAAAGCTGAAAAGGAA |
| W5 | rs77837946 | 208 | ACGTTGGATGTCACGTCAGACTACACTGAG | 482 | ACGTTGGATGGATTATAGGCATGAGCCAC | 756 | tcagcCTACACTGAGCTACCACA |
| W5 | rs1342995 | 209 | ACGTTGGATGCATTGCTTGGGTCTTTCAG | 483 | ACGTTGGATGGGGTTCGGCAGATATATCC | 757 | ccccccCCTTCCATGGACTCATTA |
| W5 | rs4311632 | 210 | ACGTTGGATGGGTTTATTGGAAATGAAGTC | 484 | ACGTTGGATGATCCTACTTACTTCCAGTC | 758 | tcTTTAAAGTGCTACATCTATGAA |
| W5 | rs13269702 | 211 | ACGTTGGATGAAGAATGAAAGTGATGAG | 485 | ACGTTGGATGCTAGGCTTGTTCACTATTTG | 759 | cGTGATGAGATTTCTATCATACAA |
| W5 | rs2993531 | 212 | ACGTTGGATGCACTGAGAGATACAGGAAAG | 486 | ACGTTGGATGCTTGTTTCCCAACATAAGG | 760 | agcGAGATACAGGAAAGTGTAAAT |
| W5 | rs1372688 | 213 | ACGTTGGATGCTTGTTAAATGTGTTCC | 487 | ACGTTGGATGTGTCCCTCAGTTTAGTTTGTC | 761 | tttcAAATGTGTTCCATCATCTA |
| W5 | rs1720839 | 214 | ACGTTGGATGATGAAGCATAAGTC | 488 | ACGTTGGATGAGATGTTGCAAAGATGCAAG | 762 | ATGATGAAAGCATAAGTCTTTTAAT |
| W5 | rs6582294 | 215 | ACGTTGGATGAGTGAGACTTAACCGTGTGAG | 489 | ACGTTGGATGCACCCCACATTAGCAAAAG | 763 | aaatTGAACTGTAGCAAGAAACAAA |
| W5 | rs10234234 | 216 | ACGTTGGATGCTTCTTTCCCTGCATCATC | 490 | ACGTTGGATGAGGGAAGTGTTGTAGCATGG | 764 | catccGTTTTCCCTCTTGACTGAAT |
| W5 | rs11221881 | 217 | ACGTTGGATGCTGCCTATTCTTCTTCACGTC | 491 | ACGTTGGATGCAGAAACATGCTTGTAGCAG | 765 | gtcgTCTACGGTCTTTTTTCTTATCAA |
| W5 | rs494220 | 218 | ACGTTGGATGCTTTTGCTCACAAGAAAGTTGG | 492 | ACGTTGGATGCCCCCCAGGCAATGATTTTC | 766 | TTGGAACTATCGTTCAAAAAGTATTA |
| W5 | rs9428474 | 219 | ACGTTGGATGTGTGGAGGCCACTCTGATTAAAG | 493 | ACGTTGGATGATGAGACACAGCTAGCACTTTCC | 767 | ggTTAAAGGAGACAATGTATGTAAAT |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W5 | rs7294836 | 220 | ACGTTGGATGACTCCCCTACCTATCTCTTG | 494 | ACGTTGGATGTCCACAGCCACTGAATAGTC | 768 | gtcgCTTTGAAAAGCCTTAACCATTAA |
| W5 | rs614004 | 221 | ACGTTGGATGTGTTACAGCAGCTAGTGTTG | 495 | ACGTTGGATGCCTCTTAATAGCACCCAGTTC | 769 | tcGCTAGTGTTGCACTAATAACCTAT |
| W5 | rs2304748 | 222 | ACGTTGGATGCACCAGTCCCCTCAAATAAC | 496 | ACGTTGGATGGCAGTTCTTAAAGACCTCGG | 770 | acaAGTCCCCTCAAATAACCTATCAAAT |
| W5 | rs2435556 | 223 | ACGTTGGATGCCCTAGGATTTTCAGAATGG | 497 | ACGTTGGATGGGCTGACTCATTGTTAGGG | 771 | cacTGGTTTCAACTAAAATCGCCAAAT |
| W5 | rs550408 | 224 | ACGTTGGATGGTGTGCTTAGGAAATGTTTGTTG | 498 | ACGTTGGATGCGTGAATACATGAGAAGGC | 772 | AATGAAAGAGATATAATCATCTTAAAAA |
| W5 | rs7818415 | 225 | ACGTTGGATGGAGGAGTTATAAGACCTAGAG | 499 | ACGTTGGATGACCATATCACAGTTGTTGGG | 773 | tgaagGAGAGCTTAACTAAAATAAACAA |
| W6 | rs6488494 | 226 | ACGTTGGATGTATCCATCCTTCAGACACCC | 500 | ACGTTGGATGATGATGGACAGTAACTGCAGAC | 774 | AGACACCCAGGCCAA |
| W6 | rs10840805 | 227 | ACGTTGGATGCCTACCTTGCTCTGAGAAAC | 501 | ACGTTGGATGATGCTTCCTGCTTTTAAGCAGTC | 775 | AGCCTGCACTGTGAA |
| W6 | rs11773909 | 228 | ACGTTGGATGTTTTTGAAAATGGCCCAAGG | 502 | ACGTTGGATGTAATCTTGGAGGCTCTCTG | 776 | TGGCCCAAGGAGAAAT |
| W6 | rs4764597 | 229 | ACGTTGGATGAGAGATCCTCCAGCTCATCTTC | 503 | ACGTTGGATGATGATTTGGCCCTGAGGCTTATC | 777 | GCTCATCTTCCTCTGAA |
| W6 | rs2820107 | 230 | ACGTTGGATGAGAGATTGGTCCCTACACAATGG | 504 | ACGTTGGATGATGATATGTTGCTTCCTTTGG | 778 | AGTCTTTTGAGCCCAA |
| W6 | rs13331222 | 231 | ACGTTGGATGGGAATACATGTGGGTATGTG | 505 | ACGTTGGATGCTTGTAAGGCAGGTCTGATG | 779 | GAGAGCCATGAGTGAAA |
| W6 | rs12675087 | 232 | ACGTTGGATGAGCCACCAAAACCAAGTTC | 506 | ACGTTGGATGACTAGTTGGAATGGGCTTGG | 780 | tgAGCAAGTGCTGAGGG |
| W6 | rs725849 | 233 | ACGTTGGATGTTGTGTCTATCTTACACTG | 507 | ACGTTGGATGACTAGTGTCCTAGCCAAA | 781 | cGTAGCTTCCTAGCCAAA |
| W6 | rs910500 | 234 | ACGTTGGATGACTGATACCCTACAGTGTGC | 508 | ACGTTGGATGTGCTCAGAGACACTTAAACG | 782 | TGGATATGACTTGCCCAA |
| W6 | rs1916803 | 235 | ACGTTGGATGTTGACTCACCACTTCTGTC | 509 | ACGTTGGATGTGTTGATGAGGTGAAGAGGG | 783 | ACTTCTGTCTCAGTATCCA |
| W6 | rs6431221 | 236 | ACGTTGGATGTCAATCAGTCATGCCTGTG | 510 | ACGTTGGATGCTAATCTGAAGGCTCCACTG | 784 | cccTGCCTGTGTGATGAAA |
| W6 | rs4488809 | 237 | ACGTTGGATGCAAGCATCTGCTCTTGAGG | 511 | ACGTTGGATGCTGTGTAAAGAGTTTGAGG | 785 | cgGCTCTTGAGGCAGTAAA |
| W6 | rs3816551 | 238 | ACGTTGGATGGGTGGAGATGGGATTCTCTG | 512 | ACGTTGGATGAACCAGTCTACACACAG | 786 | GGGATTCTCTGGTTGTAAA |
| W6 | rs7205009 | 239 | ACGTTGGATGTATCTCCCACTCTTGTACC | 513 | ACGTTGGATGCTGGAATACAACATTCTGG | 787 | cCTCTTGTACCCCAGAAAAA |
| W6 | rs2322301 | 240 | ACGTTGGATGTGTTTTTCCTCTGTACCCTGC | 514 | ACGTTGGATGTACATGTGGTTAGAGTCTGG | 788 | aaaTGCAATCTGTCTGGAAA |
| W6 | rs17074340 | 241 | ACGTTGGATGAAATGCTACTCCAACAGAGG | 515 | ACGTTGGATGCTTCATTATCCCCACTGCTG | 789 | GGAGGTGACATAAGTAAGTA |
| W6 | rs9356029 | 242 | ACGTTGGATGATCCTGGGCTTTCCTTTGTC | 516 | ACGTTGGATGGAGTCTAGTGGACAAGAGAG | 790 | acTTGTCACACCTCTTCAAAT |
| W6 | rs10898954 | 243 | ACGTTGGATGAGTGCAACAGAAAAGGCAGG | 517 | ACGTTGGATGGGTCCTTGGTATGTGTTCTC | 791 | CAAGTCTTCTATCAAGGAAT |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W6 | rs263025 | 244 | ACGTTGGATGGCATTATGCTAAAGGCTGTC | 518 | ACGTTGGATGTCCTCTGATTAGGCCCTTC | 792 | GGCTGTCACAGATTTATAAAA |
| W6 | rs273172 | 245 | ACGTTGGATGCTATGTTTTCCCCAGCTTG | 519 | ACGTTGGATGGCAAAAGAACAACCACCCAG | 793 | acttTGCTAGGTCTTACATGAA |
| W6 | rs9652080 | 246 | ACGTTGGATGGTTTGGTGACTATAGAAACAG | 520 | ACGTTGGATGCAGTTTAAAGTCATATTCAC | 794 | gaaggTGTTGCCAAAAGCTAAT |
| W6 | rs2451984 | 247 | ACGTTGGATGAACAATAGAGACACACTCCG | 521 | ACGTTGGATGTTTAATCCAGGGAGCTCTTC | 795 | ccctcGACACACTCCGGCTAAAT |
| W6 | rs11655850 | 248 | ACGTTGGATGCACCACTCAGGAAAGCAAAC | 522 | ACGTTGGATGAAAATCCCAGTGAAGAGCAG | 796 | cccaAGGAAAGCAAACTGCTACA |
| W6 | rs7084321 | 249 | ACGTTGGATGACAGAAGCACCACAGCTGAG | 523 | ACGTTGGATGAGGTTTCCCAAGCTAGACCC | 797 | ttgacAAGACGCAGCTGTGCAAT |
| W6 | rs7356482 | 250 | ACGTTGGATGCATCAGCAATATAATGCCGC | 524 | ACGTTGGATGTGTGATCACTGTTCACAGG | 798 | CAATCCTTTATCTCTCTCTAATAC |
| W6 | rs9818611 | 251 | ACGTTGGATGGTTCTGGATGTTGGCCATTC | 525 | ACGTTGGATGCCACATCATATGCATCTGGG | 799 | GTGCTATCTCATTGTTGTTTGAAA |
| W6 | rs7320201 | 252 | ACGTTGGATGTCATGTAACCAAGCACCACC | 526 | ACGTTGGATGGCTCATTTATAGAAGCAGTC | 800 | ccccccCCCAAAAACCTACTGAAAT |
| W6 | rs3913810 | 253 | ACGTTGGATGTTACGACCCAATCACCTTGC | 527 | ACGTTGGATGTGTGTCCCAACCACCATTC | 801 | tCCTCCTCAAACATTAAGGACAAAA |
| W6 | rs12450474 | 254 | ACGTTGGATGCCTTCTGCTCAAGGAACCAAG | 528 | ACGTTGGATGGCCAAAGACGATGTGAAATG | 802 | attaTGCTCAACTACCAAGTTAAGA |
| W6 | rs1503660 | 255 | ACGTTGGATGCCAGTCAAGCAGTAGCCAGTTTC | 529 | ACGTTGGATGTCTGATTAGGCCTAAGAGC | 803 | cCAGTTTCAATAACAGATAGTAAAT |
| W6 | rs683262 | 256 | ACGTTGGATGAGAAGCAGGTACTTACTATGGG | 530 | ACGTTGGATGATCAGACTTTTCCCAGGCAG | 804 | gTACTGAGATTGACAAGTCATTAAA |
| W6 | rs1041409 | 257 | ACGTTGGATGAACTGCTGAGGCACAAGGAGATAAG | 531 | ACGTTGGATGTACTGTTAGTGTGTCACTC | 805 | cgggACTTACTATGGGAATAGAAT |
| W6 | rs2984523 | 258 | ACGTTGGATGCTGAGGCACAAGGAGATAAG | 532 | ACGTTGGATGACTGACCTGGGTTTGACTTC | 806 | AAGGAGATAAGTAACATGTTTAAAAT |
| W6 | rs10754776 | 259 | ACGTTGGATGTGCCTAGCCTTACATCCTG | 533 | ACGTTGGATGTCAAAATAGATGATGACTG | 807 | caccTCCTGAATACTTTCTCATATAGA |
| W6 | rs2734574 | 260 | ACGTTGGATGGACCTTCTGTTCCTAGATG | 534 | ACGTTGGATGTGACTGACTGTGACATAGC | 808 | acgTTCCTGTTCTCTAGATGATCAAAT |
| W6 | rs9285190 | 261 | ACGTTGGATGAATCTTGGAGCCTTGGAGAC | 535 | ACGTTGGATGTGCTTCTCACAAAAGCCTG | 809 | gTAGTTTCTTTAGCTCTTGAATAAAT |
| W6 | rs331893 | 262 | ACGTTGGATGATCCATCTCTGTCAGAGTTC | 536 | ACGTTGGATGAGAGAACTGACCCTTCACTG | 810 | aggTCTCAAATAAAAATCAAAGGAAA |
| W6 | rs10806232 | 263 | ACGTTGGATGGAGAGGGAGAAGTAGAG | 537 | ACGTTGGATGCCCTTACTACTCAGTGATTCCTC | 811 | ggagGGTGGTTAGAGAACTCAATGAAT |
| W6 | rs12107918 | 264 | ACGTTGGATGTTTAATAGGGAAAGTATTGG | 538 | ACGTTGGATGCACACCCAGAAGCACTGATA | 812 | aaatCTAAATAGCCAAGAAAAACAGCCAA |
| W6 | rs1593443 | 265 | ACGTTGGATGTACCATGCTCATTGAACTCG | 539 | ACGTTGGATGGGAGATTTGATAGGAGTGC | 813 | aaAAAACTCAATATAGTAAAGGTATCAA |
| W7 | rs1912619 | 266 | ACGTTGGATGGCCCATCCTTCACTAACTTG | 540 | ACGTTGGATGAACAGTGGTGGCCCATCAGT | 814 | CACCCTCAGGAGGAA |
| W7 | rs1470207 | 267 | ACGTTGGATGCTGCCAGGAATAGGAGATG | 541 | ACGTTGGATGCGCTGAAAGAGACACTGAAG | 815 | GGGTGGCATCGGAAA |

TABLE 11A-continued

SNPs and PCR and Extend primer sequences used for multiplex assays with Tsp509I enzyme

| Multiplex | SNP_ID | SEQ ID NO: | 2nd-PCR Primer | SEQ ID NO: | 1st-PCR Primer | SEQ ID NO: | Extend Primer |
|---|---|---|---|---|---|---|---|
| W7 | rs7725509 | 268 | ACGTTGGATGTGTTACAGTTGAGAGCCACTGC | 542 | ACGTTGGATGTGCCATTCATTGCTCTACAC | 816 | CACCGAGCTTGCAATA |
| W7 | rs2792780 | 269 | ACGTTGGATGGAAGTCATTTGAGGCCCATCC | 543 | ACGTTGGATGCACTTCCAGTCGTGCTTCC | 817 | gCATCCTGGCTGAAA |
| W7 | rs6592545 | 270 | ACGTTGGATGTCTAGGTTGAGACTCAGGTG | 544 | ACGTTGGATGGGGTTTAAGCAACATGAAAGC | 818 | cTGGCTGACTGGGGA |
| W7 | rs6019378 | 271 | ACGTTGGATGTACGACCAGAATGGAAGAG | 545 | ACGTTGGATGATTGAACCCTGGAAGGTGG | 819 | cGAAGGAGGGCTTGAA |
| W7 | rs313937 | 272 | ACGTTGGATGACTTAACCCCAGTGTGATG | 546 | ACGTTGGATGCACTTATCCCATTCACGAGG | 820 | GTGATGGTGTTAGGGAA |
| W7 | rs10851704 | 273 | ACGTTGGATGACTCTCACACAAAGTTTGCC | 547 | ACGTTGGATGCGGTATTGTCTTAAGACTGA | 821 | CAAAGTTTGCCTGACAAA |
| W7 | rs6929257 | 274 | ACGTTGGATGGTCAGAGATTTCTGCCTAAG | 548 | ACGTTGGATGCATCGCCATGATGATCCTG | 822 | TCTGCCTAAGGTGTTAAA |
| W7 | rs11082446 | 275 | ACGTTGGATGACCCAGTGACCGAATAAAG | 549 | ACGTTGGATGGTAGCTACGTTCTTTGGAGG | 823 | TGGTATAGGTTTTGGGAA |
| W7 | rs4815732 | 276 | ACGTTGGATGGAGCTTCTATCCTTCTGCTAC | 550 | ACGTTGGATGGGTTCTGCCAAAAACCTTG | 824 | cACGTGAAAAACATGTTGAA |
| W7 | rs10795112 | 277 | ACGTTGGATGCAGTCTATTCTTGCTCTAC | 551 | ACGTTGGATGGAAGACCATTATGTTTCTGAC | 825 | TGCTCTACAATCACCTTAAT |
| W7 | rs1054067 | 278 | ACGTTGGATGCAGCAGCCAGCCTTTGAAAGTAAG | 552 | ACGTTGGATGTCAGCAGCTTACGGTTTCAG | 826 | ccTCAAAACAAACACAGACA |
| W7 | rs3902451 | 279 | ACGTTGGATGCTGGTTCTGTGAAATAAGAC | 553 | ACGTTGGATGGTGTCTTTACCTCTTTAC | 827 | ATGAACAAAACCTTTGAGAA |
| W7 | rs9352730 | 280 | ACGTTGGATGGGTCACTAGTATATATTTG | 554 | ACGTTGGATGACCTTACTCAGTTCTATTC | 828 | AAGGGATAGTTGTAGTATGA |
| W7 | rs2207800 | 281 | ACGTTGGATGCAAAAGAAGAGCTGATTGCTC | 555 | ACGTTGGATGCCAAGAAAGGCAATGTTGGG | 829 | ctCTGGATTGCTCACTGGAA |
| W7 | rs1870836 | 282 | ACGTTGGATGGAGGAGAAGGTGATGTGAAG | 556 | ACGTTGGATGCCCTGGAGTTCCTTTTCTTG | 830 | ATGTGAAGATGGAGGTAGAAA |
| W7 | rs264039 | 283 | ACGTTGGATGATCCCTCATTCTTTTCTCCAC | 557 | ACGTTGGATGAGAGAAGCTGAGGAAGCAAAG | 831 | CATTCTTTCTCCACTAGATAAA |
| W7 | rs2826737 | 284 | ACGTTGGATGATGCTAAGGATTCTGGGGTC | 558 | ACGTTGGATGACCATATGCTAAGAGCCAGGAC | 832 | ctTGGGTCAGACAGATTTGAAT |
| W7 | rs9554894 | 285 | ACGTTGGATGGGGCATGACACACTCAAAC | 559 | ACGTTGGATGACCTGAGTTTTCAGCCGTTG | 833 | ctgcCACAACTCAAACTTTGGAA |
| W7 | rs12034424 | 286 | ACGTTGGATGAACAGAGGGTTTAACAGCAC | 560 | ACGTTGGATGACCTTACTCAGTTCTATTC | 834 | TCAGATATGTTCAGTCAATGAAT |
| W7 | rs10880400 | 287 | ACGTTGGATGCCAATATTTTTTCCCTAGGT | 561 | ACGTTGGATGTGTGTCATTAAATCCTCCCCC | 835 | ggggCCCTAGGTACAAAGGCTA |
| W7 | rs9314663 | 288 | ACGTTGGATGTAAGCTCCCCATCCAAGAC | 562 | ACGTTGGATGCACACAGTCTACCTTGATTTC | 836 | ccccTCCATCCAAGACACTGGAAA |
| W7 | rs7769867 | 289 | ACGTTGGATGTATCTGGGTCATTGTAAGGC | 563 | ACGTTGGATGTTCCCAAACATAATCACAG | 837 | gCATTGTAAGGCAAATGTAATAAA |
| W7 | rs2522215 | 290 | ACGTTGGATGAGGGCACAAAGACATCAAAG | 564 | ACGTTGGATGGGCATAGCCCTGTGCTTAA | 838 | gCATGCAAATCTTTCACATTAATAA |
| W7 | rs10777944 | 291 | ACGTTGGATGGGCAGGCACTCCTATCAATAC | 565 | ACGTTGGATGTGTTTGTTGCTGCGTGCTTC | 839 | cagtCACTCTATCAATACAGGAATG |

TABLE 11A-continued

SNPs and PCR and Extend primer sequences used for multiplex assays with Tsp509I enzyme

| Multiplex | SNP_ID | SEQ ID NO: 2nd-PCR Primer | SEQ ID NO: | 1st-PCR Primer | SEQ ID NO: | Extend Primer |
|---|---|---|---|---|---|---|
| W7 | rs2373814 | 292 ACGTTGGATGAGGGTATAGGAAACAGCTTC | 566 | ACGTTGGATGATCCTCTCTCCTAACACCAG | 840 | ttcgTGTAAACAAGAGAAATCATGG |
| W7 | rs6941784 | 293 ACGTTGGATGCATTTACCCACAAAGGTAAG | 567 | ACGTTGGATGTAGTCCCTGACATTGGAGAG | 841 | GGAATGAAGAGATTAAAATAGATAA |
| W7 | rs1597205 | 294 ACGTTGGATGGATGCAGAATAAGCATTTGAC | 568 | ACGTTGGATGGAGGCACTTTTTTCTGTTCC | 842 | acTAAGCATTTGACAAAATCTGATAT |
| W7 | rs11727770 | 295 ACGTTGGATGCTGTCTCAAGTGTCTGGTTC | 569 | ACGTTGGATGATCCATCCACCCATCCATTG | 843 | ggCTGGTTCATAGTTAAAAGTCAATA |
| W7 | rs4678766 | 296 ACGTTGGATGGTCCTAAGTTAAAAGAATGG | 570 | ACGTTGGATGCTCATGCCGACAAAACTTCC | 844 | CAAAGAAAAAGTAGATTTGTGAAAAA |
| W7 | rs3128688 | 297 ACGTTGGATGATCAAGAGAGGAAAATGGACAG | 571 | ACGTTGGATGATTTACTCAACTCTCTGGG | 845 | taatAGGAAAATGGACAGAAGTTGAA |
| W7 | rs2168524 | 298 ACGTTGGATGCTCCCCACTTTGTTCTGAG | 572 | ACGTTGGATGTCAACTAAAGGGCAGTAACC | 846 | TCAGCTACTCTGTATTTAAAATAAAT |
| W7 | rs11125229 | 299 ACGTTGGATGACTGTGCCTGGACAAAGAAG | 573 | ACGTTGGATGTAGCACCAGGCTTACTAGAC | 847 | gggaCAAAGAAGAGACCTGAAGTACACA |
| W7 | rs6005754 | 300 ACGTTGGATGGACAGTTTTTAAATCTTTTAC | 574 | ACGTTGGATGTCTGTATTCCCATACTACTTG | 848 | TTTTTAAATCTTTTACATCAATAACTAA |
| W7 | rs6962207 | 301 ACGTTGGATGTGAGTGATAGGTCCTCTCTG | 575 | ACGTTGGATGAGCTCACAAAACTAACACAC | 849 | GTCATTTTTAAAATGGAAATCAATAAA |
| W7 | rs12442455 | 302 ACGTTGGATGCAAAAGAACCTGGCTCATGG | 576 | ACGTTGGATGATGATATGTCACGCATAGCCCAG | 850 | aaggcAGTCAGTGATTATCCTTGGAAT |

TABLE 11B

| SNP_ID | SEQ ID NO: | Corresponding Genomic Sequence with Alleles provided in Brackets |
|---|---|---|
| rs12007 | 851 | AATTTTAATCTTTGGTCTCTAAAAAGTAAATTTCAAATTTATGAGTTTAATCACTTCAAATATGAATAGCAAAAATGAGAGCTTGCTTACTTCTAAAAA[T/C]TGAGGTTAAGATATAGCTAGTGTCTGAACGACACTCCTTAAAGTAAGTTCAAATGTAAAACACTCCTTAAGTCCAAATGTTTCCGCTAATAGTCTGT |
| rs691 | 852 | TACATGCATTCTTTTAGTGATAGATGACACAAACACACAAAGGATCCAGCCATTATGGGAAGATCACGTGTGTGGCCATATTGTAACACATTTTCTGCAAAT[C/T]ACCTCTTTCATTTAACAGCCCTTATTCAATGGCCTTTTCTTTTCAGTAGTACATAACATCTGTGTCATTTGTTGAATGACGACATGAATGTTTTGTA |
| rs163027 | 853 | GTGAATCATGAAGTCATATCATCACTGTATTACAAAAGCCAAAAGCAGGCTTCTTCCATCATTCCTTAGACTCACTGTGGTAGATCACAACTGGCCACAA[A/G]TTATTCCCCTCCAAATATGCCACCACCATTAGCAATGACTAGTTACTTCTACCATGAGAAGGTCAAGTTTATTTACCCACTCACTGAAATTTGTGCC |
| rs179596 | 854 | AGAAGCACTAACCTAAACCAGTGGTTCTCAACTGGGCTGAATACTAGAATCGTGCAGAGAACTTTAAAAAATAGAATAGCCCAGGCTGAACCCCAAACCA[A/G]TTAGATGCTATGGAGGTAAGATCCAGACATTAGTCATTTTTAAGGCTCCCCAGGTTATTCTAACGCAAAAAAAAGAAAGTTGCCCTAAACCAGCTTTTTA |
| rs166576 | 855 | AAGTGATATATATTGCTATTACCTCCTGCGATCTGTTTGCAGCCGTATTGCATGCTGTTTTTAAAACATGGTGCCAAAA[A/T]TCAGAGCCTTATGTTTGATGCCTTTTCATGAGATGTAGGCCCACATCCAACAGCCTGCTAGATATTGCCAATTGCATATCCTACACCTATATATGT |
| rs302137 | 856 | GATCAGTGATACTGAGCTTTTTTTTCATATGCTTGTTGGCCACATGTGTGTCTTCTCTTTTGAAAAGTGTCTTCATGTCTTGCCCATGTTTAATGGAA[C/T]TGACAAACCACAATCTGATTGCTTAATACAATAAAGGATTATTTCTCACACGTCACCATGTAGTTAGTATTCGTGGGTAAGGGGACAGGTGTT |
| rs264039 | 857 | TAGCCACAGCCATACAGGATAATAATTGCCCCATAATCTTCACACCTCCAAGTTTTGGACAATCTAACAGAAGATCTCATTCTTTCCACTAGATAAA[T/C]TCATTAATCCTCAAGTCCCCTCCACTTGTCATTTCTTTGCTCTCCAGCTTCCCAGCTTGTCTTCCTGTGTCCACCAGTTGGGCTCCGATCGGCCAATG |
| rs247852 | 858 | CACCGGACTGGGAGCCACTGCGGGGCAGGAGTGCCTTCTTCATTTCCCAAGAAGCTGCCTTTCTGCCGAATCAATCACAGCGGCTCATCAGCGCATCATCCTCTGCAAT[G/T]GTTCCTTCCTTTCCAGGAGGTTTGGTCACGGCCAATGCTGTCCTGCTTCAGTGTTCTCTGTGTCCACACAGCTTCCGCCATCATGCTACCGTGATGGTT |
| rs331893 | 859 | AATGATAAAATGTTCGTTCTTTTGGAAGTAACTCTTTTTTCTTTTTCTTTGTCTTCAGTCATCCATCTCCTCAGTTTATCGTCTCTTGCATTAGTGAATGGAAT[C/T; T/C]CGTATTCTTTCATGTAGAGCAGAACATCTTCCTACATAGTAAATAAAAAGAGTAAAAGAGACCACCTGTATTGAGAATGAATCAAGGAAGAAAGCAACCCAA |
| rs230526 | 860 | CTAAACTCTTCAGCAGATTACTCTCCACAGATACTCATAGCATAGAGAGGTTCCATGGGCTTAGGTACCATGGCCATATCTTAGTGTACAAATATC[G/A]ATTAATACCATTTTCGTAGTAAGATTACGGGAAAAGTGATTCTTGTTTACAGAGCCCTTTCAGTTTTTTCTTTCTCATTAGTAGAACATA |
| rs299080 | 861 | CTTTGAACCTGAGTGACTATTCCCACCTGACTATTCCCACCTGATTCTTCCACTGATTCTTCCACTGATTCCTCCCCAACATACGTTTATCGTCTCTTGCATTAGTGAATGGAAT[C/T; T/C]CGTATTCTTTCATGTAGAGCAGAACATCTTCCTACATAGTAAATAAAAAGAGTAAAAGAGACCACCTGTATTGAGAATGAATCAAGGAAGAAAGCAACCCAA |
| rs299080 | 862 | CTTTGAACCTGAGTGACTATTCCCACCTGACTATTCCCACCTGATTCTTCCACTGATTCTTCCACTGATTCCTCCCCAACATACGTTTATCGTCTCTTGCATTAGTGAATGGAAT[C/T; T/C]CGTATTCTTTCATGTAGAGCAGAACATCTTCCTACATAGTAAATAAAAAGAGTAAAAGAGACCACCTGTATTGAGAATGAATCAAGGAAGAAAGCAACCAACCAA |
| rs273172 | 863 | TCAATAATGTCTGAAGAGCTTGTAAAGAGATAAGTAGATGAAAACCCTTGTAAGTATTCAGTTCTCTCAAAAAACCCTTGTAAGTATTCAGTTCTCTCAAACGCAAAAGAACACACCCAGGGCCCTTTTA[G/A]TTCATGTAAGACCTAGCACATGGAAATCTAGCAAGCTGGGGGAAAACATAGAGGCAGGAAATCTGTGGCTTCTCAGAAGACAAGGATCGAATCCTTC |
| rs263025 | 864 | GCCCTGAAAGGATGGTAGATAGGCCATATCTGCTTTCTTTGGAGGAAAACAAATAATTATTATTGCATTATGCTAAAGGTGTCACAGATTTATAAAA[T/C]TGTAGCAAAGTGCCTGAGACATGAAGAGGCCTAAATCAGGAATAGTAGTAGAATGAATGAGAAACTTCACGGAATATATCAGACAACATAGCGCTCTTTAGAGAAAA |
| rs309564 | 865 | CTGAGTTTGACTTCAGTCTGAAATTTGCTCCATAAGTCTGGGCCTTTCTTCCATAAGTCTGGGCCTGACCACCAATATCTGTCTCCTCATCCTGCAATACTTTCTACTTGGACCCAA[C/T]TTCCACATGCTTGAATGTGAAAAAACGCTTTAGAGAAAAAAGCGCTAAATCACGGAGAATAGTAGTAGAATGAATGAGAAACTTCACGGAGTGAGCTCACTTTGTATGTTTTGCTTCTCAAGGGTTACAGCAC |
| rs269882 | 866 | CTAGAAATAATGCCCTCTGGCCACTGCCCAGTGCATTCTTATAGTGACACGTGATAAATCATAGTAAAAATATATCCTCCTTTGAAACTTGCCTACA[G/A]TTCTTATCATTGAAGTTTATGTCCTTGATAAATGAAGTTTATGTCCTTGATATAGAAGGTATTTTCATTTTCACCAACTCTGTAAAAAAAAAACTACTTCTGGATTATATAAATACTAT |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs313937 | 867 | AGTTTAAGTAATATTTCAGAATGACACTGCTATGGCTTGAATATTGTCTCCAAAATCATGTTGAAACTTAACCCCAGTGTGATGGTGTTAGGGAA[C/T]TGGGCCTTTAGGAGGTGATTAAGTCACGAGGGTAGAGCCCTGTGAATGGGATAAGTGGCCTTATAAAAGGGGTGAGGGAACTAGGTAGGCCCTTTTTG |
| rs664358 | 868 | TTATAACACCTCCTTAACAGTGTTTCACCTGATGACGCCTGAGATGAAGTGCATTATCTTCATGTCCCAGGAGGACATGGAGGAGGAAAGCTGAAAGGAA[C/T]TGTATTATGAAACTACGTTCATAAACTTGGTAATACATATACATTTACATATGAATATGATAACTACTGCTGATTAACTGTGAAAATGTTCATTTACTTTCC |
| rs550408 | 869 | TTTTTAATGTGAAATGCTTGGCACAGTTCCTGCTCAGAGTTAGTGCTTAGGAAATGTTTGTTGAATGAAGAAATGAAGAATATAATCATCTTAAAAA[T/C]TGTATTGAGTACTTATTATGAAGCCTTTCTCATGTATTCACGTATTTAACTTCACAGTGACACCAAGAGGGTACTTTTTATTATCCCCTTTAAAGACA |
| rs614290 | 870 | TGGTTAAGACCTTGATTAAAAGTAGATTGATTTATTCTGTCAGTAGTTTAGACCTTCCCCCGCTCTTTTAAACATTTGTTTATGGATATTGACACTTACC[G/A]ATTCTTTTTTCAAGGTATGTGGCTATGATATAGCATCCCTAACGCCAGTCCGCTCTTCAGAGTTCCGATCACTGCAGTTATAGCAAGTAAGTAAC |
| rs686851 | 871 | AGGAAGGAGGCTATACATATAGAAAAAATTTTACACCAGTGTGACAGATTAGAATCTCAAAGGGCTTTTACAGACTAGCGTGACGACCCAATCTAAT[C/T]TGTTGTCTAGGTCTCAGTTTTCTCAGCTGTGAAATGGGGATCGTGAGATTATCATTCCAATAGGATTGCTGTGAGATTCAATAAAATAATGGATTAAA |
| rs614004 | 872 | TCCATTTCATTTGTACTCAGAGTAACTAATCTTCATCTCCATTATAACTCCTCTAATAGCACCCAGTCTCTTTTCATTCACACGTGTTTCTCATAGTTTA[G/A]ATTTTTTATTAGTGCAACACTAGCTGCTGAACATAACTCCCAAATGTACTGGTTTGACACGATAGCTTTCTCCCCTCAGCCATTTAGGAACCCCAG |
| rs558692 | 873 | GCCAATATCTGTCTCTAAAGACTTTGTCCAATAACTTTCTCCGTTCCTGAATATGTCCGTTCTGACTCAGTCAAAATGTCATCAATCAG[C/A]ATTTTCAGTAAATAATAGTGTAGAGCTTGTTCCCTGAGCCCGACAGTGAATGATTGTCCCACAACACTGGTGTTCTGAATTATTAGAGTAGGAAAGAGTC |
| rs474077 | 874 | TTAAATAAGAAAGAATAATATGTGACATAGGCCATATGTGGCTCACAAAGCATAAACATTTACCATCTAGCTCTTCATAGATAAAGTTGCTGACTATG[G/A]ATTAGAAGAATATATCATATAAAATATAAAGAGACCTTTACGGAAACGCAAATCAAAATCCATAATGAGATATTATTTCATACACACTAGGAAGGCTG |
| rs650616 | 875 | ATTGCCTAAATCAGCGTCAACATGCAGTCAGTAGAAGGTTGTCTATCCTTCTTGTATCTCTTGAGGAGAACGCATCATCCTTCTAGTTTCCATTCAGT[G/A]ATTCCCACCCCTCGGTCTACTAGCAACAACTTTCTTGTGTAGGGGAACCATCATTCACAGTTAAAAGAGACAGTCCA |
| rs453609 | 876 | CCTTTATTTGGCCACCTTTTTCTGTGTATTTCTCAATGGAGCTCAAGGCTTTCAAGGCTTTCATAATGAAGCAGGAAAAT[T/C]TTCCCCGACCCCCTCATGGGTAGGAACGTGGTGTGCAGGGGCTGGGGGCTAGCCGGCCACTTCGGACACCAGCTGAGGCAAACTCTACTCATTGGAACCGGTT |
| rs561470 | 877 | AGTCCAACTGCACGTGCAAGGCTCTCGGGGGAAATCCCTACCCCCGTGAAATAGGAGCTTGCTGTTAAGTTCTTGGGTTCCTCCTTGTCACTGATTGGCTGAAA[G/A]TTAAATAAGCTAGTGTTTGAGTGAGGGGCTTTATCGTTCTTTAGACCATCTAAAATAGGACTCAACCAGCCTGCTTGTCTTAATCATCATATAAATTTA |
| rs356643 | 878 | CCCCACTCATCCAAAAGCTCAGACCAGTTGCTTGGCCTACCATTCAGACTGCGCCGTCGGTCTCCCGGGCTGCCTCCCCGATCTACACCCCTCAAAGCCACCTCATGTTCTTG |
| rs683262 | 879 | TATGTGAATGTGAAGTTGCACACGCCCTGACGCCCCTGACGCGCCCTGAGCGGCCCATAGTCTTACTCTTATATCACAGACTTTTCCCAGGCAGACATGGAGGTTGTATTTCCTAGTGCA[G/A]TTTAATGACTTGTCAATCTCAGTATTAGAAAACCAACAGGACATCCTGGTTTCCAGTTTATTGTATAACAACAAACTTTTTTTTTTTTTTTGAGACAGA |
| rs586030 | 880 | TTTCTTCTTTTCTTTTTTTTTTTTTGGCCTTCTTATTTGCATTCAGTGAGGAGGTGACACATTGTAGAACATAACCTCCCTTTTTCATTCCATGAATCTAAT[C/T]TGTTATTCTGTGTTTGTGAAAGATAAAGGATTAGCAAGAAACCGCTTTTGCATTAAGTCGACATTTAAATGCTTTATAGTTTATTATTTATGAAATTATCCTGCA |
| rs644818 | 881 | ATCCTGGCTACAATTTAGTTCCTTTTTGAAATCTGACATTTCGACATCTTCCATGAGTTGGCTGGGCCGCTGGTCTCAGTTCAGTCAGATAGTGCTTGAGAGGAGAAAAAAGTCTCTAAAACTCAAATCAA[A/G]TTTCTGTGGGCCTTCAGACAAGTCTGACAAGTTCGACATTCTTCGACATTCAGTGGGATAATACTGACACTTCACCCCAGCAAACCAAAAA |
| rs623052 | 882 | GCTACTTTGTCCAGGTACTATGCTACGGTTTTGGATACAGTATCTTATTTAATCAGCACACAACTTCAGGAGGTGCGCCACTAAGCCACCAGGATGA[G/A]TTGATGTCTCAAGCTGTCCAGAAACAGCCCTGTAGCCACTGCAGTCCCCTTCTCACTGTCATATCCTCATTGTATTTTACACTGGTGCTTTCAAACCCT |
| rs1342995 | 883 | TACCTTGTGGAACTGACACCTGTCCTATACCTTAGTCCCAGTGAAATGGTTCTGAATAACATTGTTGGTCTTCTTCAGCTCTTCATGGGACTCATTA[A/T]TTCCCTGTTCCTTTATTGCATATGAATATCTGCCAGAACCCACTGCCCTTGTCATATCTCATAATCTAGATTCGTCATATGCCCTATGCTTGG |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs1070036 | 884 | AATTAAAATCCAAAATGCTCTAAAATATGAAAATTTTGAGTGCCAGCATGACACTCAAAGAAATGCTCACTGGAGCATTCAGATCTTAAGTTTTAC[G/A]ATTAGGGATAATCAACCTAAGTATAATGAAAATATTCCAAATCCTAAACACTTCTTTTCCAAGCAATCTCAAATAAGGGATACTCCATCTGTATGTTTG |
| rs1003016 | 885 | CTAGGTGAATTTTTCTTCCTCTTAAGCCTTTGTGACAGGCTTAAAGGGTGGGTCCTGGGCCATCCCCTCTTTATACCCCATCTGTCTGTTAATCATTAATT[T/C]GCCAAGAGAGCTCCTCCTGGGATGGGGTGACTCCTGGCTATGGGGGATGCTGATATCAGGATGCTCTAATTCAGAAGAAGCCAAACTGTTTCTTGGCCCAAACTTTCT |
| rs725849 | 886 | TAAAATGACAACTGCAGTAGAAACAGCTAGGTTCCACAAACAATTGTGCTATCTTACACTGTTTAGAAATCTTACTGAGAAGTAGCTTCCTAGCCAAA[T/C]TACATTTTCCAAGCCCATTCCAACTAGTTGGTCCTAGGTGACTAGTTCTGCCAGTGAAATATTAGCAGAAGCCAAAGCGCATCGCTTCTGGGATAGGACTC |
| rs1004395 | 887 | CAAGATTTAGGGTTATTTGGTTAAAAAAAAAAAACAGGAAAAAAATCTTGTTCATTTATTACTTCAGTAGTCGGGTAATGAGACAGTTTCACCAGTAA[A/T]ATTACATGAGAGCACAATCAGAGGTAATATTAACGTTTATATGGGCACCCAAAATGTGAATAACCCAAAAGGAGATATGTAATTTCATTAGTACATCTC |
| rs910500 | 888 | CTGAAGTCGAAAATGCATTTGATATACCTAAGCTATCAAGCATCATAGCCTTAGCCTCACCTGCTTCATTGTGCTCAGAGCACTTAAACGTTAGCCTGCA[A/G]TTGGGCAAGTCATATCCAAACAATGCTGACAGCACCGACACTGTAGGGTATCAGTTGTTTAACTTCGTGACCGTGTGCTGACTGAGAGCTGTGAATCA |
| rs1026791 | 889 | TGGAATAACAATCCTTCTGGCTGCAGAGATTCAGACAACAGGCACACCCCAGATGTCCAAGCACCCAAACACCGAGTCAAACAAACTAAGCCAAGATCATCATTTAAAAT[T/G]GGAGAGTTTGTTTTGGCAGAGAGTGGAAGCAGTATGTACTAAGTAAGAACTGTACACTTTGAGCTGTCAACAGAGAATTAATAAAAGTGAAAACCTGTTG |
| rs748773 | 890 | CAGGAAAAACCTTCCATGTTTCGATTTTTTTTTTTCTTTGTCTTTCCTACAACCACCAGTGCAAACACCACAGTCCAGGCTCCTGAGTACTCAGCTGAGACTACAGTCTCGAGCCACTGCGCTTGACCCCAGA[G/A]ATTTAACTCCTTCCAAACAATCAGGTCTTAGCCCTCCCCACTGCATTTGAGAGTCAAATATGCAACTAAAGCTAACACACATTGGACGTGG |
| rs1010479 | 891 | TAGCTCACTGCAGCCTCAAACTCTCAGGCTCAGTGATCTCCCCACTTCAGGCTCGCAGTGACTACAGTCTCGTCTTCAGCAGTGATCATCAGGAGAATT[C/T]GGCTTTTTTATTTTATTTTACTTTTGGGAACAGGGTTCTCTCTGTAACGTGAGTGCCCTAGGCTGGAGTGCCCTAGTGTGATTGTGGCTCACTGCCATCCTGGA |
| rs1259733 | 892 | AAGGCAGCTCTGGGGGAAATTGCTGCTGTCAACGCTCTGGGTGCTATGCAGGCCTATGCAGCACAACAGGCAAGCAGTCTCCATCGAGCAGCAGT |
| rs726395 | 893 | GAACAGATCTCAAGGAAACACAGGAGAATTCCTGAACGCAAAACCCTGAATGCTCCTTTTGAATAAGAAGACCAGGTGTTTCCTTTGTATCAGGAGCATCACTGTTAA[T/G]TAACTGTTGATACACTTAAAACAGCTTGGTTGGCAATGCTTCAGGATGAACTAGACAATGCTGTCACA |
| rs1335075 | 894 | AGAAGCTGAGCCCTGACTTCAGGACACATGAGGTGCAGGACCAGAGTCGCCCCTAATCAGCTTCAGGCTTCAGCTTGTTCAGGACCGATTGCTGTGTTATTCCACTTATGAAACAGC[A/C]ATTGCAGATCCTATTGTGGCCTTCTCGGGAGAATAACTGCTTCAGGCTTTGGGGATAGTTAATTTTATTGTAAAATTTACACGGATTGGGCATAAGGTTG |
| rs1054067 | 895 | GGAGTGGAAGCTCTAAGGGATACGAAATCTGATTTATCCAAAGAAATCACAGCAGCTTTGAAAGAACACATTCAAATTTCAAACAACAGACA[A/T]TTCAAAACCAGGCCGCCTCTGCTTATTCACTGAAACCGTAAGCTGTCGAAAGCTTCAGGGAAAACTGGTCTTAAAGCTTCAGGCCAAACAATGC |
| rs1029176 | 896 | TGGGGTTTTAGCTGGAATCTGTGATAAAGTTAATGAATCAGGCTTAGAGGCTATGGACCAGCCAAAGTCTGTCTCATAATAGTTGCTAACAATAGAAACCATTGTAGCTAAT[A/T]CATGTAGTTGAAAGCATATATTATGACTGCTAGAGATTTCAGGCTTGAACTTTCTGGGATTTCATTCTGGGATTTCATTCTGACACGTGACATCTGCTGCTGGCACTGGCTGGGAAAAA[T/G]TTCAGAGGGCCCATATCCCATAACTACTCATGTGAAACTGTGAACTTCTCGGGATTTCATTCTGACACGTGACATCTGCTGCTGGCACTGGCTGGGAAAAA[T/G]TTCAGAGGGCCCATATCCCATAACTACTCATGTGAAACTGTGAACTTCTGTCCCCAAGGGAGC |
| rs880385 | 897 | CTAAAGTGCCATCCTCACGTGAGGGGTGTGTTGCTGACAACGTGTGTGAAAAGGCCACAAAGCTGTTGACATCTGCTGCTGGCACTGGCTGGGAAAAA[T/G]TTCAGAGGGCCCATATCCCATAACTACTCATGTGAAACTGTGAACTTCTGTCCCCAAGGGAGC |
| rs1458207 | 898 | CATTGCTCTACAGCCTGGGGACAAGAGCAAAGCCAAAACTTCACCTCAATAAAATAAATAAATAATTCCACTTAGATATTTGAGAAATATCATATACATAAGAACTAATGTTATTCCACTATACCCTAAACCCACTTTTACCCAGT |
| rs1376827 | 899 | ATCAAAATAATAAATAAAACAGAGAAAATGATTTTGTGGAGAGCCATGACACATTTGTTGTCCATAGGGAACTAACACTTCCAGTGACATCA[G/A]TTCAAGAAAAAAAATAGCAGGAGTGAGAATGTCATCTGTCAACCCGAAAATGATTTTGTTAAAATAATGACAACAACAAACTAAATATC |
| rs2663506 | 900 | AAGTATGGGGAAAGAAAGTTAAAAGAGGAGGCAGAAATAGAAACTATTTTAGGTGAGATAAACTCTTTAAGGACTCCTACTCATTCAAGTCTTCTAA[A/G]TTCCTTCCCCTGAGGCTTGTTTATTTCTGAAATGGATCCTGATTCTCATAAACCCTTAAACTGAAGTACTTTGGTTTCCAGTATTATGGCCCAATTCT |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs1593443 | 901 | CCTTTCTATGAAAATTTCAGAGTGAGCTTGGCAATCTCTATAGAATCACTTACTGGAGAGTGCATTAAACATATATAAATGTGAAGAGA[G/A]TTGATA<br>CCTTTACTATATGAGTTTTCAGTTTCAATGAGCATGGTATGTTTCCAAGTATTTAAATCATCTTGACTGATTTCATTAGCATTTTAATT |
| rs2401505 | 902 | AGTAGATGACCAGCGATGCTGTTACTACATCCTACCCATGCGAGATGAGTTGGGACCATCTCGGTAGGAAAGAGTTGACAGGAAGAAGAAA[T/C]TGC<br>AGAGTCCCTGCCTGTCCCAGAGATACTAACAACCTACAGTTGATCTATATGGAAGAGATTTCAGCAAACATGACAAACACAGTTAATATGGAAGAAGA |
| rs2367059 | 903 | AAGGAAGAAGAAGAAATGCTAAAGCTACAGTTTATGTTTTGTTTGCATGATTTCTGCTTCAAATAGGCTGGGATGATGAGCTATATTCTAACA[A/T]TTAAAA<br>TGCTGTCAATACTAGAACTGTAATACCACACTTCCTTTAAACAAGAAAAAGCCACATTTCTGTTTTGTGGTTGACTACATGATTTAAGTTTTTG |
| rs1367452 | 904 | CCACAGCCAAGAGTTAGAGACACAGCCAGGACCAGAACTTACTGAAAAGCAATAATCCAAGGTCTGACTTGGGTTCTGAGGATTTGCTCAGTTATAGATGT[C/A]ATTC<br>TCGATTTGGCCTGAAGAGGGCAGACACTTGCCATTCATGGAGTGAAGAGCTTGTTTTAAGGCTGGACTAACATCTCCCAATAAGGTCATTTGGT |
| rs2241491 | 905 | AGGACCAAGGATACAGTCCAGATGTGTCATATAAAATAAGACCCCTTGCAGTCCAGCAGTCCACAGCATATTAAGTTTATATATCCATAGTTATA[T/A]TTGGG<br>AGAGCTTTGGGAGAAATAATGGTATTCATTATAAGAGGCTTTTAAAAAAATATTTCAGCTAAAAAAAGTATTTGAGGCATGCTCTTTAAATTGTTTAC |
| rs2007475 | 906 | CCTGCCTGTTTCCTGGACAGCCCAGCCTTGCACTATAGCTTGGGCTACAGTCGTAGGTAGAAAAGATTTGGGACAACAAAGGAGAATCAGCGTTTCACGTTCAAAA[T/C]TGAA<br>CTGGAAGCTGTTTTGCTTTAAGTTAAATACAATGAATAGATCGAAACAGAGAAGAAAGCATTAAAAAGTCCCCTGAAATTCATTG |
| rs1372688 | 907 | TTTTCCAGTAATGAACCATATAGACATCATTTACTCCCTTATATAATACAGGGATAATAACACTTATACCTTAATGCTTGTTAAATGTGTTCCATCATCTA[T/A]TATGAG<br>AAAATGTCAGACAAAACTAAACTGAGGGATATTCTACAAAAACAAATTGGTAAGACTACTTTTCAAATATGTCAAGCTCTGTCTCAATGTCTCAGT |
| rs2304748 | 908 | GGAGGGGCTGCATACTTCTCCAGGGCTTTCTATTAGATCACCGAGGTCTTTAAGAACTGCATCTTTCACATTGCTCCCCCAGTGTCTCCGGGCATTCCGCGACCGTGCACAGTCAAATACCTATCAAAT[T/C]CTG<br>TGGCTTCATTAGATCACCGAGGTCTTTAAGAACTGCATCTTTCACATTGCTCCGTCGCTGCCTCCGTCGGGCAAGACAGTGTAAAATCTTGGAGAA |
| rs2207800 | 909 | GCACGAGCTAAGGGGCCGATGATTCTGAAGAGTATTCCACTACCAAGAAAGGCAATGTTGGAAGAACCTTTTGGTCAACTTCCACCACTTGTTAAATTTCTCTTGACTTGTCTTACT[G/A]TTCC<br>AGTAGAGCAATCCAGCTTCTTTTTGTCATCTCCTTTATCTTCCCTCTTTATCATCCAGAGAGCCCATAAGCACTGTTTAAATTTCTCTTGACTTGTCTTACT |
| rs2373814 | 910 | GAATGTCACAAAACCCAGAAGTCTAACCACAGTATTGTTTCTTCTGTTTCTTCTTCTGTGGTGTTCTACCAAGCTGATTTTTAAAAAATG[T/C]CCATGA<br>TTTCTCTTTGTTTACAAGAGTCGTTTCCTATACCTATTCTTGAAGGATAAAGAAAATAGTCATTCAAAGAAAATATCTGGCTTTTTCACAGTGTT |
| rs1543513 | 911 | ATATAACATTTGGCACTTATAGAAAAAATAATAACAAGGAGAAAATTATTCCACATTCAGAGACAACTAGTTTTTTTCATATGTATGTGTAAAAGTACATATAA[C/A]TTTATTTT<br>GCCTGCTTTAAACAGAACTTACTCACCAGTTCTTTAAAAGCAAAATTTCTGAAAGCAAAATTTGTTCTTCCATAGGCAGTTAGTTCAGTAATCCAAGTTTTTATT |
| rs1904161 | 912 | TCATTTGTTGAAACAACAACTTATTGTTTCTCTGTTTAGAAACTATATCTGTGTATTTATTATATATTAAGCATCCATGAGACCTACCACCCAAAT[T/C]GAGAGCTA<br>GCTCTCTTTTTTGTGTAACTACATCTGAGCACATTTACCACCTGCCTCACCACTGGGTAACCATCAGTCCACTTCTACATTCCTCAACC |
| rs1444647 | 913 | ATATTATGTACAACTACTATATGAATTTAAGATGATTTCTTTATCTAGTCCCATCTATGATTTCCAGTTTTGTCTTCAAATCATGCCTCTATTGACA[T/A]TTTTGTGT<br>GTGTCCCAGATATAGAGACATGTAGAGATAGTTCGTTGTGATATGTTCCTGGAAATAGAATTGGTGAGTTGAGTGACTCATAACCTTAACTTT |
| rs1420562 | 914 | CCAGAATTCAAATCAATGCTAACCCCAGACTCGCATTTTAAAACCCTACACCACACTGGCTCCATTCAAGTGTGTATATGAGCCTCTGAGACTGAAAT[T/C]AAAAC<br>AAGCAGATTTCGTTCAACTTATTTAACACAAAACCTTCTTTTGTAGAATAATAAACTTATACTTAGGTCTCACGAACTTCACCATCCCGTGTTGGAAGATGCCAGC |
| rs1850422 | 915 | AATATATAATACGTGAGAGGTGATAAGCCTTATGTAGAAATTAAGCAGGATTAAGCAAGTATACTTAGGTCTCTGTTCTTAATATGTTCCAGCTCTGCATGGTCCATGT[T/A]TCAG<br>AGATGTTCTTTCAGTCAAGAACAAGCAAGTATTATTCAAGGTTTATTGGTCACATTTGTGACAGTTGACACTTGTCAGGGCATGAAGCAGGATCAGGGAGGAGC |
| rs1916803 | 916 | TGAGCAGGTTCCTAGCTCGGTGCCTTGCCACAAAACTGAGCTTAATGTTGTTGATGAGGTGAAGGGGATACTTATCAGGGCCACATTCATGGGAA[T/G]TGG<br>ATACTGAGACAGAAGTGGGTGAGTGAAGTGACACTTGTGACAGTTGACACTTGTCAGGGCATGAAGCAGGATCAGGCGGGAGGAGC |
| rs2451984 | 917 | TCTTGTTTTCTGGAGACCTTGTTATTCAGCCTTTCTTTAATCCAGGGAGCTCTTCCCATATTTTCAAATATCCTCAGTTTTTGTTTTTACTT[C/A]ATTAGCC<br>GGAGTGTGTCTCTATTGTTGCCAATGATCTAAAGGATATAGTTCGTTAGTATTTGACAAATACCCTCTAATTGTCTTCCAATCGGAGGTAG |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs2462049 | 918 | TTAAAAAGTTCTCTATAGAGTGGGATTTTTAATAATACGAAGTTGGGAAGGGAAGTGTTTGTCTCAGCTCATATTCTTCTGCAA[G/T]TAAATATTCTTGCTCCTTTCAAACTGTACCAAAACACCCTCATTAAGCAGTCAAGCTATAACCACAGCATCCACCACCCTCAAGAACAGTTGAGTTT |
| rs1503660 | 919 | GAATTAAGTAGAACCACTGTCACCACAACTTAACAACTACATGATGTGCCAAGAGGTTTCATAGACTTTATAGTCTGATTAGGCTCAAGAGCTGGCTTTTAG[A/T]ATTTACTATCTGTTATTGAAACTGCTTCCTTGACTGGTATATCTAAACTTGGTCAGATAACTTCATCCTAAAATTACAAGAAGTGAGAGGGGTTAAAG |
| rs2092797 | 920 | AAAAATTGAAGGTCTGCAGCAACTCCATTTTGAGCAAGTACACTATATTAGCACTATATTCCAACAGTGATGCTGCTCATAACTCTGTCACGTTTCAGTAA[C/T]TCTTGCAATATTTCAAAACTTTCATTATTATTATATCGTTACGATACTGTTTTGTTTTTGTTTGTTTTTATTTGTTTGAGACGGAGTCTCGCTCTGTTA |
| rs1401454 | 921 | AAAGGGTACAAAGTTGCAGGTATGTAGGATGAATAAGTCTATAGCTTCTACTCACAACATAAAAACTGAAGTTGATAATATTGTGCTGACTGTAAAT[C/T]TGCTAGGAGGTATATTTTAGGTGCTTTTACCACACACAGAACAGAAGTAACTATGTAGAGTGATGCATATGTTAATTGCTTGACTAGTAATCATTTC |
| rs2427102 | 922 | CACTCTTCCCCACTCCAGTTCCCTATTGCAAGAATCCCAGCCTGACCTCGGCCACCTGGCACCTGGCACCTGGCACCACCCTCGGAAGCTCTGGAATCAAT[G/T]GAGCTGGGGGACCCCAGCTGAACAATATCCAGGAACCCAAGAGGCCTGTGAGAGCCTGAGCCAGGCAGGGCCATCCCAGGCAGGACAGCAGCATCAGTGCTC |
| rs1912619 | 923 | AAGCTGCAGCACACTCATTCCACTTTGAATATAATAGGAAGAGAAATGCCCATCCTTCACTAACTGGAACTACAAGATTATTTCCACCCTCAGGAGGAA[C/T]TGGTCTTTTCCCACCACTGATGGGCCACCACTGTTGCAGGATTTAAGTGTTACCTGCGAAATACCAAAAAGATAGTTCTATTACAATGTTGTATCCTATA |
| rs1378933 | 924 | TCACATACTTATTGTGTGCCAGTTGCTGTAGTGGGCACTGTAATACAAAGGTGAATGAGGCACAGGCTTTAACTTTCAATGGAAGACAGAAT[T/C]GTAAGCAATAGTTGTGATACCATGTGTGAGAGGGATGGTAGAGACAAGAACAGGATGTCATGGGATACCTGCCCAGTACCTGCCCAGCTGAGG |
| rs2034877 | 925 | GTCAGGTATTTTGCAAAATGTCCTTCAATTGGGGTCATCTGAATATTTTCCTATGATTAGTTTCCTATGATTAGTTTCATCCTGACTTCTCATCCGTAACATGCCTCTTGTATTATCTCCAGTCCTTTGCC[T/C]TGTAATCTGGATTTTGTGAATAGGTAGACATTTAGTTCACTTTCACTTTCATCCTGACTTCTCATCCGTAACATGCCTCTTGTATTATCTCCAGTCCTTTGCC |
| rs1548605 | 926 | AGTGCACGGCCAATGAGGCCTTGTGAAGTCAAGTTCCCTATCTACACAAGACTGAATGCAGGCTATTCAGTTCGTGTGCTGAATGTCTCTCTTGTTT[G/T]CCACAACGAGATATAAACCTTACATGAAGTTGATGTGATAATGGATGATTGGATGGTGATAATGAAGAGAAATGAAGAGAAATCAGAGCCAGTGAATCAGAGGATTAAGTAAGAAC |
| rs1540885 | 927 | TCAATGATAACTTCCTCACTGCTCTGCAAAACATATGTCTCTTGGAGAAAACATATGCTTTGGGAGAAAACATAAGACGCCAGCTGCCAGCAGCCAGTCAGTAGCCTAGCTAACGGGC[G/A]ATTGTTCAAAACCTGGGGGCACATGGGAGTATGTCATAAGATCATGTCATAAGTCATTGCCCAGCTTCATGAAAGGATTAAGGATTAAGAAC |
| rs1870836 | 928 | AGGATGGACTGTAAATCCAATGAGAAGTGTTCTTATAAGAGAAGGAAGAAACATAAGAGGAAGGAAAACATAAGACGCATGGAATGAATTCTCCCTCGAGCCTCTAGAA[C/T]TGGAGTGACATCTGCAAGAAAAGAACTGCAAGAAAAGAACCTGAAATTAAAGTGGCTACATATAAAGTGGCTACATATAAAGTCCCAAGAGCTCCACAGAGTCTG |
| rs1822243 | 929 | CTCTACTTCTCTGTCAACCTGGAGAAAGTCACTTAACCTTCAGCACTTTCAGCACTTTCAGCACTTTCAGCACTTTCAGCACTTTCAGGATGGATGGTTGAAAGACTGAAAGACTGAAAGACTGAAAGACTG[C/T]TCTAAGTCCAATACGATCACAGAAAAATAAAGTGGCTACATATAAAGTGGCTACATATAAAGTCCCAAGAGCTCCACAGAGTCTG |
| rs1536069 | 930 | GGAGTAGTAGACCTGAGGTTGTCAGCAAGTTGCTCAGCAAGTTGCTCAGCAAGTTGCTCAGCAAGTTGCTCAGCAAGTTGCTCAGCAAGTTTGTCACATAATCTCAGGGGAACAAATGCCAATTGCCAATTGCCAATTGCCAATTGC[G/T]TGGATTATTTCCCTGAGTCAGTCAGTTTTCCGTGTCACATAATCTGTCACATAATCTCAGGGGAACAAATGCCAATTGCTTTACTAGATCTCAATATACTCCTCAGATGGCAACT |
| rs1363267 | 931 | AGATGATGAGTCTGGACATTTAAAAAGCACAGTAGTACATCCAGGGTCACATCACAGATTGAAATGAAAAAAGTCTTGTTGTCATTTTATTCACCA[A/G]TTGGAATAAGTTTCAACTTGTGAAAAGTGCTGCACAAAGTCCTGGAAACTGAAATTCTTTACTAAAGCACAGGGAAGTGCAGGGCAATCAATGCAATAT |
| rs1797700 | 932 | CTGGTCTTGAACTCCTGACCTCAGGTGATTGCCCGCCTCAGCCTCCCAAAGTGCTGGGATTACAGGAGTGAGCCACCACCGCCTGGCCAGAACTAATCAA[C/T]TATGTTTTTGTTGCATCTTTGCCTGTCCTCTCCCACTGGCTCATTTGAAACTGGTCAAGTCTTAGAACTGGTCAAGTCTTAGAACTGGTCAAGTCTTAGAA |
| rs2435556 | 933 | AAGAAGATGCCATCCAGGACTTTCATGACAAGAGAGGGGAAACCAATGCCTCGCTTCTCAAAGCTTCAAAGGACAGCCTGACTCATTGTTAGGGGCTCATG[C/A]JATTGCATTTAAGTTGAAACCAATTGAAACCAATTCATTTACCATTCTTAAAATCTCATTTAGAACTGGTCAAGTCTAAGTCTAAGTCAAGTCTTAGAAAT |
| rs2126316 | 934 | TTCTATGAGGCCAGTATCATCCTGATACAGAAACCTGCAGAAATACAACAAGCTCAGCAGCACATCAAAAATAGAACACTTAGGCCAATATCCTAATGAATATCGATGTGAA[A/G]ATTGTCAACAAAATACTAGCAAATACTAGCAAATGAATTCACCACCAATCAAGTAGGCTTCATCCCGGGGTTAGTTCA |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs1418136 | 935 | GTACAATCTCCAAGACAATTTAATTTCACCCTGTCTTTATCTGACAGAGTTACCTGCATATTTCTTATATATCGTCACCTTATATTTCAGAAAAATA[A/T]TTGTACTT CAATAGAAATCTCATGCATGCTCTGTAGCATGCTCCAGGTTACCTGAATCTGATTTTATGGAAACTATTTTATAAGTCCGTAAGTCATAGA |
| rs1432865 | 936 | CCATGCTACTTCTCCAGTTCACAGTCCAGCCAGCTGCAGCAGCACAGAAAACCCAGACTCGCTCTCGGGGCCTTTGCACTTACTGCTTCCCTTAAGATTCTCACATGAATA[A/G]TTCCT TCTGTCATTCAGTTTCAGCTTAAATGTCACCTGTCTGAGCTCCGTTTGGAGTAGACTTCCTGCATTTAATTGCGAATGCTCCTCTTTATCACTTTGCCCTATT |
| rs1885121 | 937 | TTTCCATTTTCATTAGCCCACTGTCCACATGTCTGACCATTCTCAGAGTCGGGATCTGACCATTGACTCTCATAATATATAATCATAA[G/A]TTGTG TCCTTTGTCTTATAGTTGTTCCTAGAGAATCGTCAAGAATCCTGGCATTTAATTGTACAAATCTACATCGCTACTGTGCACAAA |
| rs1720839 | 938 | TTAAAGTATTGAAAATCCACATTGGCCAAGACTTATTCTATTTCAAGTGCAAGAGATGTGCAAAGATGCAAGATTCTCAAAATATAGTGAAAGGTTGAA[A/G]ATTAAA AGACTTATGCTTTCATCATCTTTTCTTTATCATCATGCATAAATGTTCTTATAGACTGATATGACCAGGTCCTTCAGTACCATATGCTCACAG |
| rs2030926 | 939 | GAAAGTTCTTCATTTTACGGGCTGTGAAAAGGGGCATCACAAGTGACCAGTCCAAGGGCACACAAATGGATAGGGACAAGAAACCAAA[T/C]TTC CTCAATGCCAACCAGTGCTTCCTCATACCCTGCTGCTCACCTTTAACTACACAAGATGTCAAACATCAAGATAAAATAGCATGCTTGCCGGGTGCGGTGGC |
| rs2247858 | 940 | ATTGGCTCTTGAAACAGTTGATGCTTTGCCCACATGAAAAAAAAGCAGTTCATAATATGGCTGTATCAATAGCCTAGCTACAATAGACCTTGTTCCTAGAAACAA[C/T]TGCTT AACCTATTGTGTACAGAGTCCTGGACATACTGAACTTTCTGATTATCACAATGCACCAAATAACATCACTACTATGCACTGTATATAAAT |
| rs1597205 | 941 | TAATGTTAGCTGTGGTTTTGTCATATATGGCTTTATTGAGGCACTTTTCTGTCCTAGTTGTTGAGACTTTCTCTTTTGTAATCAATAAAT[G/T]ATATCAGA TTTTGTCAAATGCTTATTCTGCATCTATTGAGATTATTGTAACTTTGTATGTTTCCTTATTCTGTGATTATGGTGTATCACATTAACTAATTTT |
| rs1346718 | 942 | ATAATGTATACATAGGTTTTCTGAGGGTGTAAAAGTTCATGTGAATTCACGTCTCTTGGAAAGATGGAGCTGAAGAAATGCTTCCCATTGGGTTAGCAGCTGA[A/G]TTGGT CTGAAGGGATAGTCAAGGAGAAGGCTTGCATCCATACAAAAGAAAAGTAATAAACCGAGATCACAAAAGTATATGAGGGCTTCCTGACACCTA |
| rs1514424 | 943 | TAATTCTTCTACTTGCCTGATACTCATGGCATATCAATCAACATTACTTTCTTTGATGAAAAACATTAAATCTCTTGATTAAATGCCTGCAGGTAATATCAAGTAT[G/A]ATTACC TCTCACAGCCTATTACACATGTTAGGAAAGACGTTAAAAACAAGCAAACTATTCGAACATTAATGCTGTAGTTGTGTTAACCTGTAACTGA |
| rs2168524 | 944 | AGAACTCAAAAACAGAAGCAAGCACCATGGTCAAAAATCCCCACTGTCACAATGTGATAGAGAACCACTGGGTAAACATATTTCAGATAATAAGTCCAAGGCGCTTGAATAAGCTAGAATACCCAAAT[G/T]GGTTT TGAAAATAGGTTACTGCCCTTTAGTTGATGACTAAAACAGAGACGTGCAAATTGCAAAACATTTAAAAATAAGCCAAAACATATCTC |
| rs1910369 | 945 | GACTCCATCCCCTACCACCATGTCACAATGTGATAGAAACCACTGGGTAAACATATTTCAGATAATAAGTCCAAGGCGCTTGAATAGCTAGAATACCCAAAT[C/T]CCCTT TTATCTTTATCTTGAACTGCGTCTGGCCTCCAGATCTCTAGCTAGGTAATCAAGATCTGGTTTTTATTCTTTCATGTTGCAACACTAGAGA |
| rs1445496 | 946 | ACACTAACTTACCATAATAAACATCTTTAAACATATTTCCATATCATTAAGATATCAAGTATCCATCATTAATTGTTCCAATGGTAAAACAAAAGAATTCTATAGCCTCA GAAAAAGCTAGATTCCTGAGGTTATGGCATTTGAAAGATCATTTAGAAAGATCATTTAGAAAGATCAAGTATCACAGTAACAGTAAACTAGC[A/G]ATTAATA |
| rs1462685 | 947 | TCATGATAACACACCAAAAGGCTGTGGCAGCTGTGGCAGCAGCGCTGTCGCAGAGTTATCTATCCACCATCAATTCTTATAATAGGGGCTGCCAGCATTCTGAATGAATGTAATAGATATT[A/G]ATTTGC ACACCCAGGTGTGAATATGTGATTTCCTTTTACACCCTTCCAGCTTGCAAATAAATGAGCTTCTACTGTTTGCTCCTTTCCTCATTC |
| rs2298810 | 948 | AATTTCTCATTCTGGGTACCTCATATTGCAAAGAGCCTGTGCCTGTGGCCTCTGAGCTGACTGTGGAAAACAGGGAAAAACAGTTCGTATTCAGAAT[T/C]GACT GTCACAGCCTTGAGACCTTGAAATGTAGCCCCCATCCATGAGTCAGTGAAATATCTGTATTCTTAATTTCCTTAAAACCACACTCTCCCTG |
| rs2191076 | 949 | TCTTTGCCATTGTGAAGAGTGTGGCAATAAACATTTGCGTTCATATGTCCTTATAGTAGAATGATTTATATTCCTCTGGATAATGTCCAGTAATGAAAT[T/A]CCTGGGT CAAACAGTATTTCTGTTTTTAGCTTTTGTGGAGGCACCATACCGCTTTCCACCACGATAAACTAATTTACACTCCCACCACAGTGTATAAA |
| rs1439047 | 950 | TTTCAATACTGCAAAATGTTTGCACAAGCATCCTTATTCATGCTTTTACACATGTACAAGTGCAAAGTTTTCTAGAATACACAGAAAGAAGCAG[A/G]ATTGTTG GTTTATGTGGTTTGCACATGAAAAAATGCTGTATCTATTATGCCCACCCTAACAAGGTATACCTTGATATTGCAACTTGTTAGTGTTTG |
| rs1904185 | 951 | AATTTAAAATTTAATTTCAAAATAGGAAATACATAGAAACAAATCTGACAAAGATATAAAAGTGTACCCTAAACATGTGAAACATTGTGACAA[C/A]TTAAAGA CCTAAATGAATGGGAAGATATATCTATACTGTGTTCATGCGATTCATTGATTAAGCTCAGTTCCATGTCCATATCAAAATCCTAGT |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs2323301 | 952 | TCAGTTGATGTCAGCTCCATCTTCCAGTGTTCAGAGGAAAGACTCAGAGTCATTCATTCTTTTCCTCCTGTACCCTGCAATCTGTCTGGAAA[T/C]TATATT AGTCCTATCATAAAAATGATTCCAGATCCTAAACCACATGATACTATCTATCTCCACTGCTACCCCAAGCAGATTCAGGTCCTCCTCCTCCACCTT |
| rs1789529 | 953 | GATTTTGCCAGAGATCATTCTTTGATGTGGAAGTGGTCCTGCATTAGAGAAGTGTCCTGTGCATTAGAGAGATGGTTCGCAGCAACCTGGCCTCTGTTAACTATTGTAAGTAGCAAA[C/T]TCCTC ACTCCTTGACACATAAATAGTCTCCACACATACATTTTCAATTGTTAAAGTCAACATGGCATAACAAGCCCAAGTCTCCAGGAGAATGCATGCAAATTGCCCCAGTGGCAACTACTTCTTCAAACTGCCC |
| rs4489023 | 954 | CAACATGTGTTGAGAATACTTTTGCAAATGTTAAAGTCAACATGGCTAAACAAGCCCAAGTCTCCAGGAGAATGCATGCATTAAAATGAATCAAA[A/G]TTTATA GAGTACAATAATAAGAGCCCTCTTACTTACATTTTCATTTAATCACATGTATATGCCATCTTGTCCATTTTGAGGTTGGGCTTTAGGGAAAGC |
| rs7266163 | 955 | CAAATTCTTACCCACAAAGTTCATGAGAAATAATATATATATTTGTTGTCTTTTCGCTAAGATTGTGTTGATCTGTCACATGGCAATATAAATGACCAA[C/T]TGAGCTA TTTTCTCAAACTTCAGGGCTATTTGTTCTTCATTGAAGTTATATACAATACTCAGGAAACTTCATATAATCATCATGTGATGTTTCTAATT |
| rs2865878 | 956 | AGTACATTCCCTTTAGGGCTCCCTGTGCTGTGAATCTCATAATTGCTCCAGATTGTGGCTGTCCTCCTGGGTCTCAGAGGGGGACGATGCAGAA[T/C]TGAG TCCCTCCCCAGGATCCAAGACAGATACCAAGTGTTGGTTACAGAGAAAATAACCCTTTGTTATTTGAACCAGGACGATGTGTGCTTATGACCCACTG |
| rs7320201 | 957 | TCCAGAACAATCCTGGGTTCAGGCATATAGGTTGTAGAACAGTAGTGTAAGATTTCTGTTGTTCAGATTTCTTTTATGTCAAAGTCTCCCAGCCAGATCCTGCAAAGCTCCTCATCTTCCTCTGAA[C/T]TGTG TAGGTTTTTGGGGAACAGGTGGTGCTTGGTTACAGAAGAAAAGTTCTTTACTGTGATTTCATGCCCCATCACCCGACCAGTG |
| rs4764597 | 958 | CGACTTGCTGTGCCTTCTGGCATCTCCGCTTCCCAATCAGAAAACCTCACACATGTCTGCAAAGTCCACCAGCCAGATCCTCCAGCTCATCTTCCTCTGAA[C/T]TGTG TTAGTTGATACATATGGAAATCCAAGAGACCCTCCAAGGATTAGAGTCCACGTCTTTTTATTTGGAACTCCTTACCTGCCGACCATCATCAAGGAC |
| rs4399565 | 959 | ATTTTGTGAGGATGTAAGCAAACTAAGAAAATGTCAGATATGTCCAGTCAGTTGACCCCAGTGTGACCCCAGTGTGGGGCAGAGAGGAGCATGTAAT[G/A]TTGT CCTCATCCTAGAGCAGCTTCACAGAAATCCAGAGGTTCTTTTAGCTCTGACACTCTCTAACTCTGGGAATCACTAAGTCAATGGAGTTCAGAGGG |
| rs6542638 | 960 | TTATACGGAGGCTGAGTCCCCAGACCTGGGCTTCCTGAAACTCAGTCCTTTGCAGGGTTATAGATTCTAGCTCCAAAGGGAAAATATTCACAGGGGACACTATAGGA GAGAGTTTTTATTTCTTCCTGAAACTCAGTCCTTTGCAGGGTTATAGATTCTAGCTCCAAAGGGAAAATATTCACAGGGGACACTATAGGA |
| rs4953843 | 961 | TTATCAAAGAAAGTGTAAGAATTAAGTTCATTCAATACAAAGTTCTCATTCAAAGCTTTGCGCATCAGGCATTTATACAAGCACAGAATAAAT[C/T]ACATTA ATATGGTTGAAAGCAAGGGTCCTGTATGTATTCTTGAAGAGAAGGGGACTTCTATCCTGCAGTAGTTATTAAAATTTAAGACATCCTTCTCCTTC |
| rs7810506 | 962 | TACATCTGCTTTAGCACCCAAGCTCTTGCTTGGTGAATTAATAGTAAACATTCATCTCTTTGAACCATCTTCAAATATCCCCTTTAGAATGACATTCAA[T/C]TATTAGG TCAGTAACCCCAAGAGAAACCGTTGTTGAGTGTATATACTGTATTACAAAATAAGGGGTGAATTCAAAGGAAAACATAAGATGCAATTCGT |
| rs4708590 | 963 | TGGTAAGAGAATCCGCACTGAAGAGACTGGGAATGGAATGAAATTTCCTCCCAAGAGAAGGCTTTGCATCCTCCAGGGCCAACTGGATAGCCGTTGGA[A/C]ATT GGCTGCGAGTGGCGTTCTTCTCGCAGTCTTCGGGCGTCTGCAGCTTCACGTCCATTATTTCTTCCGGGAGTTGTCAGCCGACGATCACCTGATGATTGCCACTCACAGGGAGA |
| rs3128688 | 964 | AAGCCTGAAGTTTAAACTACCATTTGAGATCACTACCCAGAGATTACTTCTAACTCTCCAACTCTCTGGGTTATTCTCATGTGTACAGAACATATACTTGTACATGCA[A/T]TCAACT TCTGTCCATTTCCTTGTAATCCTGTTTAATTCTCCCGGGAGTCTCAGCTAAGAACTCATGAAGTGGAGAATATATTTCCTCACCTA |
| rs7689368 | 965 | TAATCTATTCATAAGAAAAATATCTATGAACCCAAATTGAGAGACCATTCTACAAATCTGAGGTTGAGGTTATAAATATGTAAAA[A/C]TTTTCAC AATCTAGAGGATCCTGTGGAAACATGGCAACTAAAATATAATGTAGTATCCTGATAGGATAACGGGACAGAAAATAACATTAGTAAAAACTA |
| rs6962207 | 966 | TGACTTCCCCTGGCATGCCTGCAAGGAAAATACATTGACCAAGGATTTGAGTGATGAGTGATAGGTCCTCTGCAGTCATTTTTAAAATGGAAATCAATAAA[C/T]TCGTA TTCTTATTTTGTGTGTAGTTTTGAGCTTGTGAATTTGATTTGTACTGACTGACATACCATCATCAACCTGCAAAGGTTG |
| rs2647415 | 967 | AGTTTGTATTTGACTCAGATAACAATGTGAGTGCCTTTGTGAATTAAGAATATAGAGAATAGATTTGCTACGATTCAGTAAGTAACAAGGTATAAGAGCA[A/G]ATTACC ATCATAGTGTCTTTTCTTGCTCACGTCCATTTACTTACTCAACAAGACTTATTGAACATAAGGCACTGGTCCAAGGACCAGTAAGAT |
| rs6766358 | 968 | CTGTCAGACATTCAAAGAAGAATCAGTAGAATCAGTAGAATACCAATTCTATTGACACACTATTCCACATGCTAGAGAAGAAGGAATCCTCCCTAAATCATTCTATGAAGCCAAT[T/A]TCAGC CTAATATGAAAATCAGGAGGAGGACATAACAGAAGGACATAACAGAACAAAAAGAAAACTACAGACAATATCCCTGATGAACATAGATGCAGAAATCCTCAATAAAATACTA |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs4894467 | 969 | AGCACGCTTGTACTGTATTTCTCTTGGCCCCTTTCATCTAGAATTTATGCAAGAGAAGTCCTGTTAGTAGGGTTAAACATTTGGATTCAGCTATTCCT[A/G]ATTGCA<br>TTTAGTTATTACATCATGTAACCCAATACATTTCTTTTGTCTTGTGTTACTCTTTTTGCTTGATTCATTTTAATGTTCCTTTTGTATTAAT |
| rs7818415 | 970 | CTGGCATATTTAAACACTCAAAAATATTTCTGTAAAAATAGTCCTTGTTAGACCTTCCACCTATGAAACCATATCACAGTTGTTGGGTTTTTTGTCCA[T/A]TTGTTTAT<br>TTTAGTTAAGCTCATTGTTTAAGAAAACTCTAGGTCTATAATCTCTATAACTCCTCATTAAATCATCCTACAGCTCCTCTTGAGTGTCCAGTTA |
| rs2928668 | 971 | AACGACATGACTCTGGCCGACCCGCCTGGCTTCTTTCTAGTCTTCTCCTTCTCCTTGTGACCTTGTGAGCAAGTCATTTGGTCTTCGTGCCTCAGTTCCC[A/C]ATTG<br>TGGAATGGGGATAACTGGTTGCTAATATTGCTGTTTTTATGCTGTTATAATTATTTGTAAATAGAAGGTTCAGGGAAGCAAGTTGATT |
| rs2993531 | 972 | ACACAATTAATGCCAACATTTGTACTTACATTTCCATTTTATGAATTTAAGTCTTGTTCCCAACATAAGTAAAACCTTCTTGGAAAACACACCTTGT[A/C]ATTACA<br>CTTTCCTGTATCTCTCAGTTGTTTATATAAGTTGATCAGTTTTTTCCTTCAAAAATTTTTCTTCAAAAATTTTTCTTGATATATTTCAAAAGGATGTACTTT |
| rs6941784 | 973 | ATTGCATTTTATATATATGTAATGTTCCACAAAATGTTATATAAATGACATTTACCCACAAAGGTAAGAATAAGAGAGAATTAAAATAGATAA[C/T]TCTAAGT<br>TTCTCTCCAATGTCAGGGACTAGGCCTTTTACATCTTCATGCCCGGTCACTGGCACATACTGAACTTTCATATACTTTCTGCAGCATGATTG |
| rs4680921 | 974 | ATATGGATGGTGGGTGAACATGACAGTTTCAACTAATATATTGCCAAGCAACAACACTATGGTATTATCTGTATTGGTTGACACCTTTTAGTCTAAGGAGAGAAAT[C/T]GCCAA<br>GTGGCACAGTTCACTTGGTCTTAAAGAGACATGAGTTGGTCTTCACCTGTCCAAGAGCCTTGCAAGATTAGCCAGTGCAGTCTCTGAAAGCAGT |
| rs4716945 | 975 | CTTTGTAAGTGAGCTTGTGAGGTTGCAGGATCTTGACAGGATCTTAGGATCTTGCCTCAGAACTTCGCCTCAGAAGCAGCATCTAAGCACAGCTCTGTGGAGCACAGAAA[A/G]TTG<br>AAAAGAGCACCTCATTCTTGGCTTCCCTGAGGAAATGGCATTTGTTTGCGTCTGTAAGGAAAACCACACAGGGCAGTGTTTACAAGTATTTCGATTAAA |
| rs4897019 | 976 | TCAAAACTTCCTCCCCCAACTTCTAAAGTTCAGCCAAGAAGTGAATTTCAGCAAAAAGAATTTGCCCTATTGTGGGAGATTTTGCTCTTCTACCTTAAGGCAAGGCAAGG[C/T]GACTT<br>CCTTCTCCCCTTTGAAAATCTCCTTTTCTGCAAAATCTGAATTATTTAACACTGAAGACTACTCTTGAACTTGGAAAACATCAGAATTGGGAGTCCTCTTG |
| rs4467489 | 977 | AATTTTCAGAATAATTCTGTGCCTGAATTATTAATTTCATGTAAGACTCATGTAAAGTATTCCTTCATTCATTAAAGTATTCCTCCTCACTCCAAAAGAGATAAAATGACCTTTGTGCAGCATGCTGGAGCAAA[T/C]TCTAAGA<br>AACTAGAGTCCTGACAACTTCTGATAAATCTCAGGTGAAAACATCAGGGATCATCATGCAGATGGGAAGCCCGACTAGATTGCAGTTCGTGAAGTAACGTGCGGA |
| rs6929257 | 978 | TAAGTGACAGCTCATTTTCAATTTAATTCATTAAAGTATTCCTTCTCTACTCCAAAAAGAGATTGCAGACTTGTGACAGATTCTGCCTAAGGTGTTAAA[C/A]ATTGCTC<br>ATAGTTCAATGTTTAAATAGTTTAAAACAGGATCATCATGCAGATGGGAAGCCCGACTAGATTGCAGTTCCGGACAGAGATAAGTGCGGA |
| rs2657300 | 979 | AGGGTCTCTTTTCATACACCATAAACACAGAGACCCAGAGGCAGCTCCGCCAGGTCTGCTCAGGTCATGTATTAGTGAGCATCAGAGGCAGGCCAGGACCCCCA[A/G]TTG<br>CACAGGTCTAGGAGCACCATTTCATCCAAGTCTATGTTGCATGCCAAAGAGTGTCACTGACAGAGAACACAGTGAGACCACTGCTACCGCCCTGGA |
| rs7703746 | 980 | GCCATCCTAACACAATTATTATCCGTCTTGCTTGAAAGTTCCCTATTTTGAAAGTTCCTATTTCATTTTAAAACTTCATTTTATACAGCATGATGAATAAAAACCATTTAGAGAATCAGTA<br>CTGATGTTTACTTGATAATATACATATCATACTTACTTGCTATTTTAAAACTTCATTTTATACAGCATGATGAATAAAAACCATTTAGAGAATCAGTA |
| rs7151741 | 981 | TTTGTCTCTCTTCCCTTCCCCTGTTGATTTGATTTGAAACTGTGCTGCTCACAATGGCCTAGCCCATGGCCTAGAATGTTTGGGGTTAAACTCCACTGGCAGCAGTTAGTGATCCAAGAACTC[T/C]ATTT<br>GGGCACTTCAGTTCGTTGATTTGAAACTGTGCTGCTCACAATGGCCTAGCCCATGGCCTAGAATGTTTGGGGTTAAACTCCACTGGCAGCAGTTAGTGATCCAAGAACTC |
| rs6468296 | 982 | AATCCATCTAATTTTCTCTGTTTCAGTGGCAAATCAGTTCCCCTCGGCTAGAACCTTGCAGTACATTGTAGATACAGTTGGCTAGATAACTGAA[C/T]TTCCTG<br>CTCATTCCTTTTCACCCATTCTTGTCAGTTTCCCGTGCCCCATATGTGAGCCCCATAGTCCTCAGATGCTGAATGGGGCCCCTGCTGTGA |
| rs2846589 | 983 | ATTAAGGAGAAAATAAAAAAGATGCTTCTAGAATCATTTCAAAAATTCAAAATGAAGATGAGTGATATATTGAGTCTCACCTGAAAGCAAAATGTGATTTTTACAAA[G/T]TATCATT<br>AGTGAAAAAGAATGATAATGAAAAGATGAAGAAGATAAAATAGTCCCTAAAATGACAATATTTGGGCACACTTGAGAAGTAATG |
| rs3816551 | 984 | TGGGGTGAGGGATCCCCTTCACTCAGCAGGAGGGTGTTCTTTTCTATATCTCTGTGGAGATGGGGGCATCTCTGGTGAGATGGAATTCTCTGGTGTAAA[T/C]TGG<br>GTTCCTTTTGCTTGATGGGGATGGGGTCTGTGTGTGTAGACTGGGTTTTTTTTTGTTTTTTGGTTTTTTTTGAGATGGA |
| rs6431221 | 985 | CCAGACTTTGAGCGAGCCAGCCCAAACTCCAGCAGGCCTTCAGTGAGCCTTCAGATTAGTTAACACACTGGCTGCATTAATCAGATGATCCATATTCAATCAGTGATCCATATTCAATCAGTCCGTGTGATGAAA[C/A]TTCC<br>AAAAAAGTCTGACACTGAAGCTCAGTGGGACTCAGATTAGTTAACACACTGGCTGCATTAATCAGATGATCCATATTCAATCAGTCCGTGTGATGAAA |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs6582294 | 986 | CGGAACCATTCCTCAGAACCACACCAAAGAACTGGCCTGAGCAGGAAGTTACCATGGCCACCACCACCCCACATTAGCAAAAGGAATGAATCATCCCCA[G/A]TTT<br>GTTTCTTGCTACAGTTCACCTCCACGTTAAGTCTCCTTCCGCCTCTAACTTACAAAACCATAGTTACACATCTGCAGCTTAGCCACCAAGGGAGTC |
| rs3913810 | 987 | TCCTGTGAGAACTCACTATCATGAGAATAGCAAGGAGGAGAAATCACCTTCACCCTTACGACCTTACGCAGGTCCCTCCTCAAACATTAAGGACAAAA[A/C]TTCA<br>CATGCAGAAATGTGGTGGGGACACAGAGCCCAAACTGTCTATCATCTCTAAACAAGTACTTTGGGTTGATTGTTAAAAACACAAAACTTAATT |
| rs7769867 | 988 | ACATTCTTATCATCATCCTGTAGAGGCAAATTTATTCCCAAACATAACATATCACAGATTACCAAAAATAAAAAGTATTGTCATCCATGATAGGGA[G/A]TTATTA<br>CATTTGCCTACACAAGACCCAGTAAATGTAATGAACATAAATGAAGAGAAGGGACAGAGAGATATTTATGTCTCCAAACCTCTGTCTCAGCTACTA |
| rs4674824 | 989 | ACTTTGAAAGGCGGACTTCTCTTTATGTAGTGGACTTAGAACTGAAGACATGACTTCTTAGTAATGAAGTAAGTACTTGTTTATACAACAAAAT[T/A]AAAAAG<br>TTCTATACAGACTTCTGAATCATACTTTAAAAAAATGTATTACTTTAAAAATAAATATATTAAAAAATAAAATGTGTATATTACTTCCCCAATATCTCCCAATATCTGCAGTCCATAA |
| rs7294836 | 990 | TCTGCACAGGTATCCTGAACTTAAAATTAAAATATATTAAAATAGAACAAAATAAGGTTTAACTCCCTACCTATCTCTTTGAAAAGCCTTAACCATTAA[T/C]TGAGTCA<br>TGGCATTTTTAAATGGACTATTCAGTGGCTGTGGAGATGTGCTGTGTTGCTTGGTTAAGCAGAAAGTAAGTTTTCAAGGATCTCCTGCCT |
| rs6043856 | 991 | TAAATTTAATATACTCAGTCTGGTTCACATATTCTAATAAAATCCAGCAAGCTTAAAACTTTTATAGGAAATGTGCATTTAAAATCCATGTGATATTCA[G/A]TTTTTACA<br>GGGTGACGTCCTTGCTCAGGGTATTAAGTAGTTTCAGTGATGACGATAGCCCAGCTTGGCAGCAAGCTTCTGGGAAACCTCACAAATAGAC |
| rs7741525 | 992 | TTCCACTTTTTTTTTTTTTTTAACCATTTAAGCATTTATTTCTGATAATCCTCTGGGGTGAAGGCAGAGTGATAATCTCATGGCCTCACTGGCCGGCCAAGCTAGACCCTTCTCCA[G/T]TATCTCC<br>TCAGCAGTGACCCCTTCTGAGTGAAGAAGCAGTGTGACTGTGAATAGAAGATTCTCACCGGAAATAGAACCTCCAATATGCAAAGAG |
| rs7084321 | 993 | CCAGCCTCCTTCTGCCATACTGGGCGTCACTCCCGACTCCACCATCTCTTGGCCTCCAGCTGTGTGCTTCTGTGGCCAGGGATCCTGTGTATCCCAAATTCCT[A/G]ATT<br>GCACAGCTGCGCTTTTTCCCAGGGCAGTCAGCCTCAGCACCTCGACCACGTCGCTTCTGTGCTTTTTAATTGCATTGGCCTCTTCTATATTGCATTGGCCTCTT |
| rs2723307 | 994 | AAACTGACAAATGAATTCCATCTTCCCATTTTTCCCATTTTTCCCTTGATCCTTTAATTTAAACATATTAATTATGATCTCAAAATGTCCAGGCCTG[A/T][A]TTATTGA<br>GGCATGTTCCCATTTTTCACTTTTCCCTGTAGGTGTTCTCTCAAAATGTATATATGAAATTCTAAACTCTAAGGTGATACTTCTAATAGCTGAATCA |
| rs4589569 | 995 | GGAAGCAGCCACTTTCCCAGTCTTGCTGAGACCAAGTAACCCAAACCCTGGCTCAAAAATACTGTATCACGAAAATACTCCAAGTAGAACCAACCAGATA[A/G]ATTT<br>CTGGCACTACGTCTGAATGTATGTCTCCTCAAAATGTATATAATGTATATATTGAAATTCTAAACTCTAAGGTGATAGAGGGGCCCTTGA |
| rs3912319 | 996 | ACCTCCACATATGGTTCTCACTTCCCTTCTTCTTACTTACACATCTGCATGGCCCAGTTCTCCATTTCTCCACGTAGTTCTCAACACTGCCCATAGACTTCTTCTTGAGGCA[G/A]TTGTTAC<br>TTTCTCTGTTGGATTTCTCTTTTTACTTACAACATCTGCATGGCCCAGTTCTCGTTTTTCCACTGTTGTTCTGATTATTCAAAAGTCACTCTCTGAATAAG |
| rs2821312 | 997 | AGTAGAGGTTAGACCAGAGCAAGAAGACTGGAGAGGCAATGTTTAGTACCTGAAGAAGATATTTAGTACCTGAAGAAGATATTTAGAGGAAAGATTCAGATATCACCA[G/A]TTACA<br>TTGAGTGAATGAGGAGCATTAGCCGTCAAAAGATCTGTTTTTTCCACTGTTGTCTTGAAATGATAAAGCCTGCCAAGACTTCAGTCCA |
| rs2820107 | 998 | AACTAATAGAATATCAACCAGTAGTTAAGGCAAGATTTGCTGTGGGAAGGAAGTCCTGTGGGAAGGAAGGACCAATCTCTATTCTGTGTTTCTTACCATCTCTTCCACCAC[G/A]TTGG<br>GCTCAGAAAGACTTCCTGCCCCTCCCCCATTCCCCCATTCCCCATTCTGAGGACCAATCTCTATTCTGTGTTTCTTACCATCTCTTCCACCAC |
| rs7002630 | 999 | TTTTCCATGTATTCTCACAAAACCTCTCACAGGAATCCACGGAATTCACTGAAGGTATGTGAGGAGGATGTTGATGAGGATGAAAACTGACATGCA[T/A]ATTT<br>AAACTTCTACCCTAGAAAAGCACTGGCAAAAGTAAAGGCACAAGCTCAAGAACACCGAGAAAAAATCAAGTACTTCCAATGACATTGGCACCAGGAC |
| rs7041138 | 1000 | CTACATTCATCCTTTCCCTTTTCTGCTAAATCGGTACCTGGCCTGGCGTGTATCCTTACTGCCGGTTGTATCTTATCCTCTATCCACCTTCACCAGCCAAACTTCTTAAAAGAATTGGCT<br>CACGTTAAAAAAAAACTAAAATTCACTGAATCCTTGAATCCATTCACTGATCCATCATCCCATCATCCCATTCACCATCCCCACCGTCCGAGTCATCCTCTAAACCGTTCTCTTCCTATAAAAAGAATTGGCT |
| rs6019378 | 1001 | AAACCCATTCTTCTTGGCTAGAAAATGAGAAAGACCTGTTAAGTTCTCAAAGACAGGAACTTCCTGAAATACGACCAGAATGGAGGAGGCTTGGAA[C/T]TGGC<br>AGTCCGTCCATCCATCCATCCATCATCGTCATCCATCCATCCATCATCCATCATCCATCATCCATCATCCATCAACCGAGTGAATTCTATCATTCACC |
| rs4815732 | 1002 | ATTTGTATCTTCTGTGAGTGCCCACTGGCCCCAAAAATGTCTTTTCTGAGCTTCATGAACAGTGTGTTTGAAACATGTCTTCTACGTGAAAACATGTGAA[T/C]TCGTG<br>AAAGAAAACAGAACATCATCAAGGTTTTGGCAGAAACCAAGGATTTTATCTTTAGGGCTGGATATTTGGGCAACATAGTGGACCTCATCTCT |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs4488809 | 1003 | CTTGTATAGAAATAATACAAGGTACAAGGTGGGCTGAAAAACACTGACAAGCTAGCCCGGGACTGCAGATGCAAGCATCTGCTCTTGAGCAGTAAA[T/C]TGA AACAGTGATTCTTATTACTAGTTTCTGTTAAAGTTCCTCAAACTCTTTTACACAGAGATATCTGACTCTTAGATGCAGCTCTAAAATTTTGAAG |
| rs4420719 | 1004 | GCATGGCAGGGTCTTGAAGTAGAATTTGTGGGAATTTCCCTGGACCCTCAGGTGCACATGACCATCCAGTTCACATGACCATCCAGGGCACCTAGGTGATG[T/A]ATTG CAAGGCAGATCAAGGGAAAGCAGATGTTGCCATGCAGATGTGCCTGCCCTGCCCCATTCATTATTAAAAGTTGTTGTTTATTGTTGTTTTTGGCAGCAT |
| rs6488494 | 1005 | GGACACCGAGGAACAAAAAGGTGGCGTGACTTGCCCAAGGATGTTGCCAGGTTAGAAGCTGGCAGCCGTGCTATCCATCCTTCAGACACCCAGGCCAA[C/T]TT GTCTGTACCCACCTCCACTTGCCTCAAACCCTGTCTGCAGTTACTGTCCCATTCTTTTATCATTTGATCATTTGAGTATGATGACAAGGTACAGTGGAAAGAAAA |
| rs2522215 | 1006 | TGTACCCTTTACCAAAGCTAAACAAATTGCTACTTGCTGCAATCCGAGAGGGTGGGGTGCGGGGCATAGCGCCTGTGCTTAACTGTGA[G/A]TTA TTAATGTGAAAGATTTGCATGTCTTTTATGATTATAGCTGACTTTGATGTCTTTTGAAATGTTGATGTCTTGATGTCTCTTAATGATTTATTT |
| rs6142841 | 1007 | GTATGAGTGAAGATTCAGGAAACACTGCTTGTTGTTCATGTTGTTCATGAAATGTTAGTTCCAGATATTCAATAAAATGTGACGTTTTAAGAGTTCTAAAAAT[A/T]ACTCGC ACTTCCTCCACACCGCTTAAATGACTCTCACAGCCTTGAATGAGAGCAAAAGTCCCCAGCAAGGCCACCCCCTCCCAAGGAACACCC |
| rs4952502 | 1008 | AATTTACTGCTCTGTTTCTTGTTTCTCATTTTTTATTACATACATAATTAAAACCTACTGTTGTTAGCTAGCACTCCAGACTCCATTAACTTAGGTGTTATGCAGTATGCATTTCA[G/A]TTGGCTG CACAACCACCATCTCTTCTTCCAGTGACCCCGCTTCTCTGTAGTGATGTGGGCATAATTCCATAGGTGGCTGTAATCCACGG |
| rs7820949 | 1009 | CTCCTTTGGTCAAAAACTTGATATGCCCATTTGCTTTTCATGAATCTCGGTGAACTACAGCCTCTTCTCTTCTATCCTTAGAACAGC[G/A]ATTTCTC CCACTCGTATGGGATCTCAACTCGATTTGTTAGAAAGAAGAATATCCTCTATGAAATGCAGTTCCATGCTGCCACTGAGCAACACAATTG |
| rs7076662 | 1010 | GTTTTTGTGTCTGGGCCTCGGGAATGGGAAGTAACCGAGGAGACCCCATGTGAGGAGGCATGTTCTTACCATTGGGGTGGAGTGCACTGAGGAAA[T/C]T TATTGCTTCATCCGTTCCTTGGTGTTTAAATGAGGTCTTTGGCACCGGTTCTGTCCAATCCATCTTAGCTGTATTCTT |
| rs4684986 | 1011 | AGCCTAGTATACCACTGGGGTCGGGAATGGGAATGGGAATGGGGAAGTAACCGAGGAGACCGAGGAGGAGGCATGTCTTTACCATTGGGGTGGAGTGCACATGAGGAAA[T/C]T GAGGGACCCCCCGTTGTAGGAGGCTTGTCTGGCATTAGAACGAGCCCATTCTTCTCCAGTATGTGGGGCCCCAGTTATGTAGCTACTTTGACCAAG |
| rs6707911 | 1012 | TGAAACAGAAAAGGAGTACATGATTTGTGGCCTAGCAGTAGAGTACATGATTTTCTCCTCCAGCATTGTTGGGCCCAGTCAGTAGAGTAGCTGCAGTGACTCTTTCTAGGCCATAGAGA[G/A]TTA GTGTCTAGGAAATAAGAAATAAAAAGAGCCATTCTTCTCCAGTAGTAGTCAGTAGTCAGTAGATGTCTCTGACAAG |
| rs4845519 | 1013 | ATTATTGAATTTGATCATAGCCATGCAGACATTGCTCAACTGCTTCAACTGAATTATAACCTCGAATTATCCTCTTCATTTTAAAAGTGTTCATACTGTAGGCTTGAAGAGA[A/C]TTTAGAC ATTATCAGTTCTTCTCATTCACTCTTCACTCTGCAGTGCAGTGCCAAAGCGTTCAAGATCCATAGTAAGTTTGTAATGCAGATAATGACTA |
| rs4420242 | 1014 | AGGAGAGCTGGGATGATGTGGGCAAAGGCGTTCAGGGAAGACGAGGAAGCAAAGCTAAGCTAAGGCTGTCATGAATTCAGAGATCCAGAGAACAGGAA[T/G]TG GTGGGAAATATGGCTTATAAGTGCTTAGGGCTCGGGCTCCTCGAGGAATGGCGTGGGGGTGGAATCCACATTCTGTACAATGGGCACCGGGGCAGCCCT |
| rs7323716 | 1015 | ACAGTCCATTCCAGTTGTGTAATGCAGCAGCCCTAGCCTAAGTTCTTATATCTTAGGGACAAAATCTAAACCAGTGCATTTCAAATCGGCCGCCACATCAGAAT[C/T]ATGTG GGGCACTTTAAAACTACAGAAGTGAAGACACCCCCATCCTGAACGAGATTTCCGCTAGTCTAGATGAATTATTGATTACTGTAGCTTCAG |
| rs6878291 | 1016 | GTTTGGATGAGATGTCATTTACTCTAGAGCGTTATCTGTAGCCTCGTGTAATTTCACTCTAAAACAGGACAGTAAAAAACAGGTGAACA[G/A]TATAT AACATGAACCAAGATTCTATGAAGAGTTTTAAGCTTTATGAGGACAAGGACATCTTGCTTACAATTATCTTCAAATGCCTACCACAGTCTCTGC |
| rs6897414 | 1017 | CTTTGAGGTTGTTAAAATGTTGCTTCCTTTCCTTTCGTGGTTTCCAGGTTCCAGGTTCCCAGGTAGCCTCCTCATTCAGTGTTTCATTGCACTTTGTATTCTTAGCTTTTAA[T/C]TCTCAGG GACAAGGACTGACCTGGTTCAACTCTGGTTCAACTCTGTTGTAGGGCCTAGCAAAGTGCTTAACCATAGAAGACATTTGCTGACTTACAGTTGAATAGAA |
| rs4452041 | 1018 | CTTGTTGAAAGTCCTTAGGAGACTCAGGAGACATGGTATACCATCTGGACTGTTGATGGAGTGTTGTGATGCATGCCAAAATCAATGACCATCAAGGCTTCATCTTCAAATATTGAGGAAAA[T/C]TGCA CCTTTGTCACTTGCTTTGCTTTGCGTCAACTTCAAGGCCCGACTTAACTATTTCCTCAGCATTCATTTTATTAAGCACTATTATTAAGCACCTGTTTTAGGTCT |
| rs7144509 | 1019 | TTTTTTTTTTAATGAGAGTTGATGTTGATGGTATACAGTTGCTGTTGATTGAGTGTTGTGATGCATGCAGACAATGCAAAATCAAATGAGGTCATCTTCAACATATTGAAGTTCTTACTTTCA[G/A]TTGGTC TTAGGAGTGCCAGTTGCTTGCTTAATCAGATAGACAGTGACTTAATTACAGTCGACTTAATTACAGTCGACAAAACGATAGGAATGCCAAAACCTTAATCTTAACTCT |

TABLE 11B-continued

Corresponding Genomic Sequence with Alleles provided in Brackets

| SNP_ID | SEQ ID NO: | |
|---|---|---|
| rs7845628 | 1020 | GACCTAAAAATTTATAGTATTGATTATTTTTATTACATGGAAGATGCACCACTTTCTGGACATAAATAAATACATAAATAAATATAAGCCATTTAATG/T]CCTCCTCT TTCTTCACATTTTTCCCAACCTCTCCTAATCTTTGTTCTCCCACCTCTGCCTGTCTCATCATGCCTGCTTACCTCTTTCTTTCCTTA |
| rs2903113 | 1021 | AGGGATGCCTGAGGAGCAGACAGGCATGAAGGAGGGCAGAACCCTTCGTGGATCCAGGCCTGATGCACACTGTTCGCATCCTGGCCATCCCAAGCCACAAAT[C/T]CT GGACTTTCCCATGATTGATGTAAACACATAAACCAATAAACAAGTAAACTTCCTTGCCTCTGAGCTACAGGAGGTTCGTTCTTCAAATGCAGACAAAATATTTGACAAATTACC |
| rs7831906 | 1022 | CAGCCCCTCTTTCAAATATACTTCAGTCTAAACCCTTGATTTTAACCGTGTTATAGGTTAAGTCTTTTCTGTCTTCTGTCAAAAGCCAGGCTAAGGCAAAT[C/T]CATCAG GAAAAACAAGACTGGAAAACAAGTGAAAACAATGTAAACTTTATACTCTTTGAACCTCTTAAACTTTAACTTTATCCTGTATTAAATTTGATCACAGAAGAAAGCTCA |
| rs6952267 | 1023 | CACTGGAAGGAATAAATTCCAGACACAGTGGCAGCTGGCACTGTGCTGCTTACAGATCAAAGACCTACAGGATTACAAGTAAGGTTGGGTGCTTTGA/C]ATTC TCCAGGTGGTCTTCTGTCTGTCAATGTGGAGGTTCCATGAATAGGAATGTAAAGGTCATGGCAGAGGTGTGGATCCTGGGCATCTAACTACTATCACTC |
| rs4783152 | 1024 | AGAAAAAGTCTTCAAGCTATGTTATTATAAATCCTACACGCTCCTGTCTGCAGCTCCTCTGAATTCAGTCATCATGCCAAATGGAACCAGACCATGTTTTAACCCTTTAAAA[T/C]TGTGT AAAAATAGTCTGGGCACGTTGGCTCACGCGTGTAATCCAACACTTGGGAGGCCAAGGCGCGTGGATCATTTGAGGTCAGGAGTTCGAGACCAG |
| rs7094883 | 1025 | GGCAAAGGAAAGGGAATGGATGGATCCCACAGTCCTCGTGTCGCAGCTGGAGCTTCGCTGGTGCGGACACAACTTCATAAAGCCTGTGACTGTTAACCTGCTGACTTCAA[T/C]TGA AACTCTTCAGATGTTAAAACAACAACCTGTTTGGGCTAATGTCCAGCAAATGTCATGTTTTGCTAAAAGACAGCAGGTCTTGCCTCACACTGGCCTCTCTACATCCAGC |
| rs2804649 | 1026 | AAGCTCCCAACCTTTCAGCAGTCTTCCTCTACACACCCAGTCTCCTGCCACCCAGTGGCCTCCAGGGTCGCAAGGGTCTTTCAGGCCCAA[T/C]TTTT GTCTCATGGCAACCTTCCCTGGCCAGATTCCCTGCGTCTCTGAGCTAAGCAGCCTAGACAGGCCCAGTCTTTGCCTCACACTGGCCTCTCTACATCCAGC |
| rs6569474 | 1027 | CCATAGAGCCCACTAAATATAACAGCTGGAAGGGATTATTCATCTCTGGACACTAAGGAGTTAGGGCACAGTAGTTCAGTTCGTGGTTATATAA[A/T]TCTGG GAACCTATACATGATTAAATGGAAATGAGAGACCTCCAGTTACTGCAATGGAAGTAAATGGTTTTCCAGGGAATTACACTTGGACTCAAAATCA |
| rs4869315 | 1028 | TCAAAATCTCCCCACTGCGCCATTTAGGTGTTTGATCATGATGTCTAAAGACACTTAACTGAGTCTGGGATTTCTAATCTTTCTGCCA[G/A]TTGTT TGTAGGGAAGTGCTCTGTGAGCTCGTGTGACCTGAGGTCTCACATGCTCCCTCTGGCCCTCCCTCGGGCCCTCCCTTTATAGCTTCTTCCACGGAGATGCAGTCAAGT |
| rs2937415 | 1029 | TCGAGGTAGGAGGTTGGTGTTGATGATAATAAGTCTTCATTCTATGAGGATAACTTCATCTACTGTATAAAGTAAATTGACTGGTTTCTATTTCGAATCATGGAAGTGATGAGAGGAACTAA[C/T]TGATTT ATCTGAAGTCTGAATATGTAATAAGTCTTCATGAACTGCAGTGAGTGTGCATTGTTGAATGTGGCTGCATTGTTACTAATGTACAGAATTTTTCCATATGGCTT |
| rs7737946 | 1030 | TTCTCTTCTCATGCAATCATTAATTCAGCGTTGCTCCAACGTCAATGAAGCCTAGTAAAGTCTTCACGTCAGACTGCTTCACATGCTTGGGAAACTGAGGTGGGTGGATCACGAGGTCAG GGGATTAAGAAAACTATTTGGGGCTGACCCAGTGGCTGACCCAGTGGCTCAACCTCAAATTATCACCCAAATTCTTATGGTTATTGGAAAGAGGTCAATATTTAAAGTGCTACATCTATGAA[T/C]TCAAAGTT |
| rs4311632 | 1031 | TTTACCCAAGTCTTCATTTTTTCCTCCCAAATTATTACCCCAAATTCTTATGGTTATTGGAAATGAAGTCAATATTTAAAGTGCTACATCTATGAA[T/C]TCAAAGTT CACATAAAATCTACATCAAAGACTGGAAGTAAGATCCTTTAGTGTCTTCTAGCTCATTGCTTCATTTGCTTCCCCAAAAAGCATAATTTTTCATGAGA |
| rs7356482 | 1032 | GTACGTTTTGCACATACATCCATATATTTCAGTGTCGTGTCTGTGTAAATTTCCTTAAACAATCTGAACATCAGCAATCTGAACATATAATGCCCATGAAACAATCCTTTATCTCTCTAATAC[A/T]ATTGTCC CTGTGAACAGTGATCCACAGTATATATGTTCTGTCGTGTCTGAGGCTGCAGATCTTTAGCCCAGATGACTTCCCCAGGAGCAGCCTTCTCGTCATTGGCA |
| rs4928169 | 1033 | TTGCTAACAATAATTCTCTTTATCTTCTTTAATTTCCTTAAACAATCTTTAATTCATCAATTCTTTAAGTGATAATATCTTGATCATTATGAAATTCTTTGAATATGCTTGGTAAATGATGCTTGTAATAAAGTCTTCAAATGAGTGGGTCAGGTAAGACATGGGTTTTGGGGGGGTCAGGTAAGAATA[A/T]TTACATT TGTGTGAATATTCAAATGATGCTTGGTAAATGATGCTTGTAATAAAGTCTTCAAATGAGTGGGGTTTTGGGGGGGTCAGGTAAGAATA TCTTAAAATCTTTGAATATAGGCATGTG |
| rs4673821 | 1034 | AACGTGCCCAGCACCTTGGCTCATCATACCACCCATGCTGGCTTACCTGCGCAGCACCATCCAGGATACTGTTCCACACATTCAGGATACTGTTCCACACATTCAGGATCTCAGATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCC[T/C]ATCC CTAAAATGATGGTTTCTTTGAAAACTGCTAACTCTTCATACATTCTACATATACTTTACTGCATTCTTCGTGATTGAATTTGCTTCTTTAAT |
| rs7588807 | 1035 | AAAAAAAAAAAAAAGAATATAACAACCATCCATGTAGACACCATTCAGGATACTGTTTCCACACATTCAGGATCTCAGATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCCAAATGCC[G/T]CTTAG TGCTGGTGAAGTGGAGAGAGGGCCTCATTTACAACACTTACACACACTTGTAAAACCACTTCAGAAGAAGTTGGCAATGTCTTTAT |
| rs7679285 | 1036 | TCCAGAATGCTATACAGTTGGAATCATACATACATCTGTGATTCCAGATAACAACACCAATAACTTATTTAGATTAGTAGTAGATTAGTTCATCA[G/A]TTTTTAA AATACGATGATAGCTCATTTCTTAGCAGTGAATAAGCCTTCCATTGTCTGCGAATAACCCAGCAATACCATATTATCTGTTAAACTACTGAAGGACAT |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs7688917 | 1037 | GAATGGCAGTAAATATTCCTTGGGTTTCACTGAAGTCTGCTCTAAATGCTGAGTTAATGATCAAGAGCTTGGACTTCAGCATCAAATGTGAGTTCA[G/A]ATTATT TCTCCATTACCTCCTAGTTGACTAACACCTACTTCTGACTATAACAACAAATGTTACTGATAACTATTCTAGGAAATTCATTAATAACATAT |
| rs4533845 | 1038 | ATTCATCGCCACGGGTGTTCTTTCACCCACAGCCTAACTCTGCTGCTCCAAGGGCAGAACAAGGACAGAAGGTGGATGTTTCAGGGAAGTAAA[G/T]TTC AGCTAAAATATAAGGCAGAACTTTTACTAGACTTTTAGAAGAGTCAAAAAAGTCAAAAAAGTTGTCTTAAAAAGTGGTCTTCGTCTCACTCTGTTTTTAAGC |
| rs7205009 | 1039 | ATGTAGAGTTATTCTGCAGGGCTGTGATTATAGGCAAATCATAGTGTGTATATCCTTCTACCTTTTTAGTGTATCTCCACTCTTGTACCCCAGAAAAA[C/T]TAGTCT TGAGTATCCTTCCAGAAATGTTGTATTCCAGTCTGTGTATCCTGTGTACTCCAGAAGTATTATAATATTATTATATTATCCTTCCAGAAAAATCAGTC |
| rs7604667 | 1040 | TCTTTTTTCTTCAAGGGCACCACAAGTCTTGGGTGTCTGTGGAGAATTGCTGATTATTTTTTCTCCCAGACATATAATACCTTGGTCTCCTTATTGTTCAA[T/C]TGATGTA GCCTTTTCCAAATAGGCTTCTTCAGTACACTCTATGAAGGAAGCAGACAGAGCTAAGAGTCTATGTACGAGTGAAACTTACCCTAGGATACCCACTTC |
| rs4442368 | 1041 | AATGTCCAGGGCCAGAGAAGCAGGACAGCACAAGATTTTATCTTGCTAATCAGAATGGCAGAAATATCTTCTTCTGTAGACAGAAGACAAGGTGCA[A/G]TTCT AAAGAAAAGAGGGTGTTCTAATAATCTTTACATGTACTTTAGACCACCAACCAAGGAGTAATATATCATTATGTCTTTTGGCTTCTCAGATATTCTA |
| rs6575809 | 1042 | TAGAGTCCCACACACTTACTTGTACTAAACATTAACCTGCATGTCCAGTCCTCCAGTCCTCTACCCAGTGAGTCAACTTGGAAAGATAAGAGAGATATCAGAAAT[T/G]TCACC CTACCAGCAAAGGGGTGAGGGAAGACTGTTGGGGAGCATTAGAGAGCATCTAGAACACCTTGGCTTATCATCGATTCACCAAGGTAAG |
| rs6807437 | 1043 | TCATAACTGTCTCCCCACAAAAATAATGACAATTGTGCACCAACACCTCCTAACTATTATTATTCTTTGCTGTGGTTCATGAAATCACAAGTCTTAGAAT[T/C]ATTGCAT TAAGGTACTGCCACACTTAGTCCATTCAGAATGCCTAGACTCCCATACTGGTGCTATCATTGGCCTCAGAAGGCATATAAAATGAAACTCAGC |
| rs3902595 | 1044 | CAAGGCCCAGGAACAGGATGTAAGAAGGAGAAGAAAAAGCCAAAAGGCCAAAGGAATCCTCTGTCTTTAGGAAGATCCTGAAGGTGCTGAAGCTAA[T/A]TAC TTGGTGTTGATCTGAAGTTAGACACTTGGAGGACTTGTTAGTATCTTTTTTCTTAAGAACCATGTCTGAGCTAGTAGTACTGTAGTAC |
| rs7763815 | 1045 | AATGAAAAAGCAATGACAGGATGAAATGAAAAATGGAAAATGCGAAAAGTACCACGTTCAAGCTCAAGCATGCCAGCCAAACATCCAAAGACTATCATTTGATAAAAGATTTACCTGAAT[T/C]AACAG AGCTTCTTGACATTGATTAGGGTGGTGAAAATTGACTGTGAGGAGAAAAATTAAGTAAGATGATTTCTACATCTATTTAGGGAGAAGGTGGGAGAAGTGGC |
| rs3010003 | 1046 | AAGACTTTGTCTATCACAGCTCTTTCAAAGTGCAATGTTGGTGAAGGATGTTAACTGCAAGTTAACTGCAAGCTACACTGCAGTTATGCAGAAAAAGAATA[C/A]ATTGA AAGCACCCTAGGTATATGTACGTTGTTTATAAAGGAGGCTGTGATAATTTCTCACATCCCTTGTGGACATGCTCCTTTACCATGTGATCTTCCA |
| rs3902451 | 1047 | TTGAAATATGTTTTCCAATTTGTTGTTGCTTTTCTTTTTCTTTTGACTGTCTTATTCACAGGAATCTCAGGGATGCCGAGGATTCATAGATTTGTGTCTTTTACCTCTTTACATAATCCCCACA[A/G]TTCTCAA AGTTTTGTTCATTCCTTTTATTCTTTTTTCTTTTGACTGTCTTATTCACAGAACCAGTCTTCAAGCTCTGAGATTCTTTTCTCAGCTTGGTT |
| rs4683161 | 1048 | TCACTGGCCCTCAAAGCTTTGCTCAGCATCTACTTATGGGAAAATGCAAGCTACAAGGTTGAACTTCAGCTTCATCAACTTGAGACATGTTCCAGA[G/A]TTTAA AATATTCTTCACTTGTATTACCCCGTCCACAGCCAATGAATTCCCTGCTGGCCACGTTCACAGTCCTAGGATCCTTGATAA |
| rs7691446 | 1049 | CAAACTTTAACACCCCTTCTCTGAACAATTGATAGAACAAGATTCAGAACAAGTGGCAAGAAGTGCAAGAATATAGGATGCAACACCACCATCCAAAAAGAGGCTCTAA[T/C]TGATAT TTACAAAACACTCATTGACATTTACAAATATTACAAACATGCAAAACATATATTCTTTCAAGTGCTTATGACACACATACAGATAGACC |
| rs4974594 | 1050 | GATGGAAGCCCTTTGTCAGCTGTCTGTGAAGGCCTTCTCCCAGTCCATGGCTGCTGTGTTCTTAACTTTCTTGAAGAGCAGAAGTTTA[A/G]TTTTG ATAAGGTTCAGAGGATGATTTTCTTTTACAGTTGGTACATTTTGTATCCTGTCTGAAGGATGCAAAGATTTTCTC |
| rs6139756 | 1051 | GACAACTGTGACCCGAATTGTTGCAACAATTATGATGTAATAATCCTGAGATCTAGCCACTTACAGAACAGAAGGGAAGACAGCAGGCTGCCTTGAAAT[C/T]GAGC TGGCAGATGTGGGTCATTGGGGATGGTATATATGAGAAGCTCCTTGGCTCAGCTCAGAAAGGTTGCATGTGTAATACCAATTATTCCG |
| rs2889515 | 1052 | TCAGGAGAAAATTCGAATGAATAGAGAGACTAAACGAATGGAATATAGACAAAAGAAAATAACAGAGAATAACAGATACCACATGGTGAAAATTTGTAAT[G/T]GAAAT CTTAGAAGAAAAAGGAGTGAGAAAACAGGGAAAAAATAATATTTAAAAGAGTGGCTAAGAATTTCAAAAACCTGATGAAAGACACAAAGCCTC |
| rs6494229 | 1053 | GCTAGCTGTGGCTCAATATCTCAATTATTATCCCCTTCTTCATAGCCAGAATAAAGACCATATTCTTCCATCCTTCTTGCAGCTTAGTGACAACTTGGTGACAAA[A/G]TTCTAG AAAATGACGATGTAACTAACAAATGAAGCACACAACTTTCAGGTGGGCCCCTAGAATGAGGCTGACAATCTGCACTCCCCAAGCCTATCCCACCA |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs4678766 | 1054 | GTGCTTTCTATCTTAATGTATATTATAGAAAAACTAACTAACTCCCTTTAGTTTTGGCCAACTTGCTCATGCCGACAAAACTCTTTAAAATACCA[G/A]TTTTTCA CAAATCTACTTTTTCTTTGGTTTTATTCTACCATTCTTTAACTTAGACAATCCTTAAAATCTAAATGAGACTTACTTTCCCTTTA |
| rs2984523 | 1055 | TTATCTCTAATTCTTACAATAATTCTTTGAAGCAGTGATGATCATCCTTTTGCAGAGGCAGATAAGCTCAAGGAGATAAGTAACATGTTAAAAT[T/C]GTATAG TTGCTATCTGAGAATGAAGTCAAACCCAGGTCAGTCTGACTTCCAAAGTCGAATTCTTTCCAATATAGTAAGTGCCTTTCCTAAACCATTGACA |
| rs4130306 | 1056 | GGCAATGTAAACTCTACCACAAGAATAAAATCATTTCCAGCAGACAAAATCAGGTATAAAACAGGTATAGAAAACTGATGGCTCGTACTACCCAGTGGAATAAA[C/T]TCTTCT GCAATAGAAGAATGAATATGTTCTTCTATAAAGGAAAAGAGCTTATTTGTGAGCACATTTAAAGCTGAATGCGTAT |
| rs4889072 | 1057 | AGGGAGCAAGATAACACAGGGCTTTCTGTTTACCTTGCTTAAGCTGGTTAAGCTTGGGAGAATACACAGTAAGTTCCCTGAGGGCAGGACTATGCATATTCTGTTA[G/A]TTTC TCCATCTCCAGATCTCATATACTTCCTGGAACATATTAAAATGCTTAGTAAATGTGAACATGAGTGACTGGGAAGAAGGGGGCTTAG |
| rs6005754 | 1058 | CCACAATGAGAAGTATAAATCTACAGAGAATAACACTTCAAACTGGTAACACTGTTACTTCTGAAAGAACAGTTTTAAATCTTTACATCAATAACTAA[T/C]TCATACA TTACTTATGTAATGATAAAACTATAAACATTAAAAAACAACAGTATGGGAATAACAGATGGCTGAGCAAATAACACTGTTCCCAGGTTGCTG |
| rs2734574 | 1059 | ATCCAGATAGCGAGCTGCTAGCAGCTGTCCAGCAATCCTGCCTTCTGCAGCCCTCTGGGCCTGTGGCTATGTCACAGTCACAGGACATCCTTCCTGTTCTAAGGACCTTCCTGTTCTAGATGATCAAAAT[T/A; A/T]G GGACCAGCCACTCCCTTCTGAGCCACTCCCTGAGCCCTCTGGGCCTGTGGCTATGTCACAGTTTTCACAGGACATCCTTCAGAACACCCTGCAGGAA |
| rs2734574 | 1060 | ATCCAGATAGCGAGCTGCTAGCAGCTGTCCAGCAATCCTGCCTTCTGCAGCCCTCTGGGCCTGTGGCTATGTCACAGTTTTCTAAGGACCTTCCTGTTCTAGATGATCAAAAT[T/A; A/T]G GGACCAGCCACTCCCTTCTGAGCCACTCCCTGAGCCCTCTGGGCCTGTGGCTATGTCACAGTCCAGTCACAACAGGACATCCCTTCAGAACACCCTGCAGGAA |
| rs7725509 | 1061 | CGTAACTTTTCCTGCACAGCCTTAGTGTCTTATGCAGAAGAAACATTCGGTAATGCCATTCATTGCTCTACACTTTTCTAGCATCTGATTGTTTAGAAAA[G/T]TATTGC AAGCTCGTGCAGTGGCCTCTCAACTGTAATCCCAGCATTTGCAAGCCAAGAGGACTGTTTAAGCCCAGGAAATCGAGGTTGCAATGA |
| rs6592545 | 1062 | AAATTTAATAAGAACAGTTAGGGATCCGATAGTTGCCTGATAAGCAAGAGAAAAGAAGTATCTATCTAGGTTGAGACTCAGGTGGCTCAGGTGGGA[A/C]TTTA CGATATGCAACAGTTCAGAAAAGTTCAGAAAACTTTCATGTTGCTTAAACCTTTAGGCTTGAGAAATAAAATTTATCAGTTCAGTAGAAACAGATCCTGCC |
| rs2676403 | 1063 | CTGGGGGTCTCTTATAGATTCAGTCACCATCATTATGAAGCCTTGTTGAGGCTTGAGGCTTTGTTGAGGCCTAAGATAACTGTTCACTAATAGATGTTCACTAATATGATGTTCCTAAGACATTT[A/G]ATTTTT CATATTTTAAGATTATGATTTTCAGCAGCAGGTTAAAGTATGTGCTTTGGGGATATATGTAATGAGAACAGAAAAGAATCCACAACTCCTTTT |
| rs2792780 | 1064 | TCACTAACAAAACTGCCTCCCCCACCCTTCTTCCGCCCTCGCACTCAAATGACTTTCTGCACTAAATCCCAGACTTGTGTATGCAGTCATTTTGCAACCAGCCTCCCAAGCTTGCCAGAGCA GCCAGGATGGGCCTCAAATGACTTTCTGCACTAAATCCCAGACTTGTGTATGCAGTCATTTTGCAACCAGCCTCCCAAGCTTGCCAGAGCA |
| rs9599645 | 1065 | AGAAATAAATGACTTTGGTCATGATTGGGTTTCCTTACTTGTCAAAGTGAAAAAAATAGACAGATAATAATGTTATTAAAGATGAGCCCACAGGCAAAA[G/A]ATTAGT CTGATTTCTGTATGTCCCTTCTCTGATGTCTTTTTAAGGCATTTGTCTTTTTAAAGAGGACAAGAAAAACGGTAGCATTTTTGACAGATC |
| rs10898954 | 1066 | TGCTTTAAAAGTGAAATGTTTATGGTACTATGAGTGCAACAGAAAAGGCAGGGGTCAAAAGACAAGGTTCTAGACACCCAAGTCTTCATCAAGGAAT[C/T]GGCA CTTAGACAACACATAACCAAGGACACCAGGTGCTAGATTTCAAAATCTTTCTCTAATGCCCGCCTGGGCAGTCACCTGTAACTTGAACTCCTGGGC |
| rs9652080 | 1067 | GGAGATTGGGCATTCACAAAATCTCAGAATAATTGTATCCATAAGTGATGTTATCTATATCTATATACAAATATGTATCCATAAGCTATAGAATAACAGTTTAAAGTCATATTCACTTTTACTG[A/C]ATTAGCT TTTGGCAACACATTTGTTTTTATTTGTTTCGTTTTCTATAGTCACCAAAACTAAAATCTTACCTATTATCTGGTTTCCCAAATAAGCCTACCTA |
| rs9352730 | 1068 | GCCTCTTCTGTGCATTTCTAGGCCTGTGTGGTAGTAACTAATGAACTTGGTAACGCCTGCGGTAGTAACTAAGAAGAGAAAATTCTGTTATCACAGTTCACTAGTATATTTGTAAAAGGGAATAGTTGTAGTATGA[A/C]TTGCAA GTCTTGAGGTATTGTGTTGTGGGAGTCATACTAAGAAGAGAAATTCTGTTATCACAGTCATGTGCCATATAAAGGCAATTCTCGGCAATGGT |
| rs12618834 | 1069 | ACAATGTTCCAAATAAATCAGCAGATTACAAAGTAATAATTTAAGACGGATGATGTTGAAGATAAAGTGCACAATGGCAGACCATCCACATCA[A/G]TTTAC AAGAAAAGATCTTTGTCCACGACTTGGTGAAGAGAGCAACTATTAATAGCAGAAATATCAGATATAGACATTCCAACTTGTTCAGCT |
| rs11835780 | 1070 | CAAGACTACCATCCGCGAACTCACGGACTCATGGGATTCACTGGATCACTGGATTATTCACTATCATGTATTCCACACAGTTATCATGTATTCCACACAGCAGCAGCAGCCTCGACCAAGCACTCACTTTATGCCAAAGAA[G/T]GTA GCAGTGGCTCATGCTCATGAGGATTCATGGGATTCACTGGTTACCAGTTCACTGGTTACCAGTCACGGATTCATCATCATCATCCCCATCATCGTCCTTACCATGTCTTGGATTGAATGAAATGGTGCAATGGCCTTTGAA |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs11105611 | 1071 | TGTTTTTCTTAAAATGCCTTCAGTTTCCTTGGAAATGGAGAATTGTGGAGTATTTAGTTATTCCCTTTCTGGCTGTGCAACAGAAGGGCAGATC[C/A]ATTTAA CTATTATCTGCCCTCCAACATATCTTCTAGTTATATTTGTTTTGTAGGCTTCAAACCTGTGAAGAGCCCTTGACTGAGGGTTCTCATTTCTCC |
| rs12450474 | 1072 | AAATGGATTACACAAAGTAAACATTAACTTGGTAGATTCAATGTAGAATAGTTCATAACAAGCATATTGCCCTTCTGCCAACTACCAAGTTAAGA[C/A]TTTTTCA AGTATTTAACTGAGATTTTATTATGTTGACATTTGTTTCTCATTCCAATCCTCTTGGCCAAGCGCAGCACTTACAAGTCTCGATTAAC |
| rs9594249 | 1073 | TGTTTCTTCTGTCTCATTCATTTTACTATTTCTTATACCCATCACAGGGTCTGTACTGCAGGCATTCAGTACTTTTTTTTAAATGAATGAGGCCA[A/G]TTCAGGT TCTAAACTTTGAGTTTCTTCCTCCATATTTCTTTTTGCTTTATTACTGCAATAAATTATTTCTTAAATTCTGTTAATCAGAAGATTTAAGA |
| rs9285190 | 1074 | TATTAAAAGAAAAACTGTTGAGGCAAAAAGAACAAAAACATTTCACCTTTTTCCTGTAGAAGCCAGAGTGTGCTTCTTCCACAAAGCCTGTGCAACCTCC[G/A]ATTTTA TTCAAGAGCTAAAGAACTAGCAGTTCTCCAAGGCTCCAAGATTTAATTTCCAATGCATAGGATGCCCCTCACAATCAGAATTAATCAGTTTTCAT |
| rs17170027 | 1075 | AGGAAGAACTCGGGGTGTGACCAGGATTTCAAAAGCGGGTCAGAGGAGAACTCAGAAGAACTTATAGCTAGAATAGAATAGGAACTCAGAAAA[T/C]TGG TGTTGTCTTGGGCTTATTTTCTTTGGCATCTTGCTCCAAAAGGATAGAATGATCAAAAGGTCACCAAGAGCTAAGCCTAGGCCATTCCTG |
| rs7899028 | 1076 | AATTAGAACCACATATCTTAACTAGAACTACCTAGAACTAAAAGTACTTGTAAAAATATGGCATAGGGACCCCCGTGAATCAGCAGGCTTAGTATTGGAAAA[G/T]TATAAA CGCTCCAGAAATGGGGGCAGGCATGTGACTGTGATTTGTGGCCAGGATTGAATTTGTGGCCAGGATTGAGAACATCTGGCCTCCGTGAGCCAGGAGATGAAACAGCCAGCCTCCTT |
| rs11079666 | 1077 | TTTAAAACCAAGTAAACCCTCTCATTGCACCCCCTGCTACTTCAGAGGAACCTCCATTCTGATGGAAGGAACTCGTACTTGGGTCCTGGAACCCTA[T/A]TTGG GACCCAAACCTCTCCCACTTGTGTGGCCTGACGTGCCTGAGTGCTGTTTGTGTCCTTTTATTATGTTGAAACTTTGTTATTCCAAAGAAACATC |
| rs12034424 | 1078 | CTAAGCACTCTACACACTTGAGCGCAGCAGCTTTTATTGAAAGAAACTTTGCCTTTGAACAGAGAGGTTTAACAGCACCACATTATTTCAGATATGTTCAGTCAATGAAT[T/A]TCAGAT TCTTTCTTGAGTAGCAAGATATATGCAAGACTGAGTAAGGTTTCTACTTTTTAAAGAGTGCTGCAATGAACACTCATGCACACTCTGA |
| rs10276221 | 1079 | TATCAAAAGATGAGTGGGATAATGAAAATTTACTATATAGACCAAGAAAAGAAAGAGAGAAATTGTCTCATTTGCGCAAAGAGAGGAGCCAGAAGGAGATAAAT[T/G]TTAAG TGAAACAAATCAGGCACACAAAAGATGAATTAAAGTGCCTAAAAGTGCACCACAAAAATTGTGTGT |
| rs9886292 | 1080 | TATCTCCCTATCAAGCCCTACCATTTCCTCCTGTCTCATCATACCCATTATAATAACATTCATGTGAAATATAACATTCATGTTTAGACATGGTTGTGTGAAGTAAAGCTGGAAT[C/T]CAGTAT TCTCAGTTCTGTATATCATTATCACCAGCGGTGCTTAAAGCAAATGGCTTAAAGAGAATTATAGGTCTCTCTACATCTATCATACACCCTCCAGATTCAATGGG |
| rs9630712 | 1081 | TGCCTATCATAAGCCTAGAGAACTTGGGAGTTAGTAGAAATATAACATTCATGTGAAATATAACATTCATGTTTAGACATGGTTGTGTGAAGTAAAGCTGGAAT[C/T]CAGTAT TCTCAGTTCTGTATATCATTATCACCAGCGGTGCTTAAAGCAAATGGCTTAAAGAGAATTATAGGTCTCTCTACATCTATCATACACCCTCCAGATTCAATGGG |
| rs10851704 | 1082 | TTCTAAGCTCAATAAAGTGCCATTATCCTGTCCGTTAATAATAAATGTTTGGAAGATCCTTCACACACTCTCACACAAAGTTGCTGACAAAA[C/T]TTTCTG GCCAAAATGGAAGGCACTAAAAAATATAGAAGTTATTATCAGTCTTAAGACAATACGTTATATATAAATAAGACATTACCTAATTAAATTTC |
| rs10034384 | 1083 | TTTGTGGCTGTGCAACAATGGCAAGTTACTTCATTGAAATGCCAAGTAAAGTGCCAAATATGCCAAGGACTACCTCAATACGTCTAATAGCTATTTTAATTGCACGTAAGAAGACTGAG AGCTATGCACTTTCATTGTAAAAGTGCCCAGAACATAAGGAACTCACTCAATACGTCTAATAGCTATTTTAATTGCACGTAAGAAGACTGAG |
| rs12442455 | 1084 | GTGAGGACAAGGGCCAGTGTGCAAAATATTGCAAAGCAGGAAGACAGGAAGACATCAGGAAGACCTGGCTCATGGATGACATCATTAAGTCAGTGATTATCCTTGGAAT[T/C]GACT TACCCTCGGGCTATGCGTGACATATGAAACTCATTATTATGGAAAAACACTTTTTGCTAGGTTTTGTGTACTTGCAGGTAAAACACTCTTAATGATTT |
| rs12439908 | 1085 | ATGGAGGCAGATGCAGTTTCTCCTGGCTAATTTGTATTATTAGTAGGAGAGATGGGTTTAGCCATGTGGCCAGGCATGGGGGTTAGCCATGTGGCCAGGCATGGGGGGGGTTCTCAGATTGGCCTGATGCGGGTCCTGGTGCCCAA[T/C]TGT GTCCTAGCTCCAGGCTGTGTCACCCCGAGGGCCTGAACGAATGCAGACAGCCAATTTCCCTGCCTCCACCTGTAAATGGAATGCCATTACCTGTCCA |
| rs11221268 | 1086 | CATGCCACCACCTGGCTAATTTTTTGTATTTTAGTAGAGATGGGGTTTAGCCATGTTGGCCAGGCTGGTCTCGAACTCCTGACCTCAAACAATCCAAT[C/T]GCCTC AGCCTTCAAAGTGCTGGGATTACAGGCATGAGCCACCACATGCCCGGCCTATTTTTCAGTTGATTTTGTTATTAAAATGCTTATTGTCCAGTTACATGCATT |
| rs9515625 | 1087 | AAATGAGAATTGAAATCTCCCATACGCTGAAAAGAAGTCTGAGACCAAGAGTGCCAGCTAATCTAACACCGTGATTTACTAATAAGTATCAAAT[T/A]TTTAA ACCTTTCCTTTGTGGCCTCATGCTCCATGACCTTTACCTATGATGTCAACTTTACCGGGATTACAGGCATGAGCCAC |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs9322744 | 1088 | CTCTGCTGGATAACAAGTGCAGCTGCAAAAAGACCCATGTCTGTCATACTGTAAACACTCAAATAAATAAAAGCATCATTAAGTATTAGCCAAT[C/T]TCTTTG CACATCAAAAGTGCTCCATATATTTAGTTCTGAGTTTACTTATGCTCCAGTGTATAAAATTATCATCATTTGAACTGAAACTTTATGATGAATT |
| rs9864594 | 1089 | TGATCTCAGCTCACTGCACCTCCGCCTCCTGGGCTCAAGTGATTTTCCAGTCATTGTCCTGAATAGCTGGGATTACGAGGCTGCCACCAGATCCAGTA[G/A]TTTT TAGTAGAGATGGGGTTTGACATGTTGGCAGCCAGGCTGGTTTCACTCGACCTCAGGTGATCCACCCGTGGGATTACAAGGTTATCTTTTTTTTTT |
| rs9356029 | 1090 | TCTTTCATATTATTCAAATCTAGAGCAGCACTGTTCCTCCTCCTAGGTACCACCACGACATCCTGGGCTTTCCTTGTCATAGCATTTGTCACACCTCTTCAAAT[C/T]TGTTTCT TTATCTCTTCTTGTCCACTAGACTCTTGTCCACTAGACTCTTATCTGCATGCCCAGTGCCTAGCATGCTACCCAGCAAATTGTAGGCAA |
| rs10740169 | 1091 | TGGGTTGAAAGGACATCTAACTATCTTTAGTGTTTTGTGCCACCCCGTCCTGCTTTCCTTCCTTACAGAGCACTTGGACAAGAATCCTCATATCAA[G/A]TTTCAG TTCTTAGAATCTAACGTAAGATACTTTCAATCATTATTTCCCTGAAAGAATTTAAGCATTTTCAAAGCCCCTTTAATTAAAATAAAAATGTC |
| rs10964719 | 1092 | ATTAAATATCTTCTCAGCCTGTGTGTCTCCTTAAATCTAAAGTGAGTCTTTTTGTAGACGTTATTATAGTGGGATCTTGTTTGGGTTTTCGGAATC[C/T]CACTGTA TGTCTTTGATTGAGCAGTTAAATCCATTTACATTGAAAGTACTTAGTGTGTAGGAAAAGGACTTACTATTTGTCCATTTGTTAATTGCTTTTGTCT |
| rs10893402 | 1093 | ATGAAATTTCTCACAGTATTCTTTATTTCCACTCTAAAATTCGGAGAGGTAATGAAGTCTAAATAATACTCAATGTATTCATTCATAGTAGGCAATCAAGCAAT[T/C]GGTTTTC ATTTACTTGGTTTGGAAAAGCTATAAAACCTTTCTTTGTAACATGACTAATAATTACAAAAATTGTTTTGTCTCTGTTTCTATACAATAC |
| rs10956363 | 1094 | TTTCTCTGGTAAGAGCAAGGATACTAAAACATGTTTGAGTGCTGATGAAATTGATCCCATAGAGAGAAAAATGTTGAGAGTACTGGGGAAAAGGGGATA[G/A]TTGT AAGAATGAGGTATTTTAAAGTGTTAGAAGAATGAGATCCAAAGACAAGAACTGGCTTGTCTTTAGAGGAGTAGAGACAGATCTTCAATTATCAT |
| rs11771935 | 1095 | AGAGACAGAGTAACGTGTTAAATGATGCTGCAAGGATGCAATCAGCACCTCGCAAGCCCACAGGACAAACACAAGTGTACAAAACAAGTACCAGCAGTA[T/A]TTTA AAACGACGGAGTGGAATCCACAGAACATAAGACACTTGGTATATAAAACCTTATTTGGATCTCATTCAAGCTAGCAAACTGTAAGAACAGATATC |
| rs10901705 | 1096 | GAATTCACTTTTATAAGATACCCTTACCACACACATAAAGCAGAATAATTTATCTGAAGGTAGACCTCGATGATAATTCAAGTAAAATCAAGACTCTGAAGCAACCACTAA[T/C]TTTTTTT AAAGGTGTAATGATATCCTGAGAGAATTAGAATAAAGAGAACCATAAAAATCTTCAAGTAAAATCAGAAAAGGCAGAAAAGCAGAAAAGAAAACCCCTGG |
| rs9989393 | 1097 | TTATTAATATCAGAAACAATTTTGTACTATGCTTTATTATTATTATAAGGTGCCCAAACATGTTATGCTATTTGTCAAAACACTCACCAGACAAAATAA[T/A]TCTTCTTA GTAGTCCCAGAGGCGTTATGCTTCAGTTTGTTTTTCCCTGCTCTCCCTGCCACTTCATCAGCAAGTTGTTCATTCTGCTTCTGATTCA |
| rs10860857 | 1098 | TTCCTCCCATGACATGTGGAGATTATGGAGAACTATAATTCAAGATGAGTTTTGGGTGGATACAGCCAAACCATGTCAGTACCACTGATGATTTTAAAT[G/T]GACTT TGTCGCTTGCCTTGGTGGTTCATAGAGAGTGTCTGGATATGTTTGAGCAATAAAGAATGATTGGAAAGTACACAATCTCCATGTGATAA |
| rs11125229 | 1099 | GGCAAGTCATCCTGCTCAGTGCCCTCAGAACATGCTCTTTTTTTCCTTGTGTCTAGTATCCAGTATCCAGTTCAGTATTCGCAGCAAATATTCGAAGTACACTGAAGTACACAA[A/T]TTGTT GAACTGAGTCTCTTTTAATGCTCTAGTAAGCCTCGGTGCTCCAGTAAGCCTCAGCACCCTATTATATCAGCAAATATTCAGTGAGAGAATCCCCA |
| rs9992168 | 1100 | AGGTGGCTTCCTCCATTTAACCAAGGGACCAATTCTCTGGAGAAGGGGGCCAATTCTGCCTCCCTGCCACCTGAGAGTGCTCAGCTACGTGACCTGAAGTCAGGATGTAAT[C/T]TGGT ACTAGGAACTAGGCAGAGCACCAGTTGCATGTAGGTAACCAGGAGTGAGAATGCAGGGTCTTACCCACATTTGCCCCATCTGTGATTCAG |
| rs7900002 | 1101 | CCCTGCCTGAGGATTAATCCTTCCCTGCTACAGTCACACAACTGCCTCCTTCAGGGAGGGAGTGCTCAGCTACGTGACCCAAAGTTCAGGATGTAA[T/G]TGA TGTCAAAAAGAGAAGAAGAAAGTTTGCATGTAGGAGGCCATGTAGGTAACCAGGAGTGAGATCATGAGAAATCAGGGTCTTACCCACATTGCCCCATCTGTGATTCAG |
| rs11685586 | 1102 | GCTGAGCTGCTGCGCAGAGGAGGGGGCTGTGGGAACCAAGGAGGCTACCAAAGTGAACTTGGGTCTCCGAACTGAACTATGAAGTGACCAACTGCAGTGACCAACAACACCTGAGACTATGAATGGTCATCACCGCACAATGACATGGT[T/C]T CTGTGGCCAGGTTGTTCTTTTCTTCCTCCTTCCTTTATTAGTTCAAAAATATGCACTCTTTAGCTCCTTAGAAATTATATACATTGAC |
| rs12158945 | 1103 | GATGTATTCAAAATATATTTTCTGCTTTACTATGTGATATCTAATTGGATCTCAATTGTAGCCCTGTTAGTCTGATATGTGATATCTAATTGGATCTCAATTGTAGCCCCCTGTTCCAGGCACAGAAGCACAGTGAGTTGAGGCCATTAAAAGCAGGGTCTGGATTG[A/C]TATT TAAAGTCATTCCACTTTTTCCACTTTGTTTAGTTCAAAAATATGCACTCTTTAGAAAATTATATACATTGAC |
| rs12903747 | 1104 | TACCAAACAGCTGGGCAAGTTCCAGGACAAAGTTTAGGGCAGGTTCCAGGCACAGAAGACAGTGAGCCCCGTTCCGGGCACAGAAGACAGTGAGCCCCGTTCCCGGCACAGAAGACAGTGAGTTGAGGCACAGTGAGTTGAGGCCATTAAAAGCAGGGTCTGGATTG[A/C]TATT GGCCAAGCTGTATATGTCCCGACGTAGCCTGCAAGCCTGAGTTTCATCATAGTCCCTATCCACAGGG |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs11249671 | 1105 | TGTGTGCCCAGAGACAGGGCTGGGCTCTCATAGACAGCGGCGGCAGCACCTTGCAGCCCTGTGGAGCTGTTATTCTAGTGTGGAGGAAATGACCC[C/A]AT TGTCTCGACGGTGGTCCTATCAAAGAAGTCGCATAGGGTGACCTGGATGAGTACTGTTGGGACGCAGAGCCCAGGGAAACTAGGCTCCACGCTGGGTAA |
| rs17079191 | 1106 | AAGGAAGTGATGGGAGGAGAAAATCATGCAAGATAACTGTTATCTGATTCTGACCCCTGAGATTGGTGGAGGGGAGCACAAACATACATTGGGTAA[A/T]TAG AATATATAGCAGATTACACACTTAAGCTTGGAGACCATGGTCTTTCCAATTCAGTGAATTTTTTTTGAAATGCATTCAAACTTGTTTGC |
| rs10832561 | 1107 | AAATAAGCACAGACTGGATTTTAATTTTCTAAACTGATGTGCCTTTTAAATTGAATACAGAATAGTCTTCAAATGAAAGGCCACTTTTTTTACTGA[A/T]TTAATGT GAAACATACTACCACTTTATTGCTAGATTAAAATGTTAGACTAGAAGAAATAACCTAGTAGTTTGCTCATAATATCAATTGAATTATATGAA |
| rs11563997 | 1108 | CATTAACCGGATATAAACTTCTTATTGGCCTTCTTGGGACTTCAAATGCTGTACTATTCATCGAGTAAGAACTTGAAGAGAATAAATGAATA[C/A]ATTGAT ATAAAAGCCTTTATGTTTAAGTGTTTAAATCTAATAGTGATTCTAAAAAGAGAGGTAAATGATGTGTATTTTGCTCTAAGATTTCAA |
| rs10754776 | 1109 | AGAAAATGAACCTTAATCTAAACATCACAACTCATACAAAAATGAACTAACTCAAAATAGATGATGACTGTAAAATGTAAGACTTTTAGAAAAA[T/A]TCTATAT GAGAAGTATTCAGGATGTAAGGCTAGGCAAGGCATTCTTAGACTTGATATCAAGAGACATGACCCCAAAAAGAAAAAAATTGATAAATTAT |
| rs7985274 | 1110 | GCTCTTCCCTAAGGCCTCATCAGAACGAGGCCTTTATACCACAGAGGACACACACAGACTTGAGAGAGAGTTTGAGAAGGGAAGTGTTGTAGCATCTCAGAGGGCCCATGGCATGTTTTCAA[G/A]TTG CGGAGACAAAGAGAGGCCATAGTTAGGACTTAGTTCATCCCAATCGTCTCAATGTGTCAAGTGCCAGGCTGTAGAACCAGCCTGTAGAAAAACCAAAGA |
| rs10234234 | 1111 | TTGTAGAGAAATAAAACAGTGCTGAGTGCATGTCGAAGGGGTGCATGTCGAGAGAGAGAGTTTGAGAAGGAAGTGTTGTAGCATGTGTATGTGATGGGATT[A/G]ATT CAGTCAAGAGGGAAAAACTGAGTCAGGAGGAAAATGTTATCCTCATAAGTGAAAGTGTTATGAAAGTGTATCTTGTGCACAAG |
| rs9314663 | 1112 | ACCTCCACCTGGTGGGGGCCTGTCAGTGTACCACAGGTCTACCTTGATTTCAAGTCCATCTCCTCGATTTCAAGTGATAATGAAGTAAAATGTTTTCCTGCATTGAAGAA[A/C]TTTCC AGTGTCTTGGATGGGGGAGCTTAAGGAGCAGATGCATTCTTGGGTATGGAGTGGATAACTTGTAGGCAGACTGTTCTAGGAACACACGTAA |
| rs10021843 | 1113 | AAACAGTGCCAGTGCAGTTGTTGATCTCAGCTGTGTTTAATGCATGAGAAACATGTTAAACATGTCAGTATTAACTGCAGTATTAACATGTTAAACATGTCAGACTTTTCTGCAAGGAGGAGAAA[C/T]TGAGAT AATATTCCTTTGATCATGAACACAAGTGGTTAGATAGTGCTATATCCCGCCAAGTAACCTTGCTGTATATGGTACTACATGTATTCATGCAGT |
| rs11773909 | 1114 | TTTAGAAACTGAAACTAAGTAATATCTGATGTTGCTTTAGGAAACAAGTAAAGTTAACGTGACCATATTTCTTTCTTTTTCT[A/C]ATTCTCC TTGGGCCATTTCCAAAAAGCCCTAATACCCCTGATAGAAAAGCGACTACTGTGATTCATGGAAAGCTGAT |
| rs11227624 | 1115 | GCAGATAACCACAGTGGGAGGAGGCTTCCCCCTGATGACAGGAGGAGCTGTGAGGCCTTGAGGCCTTTCCGCTGTCTCATTACCCGCTGCTCCATTACCCGCTGCTCCATTATGAAGCATGCGGCCTAGAACAC ACAGGGATGGCCTTCTGCCAGTCCCCCCAGTCCCCCCTGATGACAGGAGGAGCTGTGAGGCCTTGAGGCCTTTCCGCTGTCTCCAGCATGAAGCATGCGGCCTAGAACAC |
| rs9838013 | 1116 | TGTGAGAGCCAAGGATTCTTATCTACATAATAAAACAAAAGTGAACCAATATTTTGTCCCCAACATCCCTTTGATACTACCATTGAGGTTTCAC[A/C]ATTAGG ACAGTTTTCTTCCAGCACCCTCACTCTAACGACACCCCTTACTCCATCTTGCACAATTCCCTTCCTCTTCCAGCCAAACATTCCTCTATTT |
| rs9929404 | 1117 | CAACCATGTTACCAAATGATACTAAACATAAACATTGATAATAGAGACTAAAAATGGTGTCAGGCTTCAGGGTTCTACAGCTGCTTGTTGGATGAGATGAAGACCAGTGAGATGTGAAATGTTCTA[T/A]TTCTAT TCATACATGAGCAGATTAATAGAGACTAAAAATGGTGTCAGGGTTCTACAGCTGCTTGTTGGATGAGATGAAGACCAGTGAGATGTGAAATGTTCCTGTTAACATCCATTATA |
| rs13255815 | 1118 | GGGTTTCATGTACGTGTGATGGAGGTTGGCTGACAGATGTTTGCTCAGATGCTCTGACAGTCTTGGTAATGACTACAGCCCTGGTCCCCTGAAT[T/C]CGCT TCCCTGCCTGGCCTGACCCTGCCTGACCCTGCCTGACCCTGACCATCTTCATATTTCAAACAAGCATCTTCAATGATGATAACATCCTTGGAAGGAGAAGCTTCGAAG |
| rs9987005 | 1119 | GGTAAAAAATTAAGCTTGCATTTCCTTTTACAAGCTTCTCCTCAAGCAATACATTTCAAGCAATACATTTTACAAGAGAACATGCCAGAAAGTGCCACAAAAT[T/A]TCAATAA CAGGCAACACCACTAGGCTTCAGTGACCACTGATTTCATCCTCTTCCTATATTCTTCTATAGTCCTTATACATCCATTCATCAATGTCATGGACTA |
| rs11635372 | 1120 | CCACAGGAAACTTCACAAAGGTTTACGTACAGAGAACATTTGGGGCCATGTCTGTCTTGGCTATGGGACAGGTGGGCTAAGCCGGCATCTCGCTGTCA[G/A]TTG CCAGACTGCAGAGAGGCCCTTGCCTCCTTCCACAAGTGTTTCCACAAGGGACATATTTCCTTCGTTAGAAATAACAGACTGACATAT |
| rs12674093 | 1121 | GAGGAAATGGCCATTTCTGAGGTGCTCAGAACCACAGCTCACCCCTTTCACAGGGTTAGGATGGAGCTGTTACAGGAGGTTTCCTGTACTTTAAAAAA[G/T]TTAA ACAACAGAATCCAGCCTTTGCTAGCTTTGGTATCGTCTGTAAATGATTTACTGTAACATAAAACATCGAGTGAGAAAAATATAGAATAAGTTTTTC |

TABLE 11B-continued

| SNP_ID | SEQ ID NO: | Corresponding Genomic Sequence with Alleles provided in Brackets |
|---|---|---|
| rs10260483 | 1122 | TTTAAGTGTCGTCCAAAAGAGATTAGTATTGGTCATAACATGACTCTAAAGCACCACCATTAAAAGAAGCATGTAAAAAGAAGATATTCTAGTACACAAAA[G/A]TTATTA ATGGCCTAGAATGACCTCCTTCCACTCATATGATGCAAAGAATAAAGTATATAAAATGTTTGTTACAATGGCTATCCATAAAAAGAAAACC |
| rs11759755 | 1123 | CATTTAAAAATGTGTTTATCAAAAGACACTGTTAAGATTACATAGGCCAATCACCACGGTGAAAGAAGAGATATTCAAAATACATAATATTCAACAAAGAAT[T/G]TATATCC AGTATATAAACACCACACACACACACACACCCTACAGTTAATAAGAACAAAGACAATCCAACAAAGAACATCCAAAGCAATAGGAAATTATGAAAGT |
| rs12783667 | 1124 | GTCCCTGAAGATGTGTTCTTGAGAATGACGACAAAGTTCAGGTCAACCTTGAGGTAAGTGCTGGAGGAAAAACAGTGTGAGTAAGTAAATGAAGGATGTAAT[T/C]GGGCT CCTCTCCTGGAGACTGAAAAGTAAGGACATGGCCATGGAGAAATCTTTGATTTTTGCAGTATATATCATTATCTTTAGAGGTCTAGAAAAAGTGCCTACG |
| rs9692857 | 1125 | TTTACACAGCATCCAAAAGAATAAGCTACTTCGGAATAAATTAACCAATGAGGTAGGAAACGTGTACACTGAAAACTATAAAGCATTGCTAAAAGAAT[C/T]TAAAGA TGATACAAATGAAGAAAAGACATCCTGTTTTCATGGATTGGAAGACTTAATATTGTTAAGGTGTCAATACTATTGATACAGTTGGATCTATG |
| rs9428474 | 1126 | CCTCCTGCCCGGTCCATAGAAAAATTGTCTTCCATGAAATCGATCCCTGGTGCCCAAAAGTTGAGGCCACTGGATTAAAGGAGACAATGTATGTAAAT[T/C]TTGG CTTATAATAAGTTCTTGGAAAGTGCTAGCTGTGCTTATCACTGATTATAGTATCCCAATCAAACCTTGGGGTTAGGATTATTATTTCC |
| rs16830436 | 1127 | TGTGTGTGTGTGTGTGTGTGCGCGCGCCGCGCCATGCCACGCCCACTCTGGGACATCCCTATGTTGCAGCAGGAGCATCAAAATTCAGGGTCCTTAA[T/G]TTAAAT CTAGACATTTCTTCTTGTGAAGTCCATGGAACCCTGGGACATCCCTATGTTGCAGCAGGAGCATCAAAATTCAGGGTCCTTAA |
| rs8063107 | 1128 | CTGAATTCCTGTAAAGAAGAAGAGACTCATATCCTGAAGAATGAAGACATCAAAAGACCAAGGTCTGTGGCAAGTTAGCCTTCTGGTGAGGGTTTTTCACAA[C/T]TGGA TATCCTGCTGTGTGTAGAACTGAATACCCACAGCAGGGTTATTCAGGGATGCAGCTCCAGGGATGAGAGAAAGTGTCTTGACTGATACATAATTTATCTGTC |
| rs9818611 | 1129 | AGAGTTACTGTTGCTCCACGTCCTCCAGCATTTGGTGTCAGTGTTCTCGGATGTTGGCCATTCTAATAAGTATGTAGTGCTATCTCATTGTTGTTTGAAA[C/T]TGTATT TCCCAGATGCATATGATGTGGAACGTCTTCTCATATGCTAACATGCCATCTGTATATCTTCCTTGGGGTGTCTCGCTAAGGTCTTTTGCCCAATG |
| rs10840805 | 1130 | TACTTGTTAATACTCCAATTACTTCCCAGATTAAGAGATTTGTTTCTACACAACAAATATTGTACCTACCTTGCTCTGAGAACAGCCTGCACTGTGAA[C/T]TCATTTT ATCAACAACAAGACTGCTTAAAAGCAGGAAGAAGACATAAAAAATGATGAGTTCACGTCTCTTTGTAGGGACATGCATGGTATCTGAAATC |
| rs10421748 | 1131 | GAACCCCTTCCTTGCCCCTAGACAAGCCACCTGCTGAGCAGCCTGAGAGCTCAGCAGCAGCAGCACCACCAGCCTCGTTGGGAGAATGCCAAA[T/C]TG CAGCGGAGCATGGAGCAGCTGAGGAGGCGTCAGCAGCTCCAGGAGCTTGGCTCTGCGTAAGCACGTTCACAGGTGGGCTGGATGCCACAC |
| rs10139699 | 1132 | ACTAAACAAATGTATTAAAGTTCCTGGCTCTGTACACCATCCTTAGTAGGAGAATAATGGCAGGCATTGGGTGTTTTCCAGGAGTTCCCAGCAGAAT[C/T]GACTA CCTTTGCCCAGCCAGTAATCTTAGTAATGCACACAAGTTGCTTTTTTCCTGGTGTGTTCATCGTTAAATAAACTACAAATATATGAGTAGAA |
| rs12107918 | 1133 | ATGAAATGGATTCACATTTTCACATTTTCCTAGATTACCTTGGTTATATCGATGTCTCGGGTGTGCACTGATGTCTGGGTCACTCACAGAGAAACACAGCCAA[C/T]TGAGACT TTTCTTCCTAGATTACCTTGGTTATATCAGTGCTTCGGGTGTCACTGATGTCTCACGAGAAACAGCTGCGGGTCCCCAACTAAAG |
| rs10884498 | 1134 | GATGGCATATGGAGGAGGACTTACAAAAGGGCTTCGGAAAATATTATTATTATTATTATTACAATAATCATGTATTTTGTGACGGTTAATACTGAGTGTCAAA[T/A]TGATTT GATTGTAGAATGCCAAGTTGCCAAGTTCCAAGTTGTGTTCTTTGCGAGTTCACAGAAGTTTTGAGTCAGTGGGCTGGGAAAGGCAGAC |
| rs10822434 | 1135 | AGAATGTATTATTGATCTGTGATATCTGATATCCATACACCAATAGTAACTATTTTATATAAAACTACTTTTTGAAAAGTCTTGACATAAGGTAGTATAAAT[T/C]TCTGTTGCT CTTCCTGTTTCAGTATTTCCTTTGCAACCCTCTTTAAGATTGCCTTTCACTTCTATGTAAGTTCTCAAAAGAGGTTGTTAATTTAATAA |
| rs12607335 | 1136 | AATATAAGTGGAATCATAAAATAGGTGGTCTTTTGGCTGGATTCTTTAATTTATCAAAATGCTTAGAGGTTCATTTATGTAGCATGTAGCAGTA[G/A]TTATTTC CTTTTGTTGTCAGATAATATCCATTGCCTCAATAGACCACATTTTCTTCCAATTATCACTTGATAGACATTTGAATTATTTATACTTTTTG |
| rs7915178 | 1137 | CAGAGCTATCACCTAAAAGCACTTCAAATCTTCAAAATCTTTGCCTATTTTGTTATTTGTTAAATGCCCCCAGAAGCTCGAAAGCAGGAAGTGTTTGAAGGGGATTCAGAAAAACAGGCATTCCTAAACCTGTGACATTGGTTAA[T/C]TTGTGC AGGAGTTTCTTCCTCCTGTTATTTGTTAAATGCCCCCAGAAGCTCGAAAGCAGGAAGTGTTTGAAGGGGATTCAGACAAGGTTAGCTGGGAGG |
| rs10953770 | 1138 | GTACAGTGAAAGCACTTCAAATCTTTCAAAATCTTTGCCTGTAATCATAAGAAATTATTATCTTAGGATTCTTGATATATTACATCGAAATCAAGGTTTATGTTATA[T/A]TTGAGTAA AGTTTTCAAGGATGAAAACGATTTGTTCCTCCCGTTATTTTTTCTGAAGAATCTGAAGACTCTGTTCCTGA |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs11099210 | 1139 | GCTCTGGACCAGCCACGCTGGGAGGGAAACCACCTGATTTCAGTACAGAACCACTCTCATGCTACCCTCTGCTGAGAGTTATTCCATCACTCAATAA[A/C]ATTC<br>TTCTCGCCCTCCTCACCCCTTGATTGTCAGTGTAACCTCACTCTTCTTGGACGCTGAACAAGAACTGAGGAACTGCTGAATGCAGTACAGCTGT |
| rs10785736 | 1140 | TACTTCAATAACATCTACACTTTTAAAGAAGAAGATTCAATCTCAGAGAAGATTCAATCTCAGCTGGGAATATTTATTGTTCATACTAAACA[A/G]TTGAGC<br>CAGTGGATCAGCAGTAGCTAGCTTCAATGCCAAGATTCTTAAGTAGACACATTACATTTCGTAGGGGATCAAAATGTCATTCTCAGTATGCTAAT |
| rs11221881 | 1141 | CCATCTCTAATTTCCGGGAGATTTATAATTTGTTGTATTATTTTGTGAATCATCCGTTCATGTCTCTGCCTATTCTTCACGTCTTTTCTTATCAA[T/C]TTGTAAAG<br>ACTCTAATGTAATAGCCAACTGCTACAAGCATGTTCATATGCATGTTCTGATTTGTGTTTACCTTTTGATGTCTTCTGATATTAAAAGATGCTTATATAGCTG |
| rs11727770 | 1142 | CTCCACATCTGTCTACTTGCTTGTTGACTATCTTCACCCCCTTAGGCTATAAGTACTCCACTGATCTGTCTCAAGTGTCTGGTTCATAGTTAAAAGTCAATA[A/C]TTACGT<br>GATGAATGAATAGATGAATGGAAAAATCAATGATGGTGGATTGATCTTTACAGATTAACTTGAACCAGATCATGTAAGGAGCTGTTTAA |
| rs10102733 | 1143 | TTTAGCTTCATGATTTAACAGGAATAGTGTGAGTAAATGACATGAGTCACTTAAAGCCTTTCAGAAGGAGAAGTACCAGCTTGATGTGGGAAAAAA[T/C]TGGTC<br>ATGGTGGCTCACACGTGTAATCCTAGCACTTTGGGAGGCCGAGATGGGCGAATCACAAGGTCAGGAGTTCGAAACCAGTCTGCCAACATGATGA |
| rs10030074 | 1144 | CAGGACTTTGGGAGGCCAAGGCAGGTGGATCAAGGAGGTCAGGAGTTCGAGACCAATATGGAGAAACCTCTCTACTAAAAATAAGAAA[G/A]TTA<br>GCCGGGCGTGGTGGTGGGCACCTGTAGTCCCAGATACTCGGGAGGCTGAGACAGAAAATACTTGAACCCGGAGGTGGAGGTTGCAACGAGCGGA |
| rs10510379 | 1145 | TTAGCCAGGATGGTCTTGACCTCTGACCTCCTGAAATTGTCATTATTTGCTTTTAATGTGATTGCTTTTATGAGAATAACTATGAGCTCATGAGATTTTATATAGTA[G/A]TTGTCAC<br>GCATGTCCGTGTGAAGAGAGTCCACCAACAGGCTTTGTGTGAGCAACAAGGTTGTTATTTCACCTGGGTGCAGGCGAGTCCAAAAAA |
| rs13110085 | 1146 | TGCTGTGGTTAGGAGGTATAACTTGGTTAAGTGTTTCTTATCCACCGCGTAGGCTATGTTTACATAGCCTATGTGCACATAGCCTATGTGTGCATAGTTTA[C/A]JATTTC<br>CTACCAGCCCCCCAAAAAGGAACACTTGCTTTCTTATCAACTTGCCCAAGATGTGGGTAGAAGGGCAAGTGGTAGAGCTCGCAAGC |
| rs13269702 | 1147 | TACTGTTCTCAAAAGGCAAAGTCCTGTCTAGTTCATGACTTCATGTAGTATCAAGATTCAATATGTCAGAGATAAAATAAGAATGGAAAGTGATGAGATTTCATCATCAA[A/T]TTGTCAT<br>TTCCTGTGAAAAGGCAAAGATGATTTCATAGGCTTGGCTGGACACATCTAGAAACGTTTTAAGGGCTTTGGAACATGATAGAGCACACAATCAGACA |
| rs9312864 | 1148 | CTGGCCTACAATTTTTAAAGTGATAACATGAAGAATAAAAAGCTGACAACTGTTCAGATTAAAATAAGGTAAGTAAAAATCATTATCACTAAAGGCAA[T/C]TTGAGC<br>TTTCGATTTGGCTCAGATTGTGGGGAAAGAAGGTGGGGTGGGAAAGAGGTGGAGGACATCAGTTGCCACAAAATTATTGAAACAATTGGTG |
| rs9787011 | 1149 | GATAGTCCTTAGGCCTTGAAGTCATTAGAGTGCAATGCTGTAGGGCCAGAATGCTGTAGGGTAAAGCCGGATAAACAAGGGGTTTGTGGTGAAGA[C/A]ATT<br>CACTTGAAGGGGCACTTAACATGTTATCTGATGCGCTACATATCCTGATAAGTGCTCAGTTATTTGACCTGTGATAAGTCAACAATGATGATTATGCCAATGAATACAACCTG |
| rs9555581 | 1150 | GAATATCTTTACATTGATTTCCTGATGCGCTACATATCCTGATAAGTGCTCAGTTATTTGACCTGTGATAAGTGCTCAGTTATATCCAGAAGCCAACTTAATAGATCAGAGCAGATTTAAGGCAAAATTACTTTAGGATAATGG[C/T]CAATAC<br>AGGAGTGAGGTCAGATTGCCTTTTGAGAGTAAATCCAGAGGAGCCAACTTAATAGATCAGAGCAGATTTAAGGCAAAATTACTTTAGGATAATGG |
| rs8016543 | 1151 | AATGAGGATGATGAAGGGAAGTGCTCTGTGCAGAAGTCCTGTCTAGTCCAGGGGCTTTTAACCCTTCAGGAGTTTGGCTGGCCCAGTTCATCGAGCAGAAAAGGGAGTAGTAGTACTTGTCACAAA[G/A]TTT<br>GGCTTCAGTATGCAGTTTCATAGCGTCTGGACCTGTATAGAGACCCAGGAGAATGATAGAGCTACTTCTTTGTAATGACACTTTGACACATTTG |
| rs13155942 | 1152 | CTCTGTGATTTAGATTGTGGGTTTATATTGCTGACATGCATGCTATCTGCGGTTCTCGCGGTTTTCTCTGGGTTGAGGGTACCTTTCTTTCTTCCAGGGATGA[T/A]TTGTGT<br>TTGCTTTTGTCAGACACTGAGCACTACTGAGCAATGAAACACACTGTCGAGTCAGCCATATAAACTACGTAAACAGTGTAGATTCAGTT |
| rs11655850 | 1153 | TGCACAGTCACCCTGGAGAGAACCATGCGCTGGGAATCCAGATGCCACAAGCCCAGATCCAGGACACACTGTCATGCAGGCTTCCTCCCCACCACCACTCAGGAAAGCAAACTGCTACA[A/C]TTA<br>AAAAGGAACAAGGCAAGTCTGGTGCTCCGTGCTTCTCACTGGGATTTTTTTCTTTTTTAAGACAGAGTCTCACTCTGCCATCAGGCTGCA |
| rs13331222 | 1154 | ATAAATATAATTAACAAAGAGAATAACAAGAACAAGAATCAGGTTGACTGTGTATCATGTGGGTATGTGTATCATGTAAAATGGAGAGCCATGAGTGAAA[T/C]TGTATA<br>CCAAAGGAAGCAACGTATATTCTTAAAAAAGGAAAAAAAAAGCATGAGAATGATGAGAATGAGAAAAAGAACTGGAATGATGGAATACACCCTAAAATGAGCTCATTGGTCTGTGAAATGCAGTCGTAACTACTGGAACTGAAGGTTTTAT |
| rs10110766 | 1155 | GGGCATCTTCAGTTAGTACGTGGTACTGGACAAGAAGATCAGGTTGACTGAACAAGTCAGTTCAGGTCAGGATGGTCTCGAGCTCGTTAAGGCTCATCTGTGTATCATGTAAAATGGAGAGCCATGAGTGAAA[C/T]TGGA<br>CAGGGGCTATCAAGTAGCCAGGTTTTGAGGGACTCAGTTCAGGAGAACTGGAACTGAAAGAACTGGAAAGAAAACAAGCCAGGTCCTGCTGCTTTTCTCCTTGAGAAATT |

TABLE 11B-continued

Corresponding Genomic Sequence with Alleles provided in Brackets

| SNP_ID | SEQ ID NO: | Corresponding Genomic Sequence with Alleles provided in Brackets |
|---|---|---|
| rs9554894 | 1156 | CATTCCTTCCATTACATACTTCTTTGTCGACCTGAGTTTCAGCCCGTTGCTGAAATAAAAGCAAGTATTGCACAAGAATCAGTTTGTGTTCCATCCA[A/C]TTCCAA AGTTTGAGTTGTGTCATGCCCAACAGGCAAACACACCTCACTCAGTAATTGTGTTAAGAATGAAATAGGCCAGTGCCTCACGCCTGTAATCC |
| rs17152417 | 1157 | AAACAAACAAAACAAAAACAAAAAACCCATAATTCAGCCCACCAGTGGCCTCAGTTACTGTCTGTGTACAGAGTCTGTTTGTGGGATATTCTGGCTCTCCCACAA[T/C]TTCAG CTGATGTCCAGAGTTAAAGGGCTCTAAAGCTCTATAAAGTTGCTAAGGAAAGCCCTCAATGCTAAGGCTTGATACAAAAT |
| rs17156383 | 1158 | ATAGACATTCACTAAGATATTGCATCTATGAAAAATAATTACACGCTATGTAAAAGTAGCAATAAAGTACTGAAAATGTATAA[T/C]TGACAAA CATAAACTGCATATGAACTTTGGAAGAGTAAATAAAGTATCCTGGAATATAGAACAAAAATATAGAGTAAAAAAAGAAAAATCTTAGA |
| rs11017936 | 1159 | GGAACCAAGTCCCATCATTGCAATATCTCTCTGGATTCCATTGTAATCCATTTCAGACGCAGCCACACGTGTTCATGAACTCATCAATGCAATCTGGAAA[T/C]TTGAC TTTGGCTTGTGATCTCTGACATTTTGATGTTTTAAAGTGGGTTTTCTGGAGTGGAGTCTTGGCCTCCTCTCCACACTTACCGAGTCTTCCTATG |
| rs10777944 | 1160 | CTATTTGCTTGTGTCCCTTCATCTCCTGGACCATGAGCTCCTGGAGAGCAGGATGTGTCTAATGCATGGCAGGCACTCTATCAATACAGGAATG[C/A]ATTT TATGTGGAATCTGACTTTTTTCCTCAGATGTGGAAGCACGCACAAACATATGTCTGAATCAAAAACCCGGACATAAAAGCCTCACACAGGGT |
| rs10278812 | 1161 | TTATTTGTGAGCAGTAGTATTTTAGTTTAAATGGTAGATATTAAGCCTGTACAATGATATTCAAACAATGGTATATTGAATGAGAAGAATCTGTCATAA[A/T]ATTAGAG TAATGGTTTGAAAAACCAATGTTTGTGGAGATAGCAGTCAGTGGGAGATAGTATGGGGAGAACAGAGCTAGAAGCTGAAATTACAAAGTGATCAAG |
| rs10784847 | 1162 | GGCAAGACAAAGAAAGGGAGTTCAGCCTTGTAGGGGTGGTAAATTGTGGATTTTCTCGGTATGAAAGAGTGAAGGAGGACGTTTTCTTAAACAAAAAT[T/G]TATG CCCTGCTTTCAAGCAAGTAGGGGAGGGCACACAGAGCTTTTCTGTGCCTGCTATTTCTTGATTGCCTTAAATAATTCTTATGTCAAAGAG |
| rs10179379 | 1163 | TACACAGGGCAGACATGATGGTCGGCTTGGCCCCAGTGTGGTGGCAGCAAGGGTAGTAGAAGGGTAGTTCTGGTTATATGTTAAAGATAGAGCACCAG[C/A]ATT TCCGGACAGATTGGATGGGAGGTGTCACTAAAACAGAAATCCAGGGATAACTCTGAGGTGTTTGGCCTGAGTTATTAGAATGATAATTATATTTA |
| rs17074340 | 1164 | AATGTGGTGGCCTCACACTAAGACGTAGAGAGAAGAGAAGAAGCTAGAGTCAATGAAGACTCCATAAATGCTACTCCAACAGAGGAGGTGACATAAGTAAGTA[A/T]TTCC ATGGGAGGAGGGAGTCAGCAGTGGGAGATAATGAACAAGGAATAATTATAAGAAGAAAATGTAAAAGATAAGTAAGTCATTAATTCCCT |
| rs12297215 | 1165 | ATTTGCTATCTCTGGATATCTAGCTTATTTCTAAAAATCCTCTAGTGACCATGAACTATCTTCAGACCAGAAGAACATCTTTCTGGGATGCTCTGGGTTCAA[T/C]TTATTC CGGCTCGTACCATTTACCAACTCTTTGATCATAGAAAGGAAAAGTTTATCATTATTAAACGTGCAAAAGCACTACCTGTT |
| rs1041409 | 1166 | ACCATATTAGTAAGTCTCCCCCTGCATTATGGTTAGTGTCTAGTGTGTCACTCATATCATATCAGATTCTTCACTCATAAAGTCCCCATGT[A/G]ATTCTAT TCCCATAGTAAGTACCTGCTTCTTCTAGCACCATGTACTATGTACTACTGCACAAGTAGCCAGAATCAGATTTGTCTACAGAATTGAGAACTA |
| rs2826737 | 1167 | TTTACCAGGAATTGTGATACTTCATTTATACACATACTTTATTTAATCCTTACCATGACCATAGATGACTTACATATGCTAAGAGCCAGGACTCTAGTCC[G/A]ATTCAAA TCTGTCTGACCCCAGAATCTTAGCATTTTCTTCGAAATAAAAGAGCCATATTTTTACCACCTAATGTGT |
| rs2834712 | 1168 | GGACTTACAGTCTCATTCAGGAGACCTTGACAAACAAATGCTAACAATAAAAACCACCAGACTGCTATTTAGCCATTCGTCTGGGATGACTATATATTAAT[T/C]ATTTTA TGACAGCCGTTTCTTCCTTCTGAATGGTGTTACCAGCGAGGTACCTCCTTTGCTCAATGTTGCTTAAAGACATGTCTATATATATCTGGCAAG |

Conditions Used for Testing

PCR

PCR was performed with or without the addition of Tsp509I to the PCR cocktail mix as indicated in Table 12. PCR cycling was performed for all samples with the cycling conditions in Table 13 to allow Tsp509I digestion of the DNA immediately prior to PCR amplification and in a single tube. This was used even if there was no Tsp509I added to the cocktail.

TABLE 12

| Reagents | Final Conc | | Volume per reaction (uL) |
|---|---|---|---|
| Water | n/a | | 3.125 |
| 10xPCR Buffer | 1.25x | | 3.125 |
| MgCl$_2$ (25 mM*) | 1.625 | mM | 1.625 |
| PCR Nucleotide Mix (ACGU) | 0.2 | mM | 0.5 |
| F/R Primer mix (0.5 uM) | 0.1 | μM | 5 |
| 10 U/ul Tsp509I | 0 or 0.02 | U/ul | 0 or 0.05 |
| 1 U/μl Uracil-DNA-Glycosylase | 0.05 | U/ul | 0.625 |
| HotStar Taq (5 U/uL) | 0.2 | U/ul | 1 |
| Total volume | n/a | | 15 |
| DNA - added separately | varies | | 10 |

TABLE 13

| 30 C. | 10 min | UNG digestion temperature |
|---|---|---|
| 65 C. | 15 | Tsp509I digestion temperature |
| 94 C. | 15 min | Taq activation |
| 94 C. | 20 sec | ⎤ |
| 58 C. | 30 sec | ⎥ 45 cycles - Amplification |
| 72 C. | 1 min | ⎦ |
| 72 C. | 3 min | Final extension |
| 4 C. | Forever | Storage |

SAP

SAP dephosphorylation was carried out with standard conditions including the SAP cocktail preparation below in Table 14.

TABLE 14

Table 14. SAP Cocktail preparation

| SAP Mix Reagent | Volume per Reaction |
|---|---|
| Nanopure Water | 2.95 μl |
| SAP Buffer | 0.34 μl |
| Shrimp Alkaline Phosphatase (SAP) (1.7 U/uL) | 0.71 μl |
| Total Volume | 4 μl |

TypePLEX Extend

TypePLEX Extend reaction was carried out with standard conditions including extend cocktail preparation below in Table 15.

TABLE 15

Table 15. Extend Cocktail Preparation

| Extend Reagent | Volume per Reaction |
|---|---|
| Water (HPLC grade) | 1.24 μl |
| TypePLEX buffer (10x) | 0.4 μl |
| TypePLEX Termination Mix | 0.4 μl |

TABLE 15-continued

Table 15. Extend Cocktail Preparation

| Extend Reagent | Volume per Reaction |
|---|---|
| Extend Primer Mix (3-tiered 5-15 uM stock conc) | 1.88 μl |
| Thermosequenase (32 U/uL) | 0.08 μl |
| Total Volume | 4 μl |

Digestion of Heterozygous SNPs in Genomic DNA

CEPH genomic DNA obtained from the Coriell collection was used to test the ability of Tsp509I to specifically digest one allele of each SNP. The informative allele peak area ratios of DNAs heterozygous for the indicated SNPs were determined. The informative allele, alternatively called the target allele, is defined as the allele NOT recognized by Tsp509I enzyme. Tsp509I treatment significantly increased the peak area ratio. With no Tsp509I treatment, heterozygous DNAs show median allele ratios ranging from 0.4-0.6 depending on the SNP. After Tsp509I treatment, for the majority of heterozygous DNAs, the median peak area ratio is above 0.8 with many peak area ratios at 1.0. Peak area ratios of 1.0 indicate that there is no detectable non-informative (i.e., non-target) allele peak area present.

2% Mixture Model

A DNA mixture model was prepared from CEPH genomic DNA obtained from the Coriell collection. The DNA mixture model was used to test the ability of Tsp509I to enhance the detection of one allele of a SNP when present at a low fractional concentration. Briefly, the DNA mixture model comprises 47 unique child/maternal DNA pairs mixed together such that the child's DNA (the low fractional concentration DNA) is present at only 2% of the total DNA. For the studies here, DNA was added to the PCR such that there were 20 genomic copies of the low fractional concentration DNA and 980 copies of the high fractional concentration DNA in each PCR. In these mixture studies, not all DNA pairs will yield informative data for every SNP. Informative data can only be obtained for a SNP when the maternal genotype is homozygous for the non-informative allele and the child's genotype is heterozygous for the SNP. With no Tsp509I treatment, potentially informative DNA mixtures show median informative peak area ratios at background levels. After Tsp509I treatment, the majority of DNA mixtures with potentially informative genotype combinations for the indicated SNP show median peak area ratios above 0.5 with many peak area ratios at 1.0. Peak area ratios of 1.0 indicate that there is no detectable non-informative allele peak area present. This indicates the utility of the multiplexed SNPs to detect a low fractional concentration DNA present at least as low as 2% of the total DNA present and at levels as low as 20 genomic copies of DNA.

Detection of Low Fractional Concentration DNA

Modified versions of multiplexes 2, 5, and 6 with a total of 95 SNP assays (see Table 16) were tested for their ability to detect a low fractional concentration DNA. Sample test groups included:

1) Maternal only genomic DNA used in DNA mixture models
2) 2% DNA mixtures of child/maternal genomic DNA
3) Maternal PBMC DNA (pairing to the plasma DNA below)
4) Maternal plasma DNA previously shown positive for 8 Y-chromosomal markers indicating the presence of male fetal DNA (pairing to PBMC DNA above)

For the comparison, each of the above sample types was digested with Tsp509I prior to genotyping with the TypePLEX extend assay. Separately, maternal genotypes from undigested maternal DNA was determined to identify potentially informative SNPs for each sample. For this analysis, no genotype information obtained directly from child genomic DNA or fetal genomic DNA was used.

With 95 SNP genotype assays, one would expect to have 3 or more informative genotype combinations in ~99.9% of cases with biologically related maternal and child genotypes. Therefore, detection of at least 3 informative SNP alleles present in a Tsp509I digested sample that are not present in an undigested maternal only DNA sample should allow detection of a low fractional concentration DNA. Increasing this required number of detected informative SNP alleles to greater than 3 will likely increase the specificity but at the expense of sensitivity.

In prior studies with the DNA mixtures, it was noted that in the Tsp509I digested samples, background levels of informative allele peak area could lead to artificially high detection of an informative allele peak area ratio. Therefore, preliminary threshold criteria were established to improve the accuracy of detecting informative SNP alleles arising from low fractional concentration DNA. In the data here, these thresholds are defined as follows:

1) Informative allele peak area ratios must be at least 0.4 greater in the digested DNA mixture or digested maternal plasma DNA sample versus the matching undigested maternal sample.
   —and—
2) There must be greater than 15% primer extension product generated for the SNP.

The criteria used here to determine the presence or absence of an informative SNP allele are preliminary and are only exemplary. Additionally, individual SNP assays within the multiplexes may have their own criteria. Alteration of these criteria can have significant impact on the detection of informative SNP alleles in either a positive or negative manner.

Figure 10:
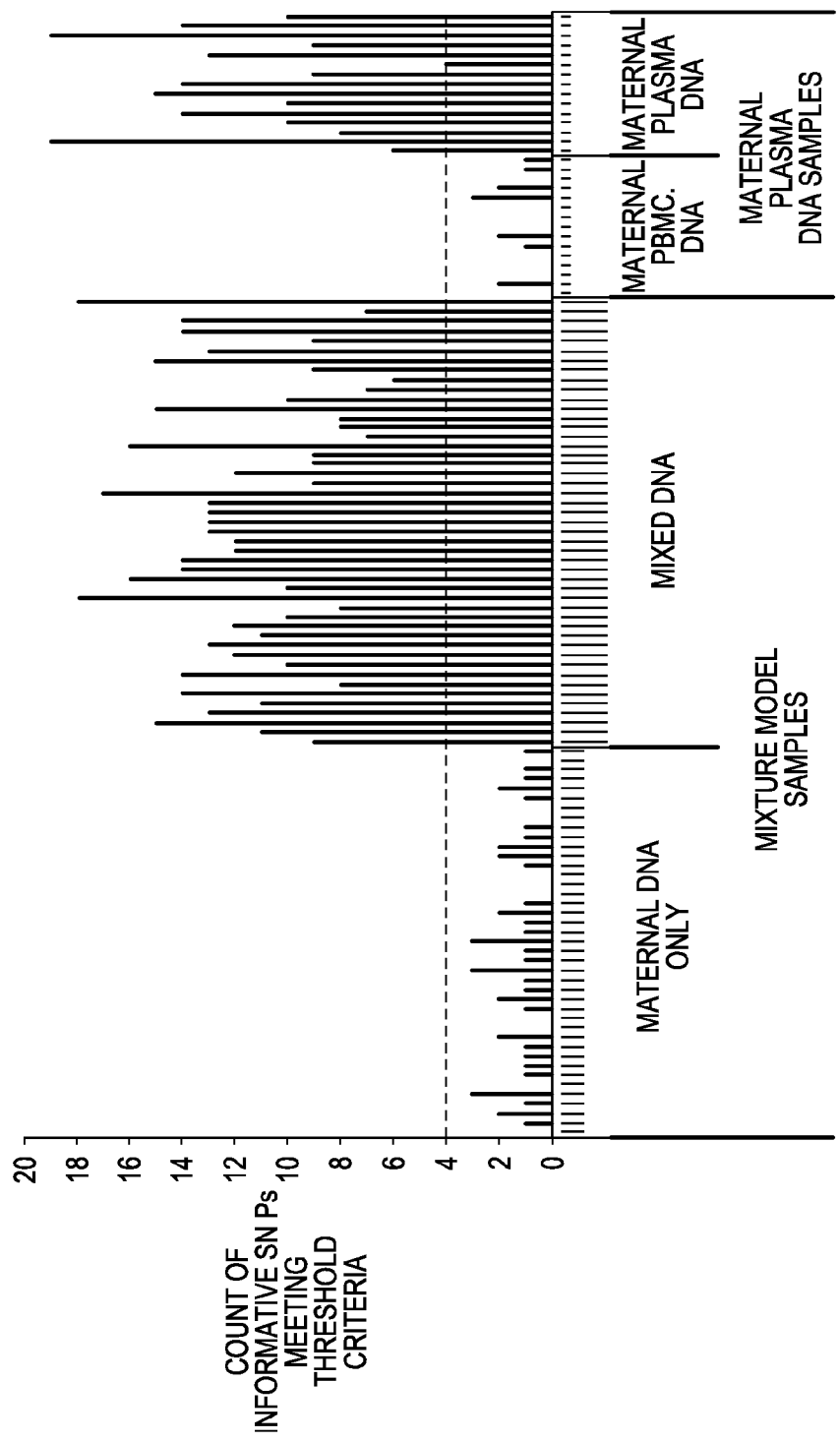
FIG. 10 shows the number of SNPs for the indicated Tsp509I digested sample with greater than 15% primer extension rate and 0.4 or higher increase in informative allele peak area ratio when compared to the matching undigested maternal DNA only (for mixtures) or undigested maternal PBMC DNA (for PBMC and plasma DNAs).

As can be seen in FIG. 10, there is a clear delineation between mixed DNAs and maternal only DNA in the DNA mixture model, where at most 3 informative SNP alleles (as defined by the criteria above) are detected in maternal only DNA and 6-18 informative SNP alleles are detected in each of the DNA mixtures containing 20/980 genomic copies of child/maternal DNA. In the plasma sample testing, this delineation, while not as clear as in the DNA mixture model, is still present between maternal PBMC DNA and maternal plasma DNA. Here, maternal PBMC DNA shows at most 3 informative SNP alleles detected while the maternal plasma DNAs show 4-19 informative SNP alleles detected. The dashed lines represents a possible cut-off value for informative and non-informative alleles. These data provide an evaluation of the utility of the method to detect low fractional concentration DNA.

Detection of Fetal Identifier Alleles in Maternal Plasma

The ability to detect fetal identifier alleles in maternal plasma DNA and non-pregnant female plasma DNA was compared. Ninety-two of the fetal identifier SNPs in Table 16 in 3 multiplexes were assayed by genotyping buffy coat, PBMC or whole blood genomic DNA from plasma samples. The samples were analyzed in parallel with and without Tsp509I digestion, and they were subsequently genotyped for the same SNPs. Genotype measurement was performed on the MassARRAY® system. A fetal identifier allele was counted as 'detected' if the undigested genomic DNA was homozygous for the cleavable SNP allele and the matching plasma DNA sample showed the presence of the non-cleavable SNP allele after digestion of the plasma DNA with Tsp509I.

Figure 11:
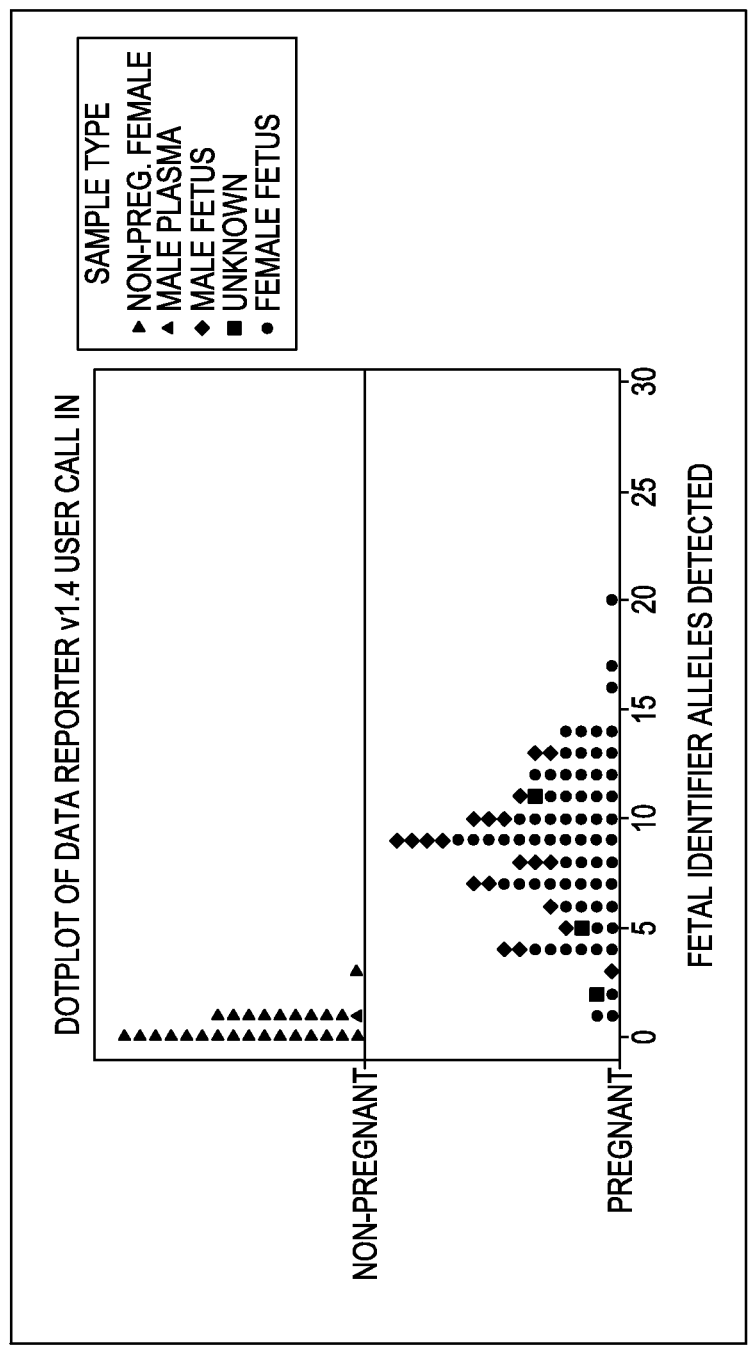
FIG. 11 shows results from 92 fetal identifiers tested in 117 plasma samples from pregnant and non-pregnant women. The x-axis of the dot plot in the top portion indicates the number of fetal identifier alleles detected in a plasma DNA sample (i.e., the number of informative SNPs). Each dot in the dot plot field represents a sample. The top portion of the panel comprises 27 non-pregnant plasma samples. The bottom portion of the panel comprises 90 pregnant, maternal plasma samples. The legend provides sample type and fetal sex (if known).

FIG. 11 shows the results from the 117 plasma samples tested for the 92 SNPs. The x-axis of the dot plot above indicates the number of fetal identifier alleles detected in a plasma DNA sample. Each dot in the dot plot field represents a sample. The top portion of the panel comprises 27 non-pregnant plasma samples. The bottom portion of the panel comprises 90 pregnant, maternal plasma samples. The legend provides sample type and fetal sex (if known).

Figure 12:
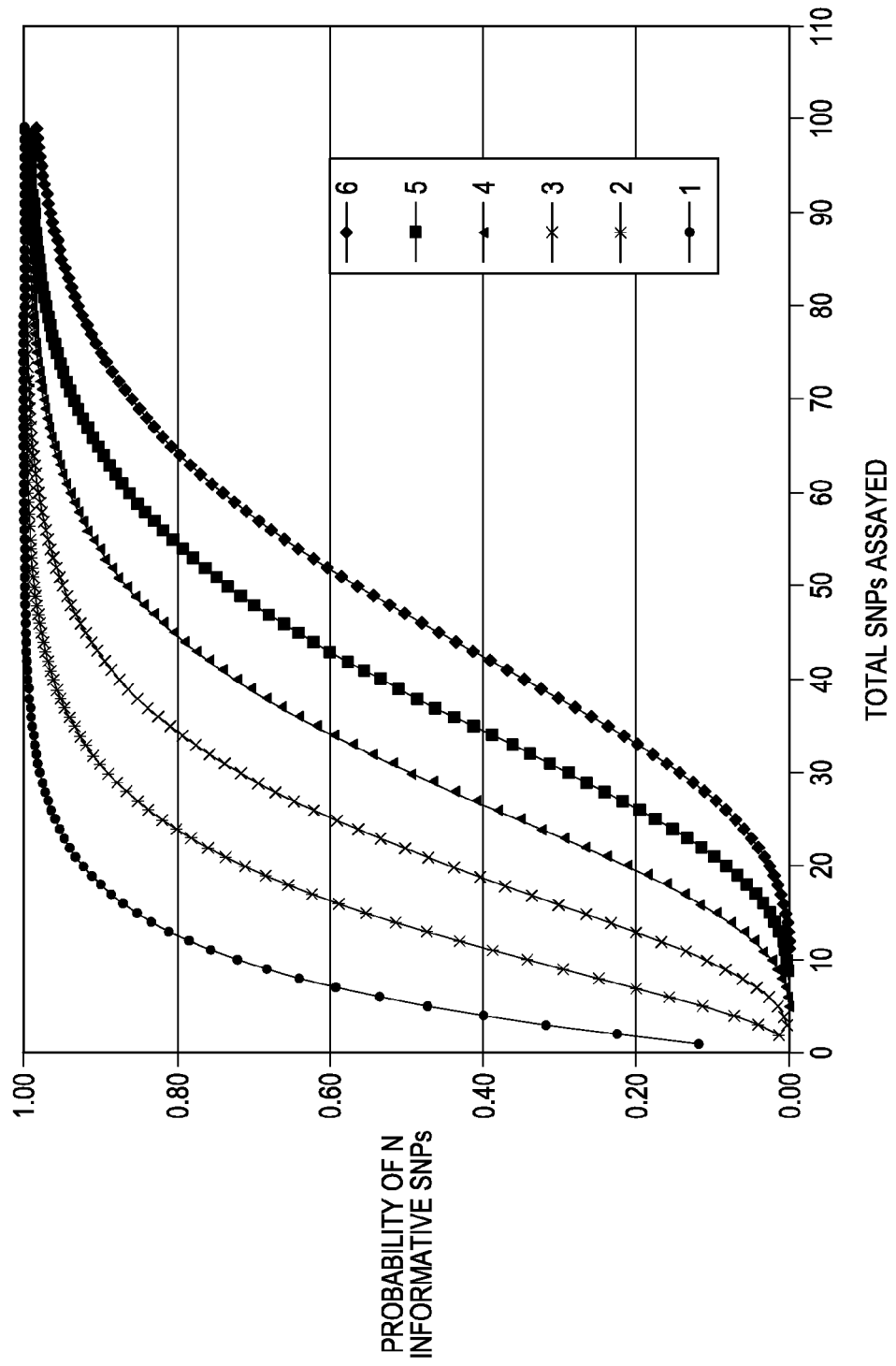
FIG. 12 is a graph showing the probability of the number of informative SNPs for each of the selected thresholds (1-6) at increasing numbers of total SNPs assayed.

As expected, the fetal identifier alleles were detected in the pregnant maternal samples and not the non-pregnant plasma samples. As the number of SNPs tested increases, the probability of the number of informative SNPs also increases. This is shown graphically in FIG. 12. The FIG. 12 graph shows the probability of the number of informative SNPs for each of the selected thresholds (1-6, shown each with a different color) at increasing numbers of total SNPs assayed. For example, if 90 SNPs are assayed, the probability of at least 4 SNPs being informative is almost 100%.

TABLE 16

| MP2.1 | | MP5.1 | | MP6.1 | |
|---|---|---|---|---|---|
| rs11835780 | rs748773 | rs7323716 | rs4311632 | rs6488494 | rs9652080 |
| rs13110085 | rs1363267 | rs10785736 | rs13269702 | rs10840805 | rs7356482 |
| rs1797700 | rs2723307 | rs7831906 | rs2993531 | rs4764597 | rs9818611 |
| rs1885121 | rs4589569 | rs12903747 | rs1372688 | rs2820107 | rs7320201 |
| rs1904161 | rs6766358 | rs4869315 | rs1720839 | rs12675087 | rs3913810 |
| rs10901705 | rs7689368 | rs6542638 | rs6582294 | rs725849 | rs12450474 |
| rs7144509 | rs7900002 | rs1346718 | rs10234234 | rs910500 | rs1503660 |
| rs8016543 | rs4489023 | rs2007475 | rs11221881 | rs1916803 | rs683262 |
| rs13155942 | rs10260483 | rs10110766 | rs494220 | rs4488809 | rs1041409 |
| rs3912319 | rs4533845 | rs11099210 | rs9428474 | rs3816551 | rs10754776 |
| rs9929404 | rs6556642 | rs4130306 | rs7294836 | rs7205009 | rs2734574 |
| rs4673821 | rs12674093 | rs1401454 | rs614004 | rs2322301 | rs9285190 |
| rs1444647 | rs7741525 | rs179596 | rs7818415 | rs17074340 | rs331893 |
| rs12007 | rs2462049 | rs9787011 | | rs9356029 | rs10806232 |
| rs6569474 | rs11105611 | rs9989393 | | rs10898954 | rs12107918 |
| rs6043856 | | rs664358 | | rs263025 | rs1593443 |
| rs6142841 | | rs1342995 | | rs273172 | |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate values thereof (e.g., 54%, 85.4%). Thus, it should be understood that although the present invention has been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claims that follow.

What is claimed is:

1. A method for detecting in nucleic acid from a sample the presence or absence of an allele of paternal origin, comprising:
   a) cleaving nucleic acid from the sample with a Tsp509I restriction enzyme;
   b) exposing the nucleic acid after (a) to amplification conditions that amplify uncleaved nucleic acid but not cleaved nucleic acid, and which amplification conditions are capable of generating amplification products comprising some or all of the single nucleotide polymorphic loci selected from the group consisting of:

| | | | | |
|---|---|---|---|---|
| rs11835780 | rs748773 | rs7323716 | rs4311632 | rs6488494 |
| rs9652080 | rs13110085 | rs1363267 | rs10785736 | rs13269702 |
| rs10840805 | rs7356482 | rs1797700 | rs2723307 | rs7831906 |
| rs2993531 | rs4764597 | rs9818611 | rs1885121 | rs4589569 |
| rs12903747 | rs1372688 | rs2820107 | rs7320201 | rs1904161 |
| rs6766358 | rs4869315 | rs1720839 | rs12675087 | rs3913810 |
| rs10901705 | rs7689368 | rs6542628 | rs6582294 | rs725849 |
| rs12450474 | rs7144509 | rs7900002 | rs1346718 | rs10234234 |
| rs910500 | rs1503660 | rs8016543 | rs4489023 | rs2007475 |
| rs11221881 | rs1916803 | rs683262 | rs13155942 | rs10260483 |
| rs10110766 | rs494220 | rs4488809 | rs1041409 | rs3912319 |
| rs4533845 | rs11099210 | rs9428474 | rs3816551 | rs10754776 |
| rs9929404 | rs6556642 | rs4130306 | rs7294836 | rs7205009 |
| rs2734574 | rs4673821 | rs12674093 | rs1401454 | rs614004 |
| rs2322301 | rs9285190 | rs1444647 | rs7741525 | rs179596 |
| rs7818415 | rs17074340 | rs331893 | rs12007 | rs2462049 |
| rs9787011 | rs9356029 | rs10806232 | rs273172 | rs6569474 |
| rs11105611 | rs9989393 | rs10898954 | rs12107918 | rs1342995 |
| rs6043856 | rs664358 | rs263025 | rs1593443 | and rs6142841, | thereby generating amplification products;
   c) analyzing a sufficient number of the single nucleotide polymorphic loci of the amplification products of step (b), whereby at least one of the single nucleotide polymorphic loci analyzed is informative of the presence of an allele of paternal origin; and
   d) determining the presence or absence of an allele of paternal origin based on the analysis of step (c).

2. The method of claim 1, wherein part (b) is conducted using amplification primer pairs selected from the group consisting of:

5'-ACGTTGGATGGGCTCTAGTTTTCAGCAGAC-3'
and

5'-ACGTTGGATGCTCAAAACCTGGCTACCTTG-3';

5'-ACGTTGGATGCTTCTTTTCCCTGCATCATC-3'
and

5'-ACGTTGGATGAGGGAAGTGTTGTAGCATGG-3';

5'-ACGTTGGATGAAGCAGGTACTTACTATGGG-3'
and

5'-ACGTTGGATGGTACTGTTAGTGTGTCACTC-3';

5'-ACGTTGGATGTTGCCTAGCCTTACATCCTG-3'
and

5'-ACGTTGGATGCTCAAAATAGATGATGGACTG-3';

5'-ACGTTGGATGCAATCAGCTACTGCTGATCC-3'
and

5'-ACGTTGGATGTGGTTTGGTTTCTCAGCTGG-3';

5'-ACGTTGGATGGAGAGAGGGAGAAAGTAGAG-3'
and

5'-ACGTTGGATGCCCTTACTCAGTGATTCCTC-3';

5'-ACGTTGGATGCCTACCTTGCTCTGAGAAAC-3'
and

5'-ACGTTGGATGCTTCCTGCTTTTAAGCAGTC-3';

5'-ACGTTGGATGAGTGCAACAGAAAAGGCAGG-3'
and

5'-ACGTTGGATGGGTCCTTGGTATGTGTTCTC-3';

5'-ACGTTGGATGTCTGAAGGTAGACCTGGATG-3'
and

5'-ACGTTGGATGCTCAGGATATCATTACACACC-3';

-continued

5'-ACGTTGGATGGTTACACTGACAATCAAGGG-3'
and

5'-ACGTTGGATGACTCTCATGTACCCTCTCTG-3';

5'-ACGTTGGATGAGAAGATATGTTGAGAGGGC-3'
and

5'-ACGTTGGATGTATTCCCTTTCTGGCTGTGG-3';

5'-ACGTTGGATGCTGCCTATTCTTCTACGGTC-3'
and

5'-ACGTTGGATGCAGAAACATGCTTGTAGCAG-3';

5'-ACGTTGGATGAATGAGAGCTTGCTTACTTC-3'
and

5'-ACGTTGGATGAGTGTCGTTCAGACACTAGC-3';

5'-ACGTTGGATGTTTAATAGGGAAAGTATTGG-3'
and

5'-ACGTTGGATGCACACCCAGAAGCACTGATA-3';

5'-ACGTTGGATGCCTTCTGCTCAACTACCAAG-3'
and

5'-ACGTTGGATGGCCAAAGACGATGTGGAATG-3';

5'-ACGTTGGATGTTTCACAGGGTTAGGATGGG-3'
and

5'-ACGTTGGATGCTAGCAAAGGCTGGATTCTG-3';

5'-ACGTTGGATGAGCCACCAAAACCAAGCTTC-3'
and

5'-ACGTTGGATGCTTGTAAGGCAGGTCTGATG-3';

5'-ACGTTGGATGGCTTGCAGAGGTTCACTAAC-3'
and

5'-ACGTTGGATGTGAGGCCATTAAAAGCAGGG-3';

5'-ACGTTGGATGAGCAAGTGTTCCCTTTTTGG-3'
and

5'-ACGTTGGATGCACGCGTAGGCTATGGTTTA-3';

5'-ACGTTGGATGCGGTTTCTTTTGAGGACTGG-3'
and

5'-ACGTTGGATGGCTCAGTGTCTGACAAAAGC-3';

5'-ACGTTGGATGAAGAATGGAAAGTGATGAG-3'
and

5'-ACGTTGGATGCTAGGCTTGTTCACTATTTG-3';

5'-ACGTTGGATGCATTGCTTGGGTCTTCTCAG-3'
and

5'-ACGTTGGATGGGGTTCTGGCAGATATATCC-3';

5'-ACGTTGGATGTATGGATGCAAGCCTTTCCC-3'
and

5'-ACGTTGGATGAGGCTGAAGAATGCTTTCCC-3';

5'-ACGTTGGATGTGTGCAGCACTTTTCACAAG-3'
and

5'-ACGTTGGATGCAGGGTCACATCACAGATTG-3';

5'-ACGTTGGATGGCTTGTTAAATGTGTGTTCC-3'
and

5'-ACGTTGGATGTCCCTCAGTTTAGTTTTGTC-3';

-continued

5'-ACGTTGGATGGATAATATTGTGCTGCATGCT-3'
and

5'-ACGTTGGATGACCTTGTTCTGTGTGTGTGG-3';

5'-ACGTTGGATGCTCCCATCTATGATTTCCAG-3'
and

5'-ACGTTGGATGATGCATATCTGGAGACACAC-3';

5'-ACGTTGGATGCCAGTCAAGGAAGCAGTTTC-3'
and

5'-ACGTTGGATGGTCTGATTAGGCCTAAGAGC-3';

5'-ACGTTGGATGTACCATGCTCATTGAACTCG-3'
and

5'-ACGTTGGATGGGAGATTTGATAGGAAGTGC-3';

5'-ACGTTGGATGAAATGCTACTCCAACAGAGG-3'
and

5'-ACGTTGGATGCTTCATTATCCCCACTGCTG-3';

5'-ACGTTGGATGGATGATGAAAGCATAAGTC-3'
and

5'-ACGTTGGATGGAGATGTTGCAAAGATGCAAG-3';

5'-ACGTTGGATGCTGGATCTTACCTCCATAGC-3'
and

5'-ACGTTGGATGACTAGAATCGTGCAGAGAAC-3';

5'-ACGTTGGATGAAGTGCTGGGATTACAGGAG-3'
and

5'-ACGTTGGATGGAGACAGGCAAAGATGCAAC-3';

5'-ACGTTGGATGGAGACGATTCTTCAGGAAAC-3'
and

5'-ACGTTGGATGCCATGACTCTAGTGACCTTC-3';

5'-ACGTTGGATGTAAGCATCCATGGACCTACC-3'
and

5'-ACGTTGGATGCAGGTGGTAAATGTGCTCAG-3';

5'-ACGTTGGATGTTGACTCACCCACTTCTGTC-3'
and

5'-ACGTTGGATGTGTTGATGAGGTGAAGAGGG-3';

5'-ACGTTGGATGAGCTTGGGCTGAATGTTAGG-3'
and

5'-ACGTTGGATGTAAAAGCAAACAGCTTCCC-3';

5'-ACGTTGGATGTTTTTCCTCCTGTACCCTGC-3'
and

5'-ACGTTGGATGTACATGTGGTTAGAGTCTGG-3';

5'-ACGTTGGATGGGGAAGGTGTTTGTCTCATA-3'
and

5'-ACGTTGGATGTGGTACAGTTTGAAAGGAGC-3';

5'-ACGTTGGATGGCATTATGCTAAAGGCTGTC-3'
and

5'-ACGTTGGATGTCCTCTGATTTAGGCCCTTC-3';

5'-ACGTTGGATGGGATCAAGAGGAAAAAATGGG-3'
and

5'-ACGTTGGATGTAGTTTCAATCTCTGTGCTG-3';

-continued

5'-ACGTTGGATGCTATGTTTTCCCCCAGCTTG-3'
and

5'-ACGTTGGATGGCAAAAGAACAACCACCCAG-3';

5'-ACGTTGGATGGACCTTCCTGTTCCTAGATG-3'
and

5'-ACGTTGGATGTGACTGGACTGTGACATAGC-3';

5'-ACGTTGGATGAGATTGGTCCCTCACAATGG-3'
and

5'-ACGTTGGATGATTTGGCCCTGAGGCTTATC-3';

5'-ACGTTGGATGCACTGAGAGATACAGGAAAG-3'
and

5'-ACGTTGGATGCTTGTTTCCCCAACATAAGG-3';

5'-ACGTTGGATGATCCATCTCTGTCAGAGTTC-3'
and

5'-ACGTTGGATGAGAGAACTGACCCTTCACTG-3';

5'-ACGTTGGATGGGTGGAGATGGGATTCTCTG-3'
and

5'-ACGTTGGATGAACCCAGTCTACACACACAG-3';

5'-ACGTTGGATGACTGGCCATGCAGATGTAAG-3'
and

5'-ACGTTGGATGCACTGCCCATAGACTCTTTC-3';

5'-ACGTTGGATGTTACGACCCAATCACCTTGC-3'
and

5'-ACGTTGGATGTGTGTCCCCAACCACATTTC-3';

5'-ACGTTGGATGAACTGATGGCTCGTACTACC-3'
and

5'-ACGTTGGATGGCTCTTTTCCCTATGATGTG-3';

5'-ACGTTGGATGGGTTTATTGGAAATGAAGTC-3'
and

5'-ACGTTGGATGGATCCTACTTACTTCCAGTC-3';

5'-ACGTTGGATGGCAAGCATCTGCTCTTGAGG-3'
and

5'-ACGTTGGATGCTGTGTAAAAGAGTTTGAGG-3';

5'-ACGTTGGATGGGGCTCTTATTATTGTACTC-3'
and

5'-ACGTTGGATGAACAAGCCCAAGTTCTCCAG-3';

5'-ACGTTGGATGGGCAGAACAAGGACAGATAG-3'
and

5'-ACGTTGGATGAGTCTAGTAAAAGTTCTGCC-3';

5'-ACGTTGGATGTACATTCAGACGATAGTGCC-3'
and

5'-ACGTTGGATGAGACCAAGTAACCCCAAACC-3';

5'-ACGTTGGATGGTCACTGAACTCTGGAGTAG-3'
and

5'-ACGTTGGATGGCAGTTTTCAAAGGAAACCC-3';

5'-ACGTTGGATGAGATCCTCCAGCTCATCTTC-3'
and

5'-ACGTTGGATGTAATCCTTGGAGGCTCTCTG-3';

-continued

5'-ACGTTGGATGTAGAGCTCACAGAGCACTTC-3'
and

5'-ACGTTGGATGAGCACTTAACTGAGTCTGGG-3';

5'-ACGTTGGATGCTTTGCTCACAAGAAAGTTGG-3
and

5'-ACGTTGGATGCCCCCAAGGCAATGATTTTC-3';

5'-ACGTTGGATGTAATACCCTGAGCAAGGACG-3'
and

5'-ACGTTGGATGGTGCATTTAAAATCCATGTG-3';

5'-ACGTTGGATGTGTTACAGCAGCTAGTGTTG-3'
and

5'-ACGTTGGATGCCTCTAATAGCACCCAGTTC-3';

5'-ACGTTGGATGGTCCATTTAACGGTGTGGAG-3'
and

5'-ACGTTGGATGGGTTCATGAAATGTTAGTTCC-3';

5'-ACGTTGGATGTATCCATCCTTCAGACACCC-3'
and

5'-ACGTTGGATGATGGGACAGTAACTGCAGAC-3';

5'-ACGTTGGATGCTCAGTTTAAAGTCACTGCC-3'
and

5'-ACGTTGGATGTAACCCTGCAAAGACTAGAG-3';

5'-ACGTTGGATGGCCAGCTTGTCCATTAAAGG-3'
and

5'-ACGTTGGATGCTGGCTTATAAATAAAAGACC-3';

5'-ACGTTGGATGCATTGCAGTAACTGGAGGTC-3'
and

5'-ACGTTGGATGGGCACAGTAGTTCAGTTACC-3';

5'-ACGTTGGATGAGTGAGACTTAACCGTGGAG-3'
and

5'-ACGTTGGATGCACCCCCACATTAGCAAAAG-3';

5'-ACGTTGGATGATCTTCATGTCCCAAGGAGG-3'
and

5'-ACGTTGGATGCCAAGTTTATGAAACGTAG-3';

5'-ACGTTGGATGCACATGCTAGAGAAAGAGGG-3'
and

5'-ACGTTGGATGTATGTCCTTCCCTGATTTTC-3';

5'-ACGTTGGATGAGGATGCCTGTTGGGTTTTC-3'
and

5'-ACGTTGGATGATCAGACTTTTCCCAGGCAG-3';

5'-ACGTTGGATGAAGCAACTGGCACTCCTAAG-3'
and

5'-ACGTTGGATGGAGTGTTGTGATGCATGCC-3';

5'-ACGTTGGATGGTATCTCCCACTCTTGTACC-3'
and

5'-ACGTTGGATGCTGGAATACAACATTTCTGG-3';

5'-ACGTTGGATGTTGTGCTATCTTACACTG-3'
and

5'-ACGTTGGATGACTAGTTGGAATGGGCTTGG-3';

-continued

5'-ACGTTGGATGACTCCCTACCTATCTCTTTG-3'
and

5'-ACGTTGGATGTCCACAGCCACTGAATAGTC-3';

5'-ACGTTGGATGTCATGTAACCAAGCACCACC-3'
and

5'-ACGTTGGATGGCTCATTTATAGAAGCAGTC-3';

5'-ACGTTGGATGCAGTGGATTTCAAATCCGGC-3'
and

5'-ACGTTGGATGTGTTCAGAGGGTGTTGGATG-3';

5'-ACGTTGGATGCATCAGCAATATAATGCCGC-3'
and

5'-ACGTTGGATGTGTGGATCACTGTTCACAGG-3';

5'-ACGTTGGATGCACCAGTGCAAACACACAAC-3'
and

5'-ACGTTGGATGCCTGATTGTTTTGGAAGGAG-3';

5'-ACGTTGGATGAGTTGCCATGTTTCCACAGG-3'
and

5'-ACGTTGGATGGACTAATACTCAGGTTGAGG-3';

5'-ACGTTGGATGTGGAAGGCAGAGTGATATAC-3'
and

5'-ACGTTGGATGGCTTTCTTCACTCAGAAGGG-3';

5'-ACGTTGGATGGAGGAGTTATAAGACCTAGAG-3'
and

5'-ACGTTGGATGACCATATCACAGTTGTTGGG-3';

5'-ACGTTGGATGCTACGTGACCCAAAGTTCAG-3'
and

5'-ACGTTGGATGTCTCACTCCTGGTTACCTAC-3';

5'-ACGTTGGATGTTATACAGGTTCCAGCCAGC-3'
and

5'-ACGTTGGATGCAGAGAGAAAAGGGAGTAGG-3';

5'-ACGTTGGATGACTGATACCCTACAGTGTGC-3'
and

5'-ACGTTGGATGGTGCTCAGAGCACTTAAACG-3';

5'-ACGTTGGATGAATCTTGGAGCCTTGGAGAC-3'
and

5'-ACGTTGGATGGTGCTTCTCACAAAAGCCTG-3';

5'-ACGTTGGATGATCCTGGGCTTTCCTTTGTC-3'
and

5'-ACGTTGGATGGAGTCTAGTGGACAAGAGAG-3';

5'-ACGTTGGATGTGGAGGCCACTGGATTAAAG-3'
and

5'-ACGTTGGATGAGACACAGCTAGCACTTTCC-3';

5'-ACGTTGGATGGTTTGGTGACTATAGAAACAG-3'
and

5'-ACGTTGGATGCAGTTTAAAGTCATATTCAC-3';

5'-ACGTTGGATGGAGCACTTATCACAGGTCAG-3'
and

5'-ACGTTGGATGGAAGGTGGGATAAACAAGGG-3';

-continued

5'-ACGTTGGATGGTTCTGGATGTTGGCCATTC-3'
and

5'-ACGTTGGATGCCACATCATATGCATCTGGG-3';

5'-ACGTTGGATGGAGATGAGTAAGAGCAGGTG-3'
and

5'-ACGTTGGATGCTCATAAGACCCTGAACACC-3';

5'-ACGTTGGATGACTGAAGCATAACGCCTCTG-3'
and

5'-ACGTTGGATGGGTGCCCAAACATGTTATGC-3';

5'-ACGTTGGATGAGAAGGAGGTCATTCTAGGC-3'
and

5'-ACGTTGGATGACATGGACTCTAAAGCCACC-3';

5'-ACGTTGGATGTGAATCCCATGAGCATGAGC-3'
and

5'-ACGTTGGATGATTCCACACAGCATTGCCTC-3';

and

5'-ACGTTGGATGCTGTCAAAAGCCAGGCTAAG-3'
and

5'-ACGTTGGATGGAGGTTCAAAGAGTATAAAG-3'.

3. The method of claim 1, further comprising contacting the amplification products with one or more extension primers.

4. The method of claim 3, wherein the extension primers are selected from the group consisting of:

5'-gCCTGGGAGAAAGAAAACAA-3',

5'-catccGTTTTTCCCTCTTGACTGAAT-3',

5'-cgggACTTACTATGGGGAATAGAAT-3',

5'-caccTCCTGAATACTTTCTCATATAGA-3',

5'-TGATCCACTGGCTCAA-3',

5'-ggagGGTGGTTAGAGAACTCAATGAAT-3',

5'-AGCCTGCACTGTGAA-3',

5'-CAAGTCTTCTATCAAGGGAAT-3',

5'-aCTGAGAGCAACCACTAA-3',

5'-cGAGGAGGGCAGAGAAGAAT-3',

5'-cccctAGAGGGCAGATAAATAGTTAAAT-3',

5'-gtcgTCTACGGTCTTTTTCTTATCAA-3',

-continued

5'-ctAGCTTGCTTACTTCTAAAAA-3',

5'-aaatcTAAATAGCCAAGAAAACAGCCAA-3',

5'-attaTGCTCAACTACCAAGTTAAGA-3',

5'-acatGGAGTTTCCTGTACTTTAAAAAA-3',

5'-tgAGCAAGTGCTGAGGG-3',

5'-gATACAGCTTGGCCAAT-3',

5'-GGGGCTGGTAGGAAAT-3',

5'-ctcTCTTTCTCCAGGGATGA-3',

5'-cGTGATGAGATTTCTATCATACAA-3',

5'-cccccCCTTCCATGGGACTCATTA-3',

5'-GACTATCCTCTTCAGACCAA-3',

5'-cccCAAGTTGAAAACTTATTCCAA-3',

5'-tttcAAATGTGTGTTCCATCATCTA-3',

5'-gggtTGCTGCATGCTGTAAAT-3',

5'-ccacATCATGCCTCTATTGACA-3',

5'-cCAGTTTCAATAACAGATAGTAAAT-3',

5'-aaAAAACTCAATATAGTAAAGGTATCAA-3',

5'-GGAGGTGACATAAGTAAGTA-3',

5'-ATGATGAAAGCATAAGTCTTTTAAT-3',

5'-agCTTACCTCCATAGCATCTAA-3',

5'-TGGCCAGAACTAATCAA-3',

5'-AAGACAAAGGACACCAA-3',

5'-caGACCTACCACCCAAAT-3',

5'-ACTTCTGTCTCAGTATCCA-3',

-continued

5'-ctAGCGTTTCACGTTCAAAA-3',

5'-aaaTGCAATCTGTCTGGAAA-3',

5'-ggtcCTTTCTGCAGCTCATATTCTGCAA-3',

5'-GGCTGTCACAGATTTATAAAA-3',

5'-cATGGGAAACATGCCTCAATAAAT-3',

5'-actTGCTAGGTCTTACATGAA-3',

5'-acgTTCCTGTTCCTAGATGATCAAAAT-3',

5'-AGTCTTTCTGAGCCCAA-3',

5'-agcGAGATACAGGAAAGTGTAAAT-3',

5'-aggTCTCAAATAAAAATGCAAAGGAAA-3',

5'-GGGATTCTCTGGTTGTAAA-3',

5'-gCCAACAGAGAAAGTAACAA-3',

5'-tCCTCCTCAAACATTAAGGACAAAA-3',

5'-tGTACTACCCAGTGGAATAAA-3',

5'-tcTTTAAAGTGCTACATCTATGAA-3',

5'-cgGCTCTTGAGGCAGTAAA-3',

5'-cGGCTCTTATTATTGTACTCTATAAA-3',

5'-atcGGTGGATGTTTCAGGGAAGTAAA-3',

5'-ggtaAGACGATAGTGCCAGAAAAT-3',

5'-agCAGATAGCCTCTTGTGAAT-3',

5'-GCTCATCTTCCTCTGAA-3',

5'-GCACTTCCCTACAAACAA-3',

5'-TTGGAACTATCGTTCAAAAGTATTA-3',

5'-cccatGACGTCACCCTGTAAAAA-3',

-continued
5'-tcGCTAGTGTTGCACTAATAAAAAAAT-3',
5'-cccccGTGTGGAGAAGTGCGAGT-3',
5'-AGACACCCAGGCCAA-3',
5'-cCACTGCCAGTGACCTAA-3',
5'-cACTTGAAAAATACTTTAGACTTTCTT-3',
5'-gATCATTGTATAGGTTCCCAGA-3',
5'-aaatTGAACTGTAGCAAGAAACAAA-3',
5'-ggatGGAAAAGCTGAAAAGGAA-3',
5'-ccctcAATCATTCTATGAAGCCAAT-3',
5'-gTACTGAGATTGACAAGTCATTAAA-3',
5'-TGGCACTCCTAAGACCAAA-3',
5'-cCTCTTGTACCCCAGAAAAA-3',
5'-cGTAGCTTCCTAGCCAAA-3',
5'-gtcgCTTTGAAAAGCCTTAACCATTAA-3',
5'-cccccCCCCAAAAACCTACTGAAAT-3',
5'-GCCGCACATCAGAAT-3',
5'-CAATCCTTTATCTCTCTAATAC-3',
5'-gaagtAATGGAGAACCTGGTTAA-3',
5'-ccCAGGATCCTCTAGATTGTGAAAA-3',
5'-agagACTGAGACAGGCAGTAGCCTAAT-3',
5'-tgaagGAGAGCTTAACTAAAATAAACAA-3',
5'-ggggcCCCAAAGTTCAGGATGGTAA-3',
5'-ACCTGATACTGAAGCCAAA-3',
5'-TGGATATGACTTGCCCAA-3',
5'-gTAGTTTCTTTAGCTCTTGAATAAAAT-3', -continued
5'-acTTGTCACACCTCTTCAAAT-3',
5'-ggTTAAAGGAGACAATGTATGTAAAT-3',
5'-gaagGTGTTGCCAAAAGCTAAT-3',
5'-gtaatTGCCCCTTCAAGTGAAT-3',
5'-GTGCTATCTCATTGTTGTTTGAAA-3',
5'-GAGCAGGTGAAATGTTTCTA-3',
5'-gaCTCTGGGACTACTAAGAAGA-3',
5'-gggcGGTCATTCTAGGCCATTAATAA-3',
5'-GAGCCCACTGCTACA-3',
and
5'-CCAGGCTAAGGCAAAT-3'.

5. The method of claim 1, wherein 20 or more of the single nucleotide polymorphic loci are assayed.

6. The method of claim 5, wherein 60 or more of the single nucleotide polymorphic loci are assayed.

7. The method of claim 6, wherein 90 or more of the single nucleotide polymorphic loci are assayed.

8. The method of claim 1, wherein four or more of the single nucleotide polymorphic loci are informative of the presence of an allele of paternal origin.

9. The method of claim 1, wherein the maternal genotype at one or more of the single nucleotide polymorphic loci is not known prior to (a).

10. The method of claim 1, wherein the target allele concentration is 10% or less of total nucleic acid concentration prior to cleaving and amplifying the nucleic acid.

11. The method of claim 1, further comprising determining whether fetal nucleic acid is present in the sample.

12. The method of claim 1, wherein the sample is from a pregnant female or a female suspected of being pregnant.

13. The method of claim 12, wherein the sample is blood.

14. The method of claim 12, wherein the sample is plasma.

15. The method of claim 1, wherein the amplification products in (b) comprise the following single nucleotide polymorphic loci:

| | | | | | |
|---|---|---|---|---|---|
| rs748773 | rs7323716 | rs4311632 | rs6488494 | rs9652080 | rs7356482 |
| rs13110085 | rs1363267 | rs10785736 | rs13269702 | rs10840805 | rs7320201 |
| rs1797700 | rs2723307 | rs2993531 | rs4764597 | rs9818611 | rs3913810 |
| rs1885121 | rs4589569 | rs12903747 | rs1372688 | rs2820107 | rs12450474 |
| rs1904161 | rs6766358 | rs4869315 | rs1720839 | rs12675087 | rs1503660 |
| rs10901705 | rs7689368 | rs6542638 | rs6582294 | rs725849 | rs683262 |
| rs7144509 | rs7900002 | rs1346718 | rs10234234 | rs910500 | rs10754776 |
| rs8016543 | rs4489023 | rs2007475 | rs11221881 | rs1916803 | rs2734574 |
| rs13155942 | rs10110766 | rs494220 | rs4488809 | rs1041409 | rs9285190 |
| rs3912319 | rs4533845 | rs11099210 | rs9428474 | rs3816551 | rs331893 |
| rs9929404 | rs6556642 | rs4130306 | rs7294836 | rs7205009 | rs273172 |
| rs4673821 | rs12674093 | rs1401454 | rs614004 | rs2322301 | rs1342995 |
| rs1444647 | rs7741525 | rs179596 | rs7818415 | rs17074340 | rs6142841 |
| rs12007 | rs2462049 | rs9787011 | rs9356029 | rs10806232 | rs1593443 |
| rs6569474 | rs11105611 | rs9989393 | rs10898954 | rs263025 | rs664358 |
| rs6043856 | and | rs12107918. | | | |

16. The method of claim 1, wherein the amplification products in (b) comprise some or all of the single nucleotide polymorphic loci selected from the group consisting of:

| | | | |
|---|---|---|---|
| rs11835780 | rs748773 | rs13110085 | rs1363267 |
| rs1797700 | rs2723307 | rs1885121 | rs4589569 |
| rs1904161 | rs6766358 | rs10901705 | rs7689368 |
| rs7144509 | rs7900002 | rs8016543 | rs4489023 |
| rs13155942 | rs10260483 | rs3912319 | rs4533845 |
| rs9929404 | rs6556642 | rs4673821 | rs12674093 |
| rs1444647 | rs7741525 | rs12007 | rs2462049 |
| rs6569474 | rs11105611 | rs6043856 | and rs6142841. |

17. The method of claim 1, wherein the amplification products in (b) comprise some or all of the single nucleotide polymorphic loci selected from the group consisting of:

| | | | |
|---|---|---|---|
| rs7323716 | rs4311632 | rs10785736 | rs13269702 |
| rs7831906 | rs2993531 | rs12903747 | rs137268 |
| rs4869315 | rs1720839 | rs6542638 | rs6582294 |

-continued

| | | | |
|---|---|---|---|
| rs1346718 | rs10234234 | rs2007475 | rs11221881 |
| rs10110766 | rs494220 | rs11099210 | rs9428474 |
| rs4130306 | rs7294836 | rs1401454 | rs614004 |
| rs179596 | rs7818415 | rs9787011 | rs9989393 |
| rs664358 | and rs1342995. | | |

18. The method of claim 1, wherein the amplification products in (b) comprise some or all of the single nucleotide polymorphic loci selected from the group consisting of:

| | | | |
|---|---|---|---|
| rs6488494 | rs9652080 | rs10840805 | rs7356482 |
| rs4764597 | rs9818611 | rs2820107 | rs7320201 |
| rs12675087 | rs3913810 | rs725849 | rs12450474 |
| rs910500 | rs1503660 | rs1916803 | rs683262 |
| rs4488809 | rs1041409 | rs3816551 | rs10754776 |
| rs7205009 | rs2734574 | rs2322301 | rs9285190 |
| rs17074340 | rs331893 | rs9356029 | rs10806232 |
| rs10898954 | rs12107918 | rs263025 | rs1593443 |
| and rs273172. | | | |

* * * * *

SEQUENCE LISTING

```
<160> NUMBER OF SEQ ID NOS: 1197

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgttggatg                                                           10

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 2
gccnnnnngg c                                                         11

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other
```

```
<400> SEQUENCE: 3
cgannnnnnt gc                                                    12

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg cacaagattc tgaaacttag                                 30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg ttgggtgcag agtagtcatc                                 30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgttggatg atgtccacct cctgctccac                                 30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgttggatg ctagcgtacc caatggaatc                                 30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgttggatg gtggtagaaa caaatgtcag c                               31

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```
acgttggatg ggcctgttca ttctcagaaa                                              30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgttggatg tagcctttag tcttgatgcc                                              30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgttggatg gcctcagtag tcacataagg                                              30

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgttggatg gctgtttaac tcagcatg                                                28

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgttggatg ttctagcttg cttctcctcc                                              30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgttggatg gaaagttgtc gtggtagagg                                              30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgttggatg ctaaccagga aaagacaccc                                              30

```
<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgttggatg ctgctaagca tgagagaaag                                    30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg tgactaggaa atcacactgg                                    30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg ccattcttgt atgttttgtc                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgttggatg ttgagatcag tgtcggttcc                                    30

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgtttaact cagcatgtgg gaa                                           23

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctccatcat ccttagc                                                  17

<210> SEQ ID NO 22
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcgtggttct agacttatgc                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caagacaccc ccatacatta                                                   20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
taagcatgag agaaagggaa ag                                                22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgaaatcac actggacatt tt                                                22

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gttttgtctt tttctgtata ctcatg                                            26

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgttcctgac tctcaaaat                                                    19

<210> SEQ ID NO 28
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 28
cacacagtta ggattyacct gagcttgtcc c                                    31

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgttggatg tgtcagactt gtctgaaggc                                      30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgttggatg ccaaagtgaa cttgggtctc                                      30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgttggatg aagcctgtgg actgttaacc                                      30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acgttggatg gtgaactttt tttgcaaggg                                      30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acgttggatg catcagcagt gtgtaagagg                                      30

<210> SEQ ID NO 34
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 34
acgttggatg tccaaggtgg tcttttggag                                         30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acgttggatg tttgttagca gctatgctgg                                         30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgttggatg gtctcttaag caacgagcgg                                         30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttggatg acactgttcg catctgcatc                                         30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgttggatg tgtttctcag gagttcccag                                         30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acgttggatg tgtgtccagt gaccataagg                                         30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 40
acgttggatg tggttccagt tctcaagctc                                    30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acgttggatg attgtggctg tgctgtcctc                                    30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acgttggatg ggaacacctc cattctgatg                                    30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttggatg acaccatctc ggtaggaaag                                    30

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acgttggatg caggaagtat atgagatctg g                                  31

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acgttggatg aagggtgagg tgagataacg                                    30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
```
acgttggatg gagtgagtcc tttgatccag                                           30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acgttggatg ctcacagtga aagtgaacag                                           30

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acgttggatg gacatataat accttggtcc c                                         31

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgttggatg gagaggttgg gaaaaatgtg                                           30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acgttggatg agctttccta aacctgtgac                                           30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acgttggatg accaccatca caaaaagagg                                           30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acgttggatg ccatgtgagg aggcatgttt                                           30

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acgttggatg gtattgggtt acatgatg                                          28

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acgttggatg gcgtgcatgg acttcacaag                                        30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acgttggatg gagcatcttc aaatatcccc                                        30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acgttggatg aatccatttc agacgcagcc                                        30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acgttggatg ggaactgatg gaagaaaagc                                        30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acgttggatg tgggcactgt aatacaaagg                                        30

```
<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
acgttggatg ctgttgccta aagttctcgc                                        30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acgttggatg gtgatattga gtctcacctg                                        30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acgttggatg tggtccagta ggaaaacagg                                        30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acgttggatg gcattttggg aaataatacc                                        30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acgttggatg taccttctat atccaaggac                                        30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
acgttggatg tcagaaggag aagtaccagc                                        30

<210> SEQ ID NO 65
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acgttggatg ctgtctgtgt gatcatcagg                                          30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acgttggatg cattgaaacc tgggatacac                                          30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acgttggatg tgctcacaca aagcctgttg                                          30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acgttggatg tgaatcccat gagcatgagc                                          30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acgttggatg gccttattag ctctcacttg                                          30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acgttggatg gaaaggccac aaagctgttg                                          30

<210> SEQ ID NO 71
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 71
acgttggatg tgcagagctg cgagaagaag                                           30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acgttggatg agcaagtgtt cccttttggg                                           30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acgttggatg aagtgctggg attacaggag                                           30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acgttggatg gagacgattc ttcaggaaac                                           30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acgttggatg taagcatcca tggacctacc                                           30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acgttggatg tctgaaggta gacctggatg                                           30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 77
acgttggatg cgagttgaag atcccatacg                                          30

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acgttggatg aagcaactgg cactcctaag                                          30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acgttggatg ttatacaggt tccagccagc                                          30

<210> SEQ ID NO 80
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acgttggatg tctcaaatat ctaagtggg                                           29

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acgttggatg cggtttcttt tgaggactgg                                          30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acgttggatg actggccatg cagatgtaag                                          30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 83
acgttggatg gagatgagta agagcaggtg                                              30

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acgttggatg gaaaaatcca tcctctgaac c                                            31

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acgttggatg gtcactgaac tctggagtag                                              30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
acgttggatg tcccctact tgcttgaaag                                               30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acgttggatg ctcccatcta tgatttccag                                              30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acgttggatg aatgagagct tgcttacttc                                              30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
```
acgttggatg cattgcagta actggaggtc         30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acgttggatg aacaccaagg aaagcggatg         30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acgttggatg taataccctg agcaaggacg         30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
acgttggatg gtccatttaa cggtgtggag         30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acgttggatg caccagtgca aacacacaac         30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
acgttggatg tgtgcagcac ttttcacaag         30

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acgttggatg ggatcaagag gaaaaaatgg g         31

```
<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acgttggatg tacattcaga cgatagtgcc                                    30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acgttggatg cacatgctag agaaagaggg                                    30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
acgttggatg agttgccatg tttccacagg                                    30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acgttggatg ctacgtgacc caaagttcag                                    30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acgttggatg gggctcttat tattgtactc                                    30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acgttggatg agaaggaggt cattctaggc                                    30

<210> SEQ ID NO 102
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acgttggatg ggcagaacaa ggacagatag                                    30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
acgttggatg gccagcttgt ccattaaagg                                    30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
acgttggatg tttcacaggg ttaggatggg                                    30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acgttggatg tggaaggcag agtgatatac                                    30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
acgttggatg gggaaggtgt ttgtctcata                                    30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acgttggatg agaagatatg ttgagagggc                                    30

<210> SEQ ID NO 108
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 108
acgttggatg gtatggtgcc tccacaaaag                                            30

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
acgttggatg atggtggtgg caatattggg                                            30

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acgttggatg accatttatt ggccctgctc                                            30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
acgttggatg agaatgacaa acccaagggc                                            30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
acgttggatg gtaggttaag agggaaaggg                                            30

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acgttggatg aaagtcagca cagtcactgg                                            30

<210> SEQ ID NO 114
<211> LENGTH: 30
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 114
acgttggatg tcgaactcct gacctcaaac                                   30

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acgttggatg gtgttcatac tgtaggcttg                                   30

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acgttggatg gtgtaatagg cttgtgagag                                   30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acgttggatg tgcttcataa ctctgtcacg                                   30

<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
acgttggatg caagtctccc tagctaagtg                                   30

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
acgttggatg catttgcggc aaagagggag                                   30

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 120
acgttggatg caccctatgc gacttctttg                                    30

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
acgttggatg tatcccccaa acctcacatc                                    30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acgttggatg atcatggaag tgatgagagg                                    30

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
acgttggatg aggacctgga gctcagcaac                                    30

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
acgttggatg tgtgcagcaa tgatcacag                                     29

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
acgttggatg acaagtaagg ttgggtggtg                                    30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
```

```
acgttggatg ggatgctata tcatagccac                                    30
```

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 127

```
acgttggatg ctctgctctg cacacataag                                    30
```

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 128

```
acgttggatg ggtgttagtc aactaggagg                                    30
```

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 129

```
acgttggatg agaggaagca aagctaaggg                                    30
```

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 130

```
acgttggatg aggaggtgac atttaagctg                                    30
```

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 131

```
acgttggatg acggctaatg ctcctcattc                                    30
```

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 132

```
acgttggatg gggcttgaat agctagatac                                    30
```

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acgttggatg gatagggata gacacaggac                                      30

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
acgttggatg ggatttctgt gaagctgctc                                      30

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acgttggatg ccatgaatgg caagtgtctg                                      30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
acgttggatg ttggtagcat atgggtctcc                                      30

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acgttggatg gccagggatt gtattcgaag                                      30

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acgttggatg cttctatgaa ccaccaaggc                                      30

```
<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgttggatg ggtaggaaac gtgtacactg                                    30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
acgttggatg atgcctattt cttgtgaccc                                    30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
acgttggatg atgacatact cccatgtgcc                                    30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acgttggatg cacgctatgt aaaagtagca                                    30

<210> SEQ ID NO 143
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
acgttggatg gaatggatag aagaatctg                                     29

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
acgttggatg cctgagtcaa ccttggaaag                                    30

<210> SEQ ID NO 145
<211> LENGTH: 30
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
acgttggatg agcctgaatc tctagcagtc                                           30

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
acgttggatg ctgcaagcta agaaacacac                                           30

<210> SEQ ID NO 147
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acgttggatg ccattatttc tcccaaagct c                                         31

<210> SEQ ID NO 148
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
acgttggatg ttgtggaagg aggcaaggg                                            29

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
acgttggatg agaagagatg gtggttgtgc                                           30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acgttggatg agtatcctcc agtttaaggg                                           30

<210> SEQ ID NO 151
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 151
acgttggatg gttgttgcta gtagaccgag                                    30

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
acgttggatg tttagtgaca cctcccatcc                                    30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
acgttggatg ggcatgcaac atagacttgg                                    30

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acgttggatg aggctttcag gatctgcttc                                    30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
acgttggatg gtggacacag gacagcattg                                    30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acgttggatg atgtgtcaag accatctggg                                    30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
                                 primer

<400> SEQUENCE: 157
acgttggatg agttattctc ccgagaaggc                                    30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
acgttggatg gacatggttg tgttgtgaag                                    30

<210> SEQ ID NO 159
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
acgttggatg actatgggta gtacatggg                                     29

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
acgttggatg tgcaagccca caggacaaac                                    30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
acgttggatg gttggtaata gctacagccc                                    30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
acgttggatg tttttgtccc caaacatccc                                    30

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 163
acgttggatg agacatcaga gagaagggac                                      30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
acgttggatg ttgttcctga cttcaagggc                                      30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
acgttggatg aaggtgctgt ggcaagttag                                      30

<210> SEQ ID NO 166
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
acgttggatg tggagaagaa actcaaaag                                       29

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
acgttggatg ccaggtctca acactgattg                                      30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acgttggatg gaaatacttc cctcgggctc                                      30

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
```

```
acgttggatg cttccctggc ttcatttcc                                    30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
acgttggatg agagattgag cttcagtccc                                   30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
acgttggatg ccacttacag aacagaaggg                                   30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
acgttggatg tgctgctgga ttcagtttgc                                   30

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
acgttggatg ttgatatgag cctctgagac                                   30

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
acgttggatg ggacgtgagc aagaaaagac                                   30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
acgttggatg gtggtctatt gaggcaatgg                                   30
```

```
<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
acgttggatg gacccatgtc tgtcatactg                                   30

<210> SEQ ID NO 177
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
acgttggatg tgtcaaaacc ccatctctac                                   30

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
acgttggatg gccaagcaac actatggtat                                   30

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
acgttggatg aatgccattt cctcaggagc                                   30

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
acgttggatg gactggtaga gtaagttctg                                   30

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
acgttggatg gtgttgatct gtcacatggc                                   30

<210> SEQ ID NO 182
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
acgttggatg gaggtgccag ctaatctaac                                        30

<210> SEQ ID NO 183
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
acgttggatg tattacatcg aaatcaagg                                         29

<210> SEQ ID NO 184
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
acgttggatg gaagtgttta ggatttgag                                         29

<210> SEQ ID NO 185
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
acgttggatg aagtcttgac ataaggtag                                         29

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
acgttggatg caaaagcttt gcgcatcagg                                        30

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
acgttggatg ttaggccaag ctcatgcttc                                        30

<210> SEQ ID NO 188
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 188
acgttggatg cagtggattt caaatccggc                                        30

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
acgttggatg caatcagcta ctgctgatcc                                        30

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
acgttggatg ctgtcaaaag ccaggctaag                                        30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
acgttggatg gcaaccagtt atccccattc                                        30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
acgttggatg gcttgcagag gttcactaac                                        30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
acgttggatg tagagctcac agagcacttc                                        30

<210> SEQ ID NO 194
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 194
acgttggatg ctcagtttaa agtcactgcc                                        30

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
acgttggatg tttacagact agcgtgacgg                                        30

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
acgttggatg ggaggatgaa atcagtggtc                                        30

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
acgttggatg tttttctgtc tcagcctccc                                        30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
acgttggatg tatggatgca agcctttccc                                        30

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
acgttggatg agcttgggct gaatgttagg                                        30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 200
acgttggatg ggctctagtt ttcagcagac                                30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
acgttggatg gttacactga caatcaaggg                                30

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
acgttggatg aactgatggc tcgtactacc                                30

<210> SEQ ID NO 203
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
acgttggatg gataatattg tgctgcatgc t                              31

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
acgttggatg ctggatctta cctccatagc                                30

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
acgttggatg gagcacttat cacaggtcag                                30

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
```
acgttggatg actgaagcat aacgcctctg                                      30

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
acgttggatg atcttcatgt cccaaggagg                                      30

<210> SEQ ID NO 208
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
acgttggatg tcacgtcaga ctacactgag                                      30

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
acgttggatg cattgcttgg gtcttctcag                                      30

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
acgttggatg ggtttattgg aaatgaagtc                                      30

<210> SEQ ID NO 211
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
acgttggatg aagaatggaa agtgatgag                                       29

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
acgttggatg cactgagaga tacaggaaag                                      30

-continued

<210> SEQ ID NO 213
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
acgttggatg gcttgttaaa tgtgtgttcc                                           30

<210> SEQ ID NO 214
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
acgttggatg gatgatgaaa gcataagtc                                            29

<210> SEQ ID NO 215
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
acgttggatg agtgagactt aaccgtggag                                           30

<210> SEQ ID NO 216
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
acgttggatg cttcttttcc ctgcatcatc                                           30

<210> SEQ ID NO 217
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
acgttggatg ctgcctattc ttctacggtc                                           30

<210> SEQ ID NO 218
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
acgttggatg ctttgctcac aagaaagttg g                                         31

```
<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
acgttggatg tggaggccac tggattaaag                                        30

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acgttggatg actccctacc tatctctttg                                        30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
acgttggatg tgttacagca gctagtgttg                                        30

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acgttggatg caccagtccc ctcaaataac                                        30

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
acgttggatg ccctaggatt ttcagaatgg                                        30

<210> SEQ ID NO 224
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
acgttggatg gtgcttagga aatgtttgtt g                                      31

<210> SEQ ID NO 225
<211> LENGTH: 31
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
acgttggatg gaggagttat aagacctaga g                                    31

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
acgttggatg tatccatcct tcagacaccc                                      30

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
acgttggatg cctaccttgc tctgagaaac                                      30

<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
acgttggatg tttttggaaa tggcccaagg                                      30

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
acgttggatg agatcctcca gctcatcttc                                      30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
acgttggatg agattggtcc ctcacaatgg                                      30

<210> SEQ ID NO 231
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 231
acgttggatg ggaatacatg tgggtatgtg                                            30

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
acgttggatg agccaccaaa accaagcttc                                            30

<210> SEQ ID NO 233
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
acgttggatg ttgtgtgcta tcttacactg                                            30

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
acgttggatg actgataccc tacagtgtgc                                            30

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
acgttggatg ttgactcacc cacttctgtc                                            30

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
acgttggatg ttcaatcagt catgcctgtg                                            30

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 237
acgttggatg gcaagcatct gctcttgagg					30

<210> SEQ ID NO 238
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
acgttggatg ggtggagatg ggattctctg					30

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
acgttggatg gtatctccca ctcttgtacc					30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
acgttggatg tttttcctcc tgtaccctgc					30

<210> SEQ ID NO 241
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
acgttggatg aaatgctact ccaacagagg					30

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
acgttggatg atcctgggct ttcctttgtc					30

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 243
acgttggatg agtgcaacag aaaaggcagg                                      30

<210> SEQ ID NO 244
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
acgttggatg gcattatgct aaaggctgtc                                      30

<210> SEQ ID NO 245
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
acgttggatg ctatgttttc ccccagcttg                                      30

<210> SEQ ID NO 246
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
acgttggatg gtttggtgac tatagaaaca g                                    31

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
acgttggatg aacaatagag acacactccg                                      30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
acgttggatg caccactcag gaaagcaaac                                      30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
```
acgttggatg acagaagcac cacagctgag                                        30

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
acgttggatg catcagcaat ataatgccgc                                        30

<210> SEQ ID NO 251
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acgttggatg gttctggatg ttggccattc                                        30

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
acgttggatg tcatgtaacc aagcaccacc                                        30

<210> SEQ ID NO 253
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
acgttggatg ttacgaccca atcaccttgc                                        30

<210> SEQ ID NO 254
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
acgttggatg ccttctgctc aactaccaag                                        30

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
acgttggatg ccagtcaagg aagcagtttc                                        30

```
<210> SEQ ID NO 256
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
acgttggatg aggatgcctg ttgggttttc                                          30

<210> SEQ ID NO 257
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
acgttggatg aagcaggtac ttactatggg                                          30

<210> SEQ ID NO 258
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
acgttggatg ctgaggcaca aggagataag                                          30

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
acgttggatg ttgcctagcc ttacatcctg                                          30

<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
acgttggatg gaccttcctg ttcctagatg                                          30

<210> SEQ ID NO 261
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
acgttggatg aatcttggag ccttggagac                                          30

<210> SEQ ID NO 262
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acgttggatg atccatctct gtcagagttc                                         30

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
acgttggatg gagagaggga gaaagtagag                                         30

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
acgttggatg tttaataggg aaagtattgg                                         30

<210> SEQ ID NO 265
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
acgttggatg taccatgctc attgaactcg                                         30

<210> SEQ ID NO 266
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
acgttggatg gcccatcctt cactaacttg                                         30

<210> SEQ ID NO 267
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
acgttggatg ctgccaggga ataggagatg                                         30

<210> SEQ ID NO 268
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 268
acgttggatg ttacagttga gagccactgc                                    30

<210> SEQ ID NO 269
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
acgttggatg aagtcatttg aggcccatcc                                    30

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
acgttggatg tctaggttga gactcaggtg                                    30

<210> SEQ ID NO 271
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
acgttggatg tacgaccaga atggaaggag                                    30

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
acgttggatg acttaacccc cagtgtgatg                                    30

<210> SEQ ID NO 273
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
acgttggatg actctcacac aaagtttgcc                                    30

<210> SEQ ID NO 274
<211> LENGTH: 30
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 274
acgttggatg gtcagagatt tctgcctaag                                        30

<210> SEQ ID NO 275
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
acgttggatg acccaggtga ccgaataaag                                        30

<210> SEQ ID NO 276
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
acgttggatg gagcttctat gaaacgtgtg                                        30

<210> SEQ ID NO 277
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
acgttggatg cagtctatct cttgctctac                                        30

<210> SEQ ID NO 278
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
acgttggatg cagcagcctt tgaaagacac                                        30

<210> SEQ ID NO 279
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
acgttggatg ctggttctgt gaaataagac                                        30

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 280
acgttggatg ggtcactagt gtatattttg                                     30

<210> SEQ ID NO 281
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
acgttggatg caaaagaagc tggattgctc                                     30

<210> SEQ ID NO 282
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
acgttggatg gaggagaagg tgatgtgaag                                     30

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
acgttggatg atccctcatt ctttctccac                                     30

<210> SEQ ID NO 284
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
acgttggatg atgctaagga ttctggggtc                                     30

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
acgttggatg gggcatgaca caactcaaac                                     30

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
```
acgttggatg aacagagggt ttaacagcac                                          30

<210> SEQ ID NO 287
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
acgttggatg ccaatatttt ttccctaggt                                          30

<210> SEQ ID NO 288
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
acgttggatg taagctcccc catccaagac                                          30

<210> SEQ ID NO 289
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
acgttggatg tatctgggtc attgtaaggc                                          30

<210> SEQ ID NO 290
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
acgttggatg agggcacaaa gacatcaaag                                          30

<210> SEQ ID NO 291
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
acgttggatg ggcaggcact ctatcaatac                                          30

<210> SEQ ID NO 292
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
acgttggatg agggtatagg aaacagcttc                                          30

-continued

<210> SEQ ID NO 293
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
acgttggatg catttaccca caaaggtaag                                    30

<210> SEQ ID NO 294
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
acgttggatg gatgcagaat aagcatttga c                                  31

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
acgttggatg ctgtctcaag tgtctggttc                                    30

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
acgttggatg gtcctaagtt aaaagaatgg                                    30

<210> SEQ ID NO 297
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
acgttggatg atcaagagga aaatggacag                                    30

<210> SEQ ID NO 298
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
acgttggatg tctccccact ttgttctgag                                    30

```
<210> SEQ ID NO 299
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
acgttggatg actgtgcctg gacaaagaag                                    30

<210> SEQ ID NO 300
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
acgttggatg gacagttttt aaatctttta c                                  31

<210> SEQ ID NO 301
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
acgttggatg tgagtgatag gtcctctctg                                    30

<210> SEQ ID NO 302
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
acgttggatg caaagaacc tggctcatgg                                     30

<210> SEQ ID NO 303
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
acgttggatg cagatagtgc ttgagaggag                                    30

<210> SEQ ID NO 304
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
acgttggatg gggagaaaga aacaacctgc                                    30

<210> SEQ ID NO 305
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
acgttggatg gacattaagc ccaaaacagg                                    30

<210> SEQ ID NO 306
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
acgttggatg aaagctggcc agggatatag                                    30

<210> SEQ ID NO 307
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
acgttggatg ctggtgagta agcattgaag                                    30

<210> SEQ ID NO 308
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
acgttggatg gttggtaaat ggtagagccg                                    30

<210> SEQ ID NO 309
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
acgttggatg ggagtagtct tcacctgtag                                    30

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
acgttggatg agaagggcaa ccaacaactg                                    30

<210> SEQ ID NO 311
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 311
acgttggatg gtagctcagg caaggagatt                                    30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
acgttggatg gcaggagagg agaaaaagac                                    30

<210> SEQ ID NO 313
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
acgttggatg gttgacgcaa agcaagtgac                                    30

<210> SEQ ID NO 314
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
acgttggatg tcttaggaaa ccacgtccac                                    30

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
acgttggatg cgtatctgtc ttggatcctg                                    30

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
acgttggatg acacaagtgg gagaggtttg                                    30

<210> SEQ ID NO 317
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 317
acgttggatg cagtttgtta ggttctctgg                                              30

<210> SEQ ID NO 318
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
acgttggatg tacacagtaa gttccctgag                                              30

<210> SEQ ID NO 319
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
acgttggatg ctggttccag cacaagtttc                                              30

<210> SEQ ID NO 320
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
acgttggatg ctacttccaa agattgttg                                               29

<210> SEQ ID NO 321
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
acgttggatg cccgtatatg tagccacttt                                              30

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
acgttggatg cgtctgcttc cttcatagag                                              30

<210> SEQ ID NO 323
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 323
acgttggatg ggaagatgca ccactttctg                                              30

<210> SEQ ID NO 324
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
acgttggatg aaaccacttc ctgctttccg                                              30

<210> SEQ ID NO 325
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
acgttggatg tatgtttgca tgttgtttg                                               29

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
acgttggatg ttaatgccag acaagcctcc                                              30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
acgttggatg agaaggtcct gttagtaggg                                              30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
acgttggatg ccactggcct tttcaaagtc                                              30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
```

```
acgttggatg aacaaccgtt ttctcttggg                                              30
```

<210> SEQ ID NO 330
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330

```
acgttggatg aatgtcagag atcacaagcc                                              30
```

<210> SEQ ID NO 331
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331

```
acgttggatg cctttgtga gcaagatgcc                                               30
```

<210> SEQ ID NO 332
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332

```
acgttggatg tccacacatg gtatcacaac                                              30
```

<210> SEQ ID NO 333
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333

```
acgttggatg acattacttg agacccacac                                              30
```

<210> SEQ ID NO 334
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334

```
acgttggatg ctctttctca ttatcattc                                               29
```

<210> SEQ ID NO 335
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335

```
acgttggatg ttcactgact catggatggg                                              30
```

```
<210> SEQ ID NO 336
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
acgttggatg gggaagtcag gatgaaagtg                                    30

<210> SEQ ID NO 337
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
acgttggatg atcctcccctt ttgaaacttg                                   30

<210> SEQ ID NO 338
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
acgttggatg gctaggatta cacgtgtgag                                    30

<210> SEQ ID NO 339
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
acgttggatg tgacgctaaa gactgagtgg                                    30

<210> SEQ ID NO 340
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
acgttggatg aaaggcaatc tcgacctcac                                    30

<210> SEQ ID NO 341
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
acgttggatg gaataactat gagctcatgg                                    30

<210> SEQ ID NO 342
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
acgttggatg attccacaca gcattgcctc                                        30

<210> SEQ ID NO 343
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
acgttggatg catctcatga gaaaggcatc                                        30

<210> SEQ ID NO 344
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
acgttggatg cacatgcatg agtatgggac                                        30

<210> SEQ ID NO 345
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
acgttggatg aagagaaggg ctttgcatcc                                        30

<210> SEQ ID NO 346
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
acgttggatg cacgcgtagg ctatggttta                                        30

<210> SEQ ID NO 347
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
acgttggatg gagacaggca aagatgcaac                                        30

<210> SEQ ID NO 348
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 348
acgttggatg ccatgactct agtgaccttc                                          30

<210> SEQ ID NO 349
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
acgttggatg caggtggtaa atgtgctcag                                          30

<210> SEQ ID NO 350
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
acgttggatg ctcaggatat cattacacac c                                        31

<210> SEQ ID NO 351
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
acgttggatg ctcggtgaac tataggaatc                                          30

<210> SEQ ID NO 352
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
acgttggatg gagtgttgtg atgcatgcc                                           29

<210> SEQ ID NO 353
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
acgttggatg cagagagaaa agggagtagg                                          30

<210> SEQ ID NO 354
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 354
acgttggatg gcaaaacttc acctcaataa                                      30

<210> SEQ ID NO 355
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
acgttggatg gctcagtgtc tgacaaaagc                                      30

<210> SEQ ID NO 356
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
acgttggatg cactgcccat agactctttc                                      30

<210> SEQ ID NO 357
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
acgttggatg ctcataagac cctgaacacc                                      30

<210> SEQ ID NO 358
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
acgttggatg ccatggctcg tgttcttaac                                      30

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
acgttggatg gcagttttca aaggaaaccc                                      30

<210> SEQ ID NO 360
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 360
acgttggatg tgaaagagtg aagggaggac                                              30

<210> SEQ ID NO 361
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
acgttggatg atgcatatct ggagacacac                                              30

<210> SEQ ID NO 362
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
acgttggatg agtgtcgttc agacactagc                                              30

<210> SEQ ID NO 363
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
acgttggatg ggcacagtag ttcagttacc                                              30

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
acgttggatg ctgcttagta acttctgtcc                                              30

<210> SEQ ID NO 365
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
acgttggatg gtgcatttaa aatccatgtg                                              30

<210> SEQ ID NO 366
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
```
acgttggatg ggttcatgaa atgttagttc c    31

<210> SEQ ID NO 367
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 367
acgttggatg cctgattgtt ttggaaggag    30

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 368
acgttggatg cagggtcaca tcacagattg    30

<210> SEQ ID NO 369
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
acgttggatg tagtttcaat ctctgtgctg    30

<210> SEQ ID NO 370
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 370
acgttggatg agaccaagta accccaaacc    30

<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 371
acgttggatg tatgtccttc cctgattttc    30

<210> SEQ ID NO 372
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 372
acgttggatg gactaatact caggttgagg    30

<210> SEQ ID NO 373
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
acgttggatg tctcactcct ggttacctac                                    30

<210> SEQ ID NO 374
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
acgttggatg aacaagccca agttctccag                                    30

<210> SEQ ID NO 375
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
acgttggatg acatggactc taaagccacc                                    30

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
acgttggatg agtctagtaa aagttctgcc                                    30

<210> SEQ ID NO 377
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
acgttggatg ctggcttata aataaaagac c                                  31

<210> SEQ ID NO 378
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
acgttggatg ctagcaaagg ctggattctg                                    30

```
<210> SEQ ID NO 379
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
acgttggatg gctttcttca ctcagaaggg                                      30

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
acgttggatg tggtacagtt tgaaaggagc                                      30

<210> SEQ ID NO 381
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
acgttggatg tattcccttt ctggctgtgg                                      30

<210> SEQ ID NO 382
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
acgttggatg cctctggata tatgtccagt                                      30

<210> SEQ ID NO 383
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
acgttggatg gccaaaaagc aggcttcttc                                      30

<210> SEQ ID NO 384
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
acgttggatg atggcaacat ctgctttccc                                      30

<210> SEQ ID NO 385
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
acgttggatg ggacctgtgc aaaactttgg                                    30

<210> SEQ ID NO 386
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
acgttggatg acttgccttg ttcttgactg                                    30

<210> SEQ ID NO 387
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
acgttggatg tctcgaacaa gctagaggac                                    30

<210> SEQ ID NO 388
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
acgttggatg cctgtaatcc cagcactttg                                    30

<210> SEQ ID NO 389
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
acgttggatg taaaccaacc cccttcttgc                                    30

<210> SEQ ID NO 390
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
acgttggatg ctctttggat taaatgcctg c                                  31

<210> SEQ ID NO 391
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 391
acgttggatg caaaacagta tcgtaacag                                         29

<210> SEQ ID NO 392
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
acgttggatg taggaagatc ctggaaggtg                                        30

<210> SEQ ID NO 393
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
acgttggatg agctcccaca catgaaagag                                        30

<210> SEQ ID NO 394
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
acgttggatg gtggagctgt tattctagtg                                        30

<210> SEQ ID NO 395
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
acgttggatg gagtggacta tagtggatgc                                        30

<210> SEQ ID NO 396
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
acgttggatg gccacattca actgcagttc                                        30

<210> SEQ ID NO 397
<211> LENGTH: 29
<212> TYPE: DNA
<213> ORGANISM: Artificial Sequence
<220> FEATURE:
<223> OTHER INFORMATION: Description of Artificial Sequence: Synthetic
```

-continued

```
         primer

<400> SEQUENCE: 397
acgttggatg ctcagctgtc tccatgctc                                              29

<210> SEQ ID NO 398
<211> LENGTH: 30
<212> TYPE: DNA
<213> ORGANISM: Artificial Sequence
<220> FEATURE:
<223> OTHER INFORMATION: Description of Artificial Sequence: Synthetic
         primer

<400> SEQUENCE: 398
acgttggatg ctcagccatc tcctgtcatc                                             30

<210> SEQ ID NO 399
<211> LENGTH: 30
<212> TYPE: DNA
<213> ORGANISM: Artificial Sequence
<220> FEATURE:
<223> OTHER INFORMATION: Description of Artificial Sequence: Synthetic
         primer

<400> SEQUENCE: 399
acgttggatg cctattcatg gaacctccac                                             30

<210> SEQ ID NO 400
<211> LENGTH: 30
<212> TYPE: DNA
<213> ORGANISM: Artificial Sequence
<220> FEATURE:
<223> OTHER INFORMATION: Description of Artificial Sequence: Synthetic
         primer

<400> SEQUENCE: 400
acgttggatg cttcccccgc tcttttaaac                                             30

<210> SEQ ID NO 401
<211> LENGTH: 30
<212> TYPE: DNA
<213> ORGANISM: Artificial Sequence
<220> FEATURE:
<223> OTHER INFORMATION: Description of Artificial Sequence: Synthetic
         primer

<400> SEQUENCE: 401
acgttggatg ccctgagatt atgtgacacc                                             30

<210> SEQ ID NO 402
<211> LENGTH: 30
<212> TYPE: DNA
<213> ORGANISM: Artificial Sequence
<220> FEATURE:
<223> OTHER INFORMATION: Description of Artificial Sequence: Synthetic
         primer

<400> SEQUENCE: 402
acgttggatg agagcttgga ctctagcatc                                             30

<210> SEQ ID NO 403
<211> LENGTH: 30
<212> TYPE: DNA
<213> ORGANISM: Artificial Sequence
<220> FEATURE:
<223> OTHER INFORMATION: Description of Artificial Sequence: Synthetic
         primer
```

-continued

```
<400> SEQUENCE: 403
acgttggatg cccagaccac tttataagcc                                    30

<210> SEQ ID NO 404
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
acgttggatg ctttgcactt actgcttccc                                    30

<210> SEQ ID NO 405
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
acgttggatg gcatgtttag tacctgcaag                                    30

<210> SEQ ID NO 406
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
acgttggatg ttacctagct agagatctgg                                    30

<210> SEQ ID NO 407
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
acgttggatg gtagttaaag gtgagcaggg                                    30

<210> SEQ ID NO 408
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
acgttggatg aaagtgttga ccccagtgtg                                    30

<210> SEQ ID NO 409
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
```
acgttggatg cttgggttct gaggatttgc                                           30

<210> SEQ ID NO 410
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
acgttggatg cctttctga tgaatgaagc c                                         31

<210> SEQ ID NO 411
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
acgttggatg ctggatattg ttcagctggg                                           30

<210> SEQ ID NO 412
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
acgttggatg ggatacagcc aaaccatgtc                                           30

<210> SEQ ID NO 413
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
acgttggatg atccatgaaa acaggatgtc                                           30

<210> SEQ ID NO 414
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
acgttggatg ctatactgca ccttagaacc                                           30

<210> SEQ ID NO 415
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
acgttggatg gaagaagaat cagagccagc                                           30

<210> SEQ ID NO 416
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
acgttggatg cttccaaagt tcatatgcag                                      30

<210> SEQ ID NO 417
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
acgttggatg actaccctga ctgctatctc                                      30

<210> SEQ ID NO 418
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
acgttggatg taatagctcc cccaacagtc                                      30

<210> SEQ ID NO 419
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
acgttggatg gagagacact gtctcactca                                      30

<210> SEQ ID NO 420
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
acgttggatg cgtaccatat acctagggtg                                      30

<210> SEQ ID NO 421
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
acgttggatg aaataagacc cttgcacccg                                      30

<210> SEQ ID NO 422

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
acgttggatg atgtctgtct tggctatggg                                           30

<210> SEQ ID NO 423
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
acgttggatg actgttagct agcactgtgg                                           30

<210> SEQ ID NO 424
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
acgttggatg ggactcccta ctcattcaag                                           30

<210> SEQ ID NO 425
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
acgttggatg ctagtttttct cttccccagc                                          30

<210> SEQ ID NO 426
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
acgttggatg gggtagtagg aagtggttag                                           30

<210> SEQ ID NO 427
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
acgttggatg ttagtgagca tcagaggcag                                           30

<210> SEQ ID NO 428
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 428
acgttggatg ctcaagggcc atagaaacac                                        30

<210> SEQ ID NO 429
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
acgttggatg tcatcgcatc atgcatcctc                                        30

<210> SEQ ID NO 430
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
acgttggatg acggagcaag actctgtctc                                        30

<210> SEQ ID NO 431
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
acgttggatg gctaggcaga ttgtgctgtg                                        30

<210> SEQ ID NO 432
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
acgttggatg aagcaccgct ggtgataatg                                        30

<210> SEQ ID NO 433
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
acgttggatg gcatcatttg aatattcaca c                                      31

<210> SEQ ID NO 434
<211> LENGTH: 30
<212> TYPE: DNA
<213> ORGANISM: Artificial Sequence
<220> FEATURE:
```

```
-continued

<223> OTHER INFORMATION: Description of Artificial Sequence: Synthetic
      primer

<400> SEQUENCE: 434
acgttggatg ttcttgtgga ttccactccg                                      30

<210> SEQ ID NO 435
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
acgttggatg agaagagctg actgtcagcg                                      30

<210> SEQ ID NO 436
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
acgttggatg tttagtgagg gtgctggaag                                      30

<210> SEQ ID NO 437
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
acgttggatg gtattaaaga tgagcccaca g                                    31

<210> SEQ ID NO 438
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
acgttggatg accagttcct acccatgaag                                      30

<210> SEQ ID NO 439
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
acgttggatg ctgctgtggg tattcagttc                                      30

<210> SEQ ID NO 440
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 440
acgttggatg acagggtctg tacattgcag                30

<210> SEQ ID NO 441
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 441
acgttggatg gccattatgt gaaatcagcg                30

<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 442
acgttggatg aaccgcaggt aaggattcag                30

<210> SEQ ID NO 443
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 443
acgttggatg cgatctccat caaaagaggc                30

<210> SEQ ID NO 444
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 444
acgttggatg tcagtcttgt gtagataggg                30

<210> SEQ ID NO 445
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 445
acgttggatg tatacccatc ccccaatgac                30

<210> SEQ ID NO 446
<211> LENGTH: 31
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 446
acgttggatg gaacacttta ggccaatatc c                    31

<210> SEQ ID NO 447
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
acgttggatg agctgaagtt cgtgagatcc                    30

<210> SEQ ID NO 448
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
acgttggatg tgctacgatt cagtaatgag                    30

<210> SEQ ID NO 449
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
acgttggatg aggttcattt atgtggtagc                    30

<210> SEQ ID NO 450
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
acgttggatg tggagcactt ttgatgtg                    28

<210> SEQ ID NO 451
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
acgttggatg gggctcaagt gattttccag                    30

<210> SEQ ID NO 452
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
acgttggatg aagaccaagt gaactgtgcc                    30

```
<210> SEQ ID NO 453
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
acgttggatg gaagcatcta agcacagctc                                        30

<210> SEQ ID NO 454
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
acgttggatg attccacatt cagagacaac                                        30

<210> SEQ ID NO 455
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
acgttggatg gagaacaaat agccctgaag                                        30

<210> SEQ ID NO 456
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
acgttggatg catgaggcca caaaggaaag                                        30

<210> SEQ ID NO 457
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
acgttggatg aggcaaaatc gttttcatcc                                        30

<210> SEQ ID NO 458
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
acgttggatg tgctcactgg agcatttcag                                        30
```

```
<210> SEQ ID NO 459
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
acgttggatg ggcaatctta aagagggttg                                        30

<210> SEQ ID NO 460
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
acgttggatg acaggaccct tgctttcaac                                        30

<210> SEQ ID NO 461
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
acgttggatg aatctggcca gggaaggttg                                        30

<210> SEQ ID NO 462
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
acgttggatg tgttcagagg gtgttggatg                                        30

<210> SEQ ID NO 463
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
acgttggatg tggtttggtt tctcagctgg                                        30

<210> SEQ ID NO 464
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
acgttggatg gaggttcaaa gagtataaag                                        30

<210> SEQ ID NO 465
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
acgttggatg gtactttgtg accttgaggc                                       30

<210> SEQ ID NO 466
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
acgttggatg tgaggccatt aaaagcaggg                                       30

<210> SEQ ID NO 467
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
acgttggatg agcacttaac tgagtctggg                                       30

<210> SEQ ID NO 468
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
acgttggatg taaccctgca aagactagag                                       30

<210> SEQ ID NO 469
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
acgttggatg atctcacgat cccccatttc                                       30

<210> SEQ ID NO 470
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
acgttggatg agaacatgcc agaaagtgcc                                       30

<210> SEQ ID NO 471
<211> LENGTH: 30
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 471
acgttggatg atggagaaac ctgtctctac                                         30

<210> SEQ ID NO 472
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
acgttggatg aggctgaaga atgctttccc                                         30

<210> SEQ ID NO 473
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
acgttggatg taaaagcaaa acagcttccc                                         30

<210> SEQ ID NO 474
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
acgttggatg ctcaaaacct ggctaccttg                                         30

<210> SEQ ID NO 475
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
acgttggatg actctcatgt accctctctg                                         30

<210> SEQ ID NO 476
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
acgttggatg gctctttccc ctatgatgtg                                         30

<210> SEQ ID NO 477
<211> LENGTH: 30
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 477
acgttggatg accttgttct gtgtgtgtgg                                30

<210> SEQ ID NO 478
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
acgttggatg actagaatcg tgcagagaac                                30

<210> SEQ ID NO 479
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
acgttggatg gaaggtggga taaacaaggg                                30

<210> SEQ ID NO 480
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480
acgttggatg ggtgcccaaa catgttatgc                                30

<210> SEQ ID NO 481
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 481
acgttggatg ccaagtttat gaaacgtag                                 29

<210> SEQ ID NO 482
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
acgttggatg ggattatagg catgagccac                                30

<210> SEQ ID NO 483
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
acgttggatg gggttctggc agatatatcc                              30

<210> SEQ ID NO 484
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
acgttggatg gatcctactt acttccagtc                              30

<210> SEQ ID NO 485
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
acgttggatg ctaggcttgt tcactatttg                              30

<210> SEQ ID NO 486
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
acgttggatg cttgtttccc caacataagg                              30

<210> SEQ ID NO 487
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
acgttggatg tccctcagtt tagttttgtc                              30

<210> SEQ ID NO 488
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
acgttggatg gagatgttgc aaagatgcaa g                            31

<210> SEQ ID NO 489
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
acgttggatg cacccccaca ttagcaaaag                          30

<210> SEQ ID NO 490
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
acgttggatg agggaagtgt tgtagcatgg                          30

<210> SEQ ID NO 491
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
acgttggatg cagaaacatg cttgtagcag                          30

<210> SEQ ID NO 492
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
acgttggatg cccccaaggc aatgattttc                          30

<210> SEQ ID NO 493
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
acgttggatg agacacagct agcactttcc                          30

<210> SEQ ID NO 494
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
acgttggatg tccacagcca ctgaatagtc                          30

<210> SEQ ID NO 495
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
acgttggatg cctctaatag cacccagttc                          30

<210> SEQ ID NO 496
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
acgttggatg gcagttctta aagacctcgg                                      30

<210> SEQ ID NO 497
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
acgttggatg ggctgactca tttgttaggg                                      30

<210> SEQ ID NO 498
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
acgttggatg cgtgaataca tgagaaaggc                                      30

<210> SEQ ID NO 499
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
acgttggatg accatatcac agttgttggg                                      30

<210> SEQ ID NO 500
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
acgttggatg atgggacagt aactgcagac                                      30

<210> SEQ ID NO 501
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
acgttggatg cttcctgctt ttaagcagtc                                      30

<210> SEQ ID NO 502

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
acgttggatg gaaacaagta aatgaggtcc                                          30

<210> SEQ ID NO 503
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
acgttggatg taatccttgg aggctctctg                                          30

<210> SEQ ID NO 504
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
acgttggatg atttggccct gaggcttatc                                          30

<210> SEQ ID NO 505
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
acgttggatg atatacgttg cttcctttgg                                          30

<210> SEQ ID NO 506
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
acgttggatg cttgtaaggc aggtctgatg                                          30

<210> SEQ ID NO 507
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
acgttggatg actagttgga atgggcttgg                                          30

<210> SEQ ID NO 508
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 508
acgttggatg gtgctcagag cacttaaacg                                        30

<210> SEQ ID NO 509
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 509
acgttggatg tgttgatgag gtgaagaggg                                        30

<210> SEQ ID NO 510
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 510
acgttggatg ctaatctgaa ggctccactg                                        30

<210> SEQ ID NO 511
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
acgttggatg ctgtgtaaaa gagtttgagg                                        30

<210> SEQ ID NO 512
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
acgttggatg aacccagtct acacacacag                                        30

<210> SEQ ID NO 513
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
acgttggatg ctggaataca acatttctgg                                        30

<210> SEQ ID NO 514
<211> LENGTH: 30
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 514
acgttggatg tacatgtggt tagagtctgg                                    30

<210> SEQ ID NO 515
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 515
acgttggatg cttcattatc cccactgctg                                    30

<210> SEQ ID NO 516
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 516
acgttggatg gagtctagtg gacaagagag                                    30

<210> SEQ ID NO 517
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 517
acgttggatg ggtccttggt atgtgttctc                                    30

<210> SEQ ID NO 518
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 518
acgttggatg tcctctgatt taggcccttc                                    30

<210> SEQ ID NO 519
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 519
acgttggatg gcaaaagaac aaccacccag                                    30

<210> SEQ ID NO 520
<211> LENGTH: 30
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 520
acgttggatg cagtttaaag tcatattcac					30

<210> SEQ ID NO 521
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 521
acgttggatg tttaatccag ggagctcttc					30

<210> SEQ ID NO 522
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 522
acgttggatg aaaatcccag tgaagagcag					30

<210> SEQ ID NO 523
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 523
acgttggatg aggtttccca agctagaccc					30

<210> SEQ ID NO 524
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 524
acgttggatg tgtggatcac tgttcacagg					30

<210> SEQ ID NO 525
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 525
acgttggatg ccacatcata tgcatctggg					30

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 526

```
acgttggatg gctcatttat agaagcagtc                                              30
```

<210> SEQ ID NO 527
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 527

```
acgttggatg tgtgtcccca accacatttc                                              30
```

<210> SEQ ID NO 528
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 528

```
acgttggatg gccaaagacg atgtggaatg                                              30
```

<210> SEQ ID NO 529
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529

```
acgttggatg gtctgattag gcctaagagc                                              30
```

<210> SEQ ID NO 530
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 530

```
acgttggatg atcagacttt tcccaggcag                                              30
```

<210> SEQ ID NO 531
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 531

```
acgttggatg gtactgttag tgtgtcactc                                              30
```

<210> SEQ ID NO 532
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 532

```
acgttggatg actgacctgg gtttgacttc                                              30
```

<210> SEQ ID NO 533
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 533
acgttggatg ctcaaaatag atgatggact g                          31

<210> SEQ ID NO 534
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 534
acgttggatg tgactggact gtgacatagc                            30

<210> SEQ ID NO 535
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 535
acgttggatg gtgcttctca caaaagcctg                            30

<210> SEQ ID NO 536
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 536
acgttggatg agagaactga cccttcactg                            30

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 537
acgttggatg cccttactca gtgattcctc                            30

<210> SEQ ID NO 538
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 538
acgttggatg cacacccaga agcactgata                            30

<210> SEQ ID NO 539
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 539
acgttggatg ggagatttga taggaagtgc                                    30

<210> SEQ ID NO 540
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 540
acgttggatg aacagtggtg gcccatcagt                                    30

<210> SEQ ID NO 541
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541
acgttggatg cgctgaaaga gacactgaag                                    30

<210> SEQ ID NO 542
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542
acgttggatg tgccattcat tgctctacac                                    30

<210> SEQ ID NO 543
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 543
acgttggatg cacttccagc tgctgctttc                                    30

<210> SEQ ID NO 544
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544
acgttggatg ggtttaagca acatgaaagc                                    30

<210> SEQ ID NO 545
<211> LENGTH: 30

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545
acgttggatg attgaaccct gggaaggtgg                                    30

<210> SEQ ID NO 546
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 546
acgttggatg cacttatccc attcacgagg                                    30

<210> SEQ ID NO 547
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 547
acgttggatg cggtattgtc ttaagactga                                    30

<210> SEQ ID NO 548
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 548
acgttggatg catctgccat gatgatcctg                                    30

<210> SEQ ID NO 549
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 549
acgttggatg gtagctacgt tctttggagg                                    30

<210> SEQ ID NO 550
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 550
acgttggatg ggtttctgcc aaaaaccttg                                    30

<210> SEQ ID NO 551
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 551
acgttggatg gaagaccatt atgtttctga c                                    31

<210> SEQ ID NO 552
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552
acgttggatg tcagcagctt acggtttcag                                      30

<210> SEQ ID NO 553
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553
acgttggatg tggtgtcttt acctctttac                                      30

<210> SEQ ID NO 554
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554
acgttggatg gactcccaac acacaatacc                                      30

<210> SEQ ID NO 555
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555
acgttggatg ccaagaaagg caatgttggg                                      30

<210> SEQ ID NO 556
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556
acgttggatg ccctggagtt ccttttcttg                                      30

<210> SEQ ID NO 557
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
                          primer

<400> SEQUENCE: 557
acgttggatg gagaagctga ggaagcaaag                                    30

<210> SEQ ID NO 558
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
acgttggatg catatgctaa gagccaggac                                    30

<210> SEQ ID NO 559
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
acgttggatg acctgagttt tcagccgttg                                    30

<210> SEQ ID NO 560
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
acgttggatg accttactca gttctattc                                     29

<210> SEQ ID NO 561
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
acgttggatg tgtgcattaa atcctccccc                                    30

<210> SEQ ID NO 562
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
acgttggatg cacaggtcta ccttgatttc                                    30

<210> SEQ ID NO 563
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 563
acgttggatg ttcccaaaca taatcacag                                     29

<210> SEQ ID NO 564
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 564
acgttggatg ggcatagcgc ctgtgcttaa                                    30

<210> SEQ ID NO 565
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 565
acgttggatg tgtttgttgc tgcgtgcttc                                    30

<210> SEQ ID NO 566
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 566
acgttggatg atcctctctc ctaacaccag                                    30

<210> SEQ ID NO 567
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 567
acgttggatg tagtccctga cattggagag                                    30

<210> SEQ ID NO 568
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 568
acgttggatg gaggcacttt tttctgttcc                                    30

<210> SEQ ID NO 569
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 569
```
acgttggatg atccatccac ccatccattg                                              30

<210> SEQ ID NO 570
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
acgttggatg ctcatgccga caaaacttcc                                              30

<210> SEQ ID NO 571
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 571
acgttggatg gatttactca actctctggg                                              30

<210> SEQ ID NO 572
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 572
acgttggatg tcaactaaag ggcagtaacc                                              30

<210> SEQ ID NO 573
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 573
acgttggatg tagcaccagg cttactagac                                              30

<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 574
acgttggatg ctgtattccc atactacttg                                              30

<210> SEQ ID NO 575
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 575
acgttggatg agctcacaaa actaacacac                                              30

<210> SEQ ID NO 576
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 576
acgttggatg atatgtcacg catagcccag                                      30

<210> SEQ ID NO 577
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 577
gaaggcccac agaaa                                                      15

<210> SEQ ID NO 578
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
cggggactcc aggaa                                                      15

<210> SEQ ID NO 579
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
aacctgctga cttcaa                                                     16

<210> SEQ ID NO 580
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
ttgcaaggga ggaaaa                                                     16

<210> SEQ ID NO 581
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
cttcaccagc actaaga                                                    17

<210> SEQ ID NO 582

```
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
tctggctctg ggttcaa                                                    17

<210> SEQ ID NO 583
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 583
cgctatgctg gagcaaa                                                    17

<210> SEQ ID NO 584
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
cgggtgcagt gggtgcaa                                                   18

<210> SEQ ID NO 585
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
ccactcccaa gccacaaat                                                  19

<210> SEQ ID NO 586
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
ccagagttcc cagcagaat                                                  19

<210> SEQ ID NO 587
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
tccctgtcag tgaggaaaa                                                  19

<210> SEQ ID NO 588
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 588
cctttgatga ggagctgta                                                   19

<210> SEQ ID NO 589
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 589 gagagggac gatgcagaa                                                    19

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 590
cctcgggtcc tggaaccta                                                   20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 591
agtttgacag gaagaagaaa                                                  20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 592
agatctggag gatggagaaa                                                  20

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 593
agataacgtg atccatttaa t                                                21

<210> SEQ ID NO 594
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 594
cgaaagtgca tagcttgtta a                                              21

<210> SEQ ID NO 595
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 595
tctcatgctt tcagctccaa aa                                             22

<210> SEQ ID NO 596
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 596
cacttggtcc cttattgttc aa                                             22

<210> SEQ ID NO 597
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 597
gaaactgtga agaaagagga gg                                             22

<210> SEQ ID NO 598
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 598
ctacacctgt gacattggtt taa                                            23

<210> SEQ ID NO 599
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 599
aacatcacaa aaagaggctc taa                                            23

<210> SEQ ID NO 600
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 600
tttggggagg tacatgaggg aaa                                         23

<210> SEQ ID NO 601
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 601
atgatgtaat aactaaaatg caat                                        24

<210> SEQ ID NO 602
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 602
acaagaagaa atgtctagat ttaa                                        24

<210> SEQ ID NO 603
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
ctataccctt tagaatgaca ttcaa                                       25

<210> SEQ ID NO 604
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 604
ttacctcatc aatgcaatct ggaaa                                       25

<210> SEQ ID NO 605
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
cagaatagaa taggaactca gaaaa                                       25

<210> SEQ ID NO 606
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 606
```

```
gggcgttcaa tggagaagac agaat                                          25
```

<210> SEQ ID NO 607
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 607

```
ctcgctattg ttagcattaa taagat                                         26
```

<210> SEQ ID NO 608
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608

```
gaaagcaaaa tgtgtatttt tacaaa                                         26
```

<210> SEQ ID NO 609
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 609

```
cccctaaaac agttcgtatt tcagaat                                        27
```

<210> SEQ ID NO 610
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 610

```
cttgtgggaa ataataccac atccaat                                        27
```

<210> SEQ ID NO 611
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 611

```
ggggacataa aacttcaatg ataagaa                                        27
```

<210> SEQ ID NO 612
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 612

```
gggcccagcc ttgatgtggg gaaaaaa                                        27
```

```
<210> SEQ ID NO 613
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 613
gatggctgtg tgatcatcag ggagaat                                        27

<210> SEQ ID NO 614
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 614
tctctgctga ggtatcatct ctaagaat                                       28

<210> SEQ ID NO 615
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 615
ggtcgcttca cacggacatg cgtgacaa                                       28

<210> SEQ ID NO 616
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 616
gagcccactg ctaca                                                     15

<210> SEQ ID NO 617
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 617
acatggtcgc caaaa                                                     15

<210> SEQ ID NO 618
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 618
actggctggg aaaaa                                                     15
```

```
<210> SEQ ID NO 619
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
acactgcaca gccaat                                                      16

<210> SEQ ID NO 620
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
ggggctggta ggaaat                                                      16

<210> SEQ ID NO 621
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 621
tggccagaac taatcaa                                                     17

<210> SEQ ID NO 622
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 622
aagacaaagg acaccaa                                                     17

<210> SEQ ID NO 623
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
cagacctacc acccaaat                                                    18

<210> SEQ ID NO 624
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 624
actgagagca accactaa                                                    18

<210> SEQ ID NO 625
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 625
catacgagtg ggagaaat                                                  18

<210> SEQ ID NO 626
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 626
tggcactcct aagaccaaa                                                 19

<210> SEQ ID NO 627
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 627
acctgatact gaagccaaa                                                 19

<210> SEQ ID NO 628
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 628
ggtctaagtg ggagtccaa                                                 19

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 629
ctctctttct ccagggatga                                                20

<210> SEQ ID NO 630
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 630
gccaacagag aaagtaacaa                                                20

<210> SEQ ID NO 631
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 631
gagcaggtga aatgtttcta                                                    20

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 632
ctcctctgaa ccttatcaaa a                                                  21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 633
agcagatagc ctcttgtgaa t                                                  21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 634
ggggattgaa agcagggcat a                                                  21

<210> SEQ ID NO 635
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 635
ccacatcatg cctctattga ca                                                 22

<210> SEQ ID NO 636
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 636
ctagcttgct tacttctaaa aa                                                 22

<210> SEQ ID NO 637
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 637
gatcattgta taggttccca ga								22

<210> SEQ ID NO 638
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 638
agcggatgaa gcaatacatt aa								22

<210> SEQ ID NO 639
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 639
cccatgacgt caccctgtaa aaa								23

<210> SEQ ID NO 640
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 640
cccccgtgtg gagaagtgcg agt								23

<210> SEQ ID NO 641
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 641
gaagtaatgg agaacctggt taa								23

<210> SEQ ID NO 642
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 642
ccccaagttg aaaacttatt ccaa								24

<210> SEQ ID NO 643
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 643
catgggaaac atgcctcaat aaat                                         24

<210> SEQ ID NO 644
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 644
ggtaagacga tagtgccaga aaat                                         24

<210> SEQ ID NO 645
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 645
ccctcaatca ttctatgaag ccaat                                        25

<210> SEQ ID NO 646
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 646
cccaggatcc tctagattgt gaaaa                                        25

<210> SEQ ID NO 647
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 647
ggggccccaa agttcaggat ggtaa                                        25

<210> SEQ ID NO 648
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 648
cggctcttat tattgtactc tataaa                                       26

<210> SEQ ID NO 649
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 649

```
gggcggtcat tctaggccat taataa                                          26

<210> SEQ ID NO 650
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 650
atcggtggat gtttcaggga agtaaa                                          26

<210> SEQ ID NO 651
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 651
cacttgaaaa atactttaga ctttctt                                         27

<210> SEQ ID NO 652
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 652
acatggagtt tcctgtactt taaaaaa                                         27

<210> SEQ ID NO 653
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 653
agagactgag acaggcagta gcctaat                                         27

<210> SEQ ID NO 654
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 654
ggtcctttct gcagctcata ttctgcaa                                        28

<210> SEQ ID NO 655
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 655
cccctagagg gcagataaat agttaaat                                        28
```

```
<210> SEQ ID NO 656
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 656
actgtttgac ccagg                                                        15

<210> SEQ ID NO 657
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 657
tgggaggggg aataa                                                        15

<210> SEQ ID NO 658
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 658
ggcaccttag gtgatg                                                       16

<210> SEQ ID NO 659
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 659
tagggcacgt agtaga                                                       16

<210> SEQ ID NO 660
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 660
agggaaaggg tgaaaa                                                       16

<210> SEQ ID NO 661
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 661
ttaaagcaac cccagga                                                      17

<210> SEQ ID NO 662
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 662
gacctcaaac aatccaat                                                 18

<210> SEQ ID NO 663
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 663
cctgtaggct tgaagaga                                                 18

<210> SEQ ID NO 664
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 664
ggcttgtgag aggtaaat                                                 18

<210> SEQ ID NO 665
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 665
ttctgtcacg tttcagtaa                                                19

<210> SEQ ID NO 666
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 666
gtcagatcaa caccaagta                                                19

<210> SEQ ID NO 667
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 667
ggagccagaa ggatataat                                                19

<210> SEQ ID NO 668
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 668
tttcccaccg tcgagacaat                                                 20

<210> SEQ ID NO 669
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 669
ccagaggatg tgtacactaa                                                 20

<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 670
gaagtgatga gaggaactaa                                                 20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 671
ggggtgggga gaatgccaaa                                                 20

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 672
agcaatgatc acagctataa t                                               21

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 673
ggaagttggg tggtgccttt g                                               21

<210> SEQ ID NO 674
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 674
ccacatacct tgaaaaaga at                                              22

<210> SEQ ID NO 675
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 675
gctatgcaca cataaggagt aa                                             22

<210> SEQ ID NO 676
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 676
taggaggtaa tggagaaata at                                             22

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 677
ccctccagat ccagaaacag gaa                                            23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 678
ggacactgaa tgacaagaag gaa                                            23

<210> SEQ ID NO 679
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 679
ctcccctcat tcaactcaat gtaa                                           24

<210> SEQ ID NO 680
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 680
gcttgaatag ctagataccc aaat                                         24

<210> SEQ ID NO 681
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 681
atagccacag gacaagaaac caaa                                         24

<210> SEQ ID NO 682
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 682
tggatgctct agagatgagg acaa                                         24

<210> SEQ ID NO 683
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 683 cccccttca ggccaaatcg agaat                                         25

<210> SEQ ID NO 684
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 684
ctgtagcata tgggtctcct tttaa                                        25

<210> SEQ ID NO 685
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 685
gggttcagga agctctggaa tcaat                                        25

<210> SEQ ID NO 686
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 686

-continued ccacaaccaa ggcaagcgac aaagtc                                        26

<210> SEQ ID NO 687
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 687
aaactataaa gcattgctaa aagaat                                        26

<210> SEQ ID NO 688
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 688
gggagggttt tttgccagta tgtaaa                                        26

<210> SEQ ID NO 689
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 689
gaaggtgccc cccaggtttt gaacaat                                       27

<210> SEQ ID NO 690
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 690
ccagctactg aaaatgaaaa tgtataa                                       27

<210> SEQ ID NO 691
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 691
gggcatggat agaagaatct gtcataa                                       27

<210> SEQ ID NO 692
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 692
gggaaagata agagagatat cagaaat                                       27

<210> SEQ ID NO 693
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 693
aaggcataaa tatgctttca actacatg                                            28

<210> SEQ ID NO 694
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 694
gcttggtgat ttatgcagaa aaagaata                                            28

<210> SEQ ID NO 695
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 695
ccaaagctct cccaa                                                          15

<210> SEQ ID NO 696
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 696
tctgcagtct ggcaa                                                          15

<210> SEQ ID NO 697
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 697
tggttgtgca gccaa                                                          15

<210> SEQ ID NO 698
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 698
gcctcagggg aaggaa                                                         16

```
<210> SEQ ID NO 699
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 699
gccgaggggt gggaat                                                     16

<210> SEQ ID NO 700
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 700
ccaatctgtc cggaaat                                                    17

<210> SEQ ID NO 701
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 701
cctcctagac ctgtgcaa                                                   18

<210> SEQ ID NO 702
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 702
gggcttccct gggaagaa                                                   18

<210> SEQ ID NO 703
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 703
acctggaaag gaaggaac                                                   18

<210> SEQ ID NO 704
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 704
tccacagtgg ctcccaaac                                                  19

<210> SEQ ID NO 705
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 705
ccacaatagg atctgcaat                                                  19

<210> SEQ ID NO 706
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 706
gtgaagtaaa agctggaat                                                  19

<210> SEQ ID NO 707
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 707
tggggtcagg taaggaata                                                  19

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 708
gacaacaagt accagcagta                                                 20

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 709
ccatccctgg tccctggaa t                                                21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 710
ccactaccat tgaggtttca c                                               21

<210> SEQ ID NO 711
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 711
ggacatacaa atcagactaa t                                              21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 712
attcataatg aagcaggaaa t                                              21

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 713
gggatggagg gtttttcaca a                                              21

<210> SEQ ID NO 714
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 714
cctcaaaagt ttagaacctg aa                                             22

<210> SEQ ID NO 715
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 715
gtaacaagta gaggtgctga at                                             22

<210> SEQ ID NO 716
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 716
ttcaggcttt aaataccttc aaa                                            23

<210> SEQ ID NO 717
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 717
cttcattttc cagggttgtt aat						23

<210> SEQ ID NO 718
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 718
agtcccctag tgtaatagga aat						23

<210> SEQ ID NO 719
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 719 cccccccagca ggctgccttg aaat						24

<210> SEQ ID NO 720
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 720
gggtgctagt attttgttga caat						24

<210> SEQ ID NO 721
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 721
gagaggagcc tctgagactg aaat						24

<210> SEQ ID NO 722
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 722
gggaaaagac actatgatgg taat						24

<210> SEQ ID NO 723
<211> LENGTH: 25
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 723 ccccctctgac aacaaaagga aataa                                         25

<210> SEQ ID NO 724
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 724
agcatcatta aagtatttag ccaat                                          25

<210> SEQ ID NO 725
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 725
cttaaaaacc ccatctctac taaaaa                                         26

<210> SEQ ID NO 726
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 726 gcaccttta gtctaaggag agaaat                                          26

<210> SEQ ID NO 727
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 727
gggcagaatg aggtgctctt ttcaaa                                         26

<210> SEQ ID NO 728
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 728
ggggtgttta aagcaggcaa aataaa                                         26

<210> SEQ ID NO 729
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 729
cttccacatg gcaatataaa tgaccaa         27

<210> SEQ ID NO 730
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 730
cccgtgattt actaataagt atcaaat         27

<210> SEQ ID NO 731
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 731
gacatcgaaa tcaaggttta tgttata         27

<210> SEQ ID NO 732
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 732
cctcatactt aggttgatta tccctaat        28

<210> SEQ ID NO 733
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 733
ttacgtcttg acataaggta gtataaat        28

<210> SEQ ID NO 734
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 734
aggcgcaaaa tctaaagcag agataaat        28

<210> SEQ ID NO 735
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 735
tctttccagg cccaa                      15

```
<210> SEQ ID NO 736
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 736
gccgcacatc agaat                                                        15

<210> SEQ ID NO 737
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 737
tgatccactg gctcaa                                                       16

<210> SEQ ID NO 738
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 738
ccaggctaag gcaaat                                                       16

<210> SEQ ID NO 739
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 739
ctccccattc cacaaat                                                      17

<210> SEQ ID NO 740
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 740
gatacagctt ggccaat                                                      17

<210> SEQ ID NO 741
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 741
gcacttccct acaaacaa                                                     18

<210> SEQ ID NO 742
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 742
ccactgccag tgacctaa                                                18

<210> SEQ ID NO 743
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 743
cgacggaccc aatctaat                                                18

<210> SEQ ID NO 744
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 744
ggtgttgcct gttattga                                                18

<210> SEQ ID NO 745
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 745
ggaaaccagg ccaggctaa                                               19

<210> SEQ ID NO 746
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 746
gactatcctc ttcagaccaa                                              20

<210> SEQ ID NO 747
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 747
ctagcgtttc acgttcaaaa                                              20

<210> SEQ ID NO 748
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 748
gcctgggaga aagaaaacaa                                                20

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 749
cgaggagggc agagaagaat                                                20

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 750
tgtactaccc agtggaataa a                                              21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 751
gggttgctgc atgctgtaaa t                                              21

<210> SEQ ID NO 752
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 752
agcttacctc catagcatct aa                                             22

<210> SEQ ID NO 753
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 753
gtaattgccc cttcaagtga at                                             22

<210> SEQ ID NO 754
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 754
gactctggga ctactaagaa ga                                              22

<210> SEQ ID NO 755
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 755
ggatggaaaa gctgaaaagg aa                                              22

<210> SEQ ID NO 756
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 756
tcagcctaca ctgagctacc aca                                             23

<210> SEQ ID NO 757
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 757 ccccccttc catgggactc atta                                             24

<210> SEQ ID NO 758
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 758
tctttaaagt gctacatcta tgaa                                            24

<210> SEQ ID NO 759
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 759
cgtgatgaga tttctatcat acaa                                            24

<210> SEQ ID NO 760
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 760
agcgagatac aggaaagtgt aaat                                          24

<210> SEQ ID NO 761
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 761
tttcaaatgt gtgttccatc atcta                                         25

<210> SEQ ID NO 762
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 762
atgatgaaag cataagtctt ttaat                                         25

<210> SEQ ID NO 763
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 763
aaattgaact gtagcaagaa acaaa                                         25

<210> SEQ ID NO 764
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 764
catccgtttt tccctcttga ctgaat                                        26

<210> SEQ ID NO 765
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 765
gtcgtctacg gtcttttct tatcaa                                         26

<210> SEQ ID NO 766
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 766
```
ttggaactat cgttcaaaaa gtatta                                       26

<210> SEQ ID NO 767
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 767
ggttaaagga gacaatgtat gtaaat                                       26

<210> SEQ ID NO 768
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 768
gtcgctttga aaagccttaa ccattaa                                      27

<210> SEQ ID NO 769
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 769
tcgctagtgt tgcactaata aaaaaat                                      27

<210> SEQ ID NO 770
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 770
acaagtcccc tcaataacc tatcaaat                                      28

<210> SEQ ID NO 771
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 771
cactggtttc aacttaaaat cgccaaat                                     28

<210> SEQ ID NO 772
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 772
aatgaaagag atataatcat cttaaaaa                                     28

<210> SEQ ID NO 773
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 773
tgaaggagag cttaactaaa ataaacaa                                         28

<210> SEQ ID NO 774
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 774
agacacccag gccaa                                                       15

<210> SEQ ID NO 775
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 775
agcctgcact gtgaa                                                       15

<210> SEQ ID NO 776
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 776
tggcccaagg agaaat                                                      16

<210> SEQ ID NO 777
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 777
gctcatcttc ctctgaa                                                     17

<210> SEQ ID NO 778
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 778
agtctttctg agcccaa                                                     17

-continued

```
<210> SEQ ID NO 779
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 779
gagagccatg agtgaaa                                                   17

<210> SEQ ID NO 780
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 780
tgagcaagtg ctgaggg                                                   17

<210> SEQ ID NO 781
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 781
cgtagcttcc tagccaaa                                                  18

<210> SEQ ID NO 782
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 782
tggatatgac ttgcccaa                                                  18

<210> SEQ ID NO 783
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 783
acttctgtct cagtatcca                                                 19

<210> SEQ ID NO 784
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 784
ccctgcctgt gtgatgaaa                                                 19

<210> SEQ ID NO 785
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 785
cggctcttga ggcagtaaa                                                    19

<210> SEQ ID NO 786
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 786
gggattctct ggttgtaaa                                                    19

<210> SEQ ID NO 787
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 787
cctcttgtac cccagaaaaa                                                   20

<210> SEQ ID NO 788
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 788
aaatgcaatc tgtctggaaa                                                   20

<210> SEQ ID NO 789
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 789
ggaggtgaca taagtaagta                                                   20

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 790
acttgtcaca cctcttcaaa t                                                 21

<210> SEQ ID NO 791
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 791
caagtcttct atcaagggaa t                                              21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 792
ggctgtcaca gatttataaa a                                              21

<210> SEQ ID NO 793
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 793
actttgctag gtcttacatg aa                                             22

<210> SEQ ID NO 794
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 794
gaaggtgttg ccaaaagcta at                                             22

<210> SEQ ID NO 795
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 795
ccctcgacac actccggcta aat                                            23

<210> SEQ ID NO 796
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 796
cccaaggaaa gcaaactgct aca                                            23

<210> SEQ ID NO 797
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 797
ttgacaagac gcagctgtgc aat                                           23

<210> SEQ ID NO 798
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 798
caatccttta tctctctcta atac                                          24

<210> SEQ ID NO 799
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 799
gtgctatctc attgttgttt gaaa                                          24

<210> SEQ ID NO 800
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 800 cccccccca aaacctact gaaat                                           25

<210> SEQ ID NO 801
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 801
tcctcctcaa acattaagga caaaa                                         25

<210> SEQ ID NO 802
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 802
attatgctca actaccaagt taaga                                         25

<210> SEQ ID NO 803
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 803
ccagtttcaa taacagatag taaat                                          25

<210> SEQ ID NO 804
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 804
gtactgagat tgacaagtca ttaaa                                          25

<210> SEQ ID NO 805
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 805
cgggacttac tatggggaat agaat                                          25

<210> SEQ ID NO 806
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 806
aaggagataa gtaacatgtt taaaat                                         26

<210> SEQ ID NO 807
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 807
cacctcctga atactttctc atataga                                        27

<210> SEQ ID NO 808
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 808
acgttcctgt tcctagatga tcaaaat                                        27

<210> SEQ ID NO 809
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 809
```
gtagtttctt tagctcttga ataaaat          27

<210> SEQ ID NO 810
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 810
aggtctcaaa taaaaatgca aaggaaa          27

<210> SEQ ID NO 811
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 811
ggagggtggt tagagaactc aatgaat          27

<210> SEQ ID NO 812
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 812
aaatctaaat agccaagaaa acagccaa          28

<210> SEQ ID NO 813
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 813
aaaaaactca atatagtaaa ggtatcaa          28

<210> SEQ ID NO 814
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 814
caccctcagg aggaa          15

<210> SEQ ID NO 815
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 815
gggtggcatc ggaaa          15

```
<210> SEQ ID NO 816
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 816
caccgagctt gcaata                                                    16

<210> SEQ ID NO 817
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 817
gccatcctgg ctgaaa                                                    16

<210> SEQ ID NO 818
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 818
ctggctggac tgggga                                                    16

<210> SEQ ID NO 819
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 819
cgaaggaggg cttggaa                                                   17

<210> SEQ ID NO 820
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 820
gtgatggtgt tagggaa                                                   17

<210> SEQ ID NO 821
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 821
caaagtttgc ctgacaaa                                                  18

<210> SEQ ID NO 822
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 822
tctgcctaag gtgttaaa                                                       18

<210> SEQ ID NO 823
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 823
tggtataggt tttgggaa                                                       18

<210> SEQ ID NO 824
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 824
cacgtgaaaa catgttgaa                                                      19

<210> SEQ ID NO 825
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 825
tgctctacaa tcaccttaat                                                     20

<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 826
cctcaaacaa acaacagaca                                                     20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 827
atgaacaaaa cctttgagaa                                                     20

<210> SEQ ID NO 828
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 828
aagggatagt tgtagtatga                                              20

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 829
ctctggattg ctctactgga a                                            21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 830
atgtgaagat ggaggtagaa a                                            21

<210> SEQ ID NO 831
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 831
cattctttct ccactagata aa                                           22

<210> SEQ ID NO 832
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 832
cttgggtcag acagatttga at                                           22

<210> SEQ ID NO 833
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 833
ctgccacaac tcaaactttg gaa                                          23

<210> SEQ ID NO 834
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 834
tcagatatgt tcagtcaatg aat                                          23

<210> SEQ ID NO 835
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 835
ggggccctag gtacaaaggg cta                                          23

<210> SEQ ID NO 836
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 836
cccctccatc caagacactg gaaa                                         24

<210> SEQ ID NO 837
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 837
gcattgtaag gcaaatgtaa taaa                                         24

<210> SEQ ID NO 838
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 838
gcatgcaaat ctttcacatt aataa                                        25

<210> SEQ ID NO 839
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 839
cagtcactct atcaatacag gaatg                                        25

<210> SEQ ID NO 840
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 840
ttcgtgtaaa caagagaaat catgg                                           25

<210> SEQ ID NO 841
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 841
ggaatgaaga gattaaaata gataa                                           25

<210> SEQ ID NO 842
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 842
actaagcatt tgacaaaatc tgatat                                          26

<210> SEQ ID NO 843
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 843
ggctggttca tagttaaaag tcaata                                          26

<210> SEQ ID NO 844
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 844
caaagaaaaa gtagatttgt gaaaaa                                          26

<210> SEQ ID NO 845
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 845
taataggaaa atggacagaa gttgaa                                          26

<210> SEQ ID NO 846
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 846
```

```
tcagctactc tggtatttaa aataaat                                              27
```

<210> SEQ ID NO 847
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 847

```
gggaacaaag aagacctgaa gtacaca                                              27
```

<210> SEQ ID NO 848
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 848

```
tttttaaatc ttttacatca ataactaa                                             28
```

<210> SEQ ID NO 849
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 849

```
gtcatttttt aaaatggaaa tcaataaa                                             28
```

<210> SEQ ID NO 850
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 850

```
aaggcagtca gtggattatc cttggaat                                             28
```

<210> SEQ ID NO 851
<211> LENGTH: 201
<212> TYPE: DNA
<213> ORGANISM: Homo sapiens

<400> SEQUENCE: 851

```
aattttaatc tttggtctct aaaaagtaaa tttcaaattt atgagtttaa tcacttcaaa          60
tatgaatagc aaaaaatgag agcttgctta cttctaaaaa ytgaggttaa gatatagcta        120
gtgtctgaac gacactcctt aaagtaagtt ccaaatgtaa aacactcctt aagttccaaa        180
tgttttccgc taatagtctg t                                                  201
```

<210> SEQ ID NO 852
<211> LENGTH: 201
<212> TYPE: DNA
<213> ORGANISM: Homo sapiens

<400> SEQUENCE: 852

```
tacatgcatt cttttagtgg atagatgcac acaaacacac aagccattat ggggaaggat          60
```

```
ccacgtgtgt ggccatattg taacacattt ttctgcaaat yacctctttc atttaacagc      120
ccttattcaa tggccttttt cttttcagt agtacataca catctgtgtc atttgttgaa       180
tgacgacatg aatgttttgt a                                               201

<210> SEQ ID NO 853
<211> LENGTH: 201
<212> TYPE: DNA
<213> ORGANISM: Homo sapiens

<400> SEQUENCE: 853
gtgaatcatg aagtcatatc atcactgtat tacaaaagcc aaaaagcagg cttcttcatc      60
tatcttagac tcactgtggt agatcacaaa ctggccacaa rttattcccc ctcccaatat     120
tgccaccacc attagcaata ggacttagtt acttctacca tgagaggtca agtttattta     180
cccactcact gaatttgtgc c                                              201

<210> SEQ ID NO 854
<211> LENGTH: 201
<212> TYPE: DNA
<213> ORGANISM: Homo sapiens

<400> SEQUENCE: 854
agaagcacta acctaaacca gtggttctca actgggctga atactagaat cgtgcagaga      60
actttaaaaa atagagatgc ccaggctgaa ccccaaacca rttagatgct atggaggtaa     120
gatccagaca ttagtcattt ttaaggctcc ccaggttatt ctaacgcaaa aaaaagaaag    180
ttgccctaaa ccagcttttt a                                              201

<210> SEQ ID NO 855
<211> LENGTH: 201
<212> TYPE: DNA
<213> ORGANISM: Homo sapiens

<400> SEQUENCE: 855
aagtgataat attgctatta cctcctgcat gctggatctg tttgcagccg tattgcatgc      60
cttattagct ctcacttgtg tttaaacatg gtcgccaaaa wtcagagcct tatgtttgat    120
gcctttctca tgagatgtag gcccacacat ccaacagcct gctagatatt gccaattgca   180
tatcctacac ctatatatgg t                                              201

<210> SEQ ID NO 856
<211> LENGTH: 201
<212> TYPE: DNA
<213> ORGANISM: Homo sapiens

<400> SEQUENCE: 856
gatcagtgat actgagcttt ttttcatatg cttgttggcc acatgtgtgt cttcttttga      60
aaagtgtctg ttcatgtcct tgcccatgt tttaatggaa ytgacaaacc acaatcttga    120
ttgcttaata caataaagga ttatttctca ccatgtcacc atccagtttg agttagtatt   180
cgtggtaagg ggacaggtgt t                                              201

<210> SEQ ID NO 857
<211> LENGTH: 201
<212> TYPE: DNA
<213> ORGANISM: Homo sapiens

<400> SEQUENCE: 857
tagccacagc catacaggat aattgcccca taatctttca cacctccaag ttttggacaa      60
```

```
tctaacagaa agatccctca ttctttctcc actagataaa ytcattaatc cttcaagtcc    120
cctctcactt gtcattttc tttgcttcct cagcttctcc attaagcttt gttttgctt      180 gtacatccat ttcttcctac c                                              201
```

<210> SEQ ID NO 858
<211> LENGTH: 201
<212> TYPE: DNA
<213> ORGANISM: Homo sapiens

<400> SEQUENCE: 858

```
caccggactg ggagccactg cggggcagga agctgccttt tccatttccc aagaccggaa    60
tcaatcacag cggctcatcg catcatgcat cctctgcaat kgttccttcc tttccaggga    120
ggttggtcac ggccaatgct gtcctgtgtc caccaggtgg cgctcgcgat caccgcaaaa    180
cacatggcta ccgtgatggt t                                              201
```

<210> SEQ ID NO 859
<211> LENGTH: 201
<212> TYPE: DNA
<213> ORGANISM: Homo sapiens

<400> SEQUENCE: 859

```
aatgataaaa tgtttcgttc tttggaagta actctttttt tttcttctgt tcttagtcat    60
ccatctctgt cagagttctc aaataaaaat gcaaggaaa kttagcacca ctctaaaaca     120
gtgaagggtc agttctctgc ttttggatat gtaatttgaa tgggaagtgt cctaatgaca    180
attaaacaca attttctaag c                                              201
```

<210> SEQ ID NO 860
<211> LENGTH: 201
<212> TYPE: DNA
<213> ORGANISM: Homo sapiens

<400> SEQUENCE: 860

```
ctaaactctt cagcagatta ctctccacac atgcatagca tgagaggttc catgggctta    60
ggtacctggc tttttagcca tatcttagtg tacaaatatc rattaatacc attttctgta    120
gtaagattac gggaaaagtg attcttgttt acagagccct ctttcagttt catgttttc     180 ttctctcatt tagtagacat a                                              201
```

<210> SEQ ID NO 861
<211> LENGTH: 201
<212> TYPE: DNA
<213> ORGANISM: Homo sapiens

<400> SEQUENCE: 861

```
ctttgaacct gagtgactat tcccacctga ttcttttctt tctctccttt cttttcctcc    60
ccaacatacg tttatcgtct cttgcattag tgaatggaat ycgtattctt tcatgtagag    120
agcaacatct tcctacatag taaataaaag agtaaagacc actgtattga gatgagaaat    180
caagggaaga aagcaaccca a                                              201
```

<210> SEQ ID NO 862
<211> LENGTH: 201
<212> TYPE: DNA
<213> ORGANISM: Homo sapiens

<400> SEQUENCE: 862

```
ctttgaacct gagtgactat tcccacctga ttcttttctt tctctccttt cttttcctcc    60
```

| | |
|---|---|
| ccaacatacg tttatcgtct cttgcattag tgaatggaat ycgtattctt tcatgtagag | 120 |
| agcaacatct tcctacatag taaataaaag agtaaagacc actgtattga gatgagaaat | 180 |
| caagggaaga aagcaaccca a | 201 |

<210> SEQ ID NO 863
<211> LENGTH: 201
<212> TYPE: DNA
<213> ORGANISM: Homo sapiens

<400> SEQUENCE: 863

| | |
|---|---|
| tcaataatgt ctgaagagct tgtaaagaga taagtgaaaa cccttgtaag tatttagttt | 60 |
| cttctcaaac gcaaaagaac aaccacccag ggccttttta rttcatgtaa gacctagcac | 120 |
| atggaaatct agcaagctgg gggaaaacat agaggcagga aattctgtgg cttctctcag | 180 |
| aagacaagga tcgaatcctt c | 201 |

<210> SEQ ID NO 864
<211> LENGTH: 201
<212> TYPE: DNA
<213> ORGANISM: Homo sapiens

<400> SEQUENCE: 864

| | |
|---|---|
| gccctgaaag gatggtagat aggccacatc tgcttttctt tcggaggaaa caaatattat | 60 |
| tttattgcat tatgctaaag gctgtcacag atttataaaa ytgtagcaaa gtgcctgagg | 120 |
| acatgaaggg cctaaatcag aggaatagta gatgaaactt cacaggaata tatcagacaa | 180 |
| cataggcgtc tttagagaaa a | 201 |

<210> SEQ ID NO 865
<211> LENGTH: 201
<212> TYPE: DNA
<213> ORGANISM: Homo sapiens

<400> SEQUENCE: 865

| | |
|---|---|
| ctgagtttga ctcagtctct ggaaatttgc tgcataagtc tgggccctga ccaccaatat | 60 |
| ctgtctcctc atccctgcaa tactttctac ttggacccaa yttccacatg cttgaatgtg | 120 |
| gaaaaaaacg ctttagagaa aaagcaaggg gaaatgtgga gctcactttg tatgttttgc | 180 |
| ttctctcaag ggttacagca c | 201 |

<210> SEQ ID NO 866
<211> LENGTH: 201
<212> TYPE: DNA
<213> ORGANISM: Homo sapiens

<400> SEQUENCE: 866

| | |
|---|---|
| ctagaaataa tgccctctgg ccactgcccc agtgcattct tatagtgcac gctgataaat | 60 |
| catagtaaaa atatatcctc cctttgaaa cttgcctaca rttcttatca ttgaagtttt | 120 |
| atgtccttgg atatagaagg tattttcatt ttcaccaact ctgtaaaaaa aaaaactact | 180 |
| tctggattat ataaatacta t | 201 |

<210> SEQ ID NO 867
<211> LENGTH: 201
<212> TYPE: DNA
<213> ORGANISM: Homo sapiens

<400> SEQUENCE: 867

| | |
|---|---|
| agtttaagta atatttcaga atgacactgc tatggcttga atatttgtgt cctccaaaat | 60 |

```
catgttgaaa cttaaccccc agtgtgatgg tgttagggaa ytgggccttt aggaggtgat      120
taagtcacga gggtagagcc ctcgtgaatg ggataagtgg ccttataaaa ggggtggagg      180
gaactaggta ggcccttttt g                                                201
```

<210> SEQ ID NO 868
<211> LENGTH: 201
<212> TYPE: DNA
<213> ORGANISM: Homo sapiens

<400> SEQUENCE: 868

```
ttataacacc tccttaacag gtgtttcacc tgatgccctg agatgaagtg cattatcttc      60
atgtcccaag gaggacatgg agggaaaagc tgaaaaggaa ytgtattatg aaactacgtt     120
tcataaactt ggtaatacta cattttacaa tatatgatat aactactgct gattaacctg     180
gaaaatgttc atttactttc c                                               201
```

<210> SEQ ID NO 869
<211> LENGTH: 201
<212> TYPE: DNA
<213> ORGANISM: Homo sapiens

<400> SEQUENCE: 869

```
tttttaatgt gaaatgcttg gcacagttcc tggctcagag ttagtgctta ggaaatgttt      60
gttgaatgaa gaaatgaaag agatataatc atcttaaaaa ytgtattgag tacttattat     120
gaagcctttc tcatgtattc acgtatttta acttcacagt gacaccaaga ggggtacttt     180
tattatcccc ctttaaagac a                                               201
```

<210> SEQ ID NO 870
<211> LENGTH: 201
<212> TYPE: DNA
<213> ORGANISM: Homo sapiens

<400> SEQUENCE: 870

```
tggttaagac cttgattaaa agtagattga tttattctgt cagtagttta gaccttcccc      60
cgctctttta aacatttgtt tatggatatt gacacttacc rattcttttt tcaaggtatg     120
tggctatgat atagcatccc ctaacgcagg tccgctcttc agagttccga tcactgcagt     180
tatagcagca aagtaagtaa c                                               201
```

<210> SEQ ID NO 871
<211> LENGTH: 201
<212> TYPE: DNA
<213> ORGANISM: Homo sapiens

<400> SEQUENCE: 871

```
aggaaggagg ctatacatat agaaaaaatt ttacaccagt gtgacagaat tagaatcctc      60
aaagggcttt tacagactag cgtgacggac ccaatctaat ytgttgtcta ggtctcagtt     120
ttctcagctg tgaaatgggg gatcgtgaga ttatcattcc cataggattg ctgtggagat     180
tcaataaaat aatggattaa a                                               201
```

<210> SEQ ID NO 872
<211> LENGTH: 201
<212> TYPE: DNA
<213> ORGANISM: Homo sapiens

<400> SEQUENCE: 872

```
tccatttcat ttgtactcag aggtaactaa tcttcatctc cattataact cctctaatag      60
```

| cacccagttc ttttcattca cagtgtttct catagtttta rattttttta ttagtgcaac | 120 |
| actagctgct gtaacaaata actctcaaat gttactggtt tgacacgata gctttctccc | 180 |
| tcagccattt aggaacccca g | 201 |

<210> SEQ ID NO 873
<211> LENGTH: 201
<212> TYPE: DNA
<213> ORGANISM: Homo sapiens

<400> SEQUENCE: 873

| gccaatatct ggtctctaaa gactttgtcc aataactttc taagtccgtt cccttgaata | 60 |
| tgtagatttg cctgactcag tcaaaaatgt catcaatcag matttcagt aaataatagt | 120 |
| gtagagcttg ttccctgagc cgcagtgaat gattgtccca acacatggtg ttctgaatta | 180 |
| ttagatgagt aggaaagagt c | 201 |

<210> SEQ ID NO 874
<211> LENGTH: 201
<212> TYPE: DNA
<213> ORGANISM: Homo sapiens

<400> SEQUENCE: 874

| ttaaataaga aagaataata tgtgacatag gccatatgtg gctcacaaag cataaaacat | 60 |
| ttaccatcta gctcttcata gataaagttt gctgactatg rattagaaga atatatatca | 120 |
| tataaaatat aaacagagac cttagggaaa cgcaaatcaa aaccataatg agatattatt | 180 |
| tcatacacac taggaaggct g | 201 |

<210> SEQ ID NO 875
<211> LENGTH: 201
<212> TYPE: DNA
<213> ORGANISM: Homo sapiens

<400> SEQUENCE: 875

| attgcctaaa tcagcgtcaa catgcagtaa aggttgtctt caactgagct gttctagttt | 60 |
| tctcttcccc agcactgtca tctagatttt ccatttcagt rattcccacc cctcggtcta | 120 |
| ctagcaacaa caactttctt gtatcctttg aggagacgtt agggagaacc atcatttcac | 180 |
| agttaaaaga aagacagtcc a | 201 |

<210> SEQ ID NO 876
<211> LENGTH: 201
<212> TYPE: DNA
<213> ORGANISM: Homo sapiens

<400> SEQUENCE: 876

| cctttatt ggccaccttt tttcttgtgg tattttcctc taatggagct gagttttctt | 60 |
| tgttcctgac ttcaagggct ttcataatga agcaggaaat yttccccgac cccttcatgg | 120 |
| gtaggaactg gtgtgcaggg gctggggcta gccggccact tcggcaccag ctgaggcaaa | 180 |
| ctctactcat tggaaccggt t | 201 |

<210> SEQ ID NO 877
<211> LENGTH: 201
<212> TYPE: DNA
<213> ORGANISM: Homo sapiens

<400> SEQUENCE: 877

| agtccaactg cacgtgcaag gctctgggga aatccctacc ccgctgaaat aggagcttgc | 60 |

| | |
|---|---:|
| tgttaagttt cttgggtctc ttgtcactga ttggctgaaa rttaaataag ctagtgtttg | 120 |
| agtgagggc tttatcgttt cctttagacc atcttaaaat agggactcaa ccagcctgct | 180 |
| tgtcttaatc atataaattt a | 201 |

<210> SEQ ID NO 878
<211> LENGTH: 201
<212> TYPE: DNA
<213> ORGANISM: Homo sapiens

<400> SEQUENCE: 878

| | |
|---|---:|
| ccccactcat ccaaaagctc agaccaggtt gcttggccta ccattcacga ctgcgccgtc | 60 |
| ggtctcccg tgcctcccca ccctatcctt tccttctcca rttgagccca actctgctgc | 120 |
| caaacttgac cacccagctt tccctgggc tgtcctctcc acccctgact atgcacccct | 180 |
| caaagccacc tcatgttctt g | 201 |

<210> SEQ ID NO 879
<211> LENGTH: 201
<212> TYPE: DNA
<213> ORGANISM: Homo sapiens

<400> SEQUENCE: 879

| | |
|---|---:|
| tatgtgaatg tgaagttgca cacgccctga cggcccatag tcttactctt tatatcagac | 60 |
| ttttcccagg cagagcatgg aggttgtatt tcctagtgca rtttaatgac ttgtcaatct | 120 |
| cagtattaga aaacccaaca ggcatcctgg tttccagttt tattgtaata ccaaactttt | 180 |
| ttttttttt tttgagacag a | 201 |

<210> SEQ ID NO 880
<211> LENGTH: 201
<212> TYPE: DNA
<213> ORGANISM: Homo sapiens

<400> SEQUENCE: 880

| | |
|---|---:|
| tttctttctt ttttttttt tttggccttc ttatttgcat tcagtgagga ggtgacacat | 60 |
| tgtagaacat aacctcccctt tttcattcca tgaatctaat ygttatttct gtgtttgtga | 120 |
| aagataaagg attagcaaga acgctttgca ttaagtcgac atttgtaaat gctttataat | 180 |
| tatttatgaa attatcctgc a | 201 |

<210> SEQ ID NO 881
<211> LENGTH: 201
<212> TYPE: DNA
<213> ORGANISM: Homo sapiens

<400> SEQUENCE: 881

| | |
|---|---:|
| atcctgggct acaatttag ttcctttga gaatgagtca gcagatagtg cttgagagga | 60 |
| gaaaaagaa aaaaaaagt ctctctaaaa ctcaaatcaa rtttctgtgg gccttcagac | 120 |
| aagtctgaca ttcttccatg agttggctgg gccgctggtc tcagttagga atactgacac | 180 |
| ttcacccag caaaccaaaa a | 201 |

<210> SEQ ID NO 882
<211> LENGTH: 201
<212> TYPE: DNA
<213> ORGANISM: Homo sapiens

<400> SEQUENCE: 882

| | |
|---|---:|
| gcctactttg tccaggtact atgctacggt tttggataca gtatcttatt taatcagcac | 60 |

```
agcaacttca ggaggtgcgc cactaagccc agagggatga rttgatgtct caagctgtcc    120
agaaacagcc ctgtagccac tgcagtcccc ttctctactg tcatatcctc attgtatttt    180
acactggtgc tttcaaaccc t                                              201

<210> SEQ ID NO 883
<211> LENGTH: 201
<212> TYPE: DNA
<213> ORGANISM: Homo sapiens

<400> SEQUENCE: 883
taccttgtgg aactgacacc tgtcctatac cttagtccca gtgaaatggg ttctgataac    60
attgctgggg tcttctcagc tccttccatg ggactcatta wttccctgtt cctttattgc    120
atatggatat atctgccaga acccaccatt gcccttgtca tatctagatt ccacattatt    180
aggctcagtc cctatgcttg g                                              201

<210> SEQ ID NO 884
<211> LENGTH: 201
<212> TYPE: DNA
<213> ORGANISM: Homo sapiens

<400> SEQUENCE: 884
aatttaaaat ccaaaatgct ctaaaatatg aaaattttg agtgccagca tgacactcaa     60
agaaaatgct cactggagca tttcagatct taagttttac rattagggat aatcaaccta    120
agtataatga aaatattctc aaatcctaaa cacttctttt tccaagcatc tcaaataagg    180
gatactccat ctgtatgttt g                                              201

<210> SEQ ID NO 885
<211> LENGTH: 201
<212> TYPE: DNA
<213> ORGANISM: Homo sapiens

<400> SEQUENCE: 885
ctaggtgaat ttttcttcct cttaagcctt tggtgacagg ctaaagggtg ggtcctgggc    60
catcccctct ttatacccca tctgtctgtt aatcattaat ygccaagaga gctcctcctg    120
ggatggggtg actccttggc tatgggggat gctgatatcc aggatgacct tgaacttgtt    180
tttcttggcc ccaaactttc t                                              201

<210> SEQ ID NO 886
<211> LENGTH: 201
<212> TYPE: DNA
<213> ORGANISM: Homo sapiens

<400> SEQUENCE: 886
taaaatgaca actgcagtag aaacagctag gttccacaaa caattgtgtg ctatcttaca    60
ctgtttagaa tctttactag aaagtagctt cctagccaaa ytacattttc caagcccatt    120
ccaactagtt ggtcctaggt gactagttct gccagtgaaa tattagcaga agcaaagcgc    180
atcgcttctg ggataggact c                                              201

<210> SEQ ID NO 887
<211> LENGTH: 201
<212> TYPE: DNA
<213> ORGANISM: Homo sapiens

<400> SEQUENCE: 887
caagatttag ggttatttgg ttaaaaaaaa aaaacaggaa aaaatccttg ttcatttatt    60
```

```
actttcagta tctgggtaat gagagcagtt tcaccagtaa watttacatg agagcacaat    120
cagaggtaat attaacgttt atatgggcac caaattgtgg aataacccaa aaggagatat    180
gtaatttcat tagtacatct c                                              201

<210> SEQ ID NO 888
<211> LENGTH: 201
<212> TYPE: DNA
<213> ORGANISM: Homo sapiens

<400> SEQUENCE: 888
ctgaagtcga aaatgcattt gatataccta agctatcaag catcatagct tagcctcacc     60
tgccttcatt gtgctcagag cacttaaacg ttagcctgca rttgggcaag tcatatccaa    120
acaatgctga cagcaccgca cactgtaggg tatcagttgt ttaacttcgt gaccgtgtgg    180
ctgactgaga gctgtgaatc a                                              201

<210> SEQ ID NO 889
<211> LENGTH: 201
<212> TYPE: DNA
<213> ORGANISM: Homo sapiens

<400> SEQUENCE: 889
tggaataaca atccttctgg ctgcagagat tcagacaaaa acaggcaccc ccagatgtcc     60
aagcaccaaa cacagtgaaa aagccaagat catttaaaat kggagagttt gttttggcag    120
agagtggaag cagtactaag taagaactgt acactacttt gagctgtcaa cagagaatta    180
ataaaaagtg aaaacctgtt g                                              201

<210> SEQ ID NO 890
<211> LENGTH: 201
<212> TYPE: DNA
<213> ORGANISM: Homo sapiens

<400> SEQUENCE: 890
caggaaaacc ttcccatgtt tctgattttt ttttctttgt ctttcctaca accaccagtg     60
caaacacaca cacccataa tgaatggaga acctggttaa ytgtgtaaac tccttccaaa    120
acaatcaggt cttagccctc cccactgcat tgagagagc gaccaaatat gcaacttaaa    180
gctaacacac attggacgtg g                                              201

<210> SEQ ID NO 891
<211> LENGTH: 201
<212> TYPE: DNA
<213> ORGANISM: Homo sapiens

<400> SEQUENCE: 891
tagctcactg cagcctcaaa ctctcaggct caagtgatcc tcccacttca ggctcctgag     60
tagctgagac tacagtctcg agccactgcg cttgacccca ratttttttt ttattttat    120 ttttactttt tgggaacagg gtctctctct gtcacctagg ctggagtgcc ctagtgtgat    180
tgtggctcac tgcatcctgg a                                              201

<210> SEQ ID NO 892
<211> LENGTH: 201
<212> TYPE: DNA
<213> ORGANISM: Homo sapiens

<400> SEQUENCE: 892
aaggcagctc tggggaaatt cgtctgtgta actggggtgc tatgcaggcc tgtctgtttg     60
```

```
actgtcatgc aggtctgtct gtgtgatcat cagggagaat yggccggcca cattttcaat    120 cttttctcctc ttctggaaaa aataaccact cagtctttag cgtcagctca cccttcaggg    180
tttgacacct ggagcagcag t                                               201
```

<210> SEQ ID NO 893
<211> LENGTH: 201
<212> TYPE: DNA
<213> ORGANISM: Homo sapiens

<400> SEQUENCE: 893

```
gaacaagatc tcaaggaaac acaggaaatt cctgaaacag caaaaccccc tatgtgaaga    60
cgtctgttat tcctttgtgt atcaggagca tcactgttaa ktaactgttg atacacttaa    120
aacagcttgg ttggcaatgt ccttttttgaa taaagaagag ccaggtgtgt ttttcaggat   180
gaactagaca atgctgtcac a                                               201
```

<210> SEQ ID NO 894
<211> LENGTH: 201
<212> TYPE: DNA
<213> ORGANISM: Homo sapiens

<400> SEQUENCE: 894

```
agaagctgag ccctgacttc aggacacatg aggtgcagga ccagagtcgc ccctaatcag    60
ctaggcagat tgtgctgtgt tattccactt atgaaacagc mattgcagat cctattgtgg    120
ccttctcggg agaataactg cttcaggctt tggggatagt taattttatt gtaaaattta    180
cacggattgg gcataaggtt g                                               201
```

<210> SEQ ID NO 895
<211> LENGTH: 201
<212> TYPE: DNA
<213> ORGANISM: Homo sapiens

<400> SEQUENCE: 895

```
ggagtggaag ctctctaagg gatacgaaat ctgattttat ccaaagaaat cacagcagcc    60
tttgaaagac acattcagat tttcaaacaa acaacagaca wttcaaaacc aggcgctctg    120
cttattcact gaaccgtaa gctgctgaaa ctcagggaaa agcttaagaa actggtctta    180
aagcttcagg ccaaacaatg c                                               201
```

<210> SEQ ID NO 896
<211> LENGTH: 201
<212> TYPE: DNA
<213> ORGANISM: Homo sapiens

<400> SEQUENCE: 896

```
tgggttttag ctgaatctgt gataaagtta atggatatac ctttgagaga cactgtctca    60
ctcataatag ttgctaacaa tagaaaccat tgtagctaat wcatgtagtt gaaagcatat    120
ttatgactgc tagagattca ggcttagagg ctatgcagcc aaaagtctcc caactatatc    180
atagaaatgc accagcaaag a                                               201
```

<210> SEQ ID NO 897
<211> LENGTH: 201
<212> TYPE: DNA
<213> ORGANISM: Homo sapiens

<400> SEQUENCE: 897

```
ctaaagtgcc atcctcacgt gaagggttgt tgttgctgac agcgtttgtg aaaggccaca    60
```

```
aagctgttga catctgctgc ttggcactgg ctgggaaaaa kttcagaggg tcccatactc    120
atgcatgtga acttctggga tttctcattc tgggaacatt atcaagaggc actagttgac    180
tccctttgtc cccaagggag c                                              201
```

<210> SEQ ID NO 898
<211> LENGTH: 201
<212> TYPE: DNA
<213> ORGANISM: Homo sapiens

<400> SEQUENCE: 898

```
cattgctcta cagcctgggg gacaagagca aaacttcacc tcaataaata aataaataaa    60
taaatattat atattggcta ttcttaaatc tatatatcca rttggactcc cacttagata    120
tttgagaaat atcatataca tacatgtcta aacagaacta atgttattcc actataccccc  180 taaacccact tttaccccag t                                              201
```

<210> SEQ ID NO 899
<211> LENGTH: 201
<212> TYPE: DNA
<213> ORGANISM: Homo sapiens

<400> SEQUENCE: 899

```
atcaaaaata aataaataaa acaagaggaa attgattttg tggagagcat ggacacattt    60
gttgtccata gggaactaac aataacttcc agtgacatca rttcaagaaa aaaaaatagc    120
agcagggagt gagaatgtca tctgtcaacc ccgaaaatga ttttggttaa aataatgaca    180
acaacaacaa aactaaatat c                                              201
```

<210> SEQ ID NO 900
<211> LENGTH: 201
<212> TYPE: DNA
<213> ORGANISM: Homo sapiens

<400> SEQUENCE: 900

```
aagtatgggg aaagaaaagt taaaagaggg aggcagaaat agaaactatt ttaggtgaga    60
taaactcttt aaggactccc tactcattca agtcttctaa rttccttccc ctgaggcttt    120
atttctgaaa tgggatcctt gattctcata aacccttaaa ctggaggata ctttggtttc    180
cagtattatg ggcccaattc t                                              201
```

<210> SEQ ID NO 901
<211> LENGTH: 201
<212> TYPE: DNA
<213> ORGANISM: Homo sapiens

<400> SEQUENCE: 901

```
cctttctatg aaaatttcag agtgagcttg gcaatctcta tagaatcact tactggagat    60
ttgataggaa gtgcattaaa catatataaa tgtgaagaga rttgatacct ttactatatt    120
gagttttcga gttcaatgag catggtatgt ttctccaagt atttaaatca tctttgactg    180
atttcattag catttttaat t                                              201
```

<210> SEQ ID NO 902
<211> LENGTH: 201
<212> TYPE: DNA
<213> ORGANISM: Homo sapiens

<400> SEQUENCE: 902

```
aggtagatga ccagcgatgc tgtttactac atcctacgca tgctgagata gatgagtggg    60
```

```
acaccatctc ggtaggaaag agtttgacag gaagaagaaa ytgcagagtc cctgcctgtc      120
ccagagaacc taacaaactg atctatatgg aaaggatttt cagcaaacat gcacaaacac      180
agttaatatg ctggaagaag a                                                201

<210> SEQ ID NO 903
<211> LENGTH: 201
<212> TYPE: DNA
<213> ORGANISM: Homo sapiens

<400> SEQUENCE: 903
aaggaaggaa gaaatgctaa agctacagtt ttatgacttt tgtttgcatg atttctgctc       60
aaataggctg gaggaatggg atgatgacta tattctaaca wttaaaatgc tgtcaatact      120
agaactgtaa taccacactc ctttaaacaa gaaaaagcca catttctgtt tttgtggttg      180
actacatgat ttaagttttt g                                                201

<210> SEQ ID NO 904
<211> LENGTH: 201
<212> TYPE: DNA
<213> ORGANISM: Homo sapiens

<400> SEQUENCE: 904
ccacagcaag agttagagac acagccagga ccagaactta ctgaaaagca ataatccaag       60
gtctgacttg ggttctgagg atttgctcag ttatagatgt mattctcgat ttggcctgaa      120
gagggcagac acttgccatt catggaggtg aagagcttgt ttttaaggct ggactaacat      180
ctcccaataa ggtcatttgg t                                                201

<210> SEQ ID NO 905
<211> LENGTH: 201
<212> TYPE: DNA
<213> ORGANISM: Homo sapiens

<400> SEQUENCE: 905
aggaccaagg atacagtcca gatgtgtcat ataaaaataa gacccttgca cccgactgag       60
tccacagcat attaagttta tatatccatc catagttata wttgggagag ctttgggaga      120
aataatggta ttcattataa gaggctttta aaaaagtatt tcagctaaaa aaaattgagg      180
catgctcttt aaattgttta c                                                201

<210> SEQ ID NO 906
<211> LENGTH: 201
<212> TYPE: DNA
<213> ORGANISM: Homo sapiens

<400> SEQUENCE: 906
cctgcctgtt tcctggacag ccgcagcctg tacatagctt gggctgaatg ttaggtagaa       60
agatttggga caaggagaa tcagcgtttc acgttcaaaa ytgaactggg aagctgtttt      120
gcttttaagt taaatcaatg aatgaataga tcgaaacaga gagagagagg aaagcattaa      180
aaagtcccct gaaattcatt g                                                201

<210> SEQ ID NO 907
<211> LENGTH: 201
<212> TYPE: DNA
<213> ORGANISM: Homo sapiens

<400> SEQUENCE: 907
tttccagtaa tgaaccatat agacatcatt tactcccctta tataatacag ggataataca       60
```

```
cttatacccta atgcttgtta aatgtgtgtt ccatcatcta wttatgagaa aatgtcagac    120
aaaactaaac tgagggatat tctacaaaac aaattggtaa gtactttca aatatgtcaa     180 gctctgtctc aatgtctcag t                                               201

<210> SEQ ID NO 908
<211> LENGTH: 201
<212> TYPE: DNA
<213> ORGANISM: Homo sapiens

<400> SEQUENCE: 908 ggaggggggct gcatacttct ccagggcttt tgctacctgc cccagtgtct ccggcattcc    60
gcggagccgt gcaccagtcc cctcaaataa cctatcaaat yctgtggctt ctattagatc    120
accgaggtct ttaagaactg catctttac attgcctcgt cgtgcctccg ggcgggcaag     180
acagtgtaaa atcttggaga a                                               201

<210> SEQ ID NO 909
<211> LENGTH: 201
<212> TYPE: DNA
<213> ORGANISM: Homo sapiens

<400> SEQUENCE: 909
gcacgagcta aggggggcgga tggattctga agaagtattt ccactaccaa gaaaggcaat    60
gttgggaaga acctttttggt caacttggtc aacttctcca rttccagtag agcaatccag   120
cttcttttgt catctcctct ttatctttca tccagagagc ccacataagc actgtttaaa    180
tttctcttga cttgtcttac t                                               201

<210> SEQ ID NO 910
<211> LENGTH: 201
<212> TYPE: DNA
<213> ORGANISM: Homo sapiens

<400> SEQUENCE: 910
gaatgtcaca aaaacccaga atgtcacagt attgttttct tcttgctggt gtcctatcct    60
ctctcctaac accagccacc aaagctgatt tttaaaaaat kccatgattt ctcttgttta    120
caagaagctg tttcctatac cctattcttg aaggataaag aaatagtcat tcaaaagaaa    180
tatctggctt ttcacagtgt t                                               201

<210> SEQ ID NO 911
<211> LENGTH: 201
<212> TYPE: DNA
<213> ORGANISM: Homo sapiens

<400> SEQUENCE: 911
atataacatt tggcacttat agaaaaatat aacaaggaaa aattattcca cattcagaga    60
caactagttt tttcatatgt atgtgtaaaa gtacatataa mtttatttg cctgctttaa    120 acagaactta ctctaccagt cttctgaaag caaaatttgt gttctacata ggcagttagt    180
tcagtaatcc aagtttttat t                                               201

<210> SEQ ID NO 912
<211> LENGTH: 201
<212> TYPE: DNA
<213> ORGANISM: Homo sapiens

<400> SEQUENCE: 912
tcatttgttg aaacaaactt tatttgtttc tctgtttaga actatatctg tgtatttatt    60
```

```
ttaataatat tataagcatc catggaccta ccacccaaat ygagagctag ctctcttttt      120
tggtaactac atctgagcac atttaccacc tgccttcctc cacctgggta accatcagtc      180
cactttctac attcctcaac c                                                201

<210> SEQ ID NO 913
<211> LENGTH: 201
<212> TYPE: DNA
<213> ORGANISM: Homo sapiens

<400> SEQUENCE: 913
atattatgta caactatatg aatttaagat gatttcttta tctagtctcc catctatgat      60
ttccagtttt tgtctacttc aaatcatgcc tctattgaca wttttgtgtg tgtctccaga      120
tatgcatgta gagatagttc tctgtgatat gttcctggaa atagaattgg tgagttgtag      180
tgtactcata accttaactt t                                                201

<210> SEQ ID NO 914
<211> LENGTH: 201
<212> TYPE: DNA
<213> ORGANISM: Homo sapiens

<400> SEQUENCE: 914
ccagaattca aatcaatgct aaccccagag ctcgcatttt taaaacccta caccacactg      60
gctccattca agtgttgata tgagcctctg agactgaaat yaaaacaagc agatttcgtt      120
caacttattt aacacaaaac cttcttttgt aggatctcac gaacttcagc ttgcacacat      180
cccgtgttgg aagatgccag c                                                201

<210> SEQ ID NO 915
<211> LENGTH: 201
<212> TYPE: DNA
<213> ORGANISM: Homo sapiens

<400> SEQUENCE: 915
aatatataat acgtgagagg tgataagcgt tatgtagaaa ttaagcagga ttaagaggta      60
tagtggaaat gactgtaggt taagagggaa agggtgaaaa wtcagagatg ttctttcagt      120
caagaacaag gcaagtatta aataaactta tacttaggtc tactgttctt aatatgttcc      180
agctcctgca tggtccctgt t                                                201

<210> SEQ ID NO 916
<211> LENGTH: 201
<212> TYPE: DNA
<213> ORGANISM: Homo sapiens

<400> SEQUENCE: 916
tgagcaggtt cctagctcgg tgccttgcac aaaactggag cttaatgttt gttgatgagg      60
tgaagagggg gatacttatc aggggccaca ttcatgggaa ktggatactg agacagaagt      120
gggtgagtca aaggtttatt gggcagtgac acttgtgaca gtccagggca tgaagcagaa      180
gcaggatcag gcgggaggag c                                                201

<210> SEQ ID NO 917
<211> LENGTH: 201
<212> TYPE: DNA
<213> ORGANISM: Homo sapiens

<400> SEQUENCE: 917
tcttgttttt ctggagacct tgttattcag ccttttcttt aatccaggga gctcttccat      60
```

```
atttttcaaa tatcctgagt tttttgtttg tttttttactt matttagccg gagtgtgtct    120
ctattgtttg ccaatgatct aaaggatatg ttcgtttagt attttgacaa atacctctaa    180
ttgtcttcca atcggaggta g                                               201
```

<210> SEQ ID NO 918
<211> LENGTH: 201
<212> TYPE: DNA
<213> ORGANISM: Homo sapiens

<400> SEQUENCE: 918

```
ttaaaaagtt ctctatagag tgggattttt taataatacg aagttgggga aggggaaggt     60
gtttgtctca tatttacttt ctgcagctca tattctgcaa ktaatattct tgctcctttc    120
aaactgtacc aaaacaccct cattaagcag tcaagctata accacaacag catcaccaca    180
ccctcaagaa cagttgagtt t                                               201
```

<210> SEQ ID NO 919
<211> LENGTH: 201
<212> TYPE: DNA
<213> ORGANISM: Homo sapiens

<400> SEQUENCE: 919

```
gaattaagta gaaccactgt caccacaact taacaactat gatgtgccaa gaggtttcat     60
agactttata gtctgattag gcctaagagc tggcttttag watttactat ctgttattga    120
aactgcttcc ttgactggta tatctaacag tttggtcaga taacttcatc ctaaaattac    180
agaagtgaga aggggttaaa g                                               201
```

<210> SEQ ID NO 920
<211> LENGTH: 201
<212> TYPE: DNA
<213> ORGANISM: Homo sapiens

<400> SEQUENCE: 920

```
aaaaattgaa ggtctgcagc aactccattt tgagcaagta tattagcact atatttccaa     60
cagtgtatgc ttgcttcata actctgtcac gtttcagtaa ytcttgcaat atttcaaacc    120
ttttcattat tattatatct gttacgatac tgttttgttt gtttgttttta ttttgttttg    180 agacggagtc tcgctctgtt a                                               201
```

<210> SEQ ID NO 921
<211> LENGTH: 201
<212> TYPE: DNA
<213> ORGANISM: Homo sapiens

<400> SEQUENCE: 921

```
aaagggtaca aagttgcagg tatgtaggat gaataagtct atagctctac tctacaacat     60
aaaaactgaa gttgataata ttgtgctgca tgctgtaaat ytgctaggag agtatatttt    120
aggtgctttt accacacaca cagaacaagg taactatgtg aggtgatgca tatgttaatt    180
tgcttgacta gtaatcattt c                                               201
```

<210> SEQ ID NO 922
<211> LENGTH: 201
<212> TYPE: DNA
<213> ORGANISM: Homo sapiens

<400> SEQUENCE: 922

```
cactcttccc ccactcccta ttgcaagaat cccagcctga ccctggccac ctctggccag     60
```

```
ggattgtatt cgaagactgt caggaagctc tggaatcaat kgagctgggg accccagct     120 gaacaatatc caggaaccaa gaggcctgtg gagagccagg cagggcccg gccatcccca     180 ggcaggacag catcagtgct c                                              201

<210> SEQ ID NO 923
<211> LENGTH: 201
<212> TYPE: DNA
<213> ORGANISM: Homo sapiens

<400> SEQUENCE: 923
aagctgcagc acactcattc cactttgaat ataatggaag aagaaatgcc catccttcac    60
taacttgaac tacaagatta ttttccaccc tcaggaggaa ytggtctttt cccaccactg    120
atgggccacc actgttgcag gatttaagtg ttacctcgga ataccaaaa agatagttct     180 attacaatgt tgtatcctat a                                              201

<210> SEQ ID NO 924
<211> LENGTH: 201
<212> TYPE: DNA
<213> ORGANISM: Homo sapiens

<400> SEQUENCE: 924
tcacatactt attgtgtgcc agttgctgta gtgggcactg taatacaaag gtgaatgagg    60
cacaggcaca ggctttaact ttcaatggag aagacagaat ygtaagcaat agttgtgata   120
ccatgtgtgg agaggatggt agagacaaga acaggatgtc atgggatacc tggcccagag   180
ggccactcaa cccagctgag g                                              201

<210> SEQ ID NO 925
<211> LENGTH: 201
<212> TYPE: DNA
<213> ORGANISM: Homo sapiens

<400> SEQUENCE: 925
gtcaggtatt ttgcaaaatg tccttcaatt tggggtcatc tgatattttc ctatgattag    60
atttaggtta tgcattttgg gaaataatac cacatccaat ytgtaatctg gattttgtga   120
ataggtagac atttagttca ctttcatcct gacttcccac aggtaacatg cctccttgta   180
ttatctccca gtcctttgcc c                                              201

<210> SEQ ID NO 926
<211> LENGTH: 201
<212> TYPE: DNA
<213> ORGANISM: Homo sapiens

<400> SEQUENCE: 926
agtgcacggc caatgaggcc ttgtgaagtc aagttccagt gtggaatttg gatggtgata    60
atgagagatt gagcttcagt cccctagtgt aataggaaat kccacaacga gatataaaat   120
ccttacatga agtttcccta tctacacaag actgaatcga ggctatttca gttcgtgttg   180
ctgaatgttc tctcttggtt t                                              201

<210> SEQ ID NO 927
<211> LENGTH: 201
<212> TYPE: DNA
<213> ORGANISM: Homo sapiens

<400> SEQUENCE: 927
tcaatgataa cttcctcact gctctgcaaa acaatatgct ctctttggga gaaaatgaag    60
```

```
aagaatcaga gccagctagc tagctagcta gctaacgggc rattgttcaa aacctggggg      120
gcacatggga gtatgtcata aagtcatgtc acctgccagc ttgccagctt tctaagtagg      180
gtgaaaggat taagtaagaa c                                                201
```

<210> SEQ ID NO 928
<211> LENGTH: 201
<212> TYPE: DNA
<213> ORGANISM: Homo sapiens

<400> SEQUENCE: 928

```
aggatggact gtaaatccaa tgagaagtgt tcttataaga gaaaggaagg gagggaagaa      60
aacataagag gagaaggtga tgtgaagatg gaggtagaaa ytggagtgaa gcatctgcaa     120
gaaaaggaac tccagggatt gccagcagcc accagaagct acaagacgca tggaatgaat    180
tctccctcgg agcctctaga a                                                201
```

<210> SEQ ID NO 929
<211> LENGTH: 201
<212> TYPE: DNA
<213> ORGANISM: Homo sapiens

<400> SEQUENCE: 929

```
ctctactttc tgtcaacctg gagaaagtca cttaaccttt cagcacctgt ctcacagtga      60
aagtgaacag tttaggtcaa gaatgctttc agctccaaaa ytctaagtcc aatacgatca    120
cagaaaaata aagtggctac atatacgggt gcacacacac acagaggttt gtctgtgcca    180
agagagctcc acaggagtct g                                                201
```

<210> SEQ ID NO 930
<211> LENGTH: 201
<212> TYPE: DNA
<213> ORGANISM: Homo sapiens

<400> SEQUENCE: 930

```
ggagtagatg cctgaggttg tcagcaaata ttgaagattt ttatttccag ggggttagaa      60
acttcacgta gcttctctgc tctgcacaca taaggagtaa ktggattatt ttccctgagt    120
cagtaaggtt ttcggtgtca cataatctca ggggaacaaa tgcaattgct tagatctcaa    180
tatactcctc agatggcaac t                                                201
```

<210> SEQ ID NO 931
<211> LENGTH: 201
<212> TYPE: DNA
<213> ORGANISM: Homo sapiens

<400> SEQUENCE: 931

```
agatgatgta gctggacatt taaaaaagca cagtagtaca tgcagggtca catcacagat      60
tgaaatgaaa aaagtccttg ttgtcatttt tatttcacca rttggaataa gttttcaact    120
tgtgaaaagt gctgcacaaa tcctggaaac tgaaattctt tactaaagca cagggaagtg    180
cagggcaatc aatggcaata t                                                201
```

<210> SEQ ID NO 932
<211> LENGTH: 201
<212> TYPE: DNA
<213> ORGANISM: Homo sapiens

<400> SEQUENCE: 932

```
ctggtcttga actcctgacc tcaggtgatt tgccccgctc agcctcccaa agtgctggga      60
```

```
ttacaggagt gagccaccac gcctggccag aactaatcaa ytatgttttt gttgcatctt    120
tgcctgtctc tcccactggg ctataagctc cttgagaccg ggaattgtgg ctttgtctta    180
tatacttctg cctaacacaa t                                              201
```

<210> SEQ ID NO 933
<211> LENGTH: 201
<212> TYPE: DNA
<213> ORGANISM: Homo sapiens

<400> SEQUENCE: 933

```
aagaagatgc catccaggac tttcatagca agagagggga aaccaatgcc tggcttcaaa    60
gcttcaaagg acaggctgac tcatttgtta ggggctcatg matttggcga ttttaagttg    120
aaaccaatgc tcatttacca ttctgaaaat cctagggtcc tttagaactg gtcaagtcta    180
ccctgcctgt gctttagaaa t                                              201
```

<210> SEQ ID NO 934
<211> LENGTH: 201
<212> TYPE: DNA
<213> ORGANISM: Homo sapiens

<400> SEQUENCE: 934

```
ttctatgagg ccagtatcat cctgatacca aaacctgcca gaaatacaac aaaaaaatag    60
aacactttag gccaatatcc ttaatgaata tcgatgtgaa rattgtcaac aaaatactag    120
caaactgaat ccagcagcac atcaaaaagc ttatccacca caatcaagta ggcttcatcc    180
cggggttgca aggttagttc a                                              201
```

<210> SEQ ID NO 935
<211> LENGTH: 201
<212> TYPE: DNA
<213> ORGANISM: Homo sapiens

<400> SEQUENCE: 935

```
gtacaatctc caagacattt taattttacc ctgtctttta tctgacagag ttacctgcat    60
attttcttat atatcgtcac cttatatttt cagaaaaata wttgtacttc aatagaaatc    120
tctatgcatg ctctgtagca tgctccaggt tacctgaatc tgattttatg gaaactattt    180
tataagtccg taagtcatag a                                              201
```

<210> SEQ ID NO 936
<211> LENGTH: 201
<212> TYPE: DNA
<213> ORGANISM: Homo sapiens

<400> SEQUENCE: 936

```
ccatgctact tctccagttc acaagctgca gccacacaaa acccagacct gcctcggggc    60
ctttgcactt actgcttccc ttaagattct cacatgaata rttccttctt gtcattcagt    120
tttcagctta aatgtcacct cctgagctcc tgtttggagt agacttcctg tcaattcccc    180
tctttatcac tttgccctat t                                              201
```

<210> SEQ ID NO 937
<211> LENGTH: 201
<212> TYPE: DNA
<213> ORGANISM: Homo sapiens

<400> SEQUENCE: 937

```
tttccatttt tcattagccc cactgtccac atgctcttga ccattctcag agtcgggatc    60
```

```
tgaccatgac tctagtgacc ttcaatatat ataatcataa rttggtgtcc tttgtcttat     120
agttgtttcc tgaagaatcg tctcaaatgt atacaaatcc tggcatttaa ttgtgggaat     180
ggatctgcta ctgtgcacaa a                                                201
```

<210> SEQ ID NO 938
<211> LENGTH: 201
<212> TYPE: DNA
<213> ORGANISM: Homo sapiens

<400> SEQUENCE: 938

```
ttaaaggtat tgaaaatcca cattggccaa gagcttattc tattttcaag tagagatgtt     60
gcaaagatgc aagattctca aaatatagtg aaaggttgaa rattaaaaga cttatgcttt     120
catcatcttt tctttatcat aacatgcata aatgttctta tagactgata tgacaggtcc     180
ttcagtacca tatgctcaca g                                                201
```

<210> SEQ ID NO 939
<211> LENGTH: 201
<212> TYPE: DNA
<213> ORGANISM: Homo sapiens

<400> SEQUENCE: 939

```
gaaagttctt cattttacgg gctgtgaaaa gggggcatca caagtgacca gtccaagggc     60
acacaaatgg atagggatag acacaggaca agaaaccaaa yttcctcaat gccaaccagt     120
gcttctcata ccctgctcac ctttaactac aagatgtcaa acatcaagat aaaaatagca     180
tgcttggccg ggtgcggtgg c                                                201
```

<210> SEQ ID NO 940
<211> LENGTH: 201
<212> TYPE: DNA
<213> ORGANISM: Homo sapiens

<400> SEQUENCE: 940

```
attggtcttg aaacagttga tgctttgccc acatgaaaaa aaaagcagtg gtatcaatag     60
ccaacaccac ttagctaaat gaccttgttc ctagaaacaa ytgcttaaca ctattgtgta     120
cagagtcctg gacatactgt aacttttctg attatcacaa tgcaccaaaa tacatcatct     180
actaatgcac tgtatataaa t                                                201
```

<210> SEQ ID NO 941
<211> LENGTH: 201
<212> TYPE: DNA
<213> ORGANISM: Homo sapiens

<400> SEQUENCE: 941

```
taatgttagc tgtggttttg tcatatatgg cctttattat gttgaggcac ttttttctgt     60
tcctagtttg ttgagacttt tctttttgta atcaataaat katatcagat tttgtcaaat     120
gcttattctg catctattga gattattgtg taacttttat tccttattct gtgattatgg     180
tgtatcacat taactaattt t                                                201
```

<210> SEQ ID NO 942
<211> LENGTH: 201
<212> TYPE: DNA
<213> ORGANISM: Homo sapiens

<400> SEQUENCE: 942

```
ataatgtata cataggtttt ctgagggtgt aaaagttcat gtgattcacg tcttggaaag     60
```

```
tggaggctga agaatgcttt cccattgggt tagcagctga rttggtctga agaggatagt        120
caagggaaag gcttgcatcc atacaaaaga aaaagtaata aaccgagatc acaaagtata        180
tgagggcttt cctgacacct a                                                  201
```

<210> SEQ ID NO 943
<211> LENGTH: 201
<212> TYPE: DNA
<213> ORGANISM: Homo sapiens

<400> SEQUENCE: 943

```
taattcttct acttgcctga tactcatggc atatcaacat tactttgatg aaaaacatta        60
aatctctttg gattaaatgc ctgcaggtaa tatcaagtat ratttacctc tcacaagcct        120
attacacatg tttaggaaag acgttaaaaa aacagtattt cgaacaatta atgctgtagt        180
tgtgttaacc tgtgtaactg a                                                  201
```

<210> SEQ ID NO 944
<211> LENGTH: 201
<212> TYPE: DNA
<213> ORGANISM: Homo sapiens

<400> SEQUENCE: 944

```
agaactcaaa acagaagcaa gcaagccctc aaaggaactg agaaaatttc tccccacttt        60
gttctgaggg gtctcagcta ctctggtatt taaaataaat kggttttgaa aaataggtta        120 ctgccccttta gttgatgact aaaacagaag ccaagaagtg tgcaaattgc aaactgacat        180
gcatgagcca aacatattct c                                                  201
```

<210> SEQ ID NO 945
<211> LENGTH: 201
<212> TYPE: DNA
<213> ORGANISM: Homo sapiens

<400> SEQUENCE: 945

```
gactccatcc cctaccacca tgtcacaatg tgatagaaac cactgggtaa acatatttca        60
gataatagtc caaggggctt gaatagctag atacccaaat ycccttttat ctttatcttg        120
aactgcgtct ggcctccaga tctctagcta ggtaatcaaa gtggctggtt tttattcttt        180
tcatgttgca acacctagag a                                                  201
```

<210> SEQ ID NO 946
<211> LENGTH: 201
<212> TYPE: DNA
<213> ORGANISM: Homo sapiens

<400> SEQUENCE: 946

```
acactaactt accataataa catcttttaa actattttcc atatcattaa gtatcaagtg        60
ttgttaccct gtagtagtac agaagtaaca gtaaactagc rattaataga aaaagctaga        120
ttcctgaagg ttatggcatt tagaaagatc ttaattgttc acaatggtaa aactaggaaa        180
caaaagaatt ctatagcctc a                                                  201
```

<210> SEQ ID NO 947
<211> LENGTH: 201
<212> TYPE: DNA
<213> ORGANISM: Homo sapiens

<400> SEQUENCE: 947

```
tcatgataac accaaaaggc tgtggcagag ttatcttata cattcacaca attcttataa        60
```

```
tagggggctgc cagcattctg aatggaatgt aatagatatt ratttgcaca cccaggtgtg      120
aatattgtga tttccttta ccaccttcca gcttggaaat aaatgagctt ctactgtttg       180
ttgttgctcc tttcctcatt c                                                 201

<210> SEQ ID NO 948
<211> LENGTH: 201
<212> TYPE: DNA
<213> ORGANISM: Homo sapiens

<400> SEQUENCE: 948
aatttctcat tctgggtacc tcatattgca aaagagcctg tggcctctga gctgacttgg      60
tccagtagga aaacagggaa aacagttcgt atttcagaat ygactgtcac agccttgaga     120
cctgaaatgt agcccccatc catgagtcag tgaaatatct gtatttctta attttctttc    180
cttaaaacca cactctccct g                                                201

<210> SEQ ID NO 949
<211> LENGTH: 201
<212> TYPE: DNA
<213> ORGANISM: Homo sapiens

<400> SEQUENCE: 949
tctttgccat tgtgaagagt gtggcaataa acatttgcgt tcatatgtct ttatagtaga     60
atgatttata ttcctctgga tatatgtcca gtaatgaaat wcctgggtca aacagtattt    120 ctgttttag cttttgtgga ggcaccatac cgctttccac aatggataaa ctaatttaca    180
ctcccaccaa cagtgtataa a                                                201

<210> SEQ ID NO 950
<211> LENGTH: 201
<212> TYPE: DNA
<213> ORGANISM: Homo sapiens

<400> SEQUENCE: 950
tttcaatact gcaaaaatgt tcagcaagc atccttattc atgcttttta cacatatgta     60
caagtgcaaa gttttttcta gaatacacag aaagaagcag rattgttggt ttatgtggtt    120
tgcacatgaa aaaatggctg tatctatta tgcccaccct aacaaggtat accttgatat    180
tagcaaactt gttagtgttt g                                                201

<210> SEQ ID NO 951
<211> LENGTH: 201
<212> TYPE: DNA
<213> ORGANISM: Homo sapiens

<400> SEQUENCE: 951
aattttaaaa tttaatttca aaataggaaa tacataggaa caaatctgac aaagatataa     60
aagatgtgta ccctaacatg tgtaaaacat tgctgcacaa mttaaagacc taaatgaatg    120
ggaagatata ctatactgtg ttcatgggtc agaagcttca atatgattaa gctgtcagtt    180
ctcccatatc aaaatcctag t                                                201

<210> SEQ ID NO 952
<211> LENGTH: 201
<212> TYPE: DNA
<213> ORGANISM: Homo sapiens

<400> SEQUENCE: 952
tcagttgatg tcagctccat cttctcaggt gttcagagga aaagactcag agtcattctc     60
```

```
attctcttttt tcctcctgta ccctgcaatc tgtctggaaa ytatattagt cctatcataa      120
aaaatgattc cagactctaa ccacatgtat ctatctccac tgctacccca agcagattca      180
ggtcctcctc tcctccacct t                                                201
```

<210> SEQ ID NO 953
<211> LENGTH: 201
<212> TYPE: DNA
<213> ORGANISM: Homo sapiens

<400> SEQUENCE: 953

```
gattttgcca gagatcattc tttgatgtgg gaagtggtcc tgtgcattag aggatgcttc       60
gcagcaacct ggcctctgtt aactatttgt aagtagcaaa ytcctcactc cttgtgacaa      120
taaaaaatgt ctccacacat caccaaatgt cttatatggg caaaattggc cccagtggca      180
actacttctt caaaactgcc c                                                201
```

<210> SEQ ID NO 954
<211> LENGTH: 201
<212> TYPE: DNA
<213> ORGANISM: Homo sapiens

<400> SEQUENCE: 954

```
caacatgtgt tgagaatact tttgcaaatg ttaaagtcaa catggctata acaagcccaa       60
gttctccagg aggaatgcat gcatttaaaa tggaatcaaa rtttatagag tacaataata      120
agagccctct tacttacatt ttcatttaat cacatgtata tggccatctt gtccattttg      180
aggttgggct ttagggaaag c                                                201
```

<210> SEQ ID NO 955
<211> LENGTH: 201
<212> TYPE: DNA
<213> ORGANISM: Homo sapiens

<400> SEQUENCE: 955

```
caaatttctt acccacaaag ttcatgagaa ataatataat atttgttgtc ttttcgctaa       60
gatttgtgtt gatctgtcac atggcaatat aaatgaccaa ytgagctatt ttctcaaact      120
tcagggctat ttgttctcat tgaaagatta tatacaatac tcaggaaact tcatataatc      180
atctatgtga tgtttctaat t                                                201
```

<210> SEQ ID NO 956
<211> LENGTH: 201
<212> TYPE: DNA
<213> ORGANISM: Homo sapiens

<400> SEQUENCE: 956

```
agtacattcc cttttagggt ccctgtgctg tgaatctcat aattgctcca gattgtggct       60
gtgctgtcct cctgggtctc agagggggga cgatgcagaa ytgagtccct ccccaggatc      120
caagacagat acgaatgtta gaaagaaata acctttgtt attttgaacc aggacgatgt      180
ggtgctgctt atgacccact g                                                201
```

<210> SEQ ID NO 957
<211> LENGTH: 201
<212> TYPE: DNA
<213> ORGANISM: Homo sapiens

<400> SEQUENCE: 957

```
tccagaacat cctgggttca ggcatatagg ttgtagaaca gtaagatttc tgttcagatt       60
```

```
tcttttgttt atgctcattt atagaagcag tctttttttt watttcagta ggttttttggg      120 gaacaggtgg tgcttggtta catgaaaaag ttctttactg gtgatttctg agattttcat      180
gcccctatca cccgaccagt g                                                201
```

<210> SEQ ID NO 958
<211> LENGTH: 201
<212> TYPE: DNA
<213> ORGANISM: Homo sapiens

<400> SEQUENCE: 958

```
cgacttgctg tgccttctgg catccgcttc ccaatcagaa acctcacaca tgtctgcaaa      60
gctcccccca gccagatcct ccagctcatc ttcctctgaa ytgtgttagt tgtacatatg      120
gaaatccaga gagcctccaa ggattagagt ccacgtcttt ttttatttgg aactcttacc     180
tgccgaccca tcatcaagga c                                                201
```

<210> SEQ ID NO 959
<211> LENGTH: 201
<212> TYPE: DNA
<213> ORGANISM: Homo sapiens

<400> SEQUENCE: 959

```
attttgtgag gatgtaagca aactaagaaa atgtcagata tgtccagcta ctagtctaaa      60
gtgttgaccc cagtgtgggg ggcagagagg gagcatgtaa rttgtcctca tctctagagc      120
agcttcacag aaatccagag gttcttttag ctctgacact ctctaactct gggaatcact     180
aagtcaatgg agttcagagg g                                                201
```

<210> SEQ ID NO 960
<211> LENGTH: 201
<212> TYPE: DNA
<213> ORGANISM: Homo sapiens

<400> SEQUENCE: 960

```
ttatacgagg ctgagtcccc cagacctggg ctacttgggt ctaggaaata gaggctgaaa      60
gtactaatgg ctcagtttaa agtcactgcc agtgacctaa ytgggagagt ttttattttt     120
ctttcctgaa actctagtct ttgcagggtt atagattcta gctcccaaag gggaaaatat     180
ttcacagggg acactatagg a                                                201
```

<210> SEQ ID NO 961
<211> LENGTH: 201
<212> TYPE: DNA
<213> ORGANISM: Homo sapiens

<400> SEQUENCE: 961

```
ttatcagaag aaagtgtaag aattaaagtt ctcattacaa aagctttgcg catcaggcat      60
tttatactag gaatgctcaa aatctaaagc agagataaat yacattaata tggttgaaag    120
caagggtcct gtatgtattc ttgaagagag ggactctatc ctgcagtaga ttataaaaat    180
ttaagagcat ccttctcctt c                                                201
```

<210> SEQ ID NO 962
<211> LENGTH: 201
<212> TYPE: DNA
<213> ORGANISM: Homo sapiens

<400> SEQUENCE: 962

```
tacatctgct ttagcaccca agctcttgct tggtgaaaaa ttaatagtaa acattcatct      60
```

```
tttgagcatc ttcaaatatc cccttagaa tgacattcaa ytattaggtc agtaacccca      120
agagaaaacg gttgtttgag tgtatatact gtattacaaa ataagggtg aattcaaagg      180 aaaacataag atgcaattcg t                                               201
```

<210> SEQ ID NO 963
<211> LENGTH: 201
<212> TYPE: DNA
<213> ORGANISM: Homo sapiens

<400> SEQUENCE: 963

```
tggtaagaga atccgcacct gaagagactg ggaatgaatg gaaattttcc tcccaagaga      60
agggctttgc atcctccagg gccaactgga tagccgtgga mattggctgt gcagtgggct     120
tcttctcgca gctctgcagt cttctggggc tgtcagccac gatcacctgc gtatgcctga     180
tgattgccac tcacagggag a                                               201
```

<210> SEQ ID NO 964
<211> LENGTH: 201
<212> TYPE: DNA
<213> ORGANISM: Homo sapiens

<400> SEQUENCE: 964

```
aagcctgaag tttaaactac cattttgaga tctaccctag agatttactc aactctctgg      60
gttatttctc atgtgtacag aacatatact tgtacatgca wttcaacttc tgtccatttt     120
cctcttgata atctgtttta ttcttcccgg gagtctcagc taagaactca tgaagtggag     180
aatattattt ttcctcacct a                                               201
```

<210> SEQ ID NO 965
<211> LENGTH: 201
<212> TYPE: DNA
<213> ORGANISM: Homo sapiens

<400> SEQUENCE: 965

```
taatctattc ataagaaaaa tatctatgaa cccaattgag agacattcta caaaatacct      60
gactaatact caggttgagg ttataaaaat aatgtaaaaa mttttcacaa tctagaggat     120
cctgtggaaa catggcaact aaatataatg tagtatcctg gataggataa cgggacagaa     180
aaataacatt agtaaaaact a                                               201
```

<210> SEQ ID NO 966
<211> LENGTH: 201
<212> TYPE: DNA
<213> ORGANISM: Homo sapiens

<400> SEQUENCE: 966

```
tgacttcccc tgtggcatgc ctgcaaggaa aatacattga ccaaaggatt tgagtgatag      60
gtcctctctg cagtcatttt ttaaaatgga aatcaataaa ytcgtattct tattttgtgt     120
gttagttttg tgagcttggt taatgtgatt tcccctattt gtactgactg acataccatc     180
atcatcaacc tgcaaaggtt g                                               201
```

<210> SEQ ID NO 967
<211> LENGTH: 201
<212> TYPE: DNA
<213> ORGANISM: Homo sapiens

<400> SEQUENCE: 967

```
agtttgtatt tgactcaaat acaatgtgag tggctttgtg gaattaagat atagagatag      60
```

```
atttgctacg attcagtaat gagtacaagg tataagagca rattaccatc atagtgtctt    120
ttcttgctca cgtccattta ctcaacaaga cttattgaac ataaggcact ggtccagatt    180
tttccaagga ccagttaaga t                                              201

<210> SEQ ID NO 968
<211> LENGTH: 201
<212> TYPE: DNA
<213> ORGANISM: Homo sapiens

<400> SEQUENCE: 968
ctgtcagaca ttcaaagaag aatcagtacc aattctattg acactattcc acatgctaga     60
gaaagaggga atcctcccta aatcattcta tgaagccaat wtcagcctaa tatgaaaatc    120
agggaaggac ataacaaaaa aagaaaacta cagacaatat ccctgatgaa catagatgca    180
gaaatcctca ataaaatact a                                              201

<210> SEQ ID NO 969
<211> LENGTH: 201
<212> TYPE: DNA
<213> ORGANISM: Homo sapiens

<400> SEQUENCE: 969
agcacgcttg tactgtattt ctcttggccc ctttcatcta gaatttatgc aagagaaggt     60
cctgttagta ggggttaaac atttggattc agctattcct rattgcattt tagttattac    120
atcatgtaac ccaatacatt tcttttgttg ttgttactct ttttttgcttg attcattttt   180 aatgtttcct tttgtattaa t                                              201

<210> SEQ ID NO 970
<211> LENGTH: 201
<212> TYPE: DNA
<213> ORGANISM: Homo sapiens

<400> SEQUENCE: 970
ctggcatatt ttaaacactc aaaaatattt tctgtaaaaa tagtccttgt tagacctcca     60
cctatgaaac catatcacag ttgttgggtt ttttttgtcca wttgtttatt ttagttaagc   120
tctcatttgt tttaagaaa aactctaggt cttataactc ctcattaaat ctatcctaca    180
gctcctcttg atgtccagtt a                                              201

<210> SEQ ID NO 971
<211> LENGTH: 201
<212> TYPE: DNA
<213> ORGANISM: Homo sapiens

<400> SEQUENCE: 971
aacagcatga ctctggccga ccgcctggct tctttctagt cttccttctg tactttgtga     60
ccttgaggca agtcatttgg tctctgtgcc tcagtttccc matttgtgga atggggataa    120
ctggttgcta atattgctgt ttttattgtt ataattattt tgtaaataga agggttgaag    180
gttcagggaa gcaagttgat t                                              201

<210> SEQ ID NO 972
<211> LENGTH: 201
<212> TYPE: DNA
<213> ORGANISM: Homo sapiens

<400> SEQUENCE: 972
acacaattaa tgccaacatt tgtacttaca ttttccattt tatgaattta agtcttgttt     60
```

-continued

```
cccaacata aggtaaacct tcttggaaaa cacaccttgt matttacact ttcctgtatc     120
tctcagtgtt tatataagtt gatcagtttt tccttcaaaa attttcttg ggaagccaaa    180 ttactaaaag ggatgtactt t                                               201
```

<210> SEQ ID NO 973
<211> LENGTH: 201
<212> TYPE: DNA
<213> ORGANISM: Homo sapiens

<400> SEQUENCE: 973

```
attgcatttt atatatatgt aatgttccac aaaatgttat ataaatgaca tttacccaca     60
aaggtaagaa taagaggaat gaagagatta aaatagataa ytctaagttt ctctccaatg    120
tcagggacta ggccttttac atcttcatgc ccggtcactg gcacatactg aactttcata    180
tacttttctg cagcatgatt g                                               201
```

<210> SEQ ID NO 974
<211> LENGTH: 201
<212> TYPE: DNA
<213> ORGANISM: Homo sapiens

<400> SEQUENCE: 974

```
atatggatgt gggtgaacat gacagtttca actataattg ccaagcaaca ctatggtatt     60
atctgtattg gttgacacct tttagtctaa ggagagaaat ygccaagtgg cacagttcac    120
ttggtcttaa agagacatga gttggtcttc accttgacac agagccttgc aagattagcc    180
agtcagctct gtgaaagcag t                                               201
```

<210> SEQ ID NO 975
<211> LENGTH: 201
<212> TYPE: DNA
<213> ORGANISM: Homo sapiens

<400> SEQUENCE: 975

```
ctttgtaagt gagcttgtga ggttgcagga tcttaggatc ttgcctcaga acttcgaagc     60
agcatgaagc atctaagcac agctctgtgg agcacagaaa rtttgaaaag agcacctcat    120
tcttggctcc tgaggaaatg gcatttgttt gcgtctgtaa ggaaaccaca cagggcagtg    180
tttacaagta tttcgattaa a                                               201
```

<210> SEQ ID NO 976
<211> LENGTH: 201
<212> TYPE: DNA
<213> ORGANISM: Homo sapiens

<400> SEQUENCE: 976

```
tcaaaacttc ctcccaactt ctaaaagttc agccaagaaa aaagaattta gaaggcaagg     60
cagggaagat aaaaaccaga cattctgttt cccaaaaaat ygacttcctt cttccctttg    120
aaaatctcct tttctgcaaa atattgccct attgtgggag attttgctct tctaccttaa    180
aaactcctgg agtcctcctt g                                               201
```

<210> SEQ ID NO 977
<211> LENGTH: 201
<212> TYPE: DNA
<213> ORGANISM: Homo sapiens

<400> SEQUENCE: 977

```
aattttcaga attaatttaa ttctgtgcct gaattatttt aatttttcatg taagactgat     60
```

```
ttttgctaag ggtgtttgtt agcagctatg ctggagcaaa ytctaagaaa ctagaggtcc      120
tggaaatctg aataaatcta caggtgaaga ctactccttg aacttgggaa aacatcagaa      180
ttgctgttaa tgtacaaata a                                                201
```

<210> SEQ ID NO 978
<211> LENGTH: 201
<212> TYPE: DNA
<213> ORGANISM: Homo sapiens

<400> SEQUENCE: 978

```
taagtgacag ctcattttca atttaattca ttaaagtatt cctctctact ccaaaagaga       60
taaatagact ttgtcagaga tttctgccta aggtgttaaa mattgctcat agttcaatgt      120
ttaaatagtt taaaaaacag gatcatcatg gcagatggga ggccggacta gattgcagtt      180
ccggacagag taacgtgcgg a                                                201
```

<210> SEQ ID NO 979
<211> LENGTH: 201
<212> TYPE: DNA
<213> ORGANISM: Homo sapiens

<400> SEQUENCE: 979

```
agggtctctt ttcatacacc ataaaacaga gacccagagg cagctcgcaa cttgctcagg       60
tcatgtatta gtgagcatca gaggcaggcc aggacccccca rttgcacagg tctaggaagc     120
accatttcat ccaagtctat gttgcatgcc aaagagtgtc actgacagag aacacagtga     180
gaccactgct accgccctgg a                                                201
```

<210> SEQ ID NO 980
<211> LENGTH: 201
<212> TYPE: DNA
<213> ORGANISM: Homo sapiens

<400> SEQUENCE: 980

```
gccatcctaa caaaattatt atccgtgctt gaaagttccc tttcatttt taacatatgt        60 ttatacatat tatataggtt taagtaatga tgcatttaca rtttaaagac tgatgtttac     120
ttgataatat atcatactta cttgctattt taaaaacttc ataaattata acagcatgat     180
aaaccattta gagaatcagt a                                                201
```

<210> SEQ ID NO 981
<211> LENGTH: 201
<212> TYPE: DNA
<213> ORGANISM: Homo sapiens

<400> SEQUENCE: 981

```
tttgtctctc ttccctgcc aaagaacagt tgctcacaat gggcgtagcc cccttctgtg        60
cgatggcaag ggtgaggtga gataacgtga tccatttaat yatttgggca ctcagtggtt     120
tgattttgaa acttgtgctg gaaccagtga atgttttggg gttaaactcc actggcagag     180
cagttagtga tccaagaact c                                                201
```

<210> SEQ ID NO 982
<211> LENGTH: 201
<212> TYPE: DNA
<213> ORGANISM: Homo sapiens

<400> SEQUENCE: 982

```
aatccatcta atttttctc tggtttcagt ggcaaattca gttccctcct gagcctagaa        60
```

```
ccttgcagta cattgtagat cagttggcta gataactgaa yttcctgctc attccttttc    120
acctcattct tgtcagtttc cagtgcccca tatctggatc tgagccccat ggtctcagat    180
gctgaatggg gccctgtctg a                                              201

<210> SEQ ID NO 983
<211> LENGTH: 201
<212> TYPE: DNA
<213> ORGANISM: Homo sapiens

<400> SEQUENCE: 983
attaagggaa aataaaaatg cttctagatc atttcaaaaa ttcagaatga aagtagtgat     60
attgagtctc acctgaaagc aaaatgtgta tttttacaaa ktatcattag tgaaaaagaa    120
atgataatga gaaagagaat aatgagaaaa gaataattag tccctaaaat gacaatattt    180
gggcacactt gagaagtaat g                                              201

<210> SEQ ID NO 984
<211> LENGTH: 201
<212> TYPE: DNA
<213> ORGANISM: Homo sapiens

<400> SEQUENCE: 984
tggggtgagg gatccccttc actcagcagg gagggtgttt cttttctat aagtgattgg      60 gggggcatct ctggtggaga tgggattctc tggttgtaaa ytgggttcct tttgcttgat    120
ggggatgggg gtctgtgtgt gtagactggg tttttttgtt tgttttttgtt ttttggtttt   180 tggttttttt tttgagatgg a                                              201

<210> SEQ ID NO 985
<211> LENGTH: 201
<212> TYPE: DNA
<213> ORGANISM: Homo sapiens

<400> SEQUENCE: 985
ccagactttg agccagccca aactccacag aaaggagggg gctggagagt gcattcaatc     60
agatgatcca tattcaatca gtcatgcctg tgtgatgaaa mttccaaaaa aagtctggac    120
actgaagctc agtggagcct tcagattagt taacacactg gcgtaccagg atggtgatgc    180
atcttgattc cacagggaga g                                              201

<210> SEQ ID NO 986
<211> LENGTH: 201
<212> TYPE: DNA
<213> ORGANISM: Homo sapiens

<400> SEQUENCE: 986
cggaaccatt cctcagaacc acaccaaaga actggcctga gcaggaagtt accatggcca     60
ccaccacccc cacattagca aaaggaatga atcatcccca rtttgtttct tgctacagtt    120
cacctccacg gttaagtctc acttccgcct ctaacttaca aaaccatagt tacacatctg    180
cagcttagcc acaagggagt c                                              201

<210> SEQ ID NO 987
<211> LENGTH: 201
<212> TYPE: DNA
<213> ORGANISM: Homo sapiens

<400> SEQUENCE: 987
tcctgtgaga actcactatc atgagaatag caagggagaa atccacccTT acgacccaat     60
```

| | |
|---|---|
| caccttgcac aaggtccctc ctcaaacatt aaggacaaaa mttcacatga aatgtggttg | 120 |
| gggacacaga gccaaactgt atcatctgtc taaacaaaag tactttgggt ttgattggtt | 180 |
| aaaaaaacac aaaacttaat t | 201 |

<210> SEQ ID NO 988
<211> LENGTH: 201
<212> TYPE: DNA
<213> ORGANISM: Homo sapiens

<400> SEQUENCE: 988

| | |
|---|---|
| acattcttat catcatcctg tagaggcaaa tttattccca aacataatca cagattacca | 60 |
| aaaataaaaa agtataagta ttgtcatcca tggataggga rtttattaca tttgccttac | 120 |
| aatgacccag ataaatgtaa tgagaatgag agagagggga cagaggatat tatgtctccc | 180 |
| aaacctctgt ctcagctact a | 201 |

<210> SEQ ID NO 989
<211> LENGTH: 201
<212> TYPE: DNA
<213> ORGANISM: Homo sapiens

<400> SEQUENCE: 989

| | |
|---|---|
| actttgaaag gcgggactct cttatgtagt ggacttagaa ctgaagacat gacttcttag | 60 |
| taatgaaact gaaggtaagt acttgtttat acaacaaaat waaaaagttc tatacagact | 120 |
| tctgaatcat actttaaaaa aaatgtgat attactgtaa cccttacctt cccctacctc | 180 |
| cccaatatct gcagtccata a | 201 |

<210> SEQ ID NO 990
<211> LENGTH: 201
<212> TYPE: DNA
<213> ORGANISM: Homo sapiens

<400> SEQUENCE: 990

| | |
|---|---|
| tctgcacagg tatcctggaa cttaaaatta aaatatatta aattagaaac aaataaggtt | 60 |
| taactcccta cctatctctt tgaaaagcct taaccattaa ytgagtcatg gcattttttaa | 120 |
| atggactatt cagtggctgt ggagatgtgt gctgtgtttg cttggttaag cagaaagtaa | 180 |
| gttttcaagg atctcctgcc t | 201 |

<210> SEQ ID NO 991
<211> LENGTH: 201
<212> TYPE: DNA
<213> ORGANISM: Homo sapiens

<400> SEQUENCE: 991

| | |
|---|---|
| taaatttaat atactcagtc tggttcacat attctaataa aatccagcaa gctttaaaac | 60 |
| ttttatagga aatgtgcatt taaaatccat gtgatattca rttttttacag ggtgacgtcc | 120 |
| ttgctcaggg tattaagtag tttcagtgat gacgatgacc cagcctggca gcaagcttct | 180 |
| ggggaaacct cacaaataga c | 201 |

<210> SEQ ID NO 992
<211> LENGTH: 201
<212> TYPE: DNA
<213> ORGANISM: Homo sapiens

<400> SEQUENCE: 992

| | |
|---|---|
| ttccactttt ttttttttttt aaccatttaa gcatttatt tcctgataac ctcttggggt | 60 |

| | |
|---|---|
| ggaaggcaga gtgatatact gagacaggca gtagcctaat ktatctcctc agcagtgacc | 120 |
| ccttctgagt gaagaaagca ggtgtgactg tctcactttc tcacggaaat agaagattct | 180 |
| catgtagcat atgcaaagac g | 201 |

<210> SEQ ID NO 993
<211> LENGTH: 201
<212> TYPE: DNA
<213> ORGANISM: Homo sapiens

<400> SEQUENCE: 993

| | |
|---|---|
| ccagcctctt ctgccatact gggcgctcac tccctgactc accatctctt ggcctcactg | 60 |
| gcggccagcg ggcaggtttc ccaagctaga cccttctcca rattgcacag ctgcgtcttt | 120 |
| tccccagggc agctcagcac ctcgcacgtc ctcagctgtg gtgcttctgt ggcccaggga | 180 |
| tcctgtgtat cccaaattcc t | 201 |

<210> SEQ ID NO 994
<211> LENGTH: 201
<212> TYPE: DNA
<213> ORGANISM: Homo sapiens

<400> SEQUENCE: 994

| | |
|---|---|
| aaactgacaa atgaatttcc atcttcgata ttgtgttttt aatttctata atttgcattt | 60 |
| ggctcttctt tatagtttca atctctgtgc tgaaaatcct watttattga ggcatgtttc | 120 |
| ccatttttc ctcttgatcc tttaacatat taattatgat ctcaaaaatg tccttgtctg | 180 |
| atcgttctaa tagctgaatc a | 201 |

<210> SEQ ID NO 995
<211> LENGTH: 201
<212> TYPE: DNA
<213> ORGANISM: Homo sapiens

<400> SEQUENCE: 995

| | |
|---|---|
| ggaagcagcc acttttccca gtcttgctga gaccaagtaa ccccaaaccc tggctcaaaa | 60 |
| atactgtatc agcaaatact ccaagtagaa ccaaccagat rattttctgg cactatcgtc | 120 |
| tgaatgtatg tgtctcctca aaatgtatat attgaaattc taaactctaa ggtgatactt | 180 |
| ctaggaggag gggcccttgg a | 201 |

<210> SEQ ID NO 996
<211> LENGTH: 201
<212> TYPE: DNA
<213> ORGANISM: Homo sapiens

<400> SEQUENCE: 996

| | |
|---|---|
| acctccacat atggttctca cttcccttc ttcttcactt ctaactcatt cacctcagta | 60 |
| aggtttcttc aacactgccc atagactctt tcttgaggca rttgttactt tctctgttgg | 120 |
| atttctcttt ttacttacat ctgcatggcc agttctctca tttctctcac gtgattattc | 180 |
| aaaagtcact ctctgaataa g | 201 |

<210> SEQ ID NO 997
<211> LENGTH: 201
<212> TYPE: DNA
<213> ORGANISM: Homo sapiens

<400> SEQUENCE: 997

| | |
|---|---|
| agtagaggtt agaccagaag caagaagact ggagaggcat gtttagtacc tgcaagaaga | 60 |

-continued

```
tatttaataa ctttcttaga ggaaagattc agaatcacca rttacattga gttgaatgag    120
gagcattagc cgtcaaaaga atctgttttt ccacttgttg cttggataaa tggataaaag    180
cctgccaagg acttcagtcc a                                              201

<210> SEQ ID NO 998
<211> LENGTH: 201
<212> TYPE: DNA
<213> ORGANISM: Homo sapiens

<400> SEQUENCE: 998
aactaataga atatcaacct agttaaggca agatttgctg tggggaaggg aaggtcctga     60
gcctctattt ggccctgagg cttatcaacc tgatacttca rttgggctca gaaagactcc    120 tgcccctcc ccattccctc cctcccattg tgagggacca atctctctta ttctgtgttt     180
tcttaccatc tcttccacca c                                              201

<210> SEQ ID NO 999
<211> LENGTH: 201
<212> TYPE: DNA
<213> ORGANISM: Homo sapiens

<400> SEQUENCE: 999
tttccatgta ttctcacaaa acctctcaca ggaatccacg gattcactag aggtatgtga     60
ggaggaggag gatgttgatg aggatgaaaa ctgacatgca watttaaact tctacctcta    120
gaaagcactg gcaaaagta aaggcacaag tcaagaacac ggaaaaaat caagtacttc      180 caatgacatt ggcaccagga c                                              201

<210> SEQ ID NO 1000
<211> LENGTH: 201
<212> TYPE: DNA
<213> ORGANISM: Homo sapiens

<400> SEQUENCE: 1000
ctacattcat cctttctccc ttcccttctg ctaaatcggg taaagtattt ccctgggaaa     60
tacttccctc gggctccttc aggctttaaa taccttcaaa yttctcccac gttaaaaaaa    120
aactaaatat tcactgaatc cttacctgcg gttgtatctt atcctccacc ttcacagcca    180
aacttcttaa aagaattggc t                                              201

<210> SEQ ID NO 1001
<211> LENGTH: 201
<212> TYPE: DNA
<213> ORGANISM: Homo sapiens

<400> SEQUENCE: 1001
aaacccattc ttcttggcta gaaaatgagg aaagacctgt taagtttctc aaagacagga     60
acttcctgaa atacgaccag aatggaagga gggcttggaa ytggcagtcc gtccatccat    120
ccatccatcc atccatccat ccatccatca tccaccttcc cagggttcaa tcattcactc    180
gagtgaattc tatcattcac c                                              201

<210> SEQ ID NO 1002
<211> LENGTH: 201
<212> TYPE: DNA
<213> ORGANISM: Homo sapiens

<400> SEQUENCE: 1002
atttgtatct ttctgtgagt gcccactggg cccaaaaatg tcttttctga gcttctatga     60
```

```
aacgtgtgtt tgaaactgtt ctacgtgaaa acatgttgaa ytcggtgaaa gaaaacagaa    120
catcatcaag gtttttggca gaaaccagga ttttatcttt tagggctgga tatttgggca    180
acatagtggg acctcatctc t                                              201

<210> SEQ ID NO 1003
<211> LENGTH: 201
<212> TYPE: DNA
<213> ORGANISM: Homo sapiens

<400> SEQUENCE: 1003
cttgtataga aataatacaa ggtacaaggt ggggctgaaa acactggac aagctagccc     60 ggggactgca gatgcaagca tctgctcttg aggcagtaaa ytgaaacagt gattcttatt    120
actagtttct gttaaagttc ctcaaactct tttacacaga gatatatctg actcttagat    180
ggcagctcta aaattttgaa g                                              201

<210> SEQ ID NO 1004
<211> LENGTH: 201
<212> TYPE: DNA
<213> ORGANISM: Homo sapiens

<400> SEQUENCE: 1004
gcatggcagg gtcttgaagt agatttgtgg gaatttccct gggaccctca ggtcacatga    60
ccatttattg gccctgctct gcagggcacc ttaggtgatg wattgcaaag gcagatcaag    120
ggaaagcaga tgttgccatg gaatggccc tgcccccatt cattattaaa agttgttgtt    180
attgttgttt tttggcagca t                                              201

<210> SEQ ID NO 1005
<211> LENGTH: 201
<212> TYPE: DNA
<213> ORGANISM: Homo sapiens

<400> SEQUENCE: 1005
ggacaccgag gaacaaaaag gtggcgtgac ttgcccaagg atgttgcagg ttagaagctg    60
agccagccgt ggctatccat ccttcagaca cccaggccaa yttgtctgta ccacctcaca    120
ttgcctcaaa ccctgtctgc agttactgtc ccatttcttt atcatttggt cctggtatga    180
caaggtacag tggaaagaaa a                                              201

<210> SEQ ID NO 1006
<211> LENGTH: 201
<212> TYPE: DNA
<213> ORGANISM: Homo sapiens

<400> SEQUENCE: 1006
tgtacccttt accaaagcta aacaaattgc tacttgctgc aatcccagag gggtgggggt    60
gggggtgcgg caggggcata gcgcctgtgc ttaactgtga rttattaatg tgaaagattt    120
gcatgtgctt tttatgatta tagctgactt tgatgtcttt gtgccctgct cagggcttca    180
acatacaact ataatttatt t                                              201

<210> SEQ ID NO 1007
<211> LENGTH: 201
<212> TYPE: DNA
<213> ORGANISM: Homo sapiens

<400> SEQUENCE: 1007
gtatgagtga agattcagga aacactggtt catgttggtt catgaaatgt tagttccaga    60
```

| | |
|---|---|
| tattcaataa aaatgtgacg tttttaagag ttctaaaaat wactcgcact tctccacacc | 120 |
| gttaaatgga ctctcacagc cttgaatgag agagcaaaag tcccagcaag gccacccct | 180 |
| ccaggttccc aaggaacacc c | 201 |

<210> SEQ ID NO 1008
<211> LENGTH: 201
<212> TYPE: DNA
<213> ORGANISM: Homo sapiens

<400> SEQUENCE: 1008

| | |
|---|---|
| aatttactgc tgtttcttca tttttttatt actacataat taaaacctac tgttagctag | 60 |
| cactgtggaa aaatgttggt gttatgcagt atgcatttca rttggctgca caaccaccat | 120 |
| ctcttcttcc agtgaccccg cttctctgta gtgatgtggg tgcataattc tcagactcca | 180 |
| ttaggtggct gtaatccacg g | 201 |

<210> SEQ ID NO 1009
<211> LENGTH: 201
<212> TYPE: DNA
<213> ORGANISM: Homo sapiens

<400> SEQUENCE: 1009

| | |
|---|---|
| ctcctttggt caaaaacttg atatgcccat tttgcttttc atgaatcttc aagactcggt | 60 |
| gaactatagg aatctttctt ccttctatcc ttagaacagc ratttctccc actcgtatgg | 120 |
| gatcttcaac tcgatttgtt agaaagagaa gatatcctct atgaaatgca ggttccatgc | 180 |
| tgccactgag caacacaatt g | 201 |

<210> SEQ ID NO 1010
<211> LENGTH: 201
<212> TYPE: DNA
<213> ORGANISM: Homo sapiens

<400> SEQUENCE: 1010

| | |
|---|---|
| gtttttgtgt ctgggcctct gggccaagcc ctggacaata ttttatgagt tgctttctac | 60 |
| tgcttagtaa cttctgtcct taaatcccat cttgaatgaa rttaatgtat tgcttcatcc | 120 |
| gctttccttg gtgtttaaat gagaagtctt tgcaccgtct ctttgtttgg tggttctgtc | 180 |
| ttatcttagc tggtatttct t | 201 |

<210> SEQ ID NO 1011
<211> LENGTH: 201
<212> TYPE: DNA
<213> ORGANISM: Homo sapiens

<400> SEQUENCE: 1011

| | |
|---|---|
| aggctagtat accactgggg tgggggaatg gggaagtaac cgaggagacc cccatgtgag | 60 |
| gaggcatgtt taccattggg gtggaggtac atgagggaaa ytgagggac ccccgtgtta | 120 |
| ggaggcttgt ctggcattaa gagaaccacg tggagaaaac tgagggaacc cacatgggag | 180 |
| gaaactgatt taccattggg a | 201 |

<210> SEQ ID NO 1012
<211> LENGTH: 201
<212> TYPE: DNA
<213> ORGANISM: Homo sapiens

<400> SEQUENCE: 1012

| | |
|---|---|
| tgaaacagaa aggagtacat gatttgtggc ctgagaaatg gcagtagaga cagaatgtgg | 60 |

```
gcccaggtat gtagctgcag tactttctag gccatagaga rttagtgtct aggaaataag        120
aaaataaaaa ggagcccatt cttctctagt gattctttac caccaagagc taataaatgt        180
gcatggtact gttctgacaa g                                                  201
```

<210> SEQ ID NO 1013
<211> LENGTH: 201
<212> TYPE: DNA
<213> ORGANISM: Homo sapiens

<400> SEQUENCE: 1013

```
attattgaat ttgatcatag ccatgcagac tgttcaactg aattataacc tctaggaata        60
tcttcatttt aaaagtgttc atactgtagg cttgaagaga mtttagacat tatcagttct        120
tcattcactc tttctgtgtc agcaagaagg gggttggttt attcaaggat ccatagtaag        180
tttgtaatgg gataatgact a                                                  201
```

<210> SEQ ID NO 1014
<211> LENGTH: 201
<212> TYPE: DNA
<213> ORGANISM: Homo sapiens

<400> SEQUENCE: 1014

```
aggagagctg ggatgatgtg ggcaaagggc gttcagggaa gaggaagcaa agctaagggc        60
ctagaaatat gaaataacct gacagatcca gaaacaggaa ktggtgggaa atatggctta        120
taaagtggtc tgggcctgcg cgagagctct catggcgtgg ggtggaatcc acattctgta        180
caatgggcac ggggcagccc t                                                  201
```

<210> SEQ ID NO 1015
<211> LENGTH: 201
<212> TYPE: DNA
<213> ORGANISM: Homo sapiens

<400> SEQUENCE: 1015

```
acagtccatt ccagttgtaa tggcagccct agcctaagtt cttatatctt agggacaaaa        60
tctaaaccag tggatttcaa atccggccgc acatcagaat yatgtggggc acttaaaaa         120 ctacagaagt gaagacccca tccaacaccc tctgaacaga tttccgctag tctagatgat        180
tattgattac tgtagcttca g                                                  201
```

<210> SEQ ID NO 1016
<211> LENGTH: 201
<212> TYPE: DNA
<213> ORGANISM: Homo sapiens

<400> SEQUENCE: 1016

```
gtttggatga gatgtcattt actctagagc gttatctgtg tagctctgta atttctaata        60
ttttcactct aaaacaggac agtaaaaaaa caggtgaaca rttatataac atgaaccaag        120
attctatgaa gagttttaag ctttatgagg acaaggacat cttgcttaca attatcttca        180
aatgcctacc acagtctctg c                                                  201
```

<210> SEQ ID NO 1017
<211> LENGTH: 201
<212> TYPE: DNA
<213> ORGANISM: Homo sapiens

<400> SEQUENCE: 1017

```
ctttgaggtt tgtttaaatg ttgctttcct ttctgggttt ctccaggtag ctcctcatct        60
```

-continued

```
tcagtgttct cattgcactt tgtattctct tagcttttaa ytctcaggga caaggactga    120
cctggttcaa ctctgtattc ttagggccta gcaaagtgct taacacatag aagacatttg    180
ctgacttaca gttgaataga a                                              201

<210> SEQ ID NO 1018
<211> LENGTH: 201
<212> TYPE: DNA
<213> ORGANISM: Homo sapiens

<400> SEQUENCE: 1018
cttgttgaaa agtccttagg agactcaggg acatgagaat aatgtgtcca gtgaccataa     60
ggctgtcttt aaaagaagaa catcctgtca gtgaggaaaa ytgcaccttt gtcacttgct    120
ttgcgtcaac ttcaaggccc gacttaacta tttcctcagc attcatttag cactatttat    180
taagcacctg ttttaggttc t                                              201

<210> SEQ ID NO 1019
<211> LENGTH: 201
<212> TYPE: DNA
<213> ORGANISM: Homo sapiens

<400> SEQUENCE: 1019
ttttttttta atgagagttg atggtatacc atcttggagt gttgtgatgc atgccaaaat     60
caatgagttc atcttcaaca tattgaagtt cttactttca rtttggtctt aggagtgcca    120
gttgcttaat caggataaag tacagtgact taattacaat gccaaacag ataggaaaat    180 taaattcaaa atcttaactc t                                              201

<210> SEQ ID NO 1020
<211> LENGTH: 201
<212> TYPE: DNA
<213> ORGANISM: Homo sapiens

<400> SEQUENCE: 1020
gacctaaaaa tttatagtat tgatttattt tttattacat ggaagatgca ccactttctg     60
gacataaata aatacataaa taaaatataa gccatttaat kcctcctctt tcttcacatt    120
tttcccaacc tctcctaatc ttttgttctc ccacctctgc ctgtcttatc tatgtccttg    180
ctttacctct ttctttcctt a                                              201

<210> SEQ ID NO 1021
<211> LENGTH: 201
<212> TYPE: DNA
<213> ORGANISM: Homo sapiens

<400> SEQUENCE: 1021
agggatgcct gaggagcaga cagcatgaag gagggcagaa ccgtcgtggg atcctggtga     60
cactgttcgc atctgcatct ggccatccca agccacaaat yctggacttt cccattgatg    120
taaaccaata aaatctcctt gcctgagcta caggaggttc tgtttctttc aaatgcagac    180
aaaatatttt gacaaattac c                                              201

<210> SEQ ID NO 1022
<211> LENGTH: 201
<212> TYPE: DNA
<213> ORGANISM: Homo sapiens

<400> SEQUENCE: 1022
cagccctctt tcaaatatac tctagtctaa acccttgatt ttaaccgtgt tatagggtta     60
```

| | |
|---|---|
| agtcttttct gcttctgtca aaagccaggc taaggcaaat ycatcaggaa aaacaagact | 120 |
| ggaaaacaaa tgtaaacttt atactctttg aacctcttta aactttatcc ctgtattaaa | 180 |
| tttgatcaca agaaaagctc a | 201 |

<210> SEQ ID NO 1023
<211> LENGTH: 201
<212> TYPE: DNA
<213> ORGANISM: Homo sapiens

<400> SEQUENCE: 1023

| | |
|---|---|
| cactggaagg aataaattcc agacacagtg gcagctggca ctgtgctgct tacagatcaa | 60 |
| agacctacag gattacaagt aaggttgggt ggtgcctttg mattctccag gtggtcttct | 120 |
| gtgtcaatgt ggaggttcca tgaataggaa tgtaaaggtc catggcagag gtgtggatcc | 180 |
| ctgggcatct aactatcact c | 201 |

<210> SEQ ID NO 1024
<211> LENGTH: 201
<212> TYPE: DNA
<213> ORGANISM: Homo sapiens

<400> SEQUENCE: 1024

| | |
|---|---|
| agaaaaaagt cttcaagcct atggttatta taaatcctac acgctcctga attcagtcat | 60 |
| gccaaatgga accagaacca tgtttttaac ccttttaaaa ytgtggtaaa atagtctggg | 120 |
| cacgttggct cacgcctgta atcccaacac tttgggaggc caaggcgcgt ggatcatttg | 180 |
| aggtcaggag ttcgagacca g | 201 |

<210> SEQ ID NO 1025
<211> LENGTH: 201
<212> TYPE: DNA
<213> ORGANISM: Homo sapiens

<400> SEQUENCE: 1025

| | |
|---|---|
| ggcaaaggaa agggatggat gcccacagct cctgtcgtgc agctggagcc ttgcaaagca | 60 |
| acttcataaa gcctgtggac tgttaacctg ctgacttcaa ytgaaaactc ttcagatgtt | 120 |
| aaaaacaaac ctgttttggg cttaatgtcc agcaaatgtc atgttttgct aaaagacagc | 180 |
| atggcaggca gaccccgggg t | 201 |

<210> SEQ ID NO 1026
<211> LENGTH: 201
<212> TYPE: DNA
<213> ORGANISM: Homo sapiens

<400> SEQUENCE: 1026

| | |
|---|---|
| aagctcccaa cctttcagca gcttctacac acccagctcc tgccacccag tggcctcttt | 60 |
| aggccaagct catgcttcac aagggtcttt ccaggcccaa yttttgtctc atggcaacct | 120 |
| tccctggcca gattcctgcc tgtctcccag cagcctagac aggcccaggt cttgcctcac | 180 |
| actggcctct ctacatccag c | 201 |

<210> SEQ ID NO 1027
<211> LENGTH: 201
<212> TYPE: DNA
<213> ORGANISM: Homo sapiens

<400> SEQUENCE: 1027

| | |
|---|---|
| ccatagagcc ccactaaata atataacagc tggaagggat ttattcatct ctggacacta | 60 | aggagttagg gcacagtagt tcagttacct ggttatataa wtctgggaac ctatacaatg    120 attaaaatgg aaatgagacc tccagttact gcaatgaagg taaatggttt tccaggggaa    180 ttacacttgg actcaaaatc a    201

<210> SEQ ID NO 1028
<211> LENGTH: 201
<212> TYPE: DNA
<213> ORGANISM: Homo sapiens

<400> SEQUENCE: 1028
tcaaaatctc cccactggcg cattttaggt gttttgatca tgagtcacca ggagctctaa    60
agcacttaac tgagtctggg gatttctaat cttttctgcca rttgtttgta gggaagtgct    120
ctgtgagctc tacctctgag gctccatgct ccctctggcc ctcccttaa tagcttctct    180 tccacggaga tgcagtcaag t    201

<210> SEQ ID NO 1029
<211> LENGTH: 201
<212> TYPE: DNA
<213> ORGANISM: Homo sapiens

<400> SEQUENCE: 1029
tcgaggtagg aggttggtgt ttgatggata actctactgt ataaagttaa atttgactgg    60
ttttctattt ctgaatcatg gaagtgatga gaggaactaa ytgatttatc tgaagtctgg    120
atatgtaata aagtcttcat gaactgcagt tgaatgtggc tgcattgtta ctaatgtaca    180
gaattttttc catattggct t    201

<210> SEQ ID NO 1030
<211> LENGTH: 201
<212> TYPE: DNA
<213> ORGANISM: Homo sapiens

<400> SEQUENCE: 1030
ttctcttctc atgcaatcat taattcagcg ttgctccaac gtcaatgaag cctagtaaag    60
cttcatcatg cttcacgtca gactacactg agctaccaca wttacatggg attaaagaaa    120
actatttggg gctggaccca gtggctcatg cctataatcc cagcactttg ggaaactgag    180
gtgggtggat cacgaggtca g    201

<210> SEQ ID NO 1031
<211> LENGTH: 201
<212> TYPE: DNA
<213> ORGANISM: Homo sapiens

<400> SEQUENCE: 1031
tttaccccaa gtcttcattt ttttctccca aatttattca cccaaattct ttatggttta    60
ttggaaatga agtcaatatt taagtgcta catctatgaa ytcaaagttc acataaaatc    120
tacatcaaag actggaagta agtaggatcc tttagtggtc tagctcattt gcttctccaa    180
aaagcataat ttttcatgag a    201

<210> SEQ ID NO 1032
<211> LENGTH: 201
<212> TYPE: DNA
<213> ORGANISM: Homo sapiens

<400> SEQUENCE: 1032
gtacgttttg cacatatcca tattatttca gtgtatccct caattctgaa catcagcaat    60

```
ataatgccgc atgaaacaat cctttatctc tctctaatac wattgtccct gtgaacagtg    120
atccacagta tatatgtgtt ctgttctatc cttagcccga tgacctctgt ctccccagga    180
gcagccttct cgtcattggc a                                              201
```

<210> SEQ ID NO 1033
<211> LENGTH: 201
<212> TYPE: DNA
<213> ORGANISM: Homo sapiens

<400> SEQUENCE: 1033

```
ttgctaacat aatttcttta tcttctttta atttccttaa catagctctc ctaaaactat    60
gggtagtaca tggggttttg gggggtcag gtaaggaata wttacatttt gtgtgaatat     120
tcaaatgatg cttggtaaaa atctttgata acttcttaag tgattatttc tctcctaaaa    180
ttctttgaat ataggcatgt g                                              201
```

<210> SEQ ID NO 1034
<211> LENGTH: 201
<212> TYPE: DNA
<213> ORGANISM: Homo sapiens

<400> SEQUENCE: 1034

```
aacgtgccca gcaccttggc tcatcatacc accgtctggc ttacctgctg caggtcactg    60
aactctggag tagattgaca tcagatagcc tcttgtgaat yatccctaaa atgatgggtt    120
tcctttgaaa actgctaact cttcatacat ttctacatat actttactgc attcttctgt    180
gattgaaatt tgcttcttaa t                                              201
```

<210> SEQ ID NO 1035
<211> LENGTH: 201
<212> TYPE: DNA
<213> ORGANISM: Homo sapiens

<400> SEQUENCE: 1035

```
aaaaaaaaaa aaaaaagaa tataacaacc atccatgtag acaccattca ggatactgtt     60
tcacactatc tggtgagtaa gcattgaagt ctaatacaaa ktcttagtgc tggtgaagtg    120
gagagagggc ctcttacaca ctgctgatgg gcatgttaat tggtaaaacc acttcagaga    180
gaagttggca atgtcttcta t                                              201
```

<210> SEQ ID NO 1036
<211> LENGTH: 201
<212> TYPE: DNA
<213> ORGANISM: Homo sapiens

<400> SEQUENCE: 1036

```
tccagaatgc tatacagttg gaatcataca tactgtgtga ttccagataa actttgagat    60 aaacttatttt agattagtga tatgcattta tgtttcatca rttttttaaaa tacgatgata   120 gctcatttct ttagcagtga atagccttcc attgtctgga cataccatat tttatttatc    180
tgtttaacta ctgaaggaca t                                              201
```

<210> SEQ ID NO 1037
<211> LENGTH: 201
<212> TYPE: DNA
<213> ORGANISM: Homo sapiens

<400> SEQUENCE: 1037

```
gaatggcagt aaatattcct tgggtttcac tgaagtctgc tctaaatgca gttgagttta    60
```

```
atgatcaaga gcttggactc tagcatcaaa tgtgagttca rattatttct ccattacctc    120
ctagttgact aacacctact ttctgactat aacaacaaat gttactgata actatttcta    180
ggaaattcat taataacata t                                              201

<210> SEQ ID NO 1038
<211> LENGTH: 201
<212> TYPE: DNA
<213> ORGANISM: Homo sapiens

<400> SEQUENCE: 1038
attcatcgcc acggggtggt tcttttccac ccaacagcct aactctgctg ctcccaaggg     60
cagaacaagg acagataggt ggatgtttca gggaagtaaa kttcagctaa atataaggca    120 gaactttttac tagactttt agaagagtca aaaaaggtat tgtcttaaaa atggtggctt    180
ctgtgtcact ggttttttaag c                                             201

<210> SEQ ID NO 1039
<211> LENGTH: 201
<212> TYPE: DNA
<213> ORGANISM: Homo sapiens

<400> SEQUENCE: 1039
atgtagagtt attcctgcag ggctgtgatt ataggcaaat catagtgtgt ataccttcta     60 cctttttag tgtatctccc actcttgtac cccagaaaaa ytagtcttga gtatccttcc    120
agaaatgttg tattccagtc ttgtgtatcc ttccagaagt attataaata ttatattatt    180
atccttccag aaaaatcagt c                                              201

<210> SEQ ID NO 1040
<211> LENGTH: 201
<212> TYPE: DNA
<213> ORGANISM: Homo sapiens

<400> SEQUENCE: 1040
tcttttttct tcaagggcac cacaagtctt gggtgctgtg gagaattgct gattattttt     60
ttctcccaga catataatac cttggtccct tattgttcaa ytgatgtagc cttttccaat    120
aggcttcttc agtacactct atgaaggaag cagacgtaag agtctatgta cgagtgaaac    180
ttaccctagg atacccactt c                                              201

<210> SEQ ID NO 1041
<211> LENGTH: 201
<212> TYPE: DNA
<213> ORGANISM: Homo sapiens

<400> SEQUENCE: 1041
aatgtccagg gccagaggaa gcaggacagc acaagatttt atcttgctaa tcagaatggc     60
agaaaatatc tcttctctgt agacagaaga caaggtggca rttctaaaga aaagagggtg    120
ttctaataat ctttacatgt actttagacc acacaaggag gtaatatatc attatgtgct    180
tttggcttct cagatattct a                                              201

<210> SEQ ID NO 1042
<211> LENGTH: 201
<212> TYPE: DNA
<213> ORGANISM: Homo sapiens

<400> SEQUENCE: 1042
tagagtccca cacacttact tgtactaaac attaacctgc atgtccagtc ctacccagta     60
```

```
cctgagtcaa ccttggaaag ataagagaga tatcagaaat ktcaccctca ccagcaaagg      120
gggtggaggg aagactgttg ggggagctat tagagagcat ctagaacacc ttggcttatc      180
atctgattca ccaaaggtaa g                                                201
```

<210> SEQ ID NO 1043
<211> LENGTH: 201
<212> TYPE: DNA
<213> ORGANISM: Homo sapiens

<400> SEQUENCE: 1043

```
tcataactgt cccccacaaa aaataatgac aattgtgcac caacctccta acttattatt      60
attctttgct gtggttcatg aaatcacaaa gtcttagaat yattgcatta aggtactgcc      120
acacttagtc cattcagaat gcctagactc ccatactggt gctatcattg gcctcagaag      180
gcatataaaa tgaaactcag c                                                201
```

<210> SEQ ID NO 1044
<211> LENGTH: 201
<212> TYPE: DNA
<213> ORGANISM: Homo sapiens

<400> SEQUENCE: 1044

```
caaggcccag gaacaggatg taagaaggga ggaagaagaa aagccaaagg gaatcctctt      60
cctgtgtctt taggaagatc ctggaaggtg ctgaagctaa wtacttggtg ttgatctgaa      120
gttagacact tagctaggga gacttgttag tatcttttc ttaagaaacc atgtgctgag       180
ctagaactag tactgtagta c                                                201
```

<210> SEQ ID NO 1045
<211> LENGTH: 201
<212> TYPE: DNA
<213> ORGANISM: Homo sapiens

<400> SEQUENCE: 1045

```
aatgaaaaaa ggcaatgaga agtaaaaatg gaaaagtacc agttcaagca tggcagccaa      60
acatccaaag actatcattt gataaaagat ttacctgaat yaacagagct ttcttgacat      120
tgattagggt ggtgaaaatg actgtggagg aaaaattaag tagatgattc tatttaggga     180
agaaaaggtg ggagaagtgg c                                                201
```

<210> SEQ ID NO 1046
<211> LENGTH: 201
<212> TYPE: DNA
<213> ORGANISM: Homo sapiens

<400> SEQUENCE: 1046

```
aagactttgt ctatcacagc tctttcaaag tgcaatgttg gtgaaggatg ttaactgcaa      60
gctaagaaac acactgggtg atttatgcag aaaagaata mattgaaagc accctaggta      120
tatggtacgt tgtttataaa gaaggctgtg ataatttctc acatcccttg tggacatgct      180
cctttaccat gtgatcttcc a                                                201
```

<210> SEQ ID NO 1047
<211> LENGTH: 201
<212> TYPE: DNA
<213> ORGANISM: Homo sapiens

<400> SEQUENCE: 1047

```
ttgaaatatg ttttccaatt tgtttgcttt cttcccctcc ctctcaggga tgccgaggat      60
```

-continued

```
tcatagattt ggtgtcttta cctctttaca taatcccaca rttctcaaag gttttgttca    120 ttcctttat tcttttttct ttgactgtct tatttcacag aaccagtctt caagctctga    180
gattctttcc tcagcttggt t                                              201

<210> SEQ ID NO 1048
<211> LENGTH: 201
<212> TYPE: DNA
<213> ORGANISM: Homo sapiens

<400> SEQUENCE: 1048
tcactggccc tcaaagcttt tgctcagcat ctacttatgg gaaaatgcaa gctacaatgg    60
ttgaactttc agcttccatc aacttgagac atgttccaga rttaaaata ttcttcactt    120 gtattacccc tgtccacagg caatgaatct cctgctggcc acgtggctaa gagacttgca    180
cagtcctagg atccttgata a                                              201

<210> SEQ ID NO 1049
<211> LENGTH: 201
<212> TYPE: DNA
<213> ORGANISM: Homo sapiens

<400> SEQUENCE: 1049
caaactttaa caccccttctc tgaacaattg atagaaaaac tagatagaaa gtctgcaaga    60 ataggatg caacaccacc atcacaaaaa gaggctctaa ytgatattta caaaacactc    120
attgacattt acaaaatatt acaaacaaca tgcaaacata tattcttttc aagtgcttat    180
gaaacacata caagatagac c                                              201

<210> SEQ ID NO 1050
<211> LENGTH: 201
<212> TYPE: DNA
<213> ORGANISM: Homo sapiens

<400> SEQUENCE: 1050
gatggaagcc ctttgtcagc tgtgctgtga aggccttctc ccagtccatg gctcgtgttc    60
ttaactttct tacattgttt tctgaagagc agaagtttta rttttgataa ggttcagagg    120
atggattttt cttttacagt tggtacattt tgtatccttc taagaaattg ttgcctgtct    180
caaggatgca aagattttct c                                              201

<210> SEQ ID NO 1051
<211> LENGTH: 201
<212> TYPE: DNA
<213> ORGANISM: Homo sapiens

<400> SEQUENCE: 1051
gacaactgtg acccgaattg ttgcaacaaa ttatgatgta ataatcctga gatctagcca    60
cttacagaac agaagggaag acagcaggct gccttgaaat ygagctggca gatgtgggtc    120
attgggggat gggtataata tgagagaagc tccttgtggc tcagctcaga aaggtttgca    180
tgtgtaatac caattattcc g                                              201

<210> SEQ ID NO 1052
<211> LENGTH: 201
<212> TYPE: DNA
<213> ORGANISM: Homo sapiens

<400> SEQUENCE: 1052
tcaggagaaa atattcggaa tgaatagaga gactaaacga atggaatata gagaaaagag    60
```

```
aataacagag tacacaatga gaatgtgaaa tatttgtaat kgaaatctta gaagaaaagg    120
agtgagaaaa caggggaaaa taaatattta aaagagagtg gctaagaatt ttcaaaaacc    180
tgatgaaaga cacaaagcct c                                              201

<210> SEQ ID NO 1053
<211> LENGTH: 201
<212> TYPE: DNA
<213> ORGANISM: Homo sapiens

<400> SEQUENCE: 1053
gctagctgtg gctcaatatc tattatcccc ttcttccata gccagaataa agaccatatt    60
ttccatcctt tcttgcagct tagtgcaact tggtgacaaa rttctagaaa atgagatgta    120
actacaaatg aagcacacaa ctttcaggtg gggccctaga atgaggctga caatctgcac    180
tcccaagcct atcccacacc a                                              201

<210> SEQ ID NO 1054
<211> LENGTH: 201
<212> TYPE: DNA
<213> ORGANISM: Homo sapiens

<400> SEQUENCE: 1054
gtgctttcta tcttaatgta taatttatag aaaaactaac taactcccctt taggttttgg    60 ccaacttgct catgccgaca aaacttcctt taaaatacca rttttttcaca aatctacttt    120 ttctttggtt ttattctacc attcttttaa cttaggacaa tccttaaaat ctctaaatga    180
gactgaatta ctttcccttt a                                              201

<210> SEQ ID NO 1055
<211> LENGTH: 201
<212> TYPE: DNA
<213> ORGANISM: Homo sapiens

<400> SEQUENCE: 1055
ttatctctaa ttcttacaat aattctttga agcagtgatg atcatcctct tttgcagagg    60
cagagctgag gcacaaggag ataagtaaca tgtttaaaat ygtatagttg ctatctgaga    120
atgaagtcaa acccaggtca gtctgacttc caaagtcgaa ttctttccaa tatagtaagt    180
gcctttccta aaccattgac a                                              201

<210> SEQ ID NO 1056
<211> LENGTH: 201
<212> TYPE: DNA
<213> ORGANISM: Homo sapiens

<400> SEQUENCE: 1056
ggcatgtaaa ctctaccaca aaaagataaa tatcatttcc agcagacaaa tatatgaaaa    60
caggtataaa ctgatggctc gtactaccca gtggaataaa ytcttctgca atagaatgaa    120
tatgttcttc tataaaggaa aagagtcaca tcatagggaa aagagcttat ttggtgagca    180
catttaaagc tgaatgcgta t                                              201

<210> SEQ ID NO 1057
<211> LENGTH: 201
<212> TYPE: DNA
<213> ORGANISM: Homo sapiens

<400> SEQUENCE: 1057
aggagcaaga taacacaggg ctttctgtta ccttgcttaa gcggtggtgg gagaatacac    60
```

```
agtaagttcc ctgagggcag ggactatgca tattctgtta rtttctccat cctccagatc    120
tcatatactt cctggaacat attaaatgct tagtaaatat gtgataagtg aacatgagtg    180
actgggaaga aagggcttag                                                201

<210> SEQ ID NO 1058
<211> LENGTH: 201
<212> TYPE: DNA
<213> ORGANISM: Homo sapiens

<400> SEQUENCE: 1058
ccacaatgag aagtataaat ctacgagaat acacttcaaa ctggtaacag tggttacttc     60
tggaaaagac agtttttaaa tcttttacat caataactaa ytcatacatt acttatgtaa    120
tgataaaact ataacaataa aaaaacaagt agtatgggaa tacagatggc tgagcaaata    180
acactgttcc cagggttgct g                                              201

<210> SEQ ID NO 1059
<211> LENGTH: 201
<212> TYPE: DNA
<213> ORGANISM: Homo sapiens

<400> SEQUENCE: 1059
atccagatag cgagctggct agcagctgtc cactctccag caatcctgcc ttctggggca     60
tggttttcta aggaccttcc tgttcctaga tgatcaaaat wgggaccagc cactcccttc    120
tgagccactc ctgcctctgg gcctgtggct atgtcacagt ccagtcacaa caggacatcc    180
cttcagaaca ccctgcagga a                                              201

<210> SEQ ID NO 1060
<211> LENGTH: 201
<212> TYPE: DNA
<213> ORGANISM: Homo sapiens

<400> SEQUENCE: 1060
atccagatag cgagctggct agcagctgtc cactctccag caatcctgcc ttctggggca     60
tggttttcta aggaccttcc tgttcctaga tgatcaaaat wgggaccagc cactcccttc    120
tgagccactc ctgcctctgg gcctgtggct atgtcacagt ccagtcacaa caggacatcc    180
cttcagaaca ccctgcagga a                                              201

<210> SEQ ID NO 1061
<211> LENGTH: 201
<212> TYPE: DNA
<213> ORGANISM: Homo sapiens

<400> SEQUENCE: 1061
cgtaactttt cctgcacagc cttagtgtct tatgcagaag aaacattcgg taatgccatt     60
cattgctcta cacttttcta gcatctgatt gtttagaaaa ktattgcaag ctcggtgcag    120
tggctctcaa ctgtaatccc agcagttttg caggctgaag caagaggact gtttaagccc    180
aggaaatcga ggttgcaatg a                                              201

<210> SEQ ID NO 1062
<211> LENGTH: 201
<212> TYPE: DNA
<213> ORGANISM: Homo sapiens

<400> SEQUENCE: 1062
aaatttaata aagaacaagt tagggatccg atgatttgac agtggataag gaaaagagaa     60
```

```
gtatctatct aggttgagac tcaggtggct ggactgggga mtttacgata tgcaacaagt    120
tcagaaaagc tttcatgttg cttaaacctt taggcttgag aaataaatat ttatcagttg    180
agataattaa cagatcctgc c                                             201

<210> SEQ ID NO 1063
<211> LENGTH: 201
<212> TYPE: DNA
<213> ORGANISM: Homo sapiens

<400> SEQUENCE: 1063
ctgggggtct cttatagatt cagtcaccat cattatgtaa actgttgagg ccttggataa    60
tggttcacta atagataact attagttgcc taagacattt rattttcat attttaagat     120 tatgattttc agcacaggtt aaagtatgtg tgctttgggg atatatgtaa tggagaacag    180
aaagaatcca caactccttt t                                             201

<210> SEQ ID NO 1064
<211> LENGTH: 201
<212> TYPE: DNA
<213> ORGANISM: Homo sapiens

<400> SEQUENCE: 1064
tcactaacaa actgcctccc caccttctt ccgccctgc tcaatgccct gcacttccag      60
ctgctgcttt ctctgcttat gtaacagctt cccaatggca mtttcagcca ggatgggcct    120
caaatgactt tctgcactaa atcccagacc tttgtgtaat gcagtcattt tgcaaccagc    180
ctccccaagc ttgccagagc a                                             201

<210> SEQ ID NO 1065
<211> LENGTH: 201
<212> TYPE: DNA
<213> ORGANISM: Homo sapiens

<400> SEQUENCE: 1065
agaaataaat gactttggtc atgattgggt ttccttactt gtcaaagtga aaaaaaaata    60
gacagataat aatgtattaa agatgagccc acaggcaaaa rattagtctg atttgtatgt    120
cccttctctc tgatgtcttt ttaaggcatt tgtaaaatgt ttttaaagag gacaagaaaa    180
cggtagcatt tttgacagat c                                             201

<210> SEQ ID NO 1066
<211> LENGTH: 201
<212> TYPE: DNA
<213> ORGANISM: Homo sapiens

<400> SEQUENCE: 1066
tgctttaaaa gtgaaatgtt tatggtacta tgagtgcaac agaaaaggca ggggtcaaaa    60
gagatctggg gtctagaccc aagtcttcta tcaagggaat yggcacttag agaacacata   120
ccaaggacca ggtgctagat ttcaaaatct ttctctattg cccgcctggg cagtgtcacc   180
tgtaactttg aactcctggg c                                             201

<210> SEQ ID NO 1067
<211> LENGTH: 201
<212> TYPE: DNA
<213> ORGANISM: Homo sapiens

<400> SEQUENCE: 1067
ggagattggg catttcacaa atatctgcag aataattgta tccataagct atatacaaat    60
```

```
atctacagat aacagtttaa agtcatattc acttttactg mattagcttt tggcaacaca    120
ttttgttttt tattttctg tttctatagt caccaaacta aattcttacc tattatctgg    180
tttcccaaat aagcctacct a                                              201
```

<210> SEQ ID NO 1068
<211> LENGTH: 201
<212> TYPE: DNA
<213> ORGANISM: Homo sapiens

<400> SEQUENCE: 1068

```
gcctcttctg tgcatttcta ggcctgtggt agtaactaat gatgctttaa aaataggtc     60 actagtgtat attttgtaaa aagggatagt tgtagtatga mttgcaagtc ttggaggtat    120
tgtgtgttgg gagtcatact aagaaaggag gaaattctgt tatacagtca tgtgccatat    180
aaaggcaatt ctggcaatgg t                                              201
```

<210> SEQ ID NO 1069
<211> LENGTH: 201
<212> TYPE: DNA
<213> ORGANISM: Homo sapiens

<400> SEQUENCE: 1069

```
acaatgttcc aaataaatca gcagattaca aatgaataat tttaagacgg gatgagatga    60
tgttgaagat aaagtgcaca atggcagacc atccacatca rtttacaaag aaaagatctt    120
gtccacgact taggtgaaga gagccaacta ttaatagcag aaataaaagc caacattata    180
gacatctcaa cttgttcagc t                                              201
```

<210> SEQ ID NO 1070
<211> LENGTH: 201
<212> TYPE: DNA
<213> ORGANISM: Homo sapiens

<400> SEQUENCE: 1070

```
caagactacc atccgcggac tcacggaatg ccgtattcac tatcatggta ttccacacag    60
cattgcctct gaccaaggca ctcactttat ggccaaagaa ktgtagcagt gggctcatgc    120
tcatgggatt cactggtctt accatgttcc ccatcatcct gaagcagctg gattgataaa    180
atggtgcaat ggccttttga a                                              201
```

<210> SEQ ID NO 1071
<211> LENGTH: 201
<212> TYPE: DNA
<213> ORGANISM: Homo sapiens

<400> SEQUENCE: 1071

```
tgttttttct taaaattgcc ttcagtttcc ttggaaatgg aggaatttgt ggagtatttt    60
agttattccc tttctggctg tggcaacaga agggcagatc matttaacta tttatctgcc    120
ctctcaacat atcttctagt tatatttgtt ttgtaggctt caaacctgtg aagagccttg    180
actgagggtt ctcatttctc c                                              201
```

<210> SEQ ID NO 1072
<211> LENGTH: 201
<212> TYPE: DNA
<213> ORGANISM: Homo sapiens

<400> SEQUENCE: 1072

```
aaatggattt acacaaagta aacattaact ttggtagatt tcaatgtaga atagttcata    60
```

-continued

```
acaagcatat tgcccttct gctcaactac caagttaaga mttttttcaag tattttaact    120 gagatttttat tatgttgaca tttgtttctc attccacatc gtctttggcc aagcgccagc    180
acttacaagt ctctgattaa c                                              201

<210> SEQ ID NO 1073
<211> LENGTH: 201
<212> TYPE: DNA
<213> ORGANISM: Homo sapiens

<400> SEQUENCE: 1073
tgtttcttct tgtctcattc attttactat ttcttatacc catcacaggg tctgtacatt     60
gcaggcattc agtactttt tttttaaatg aatgaggcca rttcaggttc taaacttttg    120
agtttcttct ccatatttct ttttgcttta ttactgcaat aaattattc ttaaattctg    180 tttaatcaga agatttttaag a                                             201

<210> SEQ ID NO 1074
<211> LENGTH: 201
<212> TYPE: DNA
<213> ORGANISM: Homo sapiens

<400> SEQUENCE: 1074
tattaaaaga aaaactgttg aggcaaaaag aaacaaaaca tttcacccttt ttccctgtag    60 aagccagagt gtgcttctca caaaagcctg tgcaacctcc rattttattc aagagctaaa    120
gaaactagca gtctccaagg ctccaagatt taatttccat tgcataggat gccccctcaca    180 tcagaattaa tcagttttca t                                              201

<210> SEQ ID NO 1075
<211> LENGTH: 201
<212> TYPE: DNA
<213> ORGANISM: Homo sapiens

<400> SEQUENCE: 1075
aggaagaact cggggtgtga ccaggatttt caaaagcggg gtcagagagg aactgatgga     60
agaaaagctt atagctagaa tagaatagga actcagaaaa ytggtgttgt cttgggctta    120 ttttcttttgg catcttgctc acaaaaggat agaatgatca aggatggat gtcaccaaga    180 gctaagccta ggccattcct g                                              201

<210> SEQ ID NO 1076
<211> LENGTH: 201
<212> TYPE: DNA
<213> ORGANISM: Homo sapiens

<400> SEQUENCE: 1076
aattagaacc acatatctta actagaacta cctagaacta aaagtacttg taaaaatatg     60
gcatagggac cccgtgaatc agcaggctta gtattggaaa ktataaacgc tccagaaatg    120
ggggcagggc atgtgactgt gatttgtggc caggattgag aacactggcc tccgtgagcc    180
aggatgaaaa gcagcctcct t                                              201

<210> SEQ ID NO 1077
<211> LENGTH: 201
<212> TYPE: DNA
<213> ORGANISM: Homo sapiens

<400> SEQUENCE: 1077
tttaaaaacc aagtaaaccc ctctccattgc accccctgct acttcagagg aacacctcca     60
```

```
ttctgatgga aggaactcgt acttgggtcc tggaaccta wttgggaccc aaacctctcc      120
cacttgtgtg gcctgacgtg cctgagtgct gtttgtgtcc tttttattat gttgaaaact      180
ttgttattcc aaagaaacat c                                                201

<210> SEQ ID NO 1078
<211> LENGTH: 201
<212> TYPE: DNA
<213> ORGANISM: Homo sapiens

<400> SEQUENCE: 1078
ctaagcactc tacacacttg agcagctttt attgaaagaa ctttgccttt gaacagaggg       60
tttaacagca cattatttca gatatgttca gtcaatgaat wtcagattct ttcttgagta      120
gcaagatata tgaatagaac tgagtaaggt ttctactttt taaagagtgc tgcaatgaac      180
actcatgcac atgtatcctg a                                                201

<210> SEQ ID NO 1079
<211> LENGTH: 201
<212> TYPE: DNA
<213> ORGANISM: Homo sapiens

<400> SEQUENCE: 1079
tatcaaaaga tgagtggata atgaaaattt actatataga cacaagaaaa agaaggaaat       60
gttgtcattt gcggcaaaga gggagccaga aggatataat kttaagtgaa acaaatcagg      120
cacaaaaaga tgaatatagc atgttctctt tcatgtgtgg gagctaaaaa tgttgagctt      180
atataaccac aaaattgtgg t                                                201

<210> SEQ ID NO 1080
<211> LENGTH: 201
<212> TYPE: DNA
<213> ORGANISM: Homo sapiens

<400> SEQUENCE: 1080
tatctcccta tcaagcccta ccatttcctc gttctcatca tacccattat ccctcaaggg       60
ccatagaaac acctcccctt gtaggaccta acacttctca rttcttccca gggaagcaga      120
tcctgaaagc cttttggagg ttttgtgtca tggttataca ggaaagagta tttagattac      180
aaagttacac attggcaggg t                                                201

<210> SEQ ID NO 1081
<211> LENGTH: 201
<212> TYPE: DNA
<213> ORGANISM: Homo sapiens

<400> SEQUENCE: 1081
tgcctatcat aagcctagag aacttgggag ttagtgaaat ataacattca tgttaatcaa       60 cctttagac atggttgtgt tgtgaagtaa aagctggaat ycagtattct cagttctgta      120
tatcattatc accagcggtg ctttaaagag aaaattatag gtctctctac atctatcata      180
cacctcctca gattcaatgg g                                                201

<210> SEQ ID NO 1082
<211> LENGTH: 201
<212> TYPE: DNA
<213> ORGANISM: Homo sapiens

<400> SEQUENCE: 1082
ttctaagctc aataaagtgc cattatcctg tcggttataa agaatggtt tggaagatcc       60
```

```
ttcacagccc accactctca cacaaagttt gcctgacaaa ytttctggcc aaaatggaag    120
gcactaaaaa tatagaagtt attatcagtc ttaagacaat accgttatat aataaataag    180
acattaccta attaaatttt c                                              201
```

<210> SEQ ID NO 1083
<211> LENGTH: 201
<212> TYPE: DNA
<213> ORGANISM: Homo sapiens

<400> SEQUENCE: 1083

```
tttgtggctg tgcaacaatg ggcaagttat tgaatcttct ttttcatcac ttgtgatatg    60
aagaaaacat tatatctact tccaaagatt gttgggaaga rttaacaagc tatgcacttt    120
cattgtaaaa gtgcctggat caaaggactc actcaatacg tgctaatagc tattttttaa    180
tttgcacgta agaagactga g                                              201
```

<210> SEQ ID NO 1084
<211> LENGTH: 201
<212> TYPE: DNA
<213> ORGANISM: Homo sapiens

<400> SEQUENCE: 1084

```
gtgaggacaa gggccagtgt gcaaatattt gcaaagcagg aagaccaaaa gaacctggct    60
catggatgac atcattaagt cagtggatta tccttggaat ygacttacct ctgggctatg    120
cgtgacatat gaaactcatt attatggaaa acactttttg ctaggttttg tgtacttgca    180
ggtaaaacac tctaatgatt t                                              201
```

<210> SEQ ID NO 1085
<211> LENGTH: 201
<212> TYPE: DNA
<213> ORGANISM: Homo sapiens

<400> SEQUENCE: 1085

```
atggaggcag atgcagtttc tcctgggcaa agactgaacg aatgcagcaa ttaaggagac    60
cccaactcag attggcctga tgccgggtcc tggtgcccaa ytgtgtccta gctccaggct    120
gtgtcacccc gagggcctga gacccatgcc aacaagccaa tttccctcac ctgtaaaatg    180
ggaatgccat tacctgtccc a                                              201
```

<210> SEQ ID NO 1086
<211> LENGTH: 201
<212> TYPE: DNA
<213> ORGANISM: Homo sapiens

<400> SEQUENCE: 1086

```
catgccacca cacctggcta attttttgtat tattagtaga gatggggttt agccatgttg    60
gccaggctag tctcgaactc ctgacctcaa acaatccaat ygcctcagcc tttcaaagtg    120
ctgggattac aggcatgagc caccatgcac cacctagttg attttttgtat taaaaatgct    180 tattgtccag ttacatgcat t                                              201
```

<210> SEQ ID NO 1087
<211> LENGTH: 201
<212> TYPE: DNA
<213> ORGANISM: Homo sapiens

<400> SEQUENCE: 1087

```
aaatgagaat tggaatctcc catacgctga aaagaagtct gagaccaaga ggtgccagct    60
```

```
aatctaacac cacaccgtga tttactaata agtatcaaat wtttaaacct ttcctttgtg      120
gcctcatgct ccatgaactt ttacctataa taaagttatt ttttcaaata atatatttct      180
atgtactcta ggggatacat a                                                201

<210> SEQ ID NO 1088
<211> LENGTH: 201
<212> TYPE: DNA
<213> ORGANISM: Homo sapiens

<400> SEQUENCE: 1088
ctctgctgga taacaagtgt cagctgcaaa aagacccatg tctgtcatac tgtaaacact       60
caaaataaaa taaaaagcat cattaaagta tttagccaat ytctttgcac atcaaaagtg      120
ctccatatat tttagttctg agtttactta tgctccaggt ataaaattat catcatttga      180
actgaaactt tatgatgaat t                                                201

<210> SEQ ID NO 1089
<211> LENGTH: 201
<212> TYPE: DNA
<213> ORGANISM: Homo sapiens

<400> SEQUENCE: 1089
tgatctcagc tcactgcaac ctccgcctcc tgggctcaag tgattttcca gctattctcc       60
tgaatagctg ggattacagg cgtgccacca gatccaggta rtttttagta gagatggggt      120
tttgacatgt tggccagcct ggtttcactc ctgacctcag gtgatccacc cgctgggatt      180
acaggttatc tttttttttt t                                                201

<210> SEQ ID NO 1090
<211> LENGTH: 201
<212> TYPE: DNA
<213> ORGANISM: Homo sapiens

<400> SEQUENCE: 1090
tctttcatat tattcaaatc tagagcagct gttcctcctc taggtaccca cagcatcctg       60 ggcttttcctt tgtcatagca tttgtcacac ctcttcaaat ytgtttcttt atctctcttg    120
tccactagac tcttgcaggc cgtatgatac tcttatctgc atgcccagtg cctagcatgg      180
tacccagcaa attgtaggca a                                                201

<210> SEQ ID NO 1091
<211> LENGTH: 201
<212> TYPE: DNA
<213> ORGANISM: Homo sapiens

<400> SEQUENCE: 1091
tgggttgaaa ggacatctaa ctatctttag tgttttgtgc caccccgtcc tgctttcctc       60
tcttccttac agagcacttg acaagaatcc ctcatatcaa rtttcagttc ttagaatcta     120
acgtaagata ctttcaatca ttatttccct gaaagaattt aagcattttc aaagcccttt      180
ttaattaaaa ataaaaatgt c                                                201

<210> SEQ ID NO 1092
<211> LENGTH: 201
<212> TYPE: DNA
<213> ORGANISM: Homo sapiens

<400> SEQUENCE: 1092
attaaatatc ttctcacttt cagcctgtgt gtgtccttaa atctaaagtg agtcttttgt       60
```

-continued

| | |
|---|---|
| agacgttatt atagtgggat cttgtttggg ttttcggaat ycactgtatg tctttgattg | 120 |
| agcagtttaa tccatttaca ttgaaagtac ttagtggtag gaaaggactt actattgcca | 180 |
| ttttgttaat tgcttttgtc t | 201 |

<210> SEQ ID NO 1093
<211> LENGTH: 201
<212> TYPE: DNA
<213> ORGANISM: Homo sapiens

<400> SEQUENCE: 1093

| | |
|---|---|
| atgaaatttc tcacagtatt ctttatttcc actctaaaat tacggagagg taatgagtat | 60 |
| aatactcaat gtattcattc atagtaggca atcaagcaat yggttttcat ttacttggtt | 120 |
| tggaaaagct ataaaaacct ttctttgtaa tcatggacta ataattacaa aaattgtttt | 180 |
| gtctctgttt ctatacaata c | 201 |

<210> SEQ ID NO 1094
<211> LENGTH: 201
<212> TYPE: DNA
<213> ORGANISM: Homo sapiens

<400> SEQUENCE: 1094

| | |
|---|---|
| tttctctggt aagagcaagg atactaaaac atgtttgagt gctgatgaaa ttgatcccat | 60 |
| agagagaaaa atgttgagag tactggggaa aaggggata rttgtaagaa tgaggtattt | 120 |
| taaagtgtta gaagaatgag atccaaagag caagaactgg cttgtcttag agaggagtag | 180 |
| agacagatct tcaattatca t | 201 |

<210> SEQ ID NO 1095
<211> LENGTH: 201
<212> TYPE: DNA
<213> ORGANISM: Homo sapiens

<400> SEQUENCE: 1095

| | |
|---|---|
| agagacagag taacgtgtta aatgatgctg caaggatgca atcagcacct ctgcaagccc | 60 |
| acaggacaaa cacaagtgta caaaacaagt accagcagta wtttaaaacg acggagtgga | 120 |
| atccacaaga aacataagac acttggtata taaaccttat ttggatctca ttcaagctag | 180 |
| caaactgtaa gaacagatat c | 201 |

<210> SEQ ID NO 1096
<211> LENGTH: 201
<212> TYPE: DNA
<213> ORGANISM: Homo sapiens

<400> SEQUENCE: 1096

| | |
|---|---|
| gaattcactt ttataagata cccttaccac acataaagca gaataatttt atctgaaggt | 60 |
| agacctggat gatattgtaa actctgagag caaccactaa ytttttttaa aggtgtgtaa | 120 |
| tgatatcctg agagattaga taaaatagaa ccatataaaa tcttcaagta aaatcagaaa | 180 |
| aggcagaaaa gaaacccctg g | 201 |

<210> SEQ ID NO 1097
<211> LENGTH: 201
<212> TYPE: DNA
<213> ORGANISM: Homo sapiens

<400> SEQUENCE: 1097

| | |
|---|---|
| ttattattat cagaaacaat ttttgtacta tgctttatat tataataggt gcccaaacat | 60 |

```
gttatgctat tgtccaaaa acactcacca gacaaaataa wtcttcttag tagtcccaga    120
ggcgttatgc ttcagtttgt ttttctccct ctttgctccc tgcacttcat cagcaagttt    180
gttcattctg cttctgattc a                                              201
```

<210> SEQ ID NO 1098
<211> LENGTH: 201
<212> TYPE: DNA
<213> ORGANISM: Homo sapiens

<400> SEQUENCE: 1098

```
ttcctcccat gacatgtgga gattatgaga actataattc aagatgagtt ttgggtgggg    60
atacagccaa accatgtcag taccactgat gattttaaat kgactttgtc gcttgccttg    120
gtggttcata aagagtgtc tggatatgtt ttgagcaata aagaaatgat tggaaaaagt     180
acacaatctc ccatgtgata a                                              201
```

<210> SEQ ID NO 1099
<211> LENGTH: 201
<212> TYPE: DNA
<213> ORGANISM: Homo sapiens

<400> SEQUENCE: 1099

```
ggcaagtcat cctgctcagt gccctcagaa catgcttttt ttctttcagt atctacagtg    60
cctagaactg tgcctggaca aagaagacct gaagtacaca wttgttgaac tgagtctctt    120
ttaatgtcta gtaagcctgg tgctataact ttatccttat gcagtcagca aatattcgaa    180
tatacactga gagaatcccc a                                              201
```

<210> SEQ ID NO 1100
<211> LENGTH: 201
<212> TYPE: DNA
<213> ORGANISM: Homo sapiens

<400> SEQUENCE: 1100

```
aggtggctcc tatttaacca agggcaattc tctggagaag ggggcacctg ttcattatta    60
tcccccaaac ctcacatcac ccagaggatg tgtacactaa ytggtactag ggaactaggc    120
agagcaccag ttgcatccac tatagtccac tcttcatcta catgcttctc tcattaagtt    180
cagtccatcc agacacagct t                                              201
```

<210> SEQ ID NO 1101
<211> LENGTH: 201
<212> TYPE: DNA
<213> ORGANISM: Homo sapiens

<400> SEQUENCE: 1101

```
ccctgcctga ggattaatcc ttccctgcta cagtcacaca actgcctcct tcagggaggg    60
gagagtgctc agctacgtga cccaaagttc aggatggtaa ktgatgtcaa aaagaggaag   120
aaagtttgca tgtaggtaac caggagtgag atcatgagaa atgcagggtc ttacccacat   180
ttgccccatc tgtgtattca g                                              201
```

<210> SEQ ID NO 1102
<211> LENGTH: 201
<212> TYPE: DNA
<213> ORGANISM: Homo sapiens

<400> SEQUENCE: 1102

```
gctgagctgc tggcagaggg gaggaggctg tgggaaccaa ggaagctacc aaagtgaact    60
```

```
tgggtctccg aactcaccac agaagcgggg actccaggaa ytctgtgca ggttgtttct    120 ttctccctct actttatatg aaaaacacct gcagtgacca actcaagact atgaatggtc    180
atcaccgcac aatgacatgg t                                             201
```

<210> SEQ ID NO 1103
<211> LENGTH: 201
<212> TYPE: DNA
<213> ORGANISM: Homo sapiens

<400> SEQUENCE: 1103

```
gatgtattca aaatatattt ttctgcttta ctatgtgata tctaattgta gcccctgttc    60
tgggttcctt ttctcatttt cttgctttcc tttgcagtaa ytgagttttt aaagtcattc    120 cacttttct tcttttagtt caaaaatatg cactctttta ttctagtggt taccttagaa    180
attataatat acatcattga c                                             201
```

<210> SEQ ID NO 1104
<211> LENGTH: 201
<212> TYPE: DNA
<213> ORGANISM: Homo sapiens

<400> SEQUENCE: 1104

```
taccaacagc tgggcaaagt tccaggacaa agtttagggc aggttcccag gcacagaagc    60
aagtggagtt gaggccatta aaagcagggg tctggtattg mattggccaa gctgtataat    120
gtcccgcaag ttagtgaacc tctgcaagcc tgagttttcc actatgtgaa atgagttcat    180
catagtccct atctcacagg g                                             201
```

<210> SEQ ID NO 1105
<211> LENGTH: 201
<212> TYPE: DNA
<213> ORGANISM: Homo sapiens

<400> SEQUENCE: 1105

```
tgtgtgccca gagcagggct gggctctcat agcacagcgg cggcagcaca gaccttgcag    60
ccctgtggag ctgttattct agtgtgggag gaaatgaccc mattgtctcg acggtggtcc    120
tatcaaagaa gtcgcatagg gtgacctgga tgagtactgt tgggagcaga ggccagggaa    180
actaggctcc acgctgggta a                                             201
```

<210> SEQ ID NO 1106
<211> LENGTH: 201
<212> TYPE: DNA
<213> ORGANISM: Homo sapiens

<400> SEQUENCE: 1106

```
aaggaagtga tggggaggaa aatcatgcaa ggataactgt tatcttgatt tcccaccctg    60
agattgggtg gagggggagc acaaacatac attggggtaa wtagaaatat atagcaaatg    120
ctacacttaa gcttggagac catggtcttt ccaattcagt gaattttttt tttttgaaat    180
ggcattcaaa ctttgttttg c                                             201
```

<210> SEQ ID NO 1107
<211> LENGTH: 201
<212> TYPE: DNA
<213> ORGANISM: Homo sapiens

<400> SEQUENCE: 1107

```
aaataagcac agactggatt ttaattttct aaactgatgt gccttttaa attgaataca    60
```

```
gaatagtctt caaatggaaa gggccacttt tttttactga wttaatgtga aacatactac    120
cactttattg ctagattaaa atgttagact agaagaaata acctagtagt ttgtctcata    180
atatcaattg aattatatga a                                              201

<210> SEQ ID NO 1108
<211> LENGTH: 201
<212> TYPE: DNA
<213> ORGANISM: Homo sapiens

<400> SEQUENCE: 1108
cattaaccgg atataaactt cttattggcc ttcttgggac tcaaatgctg tactattcat     60
cgagtaagag cttagtaaac ttgaagagaa taaatgaata mattgatata aaagcctttt    120
atgtttaagt gttttaaat ctaatagtga ttctaaaaaa gagaggggta aatgatgtgt    180
attttgctct aagatttcca a                                              201

<210> SEQ ID NO 1109
<211> LENGTH: 201
<212> TYPE: DNA
<213> ORGANISM: Homo sapiens

<400> SEQUENCE: 1109
agaaaatgaa ccttaatcta aacatcacaa ctcatacaaa aagtaactca aaatagatga     60
tggactgtaa aatgtaaaac tctaagactt ttagaaaaaa wtctatatga gaaagtattc    120
aggatgtaag gctaggcaag gcattcttag acttgatatc aaagagcatg accccaaaaa    180
agaaaaaaat tgataaatta t                                              201

<210> SEQ ID NO 1110
<211> LENGTH: 201
<212> TYPE: DNA
<213> ORGANISM: Homo sapiens

<400> SEQUENCE: 1110
gctcttccct aaggcctcat cagaacgagg cctttatacc acagaggaca cacacaccac     60
acagactgga catctcagag ggcccatggc atgttttcaa rttgcggaga gcaaaagaga    120
ggccatagtt aggactgatc atagttcatc ctcaatcgtg tcaatgagtg caggtaagcc    180
aggctgtaga aaaaccaaag a                                              201

<210> SEQ ID NO 1111
<211> LENGTH: 201
<212> TYPE: DNA
<213> ORGANISM: Homo sapiens

<400> SEQUENCE: 1111
ttgtagagaa ataaaacagt ggctgaaggg ggtgtgcatg tcgagagaga gagagtttga     60
gaagggaagt gttgtagcat ggttgtatgt ggatgggatt rattcagtca agagggaaaa    120
actgatgatg cagggaaaag aaggatagtt atgaaagtgt tatccttcat aagtgagagg    180
gaatgggatc ttgtgcacaa g                                              201

<210> SEQ ID NO 1112
<211> LENGTH: 201
<212> TYPE: DNA
<213> ORGANISM: Homo sapiens

<400> SEQUENCE: 1112
acctccacct ggtggggcct gtcagtgtac cacaggtcta ccttgatttc aagtccatct     60
```

```
cctaataatg aagtaaaatg ttttccctg cattgaagaa mtttccagtg tcttggatgg      120
gggagcttaa ggagcagatg ctcattcttg gggtatggag gtgataactt gtaggcagac    180
tgttcctagg aacacacgta a                                               201

<210> SEQ ID NO 1113
<211> LENGTH: 201
<212> TYPE: DNA
<213> ORGANISM: Homo sapiens

<400> SEQUENCE: 1113
aaacagtgca gtgcagttgt tgatctcagc tgttttaatg catgaaacat gttaaaacat     60
gtcagtatta actgtgaact tttttgcaa gggaggaaaa ytgagataat attcctttga      120
atcatgaaca acaagtggtt gataagtgct atatccctgg ccagctttt tgtgttgctt     180 catagctgag ccacatcagt t                                               201

<210> SEQ ID NO 1114
<211> LENGTH: 201
<212> TYPE: DNA
<213> ORGANISM: Homo sapiens

<400> SEQUENCE: 1114
tttagaaact gaaactaagt atatctgatg ttgcttttag gaaacaagta aatgaggtcc     60
taaaaagtta aactgtgacc atattttctt tcctttttct matttctcct tgggccattt    120
ccaaaaagcc ctaataccccc gactgataga aatggatacc ttgctgtgca ctggtactac   180
tgtgattcat ggaaagctga t                                               201

<210> SEQ ID NO 1115
<211> LENGTH: 201
<212> TYPE: DNA
<213> ORGANISM: Homo sapiens

<400> SEQUENCE: 1115
gcagataacc acagtgggag ggaggcttcc cctgatgggc cagcagggtt agggcactct     60 cattcccgc tgcctgtgca gcaatgatca cagctataat ygaacaggga atggccttct    120
gccagtcccc cctgatgaca ggagatggct gaggccttct ccctgctgtg tctccagcat    180
gaagcatgcg gcctagaaca c                                               201

<210> SEQ ID NO 1116
<211> LENGTH: 201
<212> TYPE: DNA
<213> ORGANISM: Homo sapiens

<400> SEQUENCE: 1116
tgtgagagca aggattcttt atctacatat aaaataaaac aaaagtggaa ccatattttt     60
gtccccaaac atccctttga tactaccatt gaggtttcac mattaggaca gttttcttcc    120
agcaccctca ctaaacgaca ccctctact ctcatcttgc acaattccct tccttcctct    180
ccagcaaaca ttcctctatt t                                               201

<210> SEQ ID NO 1117
<211> LENGTH: 201
<212> TYPE: DNA
<213> ORGANISM: Homo sapiens

<400> SEQUENCE: 1117
caaccatgtt taccaaatga tactaaacaa ttgataagat catctccaca tggataacag     60
```

```
ctgcttatgg agatgagtaa gagcaggtga aatgtttcta wttctattca tacatgagca    120
gattaataga gagctaaaat ggtgttcagg gtcttatgag tagcactttt ggttagggtt    180
ttcctgttaa catccattat a                                              201
```

<210> SEQ ID NO 1118
<211> LENGTH: 201
<212> TYPE: DNA
<213> ORGANISM: Homo sapiens

<400> SEQUENCE: 1118

```
gggtttcatg tacgtgtgga tggaggttgg ctcagagatg tttccacatt ccagctctg    60 acagctgttg gtaatagcta cagccctggt cccctggaat ycgcttccct gcctggcctg   120
accctgcgct gacagtcagc tcttctcaaa caagcagtct caatgatgat aagcatctcc   180
ttggaaggag aagcttcgaa g                                              201
```

<210> SEQ ID NO 1119
<211> LENGTH: 201
<212> TYPE: DNA
<213> ORGANISM: Homo sapiens

<400> SEQUENCE: 1119

```
ggtaaaaaat taagcttgca tttcctttt acacagaagc tcttccacta attcaagcca    60
atacatttac aatagaacat gccagaaagt gccacaaaat wtcaataaca ggcaacacca   120
ctaggcttca gtgaccactg atttcatcct ccttctccta tattctttcc tatagtcctt   180
atacatcaat gtcatggact a                                              201
```

<210> SEQ ID NO 1120
<211> LENGTH: 201
<212> TYPE: DNA
<213> ORGANISM: Homo sapiens

<400> SEQUENCE: 1120

```
ccacaggaaa cttcacaaag gtttacgtac agaagcattt ggggccatgt ctgtcttggc    60
tatggggaca ggtggggcta agccggcatc tctgctgtca rttgccagac tgcagagaga   120
ggcccttgcc tccttccaca aggtgtttcc aataaagggg acatatttcc ttcgttagaa   180
ataaacacag actgacaata t                                              201
```

<210> SEQ ID NO 1121
<211> LENGTH: 201
<212> TYPE: DNA
<213> ORGANISM: Homo sapiens

<400> SEQUENCE: 1121

```
gaggaaatgg ccatttctga ggtgctcaga accacaggct caccccttc acagggttag     60 gatgggagct gttacaggga gtttcctgta ctttaaaaaa kttaaacaac agaatccagc   120
ctttgctagc tttgggtact gtaaatgatt tactgtaaca taaaacacat cgagtgagaa   180
aaatatagaa taagtttttt c                                              201
```

<210> SEQ ID NO 1122
<211> LENGTH: 201
<212> TYPE: DNA
<213> ORGANISM: Homo sapiens

<400> SEQUENCE: 1122

```
tttaagtgtc gtccaaaaga gattagtatt ggtcataaca tggactctaa agccaccatt    60
```

```
taaatgaagc atgtaaaaaa gaatattcta gtacacaaaa rttattaatg gcctagaatg    120
acctccttct cactcatatg atgcaaagaa taaagtatat aaaaatgttt gttacaatgg    180
ctatccataa aaaagaaaac c                                              201

<210> SEQ ID NO 1123
<211> LENGTH: 201
<212> TYPE: DNA
<213> ORGANISM: Homo sapiens

<400> SEQUENCE: 1123
catttaaaaa tgtgtttatc aaaagacact gttaagatta tgaaaaggca atccacacgg    60
tgaaagaaga tattcaaaat acatatattc aacaaagaat ktatatccag tatataaaca    120
cacacacaca cacacacacc ctacagatta ataagaacaa agacaatcca acagcaaaaa    180
acaataggaa attatgaaag t                                              201

<210> SEQ ID NO 1124
<211> LENGTH: 201
<212> TYPE: DNA
<213> ORGANISM: Homo sapiens

<400> SEQUENCE: 1124
gtccctgaag atgtgttgtt gagaatggat gacaaacagt tcaggtcaac cttgagtaag    60
tgtgaggaaa aaataaaaat aaataaatga aggatgtaat ygggctcctc tcctggagac    120
tgaaaagtaa ggactggcat ggaaatcttt gattttggc agtatatcat tatctttaga     180
ggtctagaaa aagtgcctac g                                              201

<210> SEQ ID NO 1125
<211> LENGTH: 201
<212> TYPE: DNA
<213> ORGANISM: Homo sapiens

<400> SEQUENCE: 1125
tttacaacag catccaaaag gataagctac ttcggaataa atttaaccaa tgaggtagga    60
aacgtgtaca ctgaaaacta taaagcattg ctaaaagaat ytaaagatga tacaaatgaa    120
agaaaagaca tcctgttttc atggattgga agacttaata ttgttaaggt gtcaatacta    180
ttgatacagt ttggatctat g                                              201

<210> SEQ ID NO 1126
<211> LENGTH: 201
<212> TYPE: DNA
<213> ORGANISM: Homo sapiens

<400> SEQUENCE: 1126
cctcctgccc ggtccataga aaaattgtct tccatgaaat cgatccctgg tgcccaaaag    60
tttggaggcc actggattaa aggagacaat gtatgtaaat yttggcttat aataagttct    120
tggaaagtgc tagctgtgtc ttatcactga ttatagtatc ccaatcaaac cttgacactt    180
gggttaggat tatttatttc c                                              201

<210> SEQ ID NO 1127
<211> LENGTH: 201
<212> TYPE: DNA
<213> ORGANISM: Homo sapiens

<400> SEQUENCE: 1127
tgtgtgtgtg tgtgtgtgtg cgcgcgcgcg tgtgtgtgtg tgtgtccact ggccttttca    60
```

| | |
|---|---|
| aagtctctct tttgttttgc aactttggct ttatttataa kttaaatcta gacatttctt | 120 |
| cttgtgaagt ccatgcacgc cactcttggg acatccctat gttgcagcag aggataaaaa | 180 |
| tggaaaattc agggtcctta a | 201 |

<210> SEQ ID NO 1128
<211> LENGTH: 201
<212> TYPE: DNA
<213> ORGANISM: Homo sapiens

<400> SEQUENCE: 1128

| | |
|---|---|
| ctgaattcct gtaaagaaag gagactcata tcctgaagaa tgaagacatc aaaagcaagg | 60 |
| tgctgtggca agttagccct tggtggaggg tttttcacaa ytggatatcc tgctgtgtag | 120 |
| aactgaatac ccacagcagg gttattcagg cagctccagg gatgagagaa agtgtcttga | 180 |
| ctgatacata atttatctgt c | 201 |

<210> SEQ ID NO 1129
<211> LENGTH: 201
<212> TYPE: DNA
<213> ORGANISM: Homo sapiens

<400> SEQUENCE: 1129

| | |
|---|---|
| agagttactg ttgctccacg tcctaccagc atttggtgtc agtgttctgg atgttggcca | 60 |
| ttctaataag tatgtagtgc tatctcattg ttgtttgaaa ytgtatttcc cagatgcata | 120 |
| tgatgtggaa cgtcttctca tatgctaaca tgccatctgt atatcttcct tggggtgtct | 180 |
| gctaaggtct tttgcccaat g | 201 |

<210> SEQ ID NO 1130
<211> LENGTH: 201
<212> TYPE: DNA
<213> ORGANISM: Homo sapiens

<400> SEQUENCE: 1130

| | |
|---|---|
| tacttgttaa tactccaatt acttcccaga ttaagagatt tgtttctcta caacaaatat | 60 |
| ttgtacctac cttgctctga gaaacagcct gcactgtgaa ytcattttat caacaacaag | 120 |
| actgcttaaa agcaggaaga aaaagccata aaaaatgatg agttcacgtc ctttgtaggg | 180 |
| acatggatga tactggaaat c | 201 |

<210> SEQ ID NO 1131
<211> LENGTH: 201
<212> TYPE: DNA
<213> ORGANISM: Homo sapiens

<400> SEQUENCE: 1131

| | |
|---|---|
| gaacccttc cttgcccta gacaagccac agctgacctg ctgagcagcc tggaggacct | 60 |
| ggagctcagc aaccgacgtc tggttgggga gaatgccaaa ytgcagcgga gcatggagac | 120 |
| agctgaggag gggtcagcac gccttgggga ggagatcttg gctctgcgta agcagcttca | 180 |
| caggtgggct ggatgccaca c | 201 |

<210> SEQ ID NO 1132
<211> LENGTH: 201
<212> TYPE: DNA
<213> ORGANISM: Homo sapiens

<400> SEQUENCE: 1132

| | |
|---|---|
| actaaacaaa tgtattaaat gttcctggct ctgtacacca tcctttaggt agagaataat | 60 |

```
ggcaggcatt tgggtgtttc tcaggagttc ccagcagaat ygactacctt tgcccagagc      120
agtaatctta gtaatgcaca cacaagttgt ctttttctcc tctcctgcat cgttaaataa      180
actacaaata tatgagtaga a                                                201
```

<210> SEQ ID NO 1133
<211> LENGTH: 201
<212> TYPE: DNA
<213> ORGANISM: Homo sapiens

<400> SEQUENCE: 1133

```
atgaaatgga ttcacatttt taatgttcta tgtaattact tatcattgtt gttttaatag      60
ggaaagtatt ggttatataa atagccaaga aaacagccaa ytgagacttt tcttcctaga     120
ttaccttggt tatatcagtg cttctgggtg tggtcactga tattctacag cagaaacagc     180 tagtgggtc cccaactaaa g                                                 201
```

<210> SEQ ID NO 1134
<211> LENGTH: 201
<212> TYPE: DNA
<213> ORGANISM: Homo sapiens

<400> SEQUENCE: 1134

```
gatggcatat ggagaggact tacaaaaggg cttcggaaat atttattatt attatacaat      60
aatacatgat attttgtgac ggttaatact gagtgtcaaa wtgatttgat tgtagaatgc     120
caagtattga tcctgggtgt gtctgtaagg gtgttgtcaa aggtgattaa catttgagtc     180
agtgggctgg gaaaggcaga c                                                201
```

<210> SEQ ID NO 1135
<211> LENGTH: 201
<212> TYPE: DNA
<213> ORGANISM: Homo sapiens

<400> SEQUENCE: 1135

```
agaatgtatt tattgatctg tgatatctat ccatacacca atagtaacta ttttatataa      60 actactttt tgaaaagtct tgacataagg tagtataaat yctgttgctc ttctctgttt      120
cagtatttcc tttgcaaccc tctttaagat tgcctttcac ttctatgtaa gttctcaaaa     180
gaggttgtta atttaataa a                                                 201
```

<210> SEQ ID NO 1136
<211> LENGTH: 201
<212> TYPE: DNA
<213> ORGANISM: Homo sapiens

<400> SEQUENCE: 1136

```
aatataagtg gaatcataaa ataggtggtc ttttttggct ggattcttta atttatcaaa      60
atgcttagaa ggttcattta tgtggtagca tgtagcagta rttatttcct tttgttgtca     120
gataatatcc attgcctcaa tagaccacat tttcttctca atttatcact tgatagacat     180
ttgaattatt tatacttttt g                                                201
```

<210> SEQ ID NO 1137
<211> LENGTH: 201
<212> TYPE: DNA
<213> ORGANISM: Homo sapiens

<400> SEQUENCE: 1137

```
cagagctatc acctaaaagc atcacatgga catttaaaat tctcagtaga gcatttttc       60
```

```
cttctaatga agctttccta aacctgtgac attggtttaa yttgtgcagg agtttcctcc      120
ttgtatttgt ttaaatgccc ccagaagctc ggaaagcagg aagtggtttg aaggggattc      180
agacaaggtt agctggggag g                                                201
```

<210> SEQ ID NO 1138
<211> LENGTH: 201
<212> TYPE: DNA
<213> ORGANISM: Homo sapiens

<400> SEQUENCE: 1138

```
gtacagtgaa agcacttcaa atctttcag gtgtaatcat aagaaattat ttatcttagg       60
attcttgata tattacatcg aaatcaaggt ttatgttata wttgagtaaa gttttcaagg      120
atgaaaacga ttttgcctat ttttttctga agaattacaa acacctgctt ctttcatctt      180
cctttgacac tctgttcctg a                                                201
```

<210> SEQ ID NO 1139
<211> LENGTH: 201
<212> TYPE: DNA
<213> ORGANISM: Homo sapiens

<400> SEQUENCE: 1139

```
gctctggacc cagccacgct gggagggaaa ccacctgatt tcaggtacag aaccactctc      60
atgtaccctc tctgctgaga gttattccat cactcaataa mattcttctc tgccctcctc     120
accccttgat tgtcagtgta acctcactct tcttggacgc tgaacaagaa ctgaggaact     180
gctgaatgca ggtacagctg t                                                201
```

<210> SEQ ID NO 1140
<211> LENGTH: 201
<212> TYPE: DNA
<213> ORGANISM: Homo sapiens

<400> SEQUENCE: 1140

```
tacttcaaat aacatctaca cttttttaaag aagaagattc aatctcagag aaactggttt     60
ggtttctcag ctgggaatat ttatttggtc atactaaaca rttgagccag tggatcagca    120
gtagctgatt gcaagattct taagtagaca cacattacat ttcgtagggg atcaaaatat    180
gtcattctca agtatgctaa t                                                201
```

<210> SEQ ID NO 1141
<211> LENGTH: 201
<212> TYPE: DNA
<213> ORGANISM: Homo sapiens

<400> SEQUENCE: 1141

```
ccatctctaa tttccgggag atttataatt tgtttgtatt attttgtgaa tcatccgttc      60
atgtcttctg cctattcttc tacggtcttt ttcttatcaa yttgtaaaga ctctaatgta    120
atagccaact gctacaagca tgtttctgat ttgttgttta ccttttgatg ttcttgatat    180
taaaagatgc ttatatagct g                                                201
```

<210> SEQ ID NO 1142
<211> LENGTH: 201
<212> TYPE: DNA
<213> ORGANISM: Homo sapiens

<400> SEQUENCE: 1142

```
ctccacatct gtctacttgc ttgttgacta tcttaccccc ttaggctata agtactcact      60
```

```
gatctgtctc aagtgtctgg ttcatagtta aaagtcaata mttacgtgat gaatgaatga    120
atagatggaa aaatcaatgg atgggtggat ggatgatctt tacagattaa cttgaaccag    180
atcatgtaag gagctgttta a                                              201

<210> SEQ ID NO 1143
<211> LENGTH: 201
<212> TYPE: DNA
<213> ORGANISM: Homo sapiens

<400> SEQUENCE: 1143
tttagcttca tgatttaaca ggaatagtgt gaggtaaaat gacatgagtc acttaaagcc    60
tttcagaagg agaagtacca gccttgatgt ggggaaaaaa ytggtcatgg tggctcacac    120
gtgtaatcct agcactttgg gaggccgaga tgggcgaatc acaaggtcag gagttcgaaa    180
ccagtctggc caacatgatg a                                              201

<210> SEQ ID NO 1144
<211> LENGTH: 201
<212> TYPE: DNA
<213> ORGANISM: Homo sapiens

<400> SEQUENCE: 1144
caggactttg ggaggccaag gcaggtggat cacctgaggt caggagttcg agaccggcct    60
gaccaatatg gagaaacctg tctctactaa aaataagaaa rttagcctgg cctggtggtg    120
tgggactgta gtcccagata ctcgggaggc tgagacagaa aaactacttg aacccgggag    180
gtggaggttg caacgagcgg a                                              201

<210> SEQ ID NO 1145
<211> LENGTH: 201
<212> TYPE: DNA
<213> ORGANISM: Homo sapiens

<400> SEQUENCE: 1145
ttagccagga tggtcttgac ctcctgaaat tgtcattatt tgcttttaat gtggattgct    60
tttatgagaa taactatgag ctcatggatt ttatatagta rttgtcacgc atgtccgtgt    120
gaagagagtc caccaacagg ctttgtgtga gcaacaaggt tgtttatttc acctgggtgc    180
aggcaggctg agtccaaaaa a                                              201

<210> SEQ ID NO 1146
<211> LENGTH: 201
<212> TYPE: DNA
<213> ORGANISM: Homo sapiens

<400> SEQUENCE: 1146
tgctgtggtt aggaggtata acttggttaa gtgtttctac ccacgcgtag gctatggttt    60
acatagccta tgcacacata gcctatgtgt gcatagttta matttcctac cagcccccca    120 aaaaggggaac acttgctttt cttatcaact tgcccaagat gtggggtaga agggaagggg    180
caagtggtag agctcgcaag c                                              201

<210> SEQ ID NO 1147
<211> LENGTH: 201
<212> TYPE: DNA
<213> ORGANISM: Homo sapiens

<400> SEQUENCE: 1147
tactgttctc aaaaggcaaa gtcctgtgta gttcatgact tctgtggacc atacagagat    60
```

```
aaaaataaga atggaaagtg atgagatttc tatcatacaa wtgtcatttc ctgtgaaaag    120
gcaaagatga tttcaaatag tgaacaagcc tagaaagttt ttaagggggct ttggaacatg   180 atagagacac acaatcagac a                                               201

<210> SEQ ID NO 1148
<211> LENGTH: 201
<212> TYPE: DNA
<213> ORGANISM: Homo sapiens

<400> SEQUENCE: 1148
ctggcctaca attttttttaa agtgataaca tgaagaataa aaaagctgac aaactgttcc    60
agattaaagg taagtaaaaa atcattatca ctaaaggcaa yttgagcttt cgatttggct   120
caggattgtg gggaaaggag gtggggtggg gaaaagaggt ggaggacatg agttgccaca   180
aaattattga acaattggt g                                               201

<210> SEQ ID NO 1149
<211> LENGTH: 201
<212> TYPE: DNA
<213> ORGANISM: Homo sapiens

<400> SEQUENCE: 1149 gatagtccctt aggccttgaa gtcattagag gtgcaatgct gtagggccag aatgggtaaa    60
ggagggaagg tgggataaac aaggggtttt gtggtgaaga mattcacttg aaggggcact   120
taacatgtta tctgacctgt gataagtgct cagtatttgc caatggatga attatgactg   180
aatgaataaa gtcacaacct g                                              201

<210> SEQ ID NO 1150
<211> LENGTH: 201
<212> TYPE: DNA
<213> ORGANISM: Homo sapiens

<400> SEQUENCE: 1150 gaatatctttt acattgattt cctgatgcgc tacatatcac tgcatgcatt gaaacctggg    60
atacacaaaa aagttatgct gaggtatcat ctctaagaat ycaatacagg agtgaggtcg   120
agattgcctt ttgagagtaa atccagaagc caacttaata gatcagagca gaattaaggc   180
aaaattactt taggataatg g                                              201

<210> SEQ ID NO 1151
<211> LENGTH: 201
<212> TYPE: DNA
<213> ORGANISM: Homo sapiens

<400> SEQUENCE: 1151
aatgaggatg atgaagggaa gtgtctgtgc agggctttta acccttcagg agtttggccc    60
agttcatcag agagaaaagg gagtaggtac ttgtcacaaa rttttggcttc agtatcaggt   120 tttcatatgg ctggctggaa cctgtataag gacccaggaa tggatagagc tactttgtaa   180
tgagagactt tgacacattt g                                              201

<210> SEQ ID NO 1152
<211> LENGTH: 201
<212> TYPE: DNA
<213> ORGANISM: Homo sapiens

<400> SEQUENCE: 1152
ctctgtgatt ttagattgtg ggtttatatt tgctggcatg ctatctctgc ggtttctttt    60
```

```
gaggactggg ttgagggtac ctttctttct ccagggatga wttgtgtttg cttttgtcag    120
acactgagca ctactgacat gaatcctctt aaaaatacaa tggtcagcca tataaactac    180
gtaaacagtg tagattcagt t                                              201

<210> SEQ ID NO 1153
<211> LENGTH: 201
<212> TYPE: DNA
<213> ORGANISM: Homo sapiens

<400> SEQUENCE: 1153
tgcacagtca ccctggagag aaccatgcca caagcccaga tccaggacac actgtcatgc     60
aggcttcctt ccccaccact caggaaagca aactgctaca mttaaaaagg aacaagggca    120
agtctggtgc tgctcttcac tgggattttt ttcttttttt tttttttta agacagagtc    180 tcactctgcc atcaggctgc a                                              201

<210> SEQ ID NO 1154
<211> LENGTH: 201
<212> TYPE: DNA
<213> ORGANISM: Homo sapiens

<400> SEQUENCE: 1154
ataaatatat aatttaacaa aagagaataa caagaacgaa gtaaaggaat acatgtgggt     60
atgtgtgtat ctatgtaaaa atggagagcc atgagtgaaa ytgtatacca aggaagcaa    120 cgtatattct taaaaggaa aaaaaaaga catgagaatg cattggtctt ccgtgaaatg    180
tagctactgt aaggttttta t                                              201

<210> SEQ ID NO 1155
<211> LENGTH: 201
<212> TYPE: DNA
<213> ORGANISM: Homo sapiens

<400> SEQUENCE: 1155
gggcatcttt cagttagtac gtggtactgg acaagagatc aggttgaact gtaaggctct     60
agttttcagc agactcatgg tcctgggaga aagaaaacaa ytggacaggg ggctatcaag    120
gtagccaggt tttgagggga ctcagttcag gagaaaagaa ctggaaagca ggtcctgtgc    180
tgcttttctc cttgagaaat t                                              201

<210> SEQ ID NO 1156
<211> LENGTH: 201
<212> TYPE: DNA
<213> ORGANISM: Homo sapiens

<400> SEQUENCE: 1156
cattcctttc cattacatac tttctttgtc gacctgagtt ttcagccgtt gctgaaataa     60
aagcaagtat tgcacaagaa tcagtttggt gttccatcca mttccaaagt ttgagttgtg    120
tcatgcccaa caggcaaaca cacctcactc agtaattgtg gttaagaatg aaataggcgc    180
agtggctcac gcctgtaatc c                                              201

<210> SEQ ID NO 1157
<211> LENGTH: 201
<212> TYPE: DNA
<213> ORGANISM: Homo sapiens

<400> SEQUENCE: 1157
aaacaaacaa acaaacaaaa aaacccataa ttcagcccac cagtggcctc aggttactgt     60
```

```
gtgtacaagg tgtttgtggg atatttctgg tctcccacaa yttcagctga tgtccagagt      120
taaagggctc taagtaagta ccccaccttc tataaagtgt tgctaaggaa agccctcaat      180
gctaaggctt tgatacaaaa t                                                201

<210> SEQ ID NO 1158
<211> LENGTH: 201
<212> TYPE: DNA
<213> ORGANISM: Homo sapiens

<400> SEQUENCE: 1158
atagacattc actaagatat tgcatctatg aaaaataatt acacgctatg taaaagtagc      60
aataaaaata aaaaaagcta ctgaaaatga aatgtataa ytgacaaaca taaactgcat      120
atgaactttg gaagagtaaa taagtatcc tggaatatag aacaaaataa tatagagtaa      180
aaaaaaagga aaaatcttag a                                                201

<210> SEQ ID NO 1159
<211> LENGTH: 201
<212> TYPE: DNA
<213> ORGANISM: Homo sapiens

<400> SEQUENCE: 1159
ggaaccaagt cccatcattg caatatctct ctggattcca ttgtaatcca tttcagacgc      60
agccacacgt gttcatgaac tcatcaatgc aatctggaaa yttgactttg gcttgtgatc      120
tctgacattt tgatgtttta aagtgggttt tctggagtgg agtcttgggc ctccctctca      180
cacttacgga gtcttcctat g                                                201

<210> SEQ ID NO 1160
<211> LENGTH: 201
<212> TYPE: DNA
<213> ORGANISM: Homo sapiens

<400> SEQUENCE: 1160
ctatttgctt gtgtcccttc atctcctgct ggaccatgag ctcctggaga gcagggatgt      60
gtgtctaatg catggcaggc actctatcaa tacaggaatg mattttatgt ggaatctgac      120
ttttttcctc agatgtggaa gcacgcagca acaaacatat gtcgtgaatc aaaaaccggg      180
acataaagcc tcacacaggg t                                                201

<210> SEQ ID NO 1161
<211> LENGTH: 201
<212> TYPE: DNA
<213> ORGANISM: Homo sapiens

<400> SEQUENCE: 1161
ttatttgtga gcagtatttt agttttaaat ggtagatatt aagcctgtac aatgatattc      60
aaacaatggt atattgaatg gatagaagaa tctgtcataa wattagagta atggtttgaa      120
aaaccaatgt ttgtggagat agcagtcagg gtagttatgg ggagaacaga gactagaagc      180
tgaaattaca aagtgatcaa g                                                201

<210> SEQ ID NO 1162
<211> LENGTH: 201
<212> TYPE: DNA
<213> ORGANISM: Homo sapiens

<400> SEQUENCE: 1162
ggcaagacaa aggaaaggga gttcagccctt gtaggggtgg taaattgtgg attttcctgg    60
```

```
tatgaaagag tgaagggagg acgttttctt aaacaaaaat ktatgccctg ctttcaagca         120
agtaggggga gggcacagag cttttctgtg cctgctattt cttgattgcc ttcagcttaa         180
aataattctt atgtcaaaga g                                                   201
```

<210> SEQ ID NO 1163
<211> LENGTH: 201
<212> TYPE: DNA
<213> ORGANISM: Homo sapiens

<400> SEQUENCE: 1163

```
tacacagggc agacatgatg gtggcttggc ccagtgtggt ggcagcaagg gtagtaggaa          60
gtggttagat tctggttata tgttaaagat agagcaccag matttccgga cagattggat        120
gggaggtgtc actaaaacag aaatccaggg ataactctga ggtgtttggc ctgagttatt        180
agaatgataa tattatattt a                                                   201
```

<210> SEQ ID NO 1164
<211> LENGTH: 201
<212> TYPE: DNA
<213> ORGANISM: Homo sapiens

<400> SEQUENCE: 1164

```
aatgtggtgg cctcacacta agacgtagag aagaagagaa cctagagtca atgaagctca          60
taaaatgcta ctccaacaga ggaggtgaca taagtaagta wttccatggg agagggaggt        120
cagcagtggg gataatgaag aaaggaatat tataaataca ttttgatgga aaaatgtaaa        180
aggataagtc attaattccc t                                                   201
```

<210> SEQ ID NO 1165
<211> LENGTH: 201
<212> TYPE: DNA
<213> ORGANISM: Homo sapiens

<400> SEQUENCE: 1165

```
atttgctatc tctggatatc tagcttattt ctaaaaacct ctagtgacca tgaactatct          60
tccaaggtgg tcttttggag acggatggct ctgggttcaa yttattccgg ctctaccatt        120
taccaactct ttgatcatag gaaagttggc tactcttgaa agtttatcat tattaaacgt        180
gcaaaagcac taatacctgt t                                                   201
```

<210> SEQ ID NO 1166
<211> LENGTH: 201
<212> TYPE: DNA
<213> ORGANISM: Homo sapiens

<400> SEQUENCE: 1166

```
accatattag taagtctccc ctgcattatg gtgtactgtt agtgtgtcac tcatatcata          60
tcagattcct taaacatttg tttgcataaa gtccccatgt rattctattc cccatagtaa        120
gtacctgctt ctctagcacc atgtactatg tactatgcac aagtagccag aatcagattt        180
gtctacagaa ttggagaact a                                                   201
```

<210> SEQ ID NO 1167
<211> LENGTH: 201
<212> TYPE: DNA
<213> ORGANISM: Homo sapiens

<400> SEQUENCE: 1167

```
tttaccagga attgtgatac ttcatttata cacatacttt atttaatcct taccatgacc          60
```

-continued

```
atagatgact tacatatgct aagagccagg actctagtcc rattcaaatc tgtctgaccc      120
cagaatcctt agcattttca atgtgtttct ggaaatagcc ttaccataaa ccgcagttgc      180 acttttttacc acctaatgtg t                                                201
```

<210> SEQ ID NO 1168
<211> LENGTH: 201
<212> TYPE: DNA
<213> ORGANISM: Homo sapiens

<400> SEQUENCE: 1168

```
ggacttacag tctcattcag gaagaccttg acaaacaaat gctaacataa aaaccaccag      60
actgctattt agccattctg tctgggatga ctatattaat yatttttatga cagcgtttct     120 ttccttctga atggttgtta ccagcgaggt accttttgct caatgtttgc ttaaagacat      180
gtctatatat tatctggcaa g                                                 201
```

<210> SEQ ID NO 1169
<211> LENGTH: 212
<212> TYPE: DNA
<213> ORGANISM: Homo sapiens

<400> SEQUENCE: 1169

```
acctcatcct gggcaccctg gttatatcaa cttcagctat gaggtaattt ttctctttac      60
taattttgac cattgtttgc gttaacaatg ccctgggctc tgtaaagaat agtgtgttga     120
ttctttatcc cagatgtttc tcaagtggtc ctgattttac agttcctacc accagcttcc    180
cagtttaagc tctgatggtt ggcctcaagc ct                                    212
```

<210> SEQ ID NO 1170
<211> LENGTH: 218
<212> TYPE: DNA
<213> ORGANISM: Homo sapiens

<400> SEQUENCE: 1170

```
acctcatcct gggcaccctg gttatatcaa cttcagctat gaggtaattt ttctctttac      60
taattttgat cactgtttgc attagcagtc ccctgggctc tgtaaagaat agtgggtgga     120
ttcttcatcc caaataaagt ggtttctcaa gtggtcccaa ttttacagtt cctaccatca    180
gcttcccagt ttaagctctg atggttggcc tcaagcct                             218
```

<210> SEQ ID NO 1171
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1171

```
acgttggatg ccctgggctc tgtaaagaat                                       30
```

<210> SEQ ID NO 1172
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1172

```
acgttggatg aggcttgagg ccaaccatca g                                     31
```

```
<210> SEQ ID NO 1173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1173
ttcttcatcc caaataaagt                                                   20

<210> SEQ ID NO 1174
<211> LENGTH: 122
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1174
ccctgggctc tgtaaagaat agtgtgttga ttctttatcc cagaagtttc tcaagtggtc       60
ctgattttac agttcctacc accagcttcc cagtttaagc tctgatggtt ggcctcaagc      120
ct                                                                    122

<210> SEQ ID NO 1175
<211> LENGTH: 122
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1175
aggcttgagg ccaaccatca gagcttaaac tgggaagctg gtggtaggaa ctgtaaaatc       60
aggaccactt gagaaacttc tgggataaag aatcaacaca ctattcttta cagagcccag      120
gg                                                                    122

<210> SEQ ID NO 1176
<211> LENGTH: 128
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1176
ccctgggctc tgtaaagaat agtgggtgga ttcttcatcc caaataaagt cgtttctcaa       60
gtggtcccaa ttttacagtt cctaccatca gcttcccagt ttaagctctg atggttggcc      120
tcaagcct                                                              128

<210> SEQ ID NO 1177
<211> LENGTH: 128
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1177
aggcttgagg ccaaccatca gagcttaaac tgggaagctg atggtaggaa ctgtaaaatt       60
gggaccactt gagaaacgac tttatttggg atgaagaatc cacccactat tctttacaga      120
gcccaggg                                                              128
```

-continued

<210> SEQ ID NO 1178
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1178
acgttggatg tatcaacttc agctatgagg                                      30

<210> SEQ ID NO 1179
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1179
acgttggatg cactattctt tacagagc                                        28

<210> SEQ ID NO 1180
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1180
ctttacagag cccaggg                                                    17

<210> SEQ ID NO 1181
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1181
tatcaacttc agctatgagg taattttttct ctttactaat tttgaycayt gtttgcrtta    60
rcartaccct gggctctgta aagaatagtg                                      90

<210> SEQ ID NO 1182
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1182
cactattctt tacagagccc agggtartgr taargcaaac aytgytcaaa attagtaaag    60
agaaaaatta cctcatagct gaagttgata                                      90

<210> SEQ ID NO 1183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1183
ccctgggctc tgtaaagaat                                                 20

```
<210> SEQ ID NO 1184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1184
gagcttaaac tgggaagctg                                              20

<210> SEQ ID NO 1185
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1185
ccctgggctc tgtaaagaat agt                                          23

<210> SEQ ID NO 1186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1186
ttcttcatcc caaataaagt g                                            21

<210> SEQ ID NO 1187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1187
ccctgggctc tgtaaagaat agtg                                         24

<210> SEQ ID NO 1188
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1188
ctgggctctg taaagaatag t                                            21

<210> SEQ ID NO 1189
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1189
ctgggctctg taaagaatag tg                                           22

<210> SEQ ID NO 1190
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1190
caggacagca gtagagca                                                   18

<210> SEQ ID NO 1191
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1191
caggacagca gtagagcag                                                  19

<210> SEQ ID NO 1192
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1192
gctcagtatc ttcagcagtg tccatttgaa gatcatgtaa aattagtgaa tgaagtaact     60
gaatttgc                                                              68

<210> SEQ ID NO 1193
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1193
acgttggatg cagtatcttc agcagtgtcc                                      30

<210> SEQ ID NO 1194
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1194
acgttggatg gcaaattcag ttacttcatt c                                    31

<210> SEQ ID NO 1195
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1195
cagtgtccat ttgaagatc                                                  19

<210> SEQ ID NO 1196
<211> LENGTH: 65
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1196
cagtatcttc agcagtgtcc atttgaagat cttgtaaaat tagtgaatga agtaactgaa    60
tttgc                                                                65

<210> SEQ ID NO 1197
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1197
gcaaattcag ttacttcatt cactaatttt acaagatctt caaatggaca ctgctgaaga    60
tactg                                                                65
```